US008765746B2

(12) United States Patent
Freeze et al.

(10) Patent No.: US 8,765,746 B2
(45) Date of Patent: Jul. 1, 2014

(54) HETEROARYLS AND USES THEREOF

(75) Inventors: Brian S. Freeze, Boston, MA (US); Masaaki Hirose, Kanagawa (JP); Hong Myung Lee, Cambridge, MA (US); Todd B. Sells, Bellingham, MA (US); Zhan Shi, Concord, MA (US); Leo R. Takaoka, Newton, MA (US); Stepan Vyskocil, Arlington, MA (US); Tianlin Xu, Shrewsbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/272,413

(22) Filed: Oct. 13, 2011

(65) Prior Publication Data
US 2012/0214794 A1 Aug. 23, 2012

Related U.S. Application Data

(60) Provisional application No. 61/392,515, filed on Oct. 13, 2010.

(51) Int. Cl.
*C07D 409/04* (2006.01)
*C07D 409/14* (2006.01)
*C07D 417/04* (2006.01)
*A61K 31/427* (2006.01)
*A61K 31/4196* (2006.01)
*A61K 31/5377* (2006.01)

(52) U.S. Cl.
USPC ......... 514/233.8; 514/301; 544/127; 546/114

(58) Field of Classification Search
USPC .................. 544/127; 546/114; 514/233.8, 301
See application file for complete search history.

(56) References Cited

U.S. PATENT DOCUMENTS

| | | | |
|---|---|---|---|
| 3,257,203 A | 6/1966 | Sus et al. | |
| 3,821,384 A | 6/1974 | Ariyan et al. | |
| 3,852,293 A | 12/1974 | Ariyan et al. | |
| 4,371,607 A | 2/1983 | Donges | |
| 5,134,142 A | 7/1992 | Matsuo et al. | |
| 6,015,826 A | 1/2000 | Pechacek et al. | |
| 6,608,087 B1 | 8/2003 | Charifson et al. | |
| 6,984,652 B2 | 1/2006 | Yager et al. | |
| 7,405,235 B2 | 7/2008 | Levy et al. | |
| 7,504,513 B2 | 3/2009 | Boylan et al. | |
| 7,741,348 B2 | 6/2010 | Nan et al. | |
| 8,440,664 B2 | 5/2013 | Cardin et al. | |
| 8,586,582 B2 | 11/2013 | Liang et al. | |
| 2002/0022729 A1 | 2/2002 | Kawai et al. | |
| 2003/0096816 A1 | 5/2003 | Cao et al. | |
| 2004/0116425 A1 | 6/2004 | Li et al. | |
| 2004/0198773 A1 | 10/2004 | Hart et al. | |
| 2004/0248896 A1 | 12/2004 | Dean et al. | |
| 2005/0004122 A1 | 1/2005 | Brown et al. | |
| 2005/0054697 A1 | 3/2005 | Yager et al. | |
| 2006/0041006 A1 | 2/2006 | Ibrahim et al. | |
| 2006/0074119 A1 | 4/2006 | Andrews et al. | |
| 2006/0199804 A1 | 9/2006 | Hummersone et al. | |
| 2007/0203210 A1 | 8/2007 | Boylan et al. | |
| 2008/0021217 A1 | 1/2008 | Borchardt et al. | |
| 2008/0045570 A1 | 2/2008 | Brenchley et al. | |
| 2008/0132546 A1 | 6/2008 | Basarab et al. | |
| 2008/0255120 A1 | 10/2008 | Lin et al. | |
| 2008/0293716 A1 | 11/2008 | Drewry et al. | |
| 2008/0306060 A1 | 12/2008 | Alexander et al. | |
| 2009/0012031 A1 | 1/2009 | Chinnaiyan et al. | |
| 2009/0030016 A1 | 1/2009 | Gandhi et al. | |

(Continued)

FOREIGN PATENT DOCUMENTS

DE 275870 A1 2/1990
EP 0853083 A1 7/1998

(Continued)

OTHER PUBLICATIONS

International Search Report for PCT/US11/56135 (Publication No. WO 2012/051410), mailed May 31, 2012.
4-Oxazolecarboxylic acid, 5-[(ethoxymethylene)amino]-2-(4-pyridinyl)-, ethyl ester- (CA Index Name), CAS Registry No. 885901-22-4, entered May 29, 2006.
Adib, M. et al., Facile One-Pot Three-Component Synthesis of Functionalized Pyridylfuran-2-amines, Helvetica Chimica Acta, 89(2):299-303 (2006).

(Continued)

*Primary Examiner* — Bruck Kifle
(74) *Attorney, Agent, or Firm* — Choate, Hall & Stewart LLP; Andrea L. C. Reid; Daniel A. Klein

(57) ABSTRACT

This invention provides compounds of formula I-A or I-B:

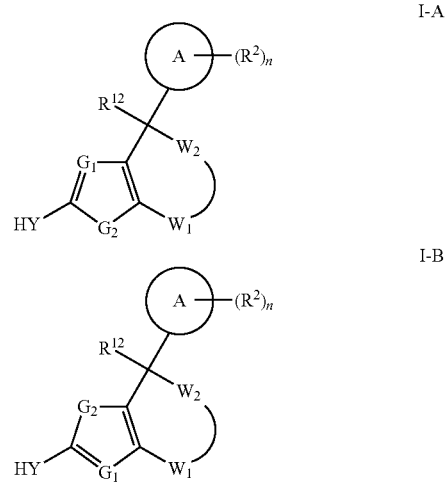

wherein HY, $G_1$, $G_2$, $R^2$, $R^{12}$, $W_1$, $W_2$, n, and Ring A are as described in the specification. The compounds are inhibitors of PI3K and/or mTor and are thus useful for treating proliferative, inflammatory, or cardiovascular disorders.

27 Claims, No Drawings

(56) References Cited

U.S. PATENT DOCUMENTS

| | | |
|---|---|---|
| 2009/0036435 A1 | 2/2009 | Curry et al. |
| 2009/0247567 A1 | 10/2009 | Do et al. |
| 2009/0325925 A1 | 12/2009 | Renou et al. |
| 2010/0075951 A1 | 3/2010 | Cardin et al. |
| 2010/0256172 A1 | 10/2010 | Shi et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0142732 A1 | 6/2012 | Cullis et al. |
| 2012/0172345 A1 | 7/2012 | Freeze et al. |
| 2012/0178723 A1 | 7/2012 | Hirose et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| GB | 874634 A | 8/1961 |
| JP | 10087490 | 4/1998 |
| JP | 2007-197324 A | 8/2007 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2006/114343 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO-2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/080873 A1 | 7/2010 |
| WO | WO-2010090716 A1 | 8/2010 |
| WO | WO-2010/132598 A1 | 11/2010 |
| WO | WO-2011/043371 A1 | 4/2011 |

OTHER PUBLICATIONS

Boppana, K. et al., Knowledge based identification of MAO-B selective inhibitors using pharmacophore and structure based virtual screening models, European Journal of Medicinal Chemistry, 44:3584-3590 (2009).

Chattopadhyay, S. K. et al., Efficient Construction of the Carbon Skeleton of the Novel Polyoxazole-Based Cyclopeptide IB-01211 via a Biomimetic Macrocyclisation, SYNLETT, 4:555-558 (2010).

Database Chemcats, Chemical Abstracts Service, Columbus, Ohio, US, XP002545555, order No. T5337328, May 2006.

Fletcher, A. N. et al., Laser Dye Stability, Part 12. The Pyridinium Salts, Applied Physics, B43:155-160 (1987).

Hernandez, D. et al., Synthesis and Antitumor Activity of Mechercharmycin A Analogues, Journal of Medicinal Chemistry, 51: 5722-5730 (2008).

Hernandez, D. et al., Synthesis of Natural Product Derivatives Containing 2,4-Concatenated Oxazoles, European Journal of Organic Chemistry, (19): 3389-3396 (2008).

International Search Report for PCT/US09/00513, 3 pages (Jun. 10, 2009).

International Search Report for PCT/US09/03607, 4 pages (Sep. 23, 2009).

International Search Report for PCT/US10/00234, 3 pages (Jun. 1, 2010).

International Search Report for PCT/US11/47245, 2 pages (Dec. 22, 2011).

International Search Report for PCT/US11/47407, 2 pages (Dec. 22, 2011).

Liang, J. et al., Crystal Structure of P13K SH3 Domain at 2.0 A Resolution, Journal of Molecular Biology, 257:632-643 (1996).

Menear, K. A. et al., Identification and optimisation of novel and selective small molecular weight kinase inhibitors of mTOR, Bioorganic & Medicinal Chemistry Letters, 19:5898-5901 (2009).

Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).

Thompson, M. J. et al., Development of a Diversity-Oriented Approach to Oxazole-5-amide Libraries, Journal of Organic Chemistry, 74(10):3856-3865 (2009).

Wang, Q. et al., Copper-Mediated Amidation of Heterocyclic and Aromatic C-H Bonds, Organic Letters, 11( 22): 5178-5180 (2009).

Written Opinion for PCT/US09/00513, 5 pages (Jun. 10, 2009).

Written Opinion for PCT/US09/03607, 5 pages (Sep. 23, 2009).

Written Opinion for PCT/US10/00234, 6 pages (Jun. 1, 2010).

Written Opinion for PCT/US11/47245, 5 pages (Dec. 22, 2011).

Written Opinion for PCT/US11/47407, 7 pages (Jun. 10, 2009).

Written Opinion for PCT/US11/56135, 13 pages (May 31, 2012).

Zhang, F. et al., Decarboxylative C-H Cross-Coupling of Azoles, Angew. Chem. Int. Ed., 49(15): 2768-2771 (2010).

Berndt, A. et al., The p110 crystal structure uncovers mechanisms for selectivity and potency of novel PI3K inhibitors, Nature Chemical Biology, 6(2):117-124 (2010).

Choi, W. et al., Synthesis and Antiproliferative Activities of 1-Substituted-3-(3-chloro-5-methoxy phenyl)-4-pyridinylpyrazole Derivatives Against Melanoma Cell Line, Bulletin of the Korean Chemical Society, 30(9):2027-2031 (2009).

Benzamide, N-[2-(5-amino-1-phenyl-1H-pyrazol-4-yl)-4-phenyl-5-thiazolyl]-4-methyl- (CA Index Name), CAS Registry No. 1017527-68-2, entered Apr. 27, 2008.

Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).

5-Thiazolecarboxamide, N-[2'-(aminosulfonyl)[1,1'-biphenyl]-2-yl]-4-(4-methoxyphenyl)-2-(1H-pyrrol-1-yl)- (CA Index Name), CAS Registry No. 1027033-64-2, entered Jun. 10, 2008.

(56) References Cited

OTHER PUBLICATIONS 1,2,4-Oxadiazole-3-ethanamine, 5-[5-(1H-imidazol-2-yl)-2-thienyl]-N,N-dimethyl- (CA Index Name), CAS Registry No. 1066888-52-5, entered Oct. 27, 2008.
1,2,4-Oxadiazole, 5-[5-(1H-imidazol-2-yl)-2-thienyl]-3-(methoxymethyl)-(CA Index Name), CAS Registry No. 1069660-66-7, entered Nov. 2, 2008.
2,7-Naphthyridine, 1,2,3,4-tetrahydro-5-[5-[5-(1H-imidazol-2-yl)-2-thienyl]-1,2,4-oxadiazol-3-yl]-6-methyl- (CA Index Name), CAS Registry No. 1069717-72-1, entered Nov. 2, 2008.
Pyrazolo[1,5-a]pyrimidin-7(4H)-one,3-ethyl-5-[5-(1H-imidazol-2-yl)-2-thienyl]- (CA Index Name), CAS Registry No. 1087437-07-7, entered Dec. 21, 2008.
3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.
Acetamide, N-(3,5-dichlorophenyl)-2-[[4-methyl-5-[4-methyl-2-(5-methyl-3-isoxazolyl)-5-thiazolyl]-4H-1,2,4- triazol-3-yl]thio]- (CA Index Name), CAS Registry No. 264626-19-9, entered May 12, 2000.
Acetamide, N-(4-chlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.
Carbamic acid, 4,4'-diphenyl[2,2'-bithiazole]-5,5'-diyl)bis-, dimethyl ester (9CI)(CA Index Name), CAS Registry No. 505060-78-6, entered Apr. 25, 2003.
Benzamide, N,N'-(4,4'-di-2-thienyl[2,2'-bithiazole]-5,5'-diyl)bis- (CA Index Name) CAS Registry No. 691381-57-4, entered Jun. 10, 2004.
Carbamic acid, N,N'-(4,4'-di-2-thienyl[2,2'-bithiazole]-5,5'-diyl) bis-,C,C'-dimethyl ester (CA Index Name) CAS Registry No. 691381-58-5, entered Jun. 10, 2004.
Benzamide, N,N'-[4,4'-bis(4-fluorophenyl)[2,2'-bithiazole]-5,5'-diyl]bis[4-methyl- (CA Index Name) CAS Registry No. 691381-60-9, entered Jun. 10, 2004.
Imidazo[1,2-a]pyridine, 6-[3-[5-(2H-tetrazol-5-yl)-2-thienyl]-1H-pyrazol-4-yl]-3-(2-thiazolyl)- (CA Index Name) CAS Registry No. 732241-18-8, entered Aug. 25, 2004).
Benzamide, N-(4'-amino-2',3'-dihydro-3',4-diphenyl-2'-thioxo[2,5'-bithiazol]-5-yl)- (CA Index Name) CAS Registry No. 879910-33-5, entered Apr. 10, 2006.
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
2-Thiazolamine, 4-[5-(2H-tetrazol-5-yl)-2-thienyl]- (CA Index Name), CAS Registry No. 937625-84-8, entered Jun. 17, 2007.
1H-Pyrazole-1-carboxylic acid, 5[2,2'-bithiophen]-5-yl-, ethyl ester (CA Index Name), CAS Registry No. 957595-63-0, entered Dec. 12, 2007.
4-Thiazolecarboxamide, 2-(4-acetyl-5-methyl-1H-1,2,3-triazol-1-yl)-N,N-diethyl-5-phenyl- (CA Index Name), CAS Registry No. 709639-21-4, entered Jul. 14, 2004.
2-Thiophenecarboxylic acid, 3-(4-chlorophenyl)-4-cyano-5(4-morpholinyl)-(CA Index Name), CAS Registry No. 883097-33-4, entered May 5, 2006.
2-Thiophenecarboxylic acid, 3-(4-chlorophenyl)-4-cyano-5(4-morpholinyl)-, methyl ester (CA Index Name), CAS Registry No. 882283-38-7, entered Apr. 30, 2006.
Abdelrazek et al., Heterocyclic Synthesis with Nitriles: Synthesis of Some Novel Thiophene and Thieno[2,3-d]Pyrimidine Derivatives, Phosphorus, Sulfur, Silicons, 71:93-97 (1992).

Al-Azawe et al., Synthesis of 2, 5-Disubstituted Thiazoles and Their Reactions with Grignard Reagents, Journal of the Iraqi Chemical Society, 13(1): 1-13 (1988).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Cudworth et al., Structure-Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Datta et al., A Novel Route to Methyl 3-3(3,4-Disubstituted 5-alkylthio/amino-2-thienyl) propenoates, Synthesis, 7:556-567 (1988).
Emmitte et al., Discovery of Thiophene Inhibitors of Polo-like Kinase, Bioorganic & Medicinal Chemistry Letters, 19(3): 1018-1021 (2009).
Fridman et al., Spectroscopy, Photophysical and Photochemical Properties of Bisimidazole, Derivatives, Journal of Photochemistry and Photobiology, A: Chemistry, 188(1): 25-33 (2007).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Sytesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathil-2-ylideneimmonium Salt, Chemical & Pharmaceutical Bulletin, 19(10): 2194-2197 (1971).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liu et al., Highly Selective and Potent Thiophenes as PI3K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Prcursors of Materials for Nonlinear Optics, Tetrahedron, 48(45): 9951-9966 (1992).
Mamedov et al., Synthesis and Some Properties of the Methyl Ester and N,N-diethylamide of 2-Azido-5-Phyenyl-4-Thiazolecarboxylic Acic, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Nagasaki et al., CASREACT 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pinto et al., The Synthesis of 5-alkoxy and 5-amino Substituted Thiophenes, Tetrahedron Letters, 41(10): 1597-1600 (2000).
Raap, Some Synthesis with Dimethyl Monothionemalonate, Canadian Journal of Chemistry, 46:13, 2255-2261 (1968).

(56) References Cited

OTHER PUBLICATIONS

Rehwald et al., New Synthesis of 2,4-Diaminothiophenes- Use of (1,3-oxathioI-2-ylidene)Malononitrile, Heterocycles, 45(3): 493-500 (1997).

Sheridan, The Most Common Chemical Replacements in Drug-Like Compounds, J. Chem. Inf. Comput. Sci., 42:103-108 (2002).

Welker et al., Recent syntheses of PI3K/Akt/mTOR signaling pathway inhibitors, Bioorganic & Medicinal Chemistry, 21(14): 4063-4091 (2013).

HETEROARYLS AND USES THEREOF

The present application claims the benefit of U.S. Provisional Application Ser. No. 61/392,515, filed Oct. 13, 2010 (pending), which is hereby incorporated by reference in its entirety.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Vacuolar Protein Sorting 34 (VPS34) is the sole Class III PI3K family member. VPS34 functions in the formation and trafficking of multiple intracellular vesicles, including vacuoles, endosomes, multivessicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionshy Science 2004; Kondo et al Nat Rev Cancer 2005; Delgato et al Immunol Rev 2009).

Clearly, it would be beneficial to provide novel PI3K inhibitors that possess good therapeutic properties, especially for the treatment of proliferative, inflammatory, or cardiovascular disorders.

1. General Description of Compounds of the Invention

This invention provides compounds that are inhibitors of PI3K, and accordingly are useful for the treatment of proliferative, inflammatory, or cardiovascular disorders. The compounds of this invention are represented by formula I-A or I-B:

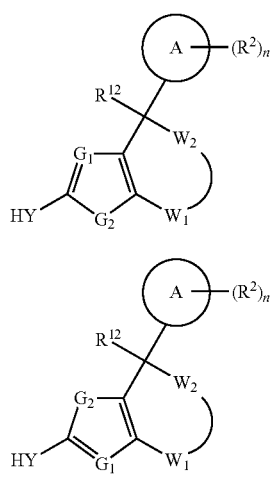

or a pharmaceutically acceptable salt thereof, wherein:

$G_1$ is N or $CR^1$, wherein $R^1$ is H, —CN, halogen, or an optionally substituted group selected from $C_{1-6}$ aliphatic, 3-10-membered cycloaliphatic, or —Z—$R^{11}$, wherein:
  Z is selected from an optionally substituted $C_{1-3}$ alkylene chain, —O—, —N($R^{1a}$)—, —S—, —S(O)—, S(O)$_2$—, —C(O)—, —CO$_2$—, —C(O)N$R^{1a}$—, —N($R^{1a}$)C(O)—, —N($R^{1a}$)CO$_2$—, —S(O)$_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, or —OC(O)—;
  $R^{1a}$ is hydrogen or an optionally substituted $C_{1-4}$ aliphatic, and
  $R^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, O, or $NR^3$, wherein $R^3$ is hydrogen or an optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2R^{12d}$, or —$V_2$-$T_2$-$R^{12d}$, and:
  each occurrence of $R^{12a}$ is independently halogen, —CN, —NO$_2$, —$R^{12c}$, —N($R^{12b}$)$_2$, —OR$^{12b}$, —SR$^{12c}$, —S(O)$_2R^{12c}$, —C(O)$R^{12b}$, —C(O)OR$^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12e}$, —N($R^{12e}$)C(O)OR$^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{12e}$ is independently hydrogen or an optionally substituted $C_{1-6}$ aliphatic group;
  each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
  $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;
  n is 0 to 4;
  $R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —OR$^{4a}$, or —SR$^{4a}$;
  or $R^2$ and $R^{12}$ form an optionally substituted 3-10-membered cycloaliphatic;

$W_1$ is selected from —C(O)C(R$^4$)$_2$—, —C(R$^4$)$_2$C(O)—, —C(O)O—, —OC(O)—, —C(O)NR$^{4a}$—, —NR$^{4a}$C(O)—, —C(=NR$^{4b}$)C(R$^4$)$_2$—, —C(R$^4$)$_2$C(=NR$^{4b}$)—, —C(=NR$^{4b}$)O—, —OC(=NR$^{4b}$)—, —C(=NR$^{4b}$)NR$^{4a}$—, —NR$^{4a}$C(=NR$^{4b}$)—, —S(O)C(R$^4$)$_2$—, —C(R$^4$)$_2$S(O)—, —S(O)O—, —OS(O)—, —S(O)NR$^{4a}$—, —NR$^{4a}$S(O)—, —S(O)$_2$C(R$^4$)$_2$—, —C(R$^4$)$_2$S(O)$_2$—, —S(O)$_2$O—, —OS(O)$_2$—, —S(O)$_2$NR$^{4a}$—, —NR$^{4a}$S(O)$_2$—, —C(S)C(R$^4$)$_2$—, —C(R$^4$)$_2$C(S)—, —C(S)O—, —OC(S)—, —C(S)NR$^{4a}$—, or —NR$^{4a}$C(S)—, wherein:

$W_2$ is —(C—$W_3$)$_r$, or any two occurrences of $W_2$ is independently —C(R$^5$)=C(R$^5$)—;

wherein each occurrence of $W_3$ is independently —(R$^5$)$_2$ or =O;

r is 0 to 3;

each occurrence of R$^4$ is independently hydrogen, halo, or an optionally substituted $C_{1-6}$ aliphatic or —C(O)OR$^{4c}$;

each occurrence of R$^{4a}$ is independently hydrogen or optionally substituted $C_{1-6}$ aliphatic;

each occurrence of R$^{4b}$ is independently hydrogen, or a group selected from optionally substituted $C_{1-6}$ aliphatic, —OR$^{4c}$, or —N(R$^{4a}$)$_2$;

each occurrence of R$^{4c}$ is independently hydrogen or optionally substituted $C_{1-6}$ aliphatic;

each occurrence of R$^5$ is independently hydrogen, halo, or an optionally substituted group selected from $C_{1-6}$ aliphatic, —C(O)N(R$^{5a}$)$_2$, 3-10-membered cycloaliphatic, 6-10-membered aryl, 5-10-membered heteroaryl having 1-5 heteroatoms independently selected from nitrogen, oxygen, or sulfur, —N(R$^{4b}$)$_2$, —OR$^{4a}$, or —SR$^{4a}$;

each occurrence of R$^{5a}$ is independently hydrogen or optionally substituted $C_{1-6}$ aliphatic;

HY is an optionally substituted group selected from:

A
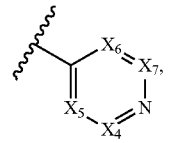

B
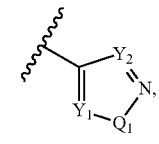

C
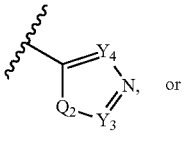

or

D
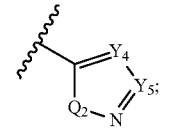

wherein each occurrence of $X_4$, $X_5$, $X_6$, and $X_7$ is independently —CR$^{10}$ or N, provided no more than two occurrences of $X_4$, $X_5$, $X_6$, and $X_7$ are N;

each occurrence of $Q_1$ and $Q_2$ is independently S, O or —NR$^6$;

each occurrence of $Y_1$, $Y_2$, $Y_3$, $Y_4$, and $Y_5$ is independently —CR$^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein R$^{10}$ is —R$^{10b}$, —V$_1$—R$^{10c}$, -T$_1$-R$^{10b}$, or —V$_1$-T$_1$-R$^{10b}$ wherein:

$V_1$ is —NR$^7$—, —NR$^7$—C(O)—, —NR$^7$—C(S)—, —NR$^7$—C(NR$^7$)—, —NR$^7$C(O)OR$^{10a}$—, —NR$^7$C(O)NR$^7$—, —NR$^7$C(O)SR$^{10a}$—, —NR$^7$C(S)OR$^{10a}$—, —NR$^7$C(S)NR$^7$—, —NR$^7$C(S)SR$^{10a}$—, —NR$^7$C(NR$^7$)OR$^{10a}$—, —NR$^7$C(NR$^7$)NR$^7$—, —NR$^7$S(O)$_2$—, —NR$^7$S(O)$_2$NR$^7$—, —C(O)—, —CO$_2$—, —C(O)NR$^7$—, —C(O)NR$^7$O—, —SO$_2$—, or —SO$_2$NR$^7$—;

each occurrence of R$^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N(R$^7$)—, —O—, —S—, —S(O)—, —S(O)$_2$—, —C(O)—, —C(O)O—, —C(O)N(R$^7$)—, —S(O)$_2$N(R$^7$)—, —OC(O)N(R$^7$)—, —N(R$^7$)C(O)—, —N(R$^7$)SO$_2$—, —N(R$^{10a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^7$)—O— or wherein $T_1$ forms part of an optionally substituted 3-7 membered cycloaliphatic or heterocyclyl ring;

each occurrence of R$^{10b}$ is independently hydrogen, halogen, —CN, —NO$_2$, —N(R$^7$)$_2$, —OR$^{10a}$, —SR$^{10a}$, —S(O)$_2$R$^{10a}$, —C(O)R$^{10a}$, —C(O)OR$^{10a}$, —C(O)N(R$^7$)$_2$, —S(O)$_2$N(R$^7$)$_2$, —OC(O)N(R$^7$)$_2$, —N(R$^7$)C(O)R$^{10a}$, —N(R$^7$)SO$_2$R$^{10a}$, —N(R$^7$)C(O)OR$^{10a}$, —N(R$^7$)C(O)N(R$^7$)$_2$, or —N(R$^7$)SO$_2$N(R$^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or R$^7$ and R$^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of R$^7$ is independently hydrogen, —C(O)R$^{7a}$, —CO$_2$R$^{7a}$, —C(O)N(R$^{7a}$)$_2$, —C(O)N(R$^{7a}$)—OR$^{7a}$, —SO$_2$R$^{7a}$, —SO$_2$N(R$^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10- membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O)$R^{6a}$, —CO$_2R^{6a}$, —C(O)N($R^{6b}$)$_2$, —SO$_2R^{6a}$, —SO$_2$N($R^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or HY is

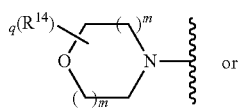

E or

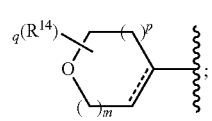

F wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —O$R^{14b}$, —S$R^{14c}$, —S(O)$_2$$R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14}$)$_2$, —N($R^{14e}$)C(O)$R^{14b}$, —N($R^{14e}$)SO$_2R^{14c}$, —N($R^{14e}$)C(O)O$R^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —N$R^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;

m is 1 or 2; and p is 0, 1, or 2, provided that for compounds of formula I-B, compounds are other than:

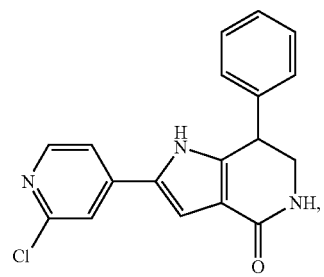

-continued

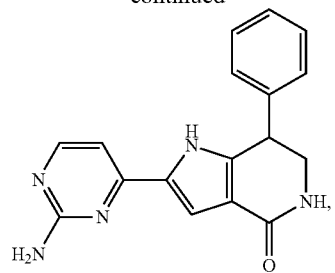
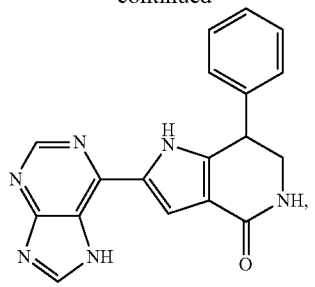
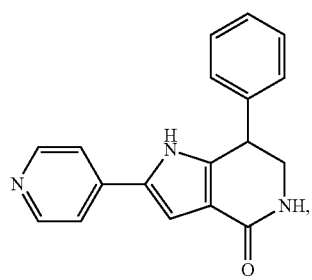
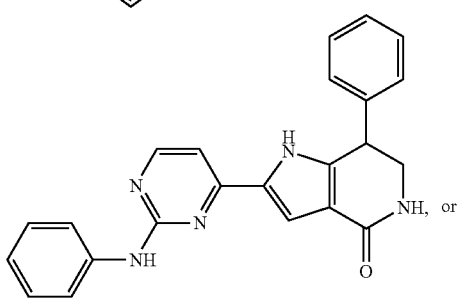
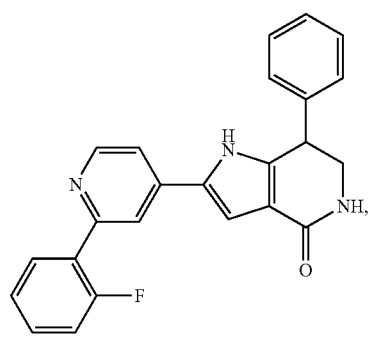
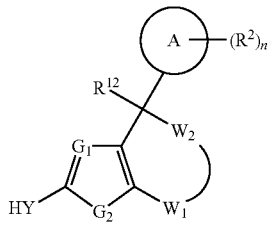
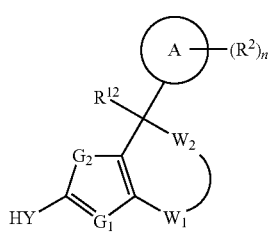

In another aspect, the compounds of this invention are represented by formula I-A or I-B:

$$\text{I-A}$$

$$\text{I-B}$$

or a pharmaceutically acceptable salt thereof, wherein:

$G_1$ is N or $CR^1$, wherein $R^1$ is H, —CN, halogen, or an optionally substituted group selected from $C_{1-6}$ aliphatic, 3-10-membered cycloaliphatic, or —Z—$R^{11}$, wherein:

Z is selected from an optionally substituted $C_{1-3}$alkylene chain, —O—, —N($R^{1a}$)—, —S—, —S(O)—, $S(O)_2$—, —C(O)—, —$CO_2$—, —C(O)N$R^{1a}$—, —N($R^{1a}$)C(O)—, —N($R^{1a}$)$CO_2$—, —S(O)$_2$N$R^{1a}$—, —N($R^{1a}$)S $(O)_2$—, —OC(O)N($R^{1a}$)—, —N($R^{1a}$)C(O)N$R^{1a}$—, —N($R^{1a}$)S(O)$_2$N($R^{1a}$)—, or —OC(O)—;
$R^{1a}$ is hydrogen or an optionally substituted $C_{1-4}$ aliphatic, and
$R^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, O, or $NR^3$, wherein $R^3$ is hydrogen or an optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, and:

each occurrence of $R^{12a}$ is independently halogen, —CN, —$NO_2$, —$R^{12c}$, —N($R^{12b}$)$_2$, —$OR^{12b}$, —$SR^{12c}$, —S(O)$_2R^{12c}$, —C(O)$R^{12b}$, —C(O)$OR^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)$OR^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —$OR^{4a}$, or —$SR^{4a}$;

or $R^2$ and $R^{12}$ form an optionally substituted 3-10-membered cycloaliphatic;

$W_1$ is selected from —C(O)C($R^4$)$_2$—, —C($R^4$)$_2$C(O)—, —C(O)O—, —OC(O)—, —C(O)$NR^{4a}$—, —$NR^{4a}$C(O)—, —C(=$NR^{4b}$)C($R^4$)$_2$—, —C($R^4$)$_2$C(=$NR^{4b}$)—, —C(=$NR^{4b}$)O—, —OC(=$NR^{4b}$)—, —C(=$NR^{4b}$)$NR^{4a}$—, —$NR^{4a}$C(=$NR^{4b}$)—, —S(O)C($R^4$)$_2$—, —C($R^4$)$_2$S(O)—, —S(O)O—, —OS(O)—, —S(O)$NR^{4a}$—, —$NR^{4a}$S(O)—, —S(O)$_2$C($R^4$)$_2$—, —C($R^4$)$_2$S(O)$_2$—, —S(O)$_2$O—, —OS(O)$_2$—, —S(O)$_2NR^{4a}$—, —$NR^{4a}$S(O)$_2$—, —C(S)C($R^4$)$_2$—, —C($R^4$)$_2$C(S)—, —C(S)O—, —OC(S)—, —C(S)$NR^{4a}$, or —$NR^{4a}$C(S)—, wherein:

$W_2$ is —(C—$W_3$)$_r$, or any two occurrences of $W_2$ is independently —C($R^5$)=C($R^5$)—;

wherein each occurrence of $W_3$ is independently —($R^5$)$_2$ or =O;

r is 0 to 3;

each occurrence of $R^4$ is independently hydrogen, halo, or an optionally substituted $C_{1-6}$ aliphatic or —C(O)$OR^{4c}$;

each occurrence of $R^{4a}$ is independently hydrogen or optionally substituted $C_{1-6}$ aliphatic;

each occurrence of $R^{4b}$ is independently hydrogen, or a group selected from optionally substituted $C_{1-6}$ aliphatic, —$OR^{4c}$, or —N($R^{4a}$)$_2$;

each occurrence of $R^{4c}$ is independently hydrogen or optionally substituted $C_{1-6}$ aliphatic;

each occurrence of $R^5$ is independently hydrogen, halo, or an optionally substituted group selected from $C_{1-6}$aliphatic, —C(O)N($R^{5a}$)$_2$, 3-10-membered cycloaliphatic, 6-10-membered aryl, 5-10-membered heteroaryl having 1-5 heteroatoms independently selected from nitrogen, oxygen, or sulfur, —N($R^{4b}$)$_2$, —$OR^{4a}$, or —$SR^{4a}$;

each occurrence of $R^{5a}$ is independently hydrogen or optionally substituted $C_{1-6}$ aliphatic;

HY is an optionally substituted group selected from:

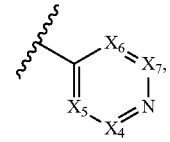

A

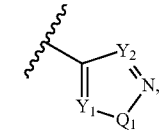

B

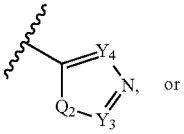

C or

-continued

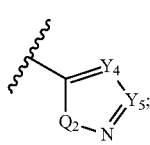

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7C(O)OR^{10a}$—, —$NR^7C(O)NR^7$—, —$NR^7C(O)SR^{10a}$—, —$NR^7C(S)OR^{10a}$—, —$NR^7C(S)NR^7$—, —$NR^7C(S)SR^{10a}$—, —$NR^7C(NR^7)OR^{10a}$—, —$NR^7C(NR^7)NR^7$—, —$NR^7S(O)_2$—, —$NR^7S(O)_2NR^7$—, —C(O)—, —$CO_2$—, —C(O)NR^7$—, —C(O)NR^7O$—, —$SO_2$—, or —$SO_2NR^7$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —$N(R^7)$—, —O—, —S—, —S(O)—, —$S(O)_2$—, —C(O)—, —C(O)O—, —$C(O)N(R^7)$—, —$S(O)_2N(R^7)$—, —$OC(O)N(R^7)$—, —$N(R^7)C(O)$—, —$N(R^7)SO_2$—, —$N(R^{10a})C(O)O$—, —$NR^{10a}C(O)N(R^{10a})$—, —$N(R^{10a})S(O)_2N(R^{10a})$—, —OC(O)—, or —$C(O)N(R^7)$—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —$N(R^7)_2$, —$OR^{10a}$, —$SR^{10a}$, —$S(O)_2R^{10a}$, —$C(O)R^{10a}$, —$C(O)OR^{10a}$, —$C(O)N(R^7)_2$, —$S(O)_2N(R^7)_2$, —$OC(O)N(R^7)_2$, —$N(R^7)C(O)R^{10a}$, —$N(R^7)SO_2R^{10a}$, —$N(R^7)C(O)OR^{10a}$, —$N(R^7)C(O)N(R^7)_2$, or —$N(R^7)SO_2N(R^7)_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —$C(O)R^{7a}$, —$CO_2R^{7a}$, —$C(O)N(R^{7a})_2$, —$C(O)N(R^{7a})$—$OR^{7a}$, —$SO_2R^{7a}$, —$SO_2N(R^{7a})_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —$C(O)R^{6a}$, —$CO_2R^{6a}$, —$C(O)N(R^{6b})_2$, —$SO_2R^{6a}$, —$SO_2N(R^{6b})_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or HY is

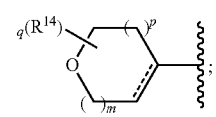

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —R$^{14c}$, —N(R$^{14b}$)$_2$, —OR$^{14b}$, —SR$^{14c}$, —S(O)$_2$R$^{14c}$, —C(O)R$^{14b}$, —C(O)OR$^{14b}$, —C(O)N(R$^{14b}$)$_2$, —S(O)$_2$N(R$^{14b}$)$_2$, —OC(O)N(R$^{14b}$)$_2$, —N(R$^{14e}$)C(O)R$^{14b}$, —N(R$^{14e}$)SO$_2$R$^{14c}$, —N(R$^{14e}$)C(O)OR$^{14b}$, —N(R$^{14e}$)C(O)N(R$^{14b}$)$_2$, or —N(R$^{14e}$)SO$_2$N(R$^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N(R$^{14b}$)—, —O—, —S—, —S(O)—, —S(O)$_2$—, —C(O)—, —C(O)O—, —C(O)N(R$^{14b}$)—, —S(O)$_2$N(R$^{14b}$)—, —OC(O)N(R$^{14b}$)—, —N(R$^{14b}$)C(O)—, —N(R$^{14b}$)SO$_2$—, —N(R$^{14b}$)C(O)O—, —NR$^{14b}$C(O)N(R$^{14b}$)—, —N(R$^{14b}$)S(O)$_2$N(R$^{14b}$)—, —OC(O)—, or —C(O)N(R$^{14b}$)—O— or wherein $T_1$ or a portion thereof optionally forms part of an optionally substituted 3-7 membered cycloaliphatic or heterocyclyl ring;

q is 0-6;
m is 1 or 2; and
p is 0, 1, or 2, provided that for compounds of formula I-B, compounds are other than:

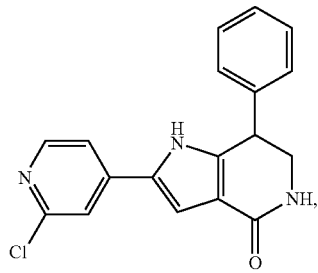

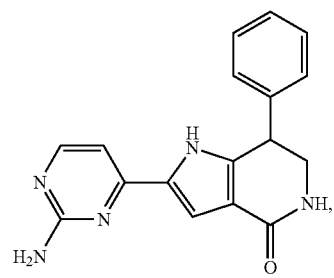

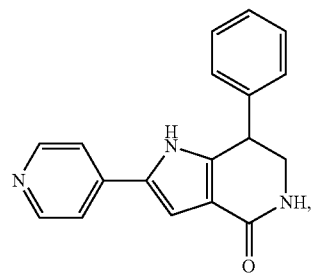

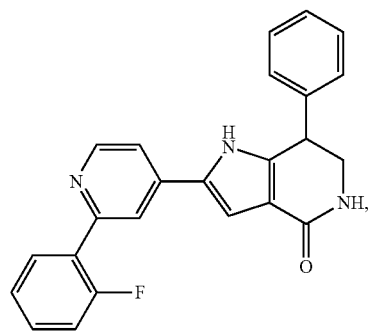

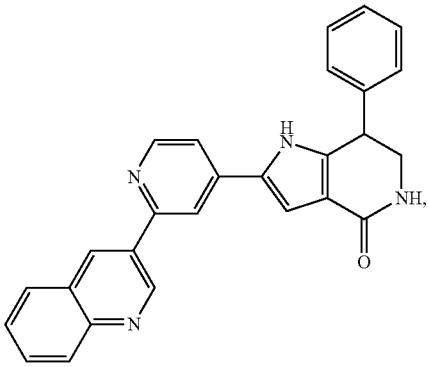

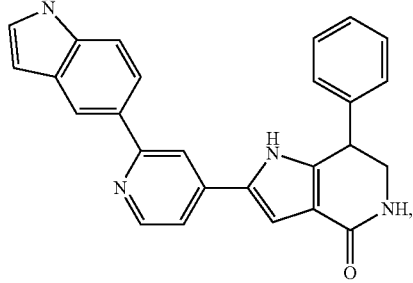

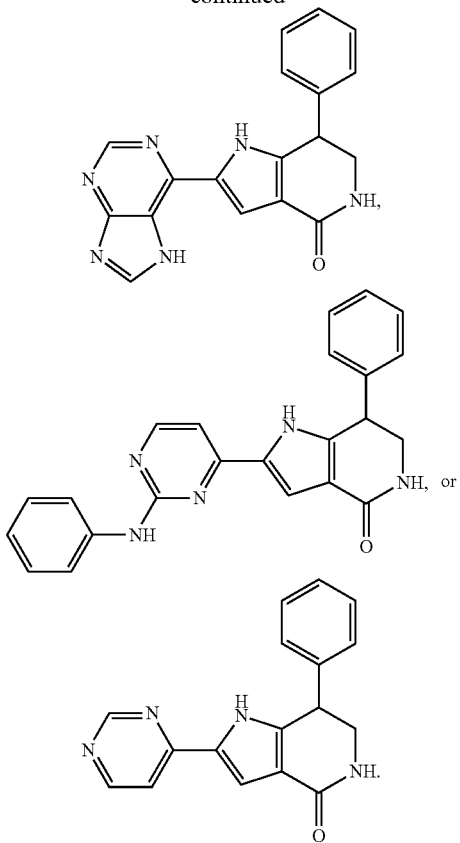

In another aspect, the compounds of this invention are represented by formula I-A or I-C:

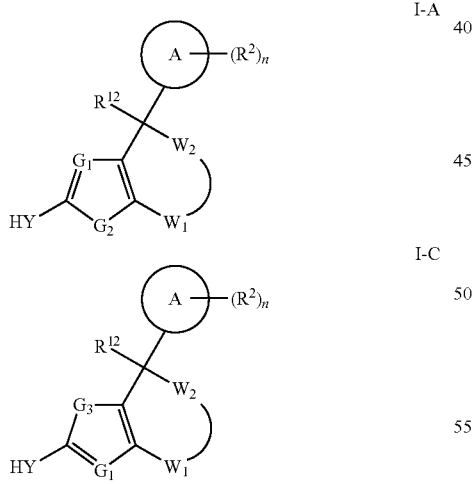

I-A

I-C or a pharmaceutically acceptable salt thereof, wherein:

$G_1$ is N or $CR^1$, wherein $R^{11}$ is H, —CN, halogen, or an optionally substituted group selected from $C_{1-6}$aliphatic, 3-10-membered cycloaliphatic, or —Z—$R^{11}$, wherein:

Z is selected from an optionally substituted $C_{1-3}$ alkylene chain, —O—, —N($R^{1a}$)—, —S—, —S(O)—, $S(O)_2$—, —C(O)—, —$CO_2$—, —C(O)N$R^{1a}$—, —N($R^{1a}$)C(O)—, —N($R^{1a}$)$CO_2$—, —$S(O)_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, or —OC(O)—;

$R^{1a}$ is hydrogen or an optionally substituted $C_{1-4}$ aliphatic, and $R^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, O, or $NR^3$, wherein $R^3$ is hydrogen or an optionally substituted $C_{1-6}$ aliphatic;

$G_3$ is S or O.

Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —$NO_2$, $R^{12c}$, —N($R^{12b}$)$_2$, —$OR^{12b}$, —$SR^{12c}$, —$S(O)_2R^{12c}$, —C(O)$R^{12b}$, —C(O)O$R^{12b}$, —C(O)N($R^{12b}$)$_2$, —$S(O)_2$N($R^{12b}$)$_2$, —OC(O)N($R^{12b}$)$_2$, —N($R^{12e}$)C(O)$R^{12b}$, —N($R^{12e}$)$SO_2R^{12c}$, —N($R^{12e}$)C(O)O$R^{12b}$, —N($R^{12e}$)C(O)N($R^{12b}$)$_2$, or —N($R^{12e}$)$SO_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N ($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein T$_2$ or a portion thereof optionally forms part of an optionally substituted 3-7 membered cycloaliphatic or heterocyclyl ring, wherein $R^{13}$ is hydrogen or an optionally substituted C$_{1-4}$aliphatic group;

n is 0 to 4;

$R^{12}$ is hydrogen, halo, or an optionally substituted group selected from C$_{1-6}$ aliphatic, —C(O)N($R^{5a}$)$_2$, 3-10-membered cycloaliphatic, —N($R^{4b}$)$_2$, —OR$^{4a}$, or —SR$^{4a}$;

or $R^2$ and $R^{12}$ form an optionally substituted 3-10-membered cycloaliphatic;

W$_1$ is selected from —C(O)C($R^4$)$_2$—, —C($R^4$)$_2$C(O)—, —C(O)O—, —OC(O)—, —C(O)NR$^{4a}$—, —NR$^{4a}$C(O)—, —C(=NR$^{4b}$)C($R^4$)$_2$—, —C($R^4$)$_2$C(=NR$^{4b}$)—, —C(=NR$^{4b}$)O—, —OC(=NR$^{4b}$)—, —C(=NR$^{4b}$)NR$^{4a}$—, —NR$^4$C(=NR$^{4b}$)—, —S(O)C($R^4$)$_2$—, —C($R^4$)$_2$S(O)—, —S(O)O—, —OS(O)—, —S(O)NR$^{4a}$—, —NR$^{4a}$S(O)—, —S(O)$_2$C($R^4$)$_2$—, —C($R^4$)$_2$S(O)$_2$—, —S(O)$_2$O—, —OS(O)$_2$—, —S(O)$_2$NR$^{4a}$—, —NR$^{4a}$S(O)$_2$—, —C(S)C($R^4$)$_2$—, —C($R^4$)$_2$C(S)—, —C(S)O—, —OC(S)—, —C(S)NR$^{4a}$—, or —NR$^{4a}$C(S)—, wherein:

W$_2$ is —(C—W$_3$)$_r$, or any two occurrences of W$_2$ is independently —C($R^5$)=C($R^5$)—;

wherein each occurrence of W$_3$ is independently —($R^5$)$_2$ or =O;

r is 0 to 3;

each occurrence of $R^4$ is independently hydrogen, halo, or an optionally substituted C$_{1-6}$ aliphatic or —C(O)OR$^{4e}$;

each occurrence of $R^{4a}$ is independently hydrogen or optionally substituted C$_{1-6}$ aliphatic;

each occurrence of $R^{4b}$ is independently hydrogen, or a group selected from optionally substituted C$_{1-6}$ aliphatic, —OR$^{4c}$, or —N($R^{4a}$)$_2$;

each occurrence of $R^{4c}$ is independently hydrogen or optionally substituted C$_{1-6}$ aliphatic;

each occurrence of $R^5$ is independently hydrogen, halo, or an optionally substituted group selected from C$_{1-6}$ aliphatic, —C(O)N($R^{5a}$)$_2$, 3-10-membered cycloaliphatic, 6-10-membered aryl, 5-10-membered heteroaryl having 1-5 heteroatoms independently selected from nitrogen, oxygen, or sulfur, —N($R^{4b}$)$_2$, —OR$^{4a}$, or —SR$^{4a}$;

each occurrence of $R^{5a}$ is independently hydrogen or optionally substituted C$_{1-6}$ aliphatic;

HY is an optionally substituted group selected from:

A

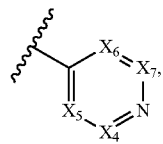

B

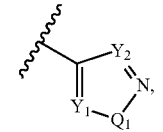

C

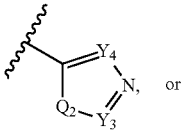

or

D

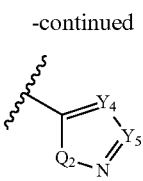

wherein each occurrence of X$_4$, X$_5$, X$_6$, and X$_7$ is independently —CR$^{10}$ or N, provided no more than two occurrences of X$_4$, X$_5$, X$_6$, and X$_7$ are N;

each occurrence of Q$_1$ and Q$_2$ is independently S, O or —NR$^6$;

each occurrence of Y$_1$, Y$_2$, Y$_3$, Y$_4$, and Y$_5$ is independently —CR$^{10}$ or N;

or wherein two adjacent occurrences of X$_4$ and X$_5$, X$_6$ and X$_7$, Y$_1$ and Q$_1$, Y$_3$ and Q$_2$, or Y$_4$ and Y$_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —R$^{10b}$, —V$_1$—R$^{10c}$, -T$_1$-R$^{10b}$, or —V$_1$-T$_1$-R$^{10b}$ wherein:

V$_1$ is —NR$^7$—, —NR$^7$—C(O)—, —NR$^7$—C(S)—, —NR$^7$—C(NR$^7$)—, —NR$^7$C(O)OR$^{10a}$—, —NR$^7$C(O)NR$^7$—, —NR$^7$C(O)SR$^{10a}$—, —NR$^7$C(S)OR$^{10a}$—, —NR$^7$C(S)NR$^7$—, —NR$^7$C(S)SR$^{10a}$—, —NR$^7$C(NR$^7$)OR$^{10a}$—, —NR$^7$C(NR$^7$)NR$^7$—, —NR$^7$S(O)$_2$—, —NR$^7$S(O)$_2$NR$^7$—, —C(O)—, —CO$_2$—, —C(O)NR$^7$—, —C(O)NR$^7$O—, —SO$_2$—, or —SO$_2$NR$^7$—;

each occurrence of $R^{10a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

T$_1$ is an optionally substituted C$_1$-C$_6$alkylene chain wherein the alkylene chain optionally is interrupted by —N(R$^7$)—, —O—, —S—, —S(O)—, —S(O)$_2$—, —C(O)—, —C(O)O—, —C(O)N(R$^7$)—, —S(O)$_2$N(R$^7$)—, —OC(O)N(R$^7$)—, —N(R$^7$)C(O)—, —N(R$^7$)SO$_2$—, —N(R$^{10a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^7$)—O— or wherein T$_1$ forms part of an optionally substituted 3-7 membered cycloaliphatic or heterocyclyl ring;

each occurrence of $R^{10b}$ is independently hydrogen, halogen, —CN, —NO$_2$, —N(R$^7$)$_2$, —OR$^{10a}$, —SR$^{10a}$, —S(O)$_2$R$^{10a}$, —C(O)R$^{10a}$, —C(O)OR$^{10a}$, —C(O)N(R$^7$)$_2$, —S(O)$_2$N(R$^7$)$_2$, —OC(O)N(R$^7$)$_2$, —N(R$^7$)C(O)R$^{10a}$, —N(R$^7$)SO$_2$R$^{10a}$, —N(R$^7$)C(O)OR$^{10a}$, —N(R$^7$)C(O)N(R$^7$)$_2$, or —N(R$^7$)SO$_2$N(R$^7$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O)$R^{7a}$, —CO$_2R^{7a}$, —C(O)N($R^{7a}$)$_2$, —C(O)N($R^{7a}$)—OR$^{7a}$, —SO$_2R^{7a}$, —SO$_2$N($R^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O)$R^{6a}$, —CO$_2R^{6a}$, —C(O)N($R^{6b}$)$_2$, —SO$_2R^{6a}$, —SO$_2$N($R^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or HY is

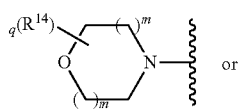

E

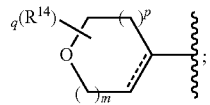

F wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —OR$^{14b}$, —SR$^{14c}$, —S(O)$_2$$R^{14c}$, —C(O)$R^{14b}$, —C(O)OR$^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2R^{14c}$, —N($R^{14e}$)C(O)OR$^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, OC(O)N($R^{14b}$)—, —N($R^{14b}$)C(O)—, —N($R^{14b}$)SO$_2$—, —N($R^{14b}$)C(O)O—, —NR$^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;

m is 1 or 2; and p is 0, 1, or 2.

In another aspect, the compounds of this invention are represented by formula II-A or II-B:

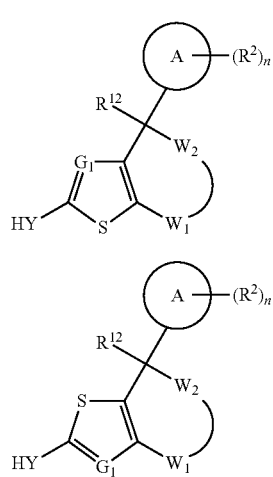

or a pharmaceutically acceptable salt thereof, wherein:

$G_1$ is N or $CR^1$, wherein $R^1$ is H, —CN, halogen, or an optionally substituted group selected from $C_{1-6}$ aliphatic, 3-10-membered cycloaliphatic, or —Z—$R^{11}$, wherein:

Z is selected from an optionally substituted $C_{1-3}$ alkylene chain, —O—, —N($R^{1a}$)—, —S—, —S(O)—, S(O)$_2$—, —C(O)—, —CO$_2$—, —C(O)N$R^{1a}$—, —N($R^{1a}$)C(O)—, —N($R^{1a}$)CO$_2$—, —S(O)$_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, or —OC(O)—;

$R^{1a}$ is hydrogen or an optionally substituted $C_{1-4}$ aliphatic, and $R^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —O$R^{4a}$, or —S$R^{4a}$;

or $R^2$ and $R^{12}$ form an optionally substituted 3-10-membered cycloaliphatic;

$W_1$ is selected from —C(O)C($R^4$)$_2$—, —C($R^4$)$_2$C(O)—, —C(O)O—, —OC(O)—, —C(O)N$R^{4a}$—, —N$R^{4a}$C(O)—, —C(=N$R^{4b}$)C($R^4$)$_2$—, —C($R^4$)$_2$C(=N$R^{4b}$)—, —C(=N$R^{4b}$)O—, —OC(=N$R^{4b}$)—, —C(=N$R^{4b}$)N$R^{4a}$—, —N$R^{4a}$C(=N$R^{4b}$)—, —S(O)C($R^4$)$_2$—, —C($R^4$)$_2$S(O)—, —S(O)O—, —OS(O)—, —S(O)N$R^{4a}$—, —N$R^{4a}$S(O)—, —S(O)$_2$C($R^4$)$_2$—, —C($R^4$)$_2$S(O)$_2$—, —S(O)$_2$O—, —OS(O)$_2$—, —S(O)$_2$N$R^{4a}$—, —N$R^{4a}$S(O)$_2$—, —C(S)C($R^4$)$_2$—, —C($R^4$)$_2$C(S)—, —C(S)O—, —OC(S)—, —C(S)N$R^{4a}$—, or —N$R^{4a}$C(S)—, wherein:

$W_2$ is —(C—$W_3$)$_r$, or any two occurrences of $W_2$ is independently —C(R)=C($R^5$)—;

wherein each occurrence of $W_3$ is independently —($R^5$)$_2$ or =O;

r is 0 to 3;

each occurrence of $R^4$ is independently hydrogen, halo, or an optionally substituted $C_{1-6}$ aliphatic or —C(O)O$R^{4c}$;

each occurrence of $R^{4a}$ is independently hydrogen or optionally substituted $C_{1-6}$ aliphatic;

each occurrence of $R^{4b}$ is independently hydrogen, or a group selected from optionally substituted $C_{1-6}$ aliphatic, —O$R^{4c}$, or —N($R^{4a}$)$_2$;

each occurrence of $R^{4c}$ is independently hydrogen or optionally substituted $C_{1-6}$ aliphatic;

each occurrence of $R^5$ is independently hydrogen, halo, or an optionally substituted group selected from $C_{1-6}$aliphatic, —C(O)N($R^{5a}$)$_2$, 3-10-membered cycloaliphatic, 6-10-membered aryl, 5-10-membered heteroaryl having 1-5 heteroatoms independently selected from nitrogen, oxygen, or sulfur, —N($R^{4b}$)$_2$, —O$R^{4a}$, or —S$R^{4a}$;

each occurrence of $R^{5a}$ is independently hydrogen or optionally substituted $C_{1-6}$ aliphatic;

HY is an optionally substituted group selected from:

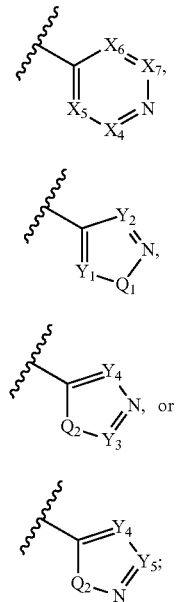

A

B

C, or

D wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is $R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7$C(O)O$R^{10a}$—, —$NR^7$C(O)N$R^7$—, —$NR^7$C(O)S$R^{10a}$—, —$NR^7$C(S)O$R^{10a}$—, —$NR^7$C(S)N$R^7$—, —$NR^7$C(S)S$R^{10a}$—, —$NR^7$C($NR^7$)O$R^{10a}$—, —$NR^7$C($NR^7$)N$R^7$—, —$NR^7$S(O)$_2$—, —$NR^7$S(O)$_2$N$R^7$—, —C(O)—, —CO$_2$—, —C(O)N$R^7$—, —C(O)N$R^7$O—, —SO$_2$—, or —SO$_2$N$R^7$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N($R^7$)—, —OC(O)N($R^7$)—, —N($R^7$)C(O)—, —N($R^7$)SO$_2$—, —N($R^{10}$)C(O)O—, —N$R^{10a}$C(O)N($R^{10a}$)—, —N($R^{10a}$)S(O)$_2$N($R^{10a}$)—, —OC(O)—, or —C(O)N($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^7$)$_2$, —O$R^{10a}$, —S$R^{10a}$, —S(O)$_2$$R^{10a}$, —C(O)$R^{10a}$, —C(O)O$R^{10a}$, —C(O)N($R^7$)$_2$, —S(O)$_2$N($R^7$)$_2$, —OC(O)N($R^7$)$_2$, —N($R^7$)C(O)$R^{10a}$, —N($R^7$)SO$_2$$R^{10a}$, —N($R^7$)C(O)O$R^{10a}$, —N($R^7$)C(O)N($R^7$)$_2$, or —N($R^7$)SO$_2$N($R^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O)$R^{7a}$, —CO$_2$$R^{7a}$, —C(O)N($R^{7a}$)$_2$, —C(O)N($R^{7a}$)—O$R^{7a}$, —SO$_2$$R^{7a}$, —SO$_2$N($R^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O)$R^{6a}$, —CO$_2$$R^{6a}$, —C(O)N($R^{6b}$)$_2$, —SO$_2$$R^{6a}$, —SO$_2$N($R^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10- membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or HY is

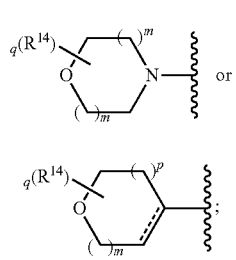

wherein each occurrence of $R^{14}$ is independently $-R^{14a}$ or $-T_1-R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —O$R^{14b}$, S$R^{14c}$, —S(O)$_2R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2R^{14c}$, —N($R^{14e}$)C(O)O$R^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —NR$^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;

m is 1 or 2; and p is 0, 1, or 2.

In another aspect, the compounds of this invention are represented by formula III-A or III-B:

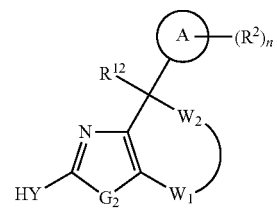

III-A

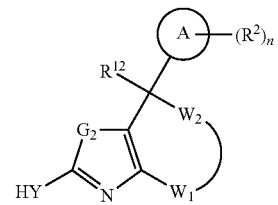

III-B or a pharmaceutically acceptable salt thereof, wherein:

$G_2$ is S, O, or N$R^3$, wherein $R^3$ is hydrogen or an optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12c}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —S(O)$_2$—, —C(O)—, —C(O)O—, —C(O)N(R^{12e})—, —S(O)$_2$N(R^{12e})—, —OC(O)N(R^{12e})—, —N(R^{12e})C(O)—, —N(R^{12e})SO$_2$—, —N(R^{12e})C(O)O—, —N(R^{12e})C(O)N(R^{12e})—, —N(R^{12e})SO$_2$N(R^{12e})—, —OC(O)—, or —C(O)N(R^{12e})—O—; and $T_2$ is an optionally substituted $C_1$-$C_6$alkylene chain wherein the alkylene chain optionally is interrupted by —N(R^{13})—, —O—, —S—, —S(O)—, —S(O)$_2$—, —C(O)—, —C(O)O—, —C(O)N(R^{13})—, —S(O)$_2$N(R^{13})—, —OC(O)N(R^{13})—, —N(R^{13})C(O)—, —N(R^{13})SO$_2$—, —N(R^{13})C(O)O—, —N(R^{13})C(O)N(R^{13})—, —N(R^{13})S(O)$_2$N(R^{13})—, —OC(O)—, or —C(O)N(R^{13})—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —C(O)N(R^{5a})$_2$, 3-10-membered cycloaliphatic, —N(R^{4b})$_2$, —OR^{4a}, or —SR^{4a}; or $R^2$ and $R^{12}$ form an optionally substituted 3-10-membered cycloaliphatic;

$W_1$ is selected from —C(O)C(R^4)$_2$—, —C(R^4)$_2$C(O)—, —C(O)O—, —OC(O)—, —C(O)NR^{4a}—, —NR^{4a}C(O)—, —C(=NR^{4b})C(R^4)$_2$—, —C(R^4)$_2$C(=NR^{4b})—, —C(=NR^{4b})O—, —OC(=NR^{4b})—, —C(=NR^{4b})NR^{4a}—, —NR^{4a}C(=NR^{4b})—, —S(O)C(R^4)$_2$—, —C(R^4)$_2$S(O)—, —S(O)O—, —OS(O)—, —S(O)NR^{4a}—, —NR^{4a}S(O)—, —S(O)$_2$C(R^4)$_2$—, —C(R^4)$_2$S(O)$_2$—, —S(O)$_2$O—, —OS(O)$_2$—, —S(O)$_2$NR^{4a}—, —NR^{4a}S(O)$_2$—, —C(S)C(R^4)$_2$—, —C(R^4)$_2$C(S)—, —C(S)O—, —OC(S)—, —C(S)NR^{4a}—, or —NR^{4a}C(S)—, wherein:

$W_2$ is —(C—$W_3$)$_r$—, or any two occurrences of $W_2$ is independently —C(R^5)=C(R^5)—;

wherein each occurrence of $W_3$ is independently —(R^5)$_2$ or =O;

r is 0 to 3;

each occurrence of $R^4$ is independently hydrogen, halo, or an optionally substituted $C_{1-6}$ aliphatic or —C(O)OR^{4c};

each occurrence of $R^{4a}$ is independently hydrogen or optionally substituted $C_{1-6}$ aliphatic;

each occurrence of $R^{4b}$ is independently hydrogen, or a group selected from optionally substituted $C_{1-6}$ aliphatic, —OR^{4c}, or —N(R^{4a})$_2$;

each occurrence of $R^{4c}$ is independently hydrogen or optionally substituted $C_{1-6}$ aliphatic;

each occurrence of $R^5$ is independently hydrogen, halo, or an optionally substituted group selected from $C_{1-6}$ aliphatic, —C(O)N(R^{5a})$_2$, 3-10-membered cycloaliphatic, 6-10-membered aryl, 5-10-membered heteroaryl having 1-5 heteroatoms independently selected from nitrogen, oxygen, or sulfur, —N(R^{4b})$_2$, —OR^{4a}, or —SR^{4a};

each occurrence of $R^{5a}$ is independently hydrogen or optionally substituted $C_{1-6}$ aliphatic;

HY is an optionally substituted group selected from:

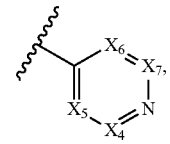

A

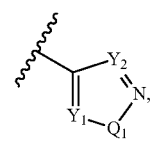

B

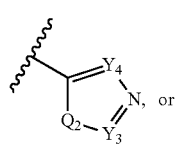

C

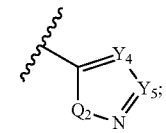

D wherein each occurrence of $X_4$, $X_5$, $X_6$, and $X_7$ is independently —CR^{10} or N, provided no more than two occurrences of $X_4$, $X_5$, $X_6$, and $X_7$ are N;

each occurrence of $Q_1$ and $Q_2$ is independently S, O or —NR^6;

each occurrence of $Y_1$, $Y_2$, $Y_3$, $Y_4$, and $Y_5$ is independently —CR^{10} or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —NR^7—, —NR^7—C(O)—, —NR^7—C(S)—, —NR^7—C(NR^7)—, —NR^7C(O)OR^{10a}—, —NR^7C(O)NR^7—, —NR^7C(O)SR^{10a}—, —NR^7C(S)OR^{10a}—, —NR^7C(S)NR^7—, —NR^7C(S)SR^{10a}—, —NR^7C(NR^7)OR^{10a}—, —NR^7C(NR^7)NR^7—, —NR^7S(O)$_2$—, —NR^7S(O)$_2$NR^7—, —C(O)—, —CO$_2$—, —C(O)NR^7—, —C(O)NR^7O—, —SO$_2$—, or —SO$_2$NR^7—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N($R^7$)—, —OC(O)N($R^7$)—, —N($R^7$)C(O)—, —N($R^7$)SO$_2$—, —N($R^{10a}$)C(O)O—, —N$R^{10a}$C(O)N($R^{10a}$)—, —N($R^{10a}$)S(O)$_2$N($R^{10a}$)—, —OC(O)—, or —C(O)N($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^7$)$_2$, —OR$^{10a}$, —SR$^{10a}$, —S(O)$_2$R$^{10a}$, —C(O)R$^{10a}$, —C(O)OR$^{10a}$, —C(O)N($R^7$)$_2$, —S(O)$_2$N($R^7$)$_2$, —OC(O)N($R^7$)$_2$, —N($R^7$)C(O)R$^{10a}$, —N(R)SO$_2$R$^{10a}$, —N($R^7$)C(O)OR$^{10a}$, —N($R^7$)C(O)N($R^7$)$_2$, or —N($R^7$)SO$_2$N($R^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O)R$^{7a}$, —CO$_2$R$^{7a}$, —C(O)N($R^{7a}$)$_2$, —C(O)N($R^{7a}$)—OR$^{7a}$, —SO$_2$R$^{7a}$, —SO$_2$N($R^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O)R$^{6a}$, —CO$_2$R$^{6a}$, —C(O)N($R^{6b}$)$_2$, —SO$_2$R$^{6a}$, —SO$_2$N($R^{66}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or HY

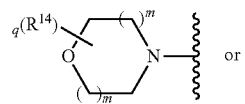

E

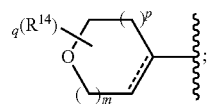

F wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —R$^{14c}$, —N($R^{14b}$)$_2$, —OR$^{14b}$, —SR$^{14c}$, —S(O)$_2$R$^{14c}$, —C(O)R$^{14b}$, —C(O)OR$^{14b}$, —C(O)N($R^{14b}$)$_2$, —S(O)$_2$N($R^{14b}$)$_2$, —OC(O)N($R^{14b}$)$_2$, —N($R^{14e}$)C(O)R$^{14b}$, —N($R^{14e}$)SO$_2$R$^{14c}$, —N($R^{14e}$)C(O)OR$^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10- membered heteroaryl having 1-5 heteroatoms independently selected from nitrogen, oxygen, or sulfur;
each occurrence of $R^{14e}$ is independently hydrogen or an optionally substituted $C_{1-6}$ aliphatic group; and
$T_1$ is an optionally substituted $C_1$-$C_6$alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —N$R^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;
m is 1 or 2; and
p is 0, 1, or 2.

In another aspect, the compounds of this invention are represented by formula VI-A or VI-B:

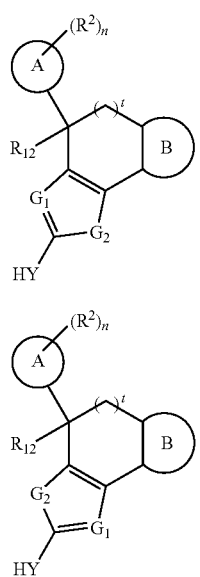

VI-A

VI-B or a pharmaceutically acceptable salt thereof, wherein:

$G_1$ is N or CR$^1$, wherein R$^1$ is H, —CN, halogen, or an optionally substituted group selected from $C_{1-6}$ aliphatic, 3-10-membered cycloaliphatic, or —Z—R$^{11}$, wherein:
Z is selected from an optionally substituted $C_{1-3}$ alkylene chain, —O—, —N(R$^{1a}$)—, —S—, —S(O)—, S(O)$_2$—, —C(O)—, —CO$_2$—, —C(O)NR$^{1a}$—, —N(R$^{1a}$)C(O)—, —N(R$^{1a}$)CO$_2$—, —S(O)$_2$NR$^{1a}$—, —N(R$^{1a}$)S(O)$_2$—, —OC(O)N(R$^{1a}$)—, —N(R$^{1a}$)C(O)NR$^{1a}$—, —N(R$^{1a}$)S(O)$_2$N(R$^{1a}$)—, or —OC(O)—;
R$^{1a}$ is hydrogen or an optionally substituted $C_{1-4}$ aliphatic, and
R$^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, O, or NR$^3$, wherein R$^3$ is hydrogen or an optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

Ring B is an optionally substituted group selected from a 5- or 6-membered heterocyclyl having 1-3 heteroatoms independently selected from nitrogen, oxygen, or sulfur, or a 5- or 6-membered heteroaryl having 1-3 heteroatoms independently selected from nitrogen, oxygen, or sulfur, provided that Ring B has no more than one occurrence of oxygen or sulfur;

t is 1 to 3;
each occurrence of R$^2$ is independently —R$^{12a}$, -T$_2$-R$^{12d}$, or —V$_2$-T$_2$-R$^{12d}$, and:
each occurrence of R$^{12a}$ is independently halogen, —CN, —NO$_2$, —R$^{12c}$, —N(R$^{12b}$)$_2$, —OR$^{12b}$, —SR$^{12c}$, —S(O)$_2$R$^{12c}$, —C(O)R$^{12b}$, —C(O)OR$^{12b}$, —C(O)N(R$^{12b}$)$_2$, —S(O)$_2$N(R$^{12b}$)$_2$, —OC(O)N(R$^{12b}$)$_2$, —N(R$^{12e}$)C(O)R$^{12b}$, —N(R$^{12e}$)SO$_2$R$^{12c}$, —N(R$^{12e}$)C(O)OR$^{12b}$, —N(R$^{12e}$)C(O)N(R$^{12b}$)$_2$, or —N(R$^{12e}$)SO$_2$N(R$^{12b}$)$_2$, or two occurrences of R$^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of R$^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12e}$ is independently hydrogen or an optionally substituted $C_{1-6}$ aliphatic group;
each occurrence of $V_2$ is independently —N(R$^{12e}$)—, —O—, —S—, —S(O)—, —S(O)$_2$—, —C(O)—, —C(O)O—, —C(O)N(R$^{12e}$)—, —S(O)$_2$N(R$^{12e}$)—, —OC(O)N(R$^{12e}$)—, —N(R$^{12e}$)C(O)—, —N(R$^{12e}$)SO$_2$—, —N(R$^{12e}$)C(O)O—, —N(R$^{12e}$)C(O)N(R$^{12e}$)—, —N(R$^{12e}$)SO$_2$N(R$^{12e}$)—, —OC(O)—, or —C(O)N(R$^{12e}$)—O—; and
$T_2$ is an optionally substituted $C_1$-$C_6$alkylene chain wherein the alkylene chain optionally is interrupted by —N(R$^{13}$)—, —O—, —S—, —S(O)—, —S(O)$_2$—, —C(O)—, —C(O)O—, —C(O)N(R$^{13}$)—, —S(O)$_2$N(R$^{13}$)—, —OC(O)N(R$^{13}$)—, —N(R$^{13}$)C(O)—, —N(R$^{13}$)SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —OR$^{4a}$, or —SR$^{4a}$;

or $R^2$ and $R^{12}$ form an optionally substituted 3-10-membered cycloaliphatic;

each occurrence of $R^{4a}$ is independently hydrogen or optionally substituted $C_{1-6}$ aliphatic;

each occurrence of $R^{4b}$ is independently hydrogen, or a group selected from optionally substituted $C_{1-6}$ aliphatic, —OR$^{4c}$, or —N($R^{4a}$)$_2$;

each occurrence of $R^{4c}$ is independently hydrogen or optionally substituted $C_{1-6}$ aliphatic;

HY is an optionally substituted group selected from:

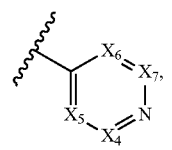
A

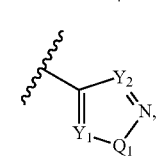
B

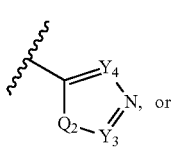
C

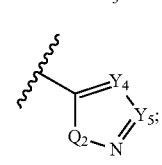
D wherein each occurrence of $X_4$, $X_5$, $X_6$, and $X_7$ is independently —CR$^{10}$ or N, provided no more than two occurrences of $X_4$, $X_5$, $X_6$, and $X_7$ are N;

each occurrence of $Q_1$ and $Q_2$ is independently S, O or —NR$^6$;

each occurrence of $Y_1$, $Y_2$, $Y_3$, $Y_4$, and $Y_5$ is independently —CR$^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —R$^{10b}$, —V$_1$—R$^{10c}$, -T$_1$-R$^{10b}$, or —V$_1$-T$_1$-R$^{10b}$ wherein:

$V_1$ is —NR$^7$—, —NR$^7$—C(O)—, —NR$^7$—C(S)—, —NR$^7$—C(NR$^7$)—, —NR$^7$C(O)OR$^{10a}$—, —NR$^7$C(O) NR$^7$—, —NR$^7$C(O)SR$^{10a}$—, —NR$^7$C(S)OR$^{10a}$—, —NR$^7$C(S)NR$^7$—, —NR$^7$C(S)SR$^{10a}$—, —NR$^7$C (NR$^7$)OR$^{10a}$—, —NR$^7$C(NR$^7$)NR$^7$—, —NR$^7$S(O)$_2$—, —NR$^7$S(O)$_2$NR$^7$—, —C(O)—, —CO$_2$—, —C(O) NR$^7$—, —C(O)NR$^7$O—, —SO$_2$—, or —SO$_2$NR$^7$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N(R$^7$)—, —O—, —S—, —S(O)—, —S(O)$_2$—, —C(O)—, —C(O)O—, —C(O)N(R$^7$)—, —S(O)$_2$N (R$^7$)—, —OC(O)N(R$^7$)—, —N(R$^7$)C(O)—, —N(R$^7$) SO$_2$—, —N(R$^{10a}$)C(O)O—, —NR$^{10a}$C(O)N(R$^{10a}$)—, —N(R$^{10a}$)S(O)$_2$N(R$^{10a}$)—, —OC(O)—, or —C(O)N (R$^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N(R$^7$)$_2$, —OR$^{10a}$, —SR$^{10a}$, S(O)$_2$ R$^{10a}$, —C(O)R$^{10a}$, —C(O)OR$^{10a}$, —C(O)N (R$^7$)$_2$, —S(O)$_2$N(R$^7$)$_2$, —OC(O)N(R$^7$)$_2$, —N(R$^7$)C(O) R$^{10a}$, —N(R$^7$)SO$_2$R$^{10a}$, —N(R$^7$)C(O)OR$^{10a}$, —N(R$^7$) C(O)N(R$^7$)$_2$, or —N(R$^7$)SO$_2$N(R$^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O) R$^{7a}$, —CO$_2$R$^{7a}$, —C(O)N(R$^{7a}$)$_2$, —C(O)N(R$^{7a}$)—OR$^{7a}$, —SO$_2$R$^{7a}$, —SO$_2$N(R$^{7a}$)$_2$, or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O) R$^{6a}$, —CO$_2$R$^{6a}$, —C(O)N(R$^{6b}$)$_2$, —SO$_2$R$^{6a}$, —SO$_2$N(R$^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and
  wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;
or HY is

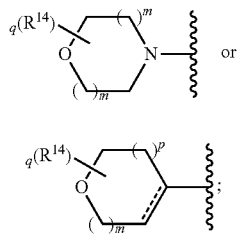

E

F wherein each occurrence of $R^{14}$ is independently —$R^{14a}$ or -$T_1$-$R^{14d}$, wherein:
  each occurrence of $R^{14a}$, as valency and stability permit, is independently fluorine, =O, =S, —CN, —NO$_2$, —$R^{14c}$, —N($R^{14b}$)$_2$, —O$R^{14b}$, —S$R^{14c}$, —S(O)$_2$$R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2$$R^{14c}$, —N($R^{14e}$)C(O)O$R^{14b}$, —N($R^{14c}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14e}$ is independently hydrogen or an optionally substituted $C_{1-6}$ aliphatic group; and
  $T_1$ is an optionally substituted $C_1$-$C_6$alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —NR$^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;
q is 0-6;
m is 1 or 2; and
p is 0, 1, or 2.

In another aspect, the compounds of this invention are represented by formula VII-A or VII-B:

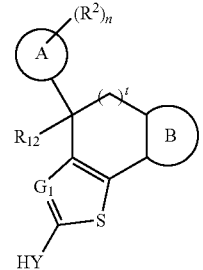

VII-A

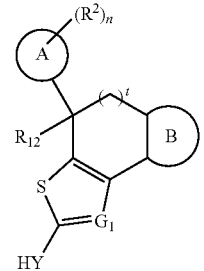

VII-B or a pharmaceutically acceptable salt thereof, wherein:
  $G_1$ is N or CR$^1$, wherein R$^1$ is H, —CN, halogen, or an optionally substituted group selected from $C_{1-6}$ aliphatic, 3-10-membered cycloaliphatic, or —Z—$R^{11}$, wherein:
    Z is selected from an optionally substituted $C_{1-3}$ alkylene chain, —O—, —N($R^{1a}$)—, —S—, —S(O)—, S(O)$_2$—, —C(O)—, —CO$_2$—, —C(O)NR$^{1a}$—, —N($R^{1a}$)C(O)—, —N($R^{1a}$)CO$_2$—, —S(O)$_2$NR$^{1a}$—, —N($R^{1a}$)S(O)$_2$—, —OC(O)N($R^{1a}$)—, —N($R^{1a}$)C(O)NR$^{1a}$—, —N($R^{1a}$)S(O)$_2$N($R^{1a}$)—, or —OC(O)—;
    $R^{1a}$ is hydrogen or an optionally substituted $C_{1-4}$ aliphatic, and R¹¹ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and Ring A is an optionally substituted group selected from 6-10-membered aryl, or 5-10-membered heteroaryl having 1-5 heteroatoms independently selected from nitrogen, oxygen, or sulfur;

Ring B is an optionally substituted group selected from a 5- or 6-membered heterocyclyl having 1-3 heteroatoms independently selected from nitrogen, oxygen, or sulfur, or a 5- or 6-membered heteroaryl having 1-3 heteroatoms independently selected from nitrogen, oxygen, or sulfur, provided that Ring B has no more than one occurrence of oxygen or sulfur;

t is 1 to 3;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —$C(O)N(R^{5a})_2$, 3-10-membered cycloaliphatic, —$N(R^{4b})_2$, —$OR^{4a}$, or —$SR^{4a}$;

or $R^2$ and $R^{12}$ form an optionally substituted 3-10-membered cycloaliphatic;

each occurrence of $R^{4a}$ is independently hydrogen or optionally substituted $C_{1-6}$ aliphatic;

each occurrence of $R^{4b}$ is independently hydrogen, or a group selected from optionally substituted $C_{1-6}$ aliphatic, —$OR^{4c}$, or —$N(R^{4a})_2$;

each occurrence of $R^{46}$ is independently hydrogen or optionally substituted $C_{1-6}$ aliphatic;

HY is an optionally substituted group selected from:

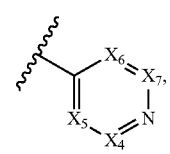

A

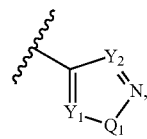

B

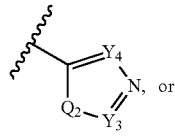

C

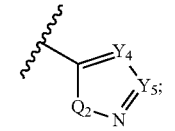

D wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—$C(NR^7)$—, —$NR^7C(O)OR^{10a}$—, —$NR^7C(O)$

NR$^7$—, —NR$^7$C(O)SR$^{10a}$—, —NR$^7$C(S)OR$^{10a}$—, —NR$^7$C(S)NR$^7$—, —NR$^7$C(S)SR$^{10a}$—, —NR$^7$C(NR$^7$)OR$^{10a}$—, —NR$^7$C(NR$^7$)NR$^7$—, —NR$^7$S(O)$_2$—, —NR$^7$S(O)$_2$NR$^7$—, —C(O)—, —CO$_2$—, —C(O)NR$^7$—, —C(O)NR$^7$O—, —SO$_2$—, or —SO$_2$NR$^7$—;

each occurrence of R$^{10a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

T$_1$ is an optionally substituted C$_1$-C$_6$alkylene chain wherein the alkylene chain optionally is interrupted by —N(R$^7$)—, —O—, —S—, —S(O)—, —S(O)$_2$—, —C(O)—, —C(O)O—, —C(O)N(R$^7$)—, —S(O)$_2$N(R$^7$)—, —OC(O)N(R$^7$)—, —N(R$^7$)C(O)—, —N(R$^7$)SO$_2$—, —N(R$^{10a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^7$)—O— or wherein T$_1$ forms part of an optionally substituted 3-7 membered cycloaliphatic or heterocyclyl ring;

each occurrence of R$^{10b}$ is independently hydrogen, halogen, —CN, —NO$_2$, —N(R)$_2$, —OR$^{10a}$, —SR$^{10a}$, —S(O)$_2$R$^{10a}$, —C(O)R$^{10a}$, —C(O)OR$^{10a}$, —C(O)N(R$^7$)$_2$, —S(O)$_2$N(R$^7$)$_2$, —OC(O)N(R$^7$)$_2$, —N(R$^7$)C(O)R$^{10a}$, —N(R)SO$_2$R$^{10a}$, —N(R$^7$)C(O)OR$^{10a}$, —N(R$^7$)C(O)N(R$^7$)$_2$, or —N(R$^7$)SO$_2$N(R$^7$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{10c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or R$^7$ and R$^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of R$^7$ is independently hydrogen, —C(O)R$^{7a}$, —CO$_2$R$^{7a}$, —C(O)N(R$^{7a}$)$_2$, —C(O)N(R$^{7a}$)—OR$^{7a}$, —SO$_2$R$^{7a}$, —SO$_2$N(R$^{7a}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{7a}$ is independently hydrogen or an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^6$ is independently hydrogen, —C(O)R$^{6a}$, —CO$_2$R$^{6a}$, —C(O)N(R$^{6b}$)$_2$, —SO$_2$R$^{6a}$, —SO$_2$N(R$^{6b}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{6a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of R$^{6b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of R$^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or HY is

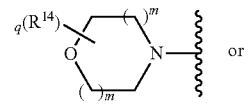

E or

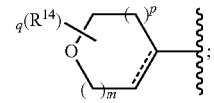

F wherein each occurrence of R$^{14}$ is independently —R$^{14a}$ or wherein:

each occurrence of R$^{14a}$, as valency and stability permit, is independently fluorine, =O, =S, —CN, —NO$_2$, —R$^{14c}$, —N(R$^{14b}$)$_2$, —OR$^{14b}$, —SR$^{14c}$, —S(O)$_2$R$^{14c}$, —C(O)R$^{14b}$, —C(O)OR$^{14b}$, —C(O)N(R$^{14b}$)$_2$, —S(O)$_2$N(R$^{14b}$)$_2$, —OC(O)N(R$^{14b}$)$_2$, —N(R$^{14e}$)C(O)R$^{14b}$, —N(R$^{14e}$)SO$_2$R$^{14c}$, —N(R$^{14e}$)C(O)OR$^{14b}$, —N(R$^{14e}$)C(O)N(R$^{14b}$)$_2$, or —N(R$^{14e}$)SO$_2$N(R$^{14b}$)$_2$, or two occurrences of R$^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{14b}$ is independently hydrogen or an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14c}$ is independently an optionally substituted group selected from C$_1$-C$_6$aliphatic, 3-10- membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —NR$^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;

p is 0, 1, or 2.

In another aspect, the invention provides compounds having the structure VIII-A or VIII-B:

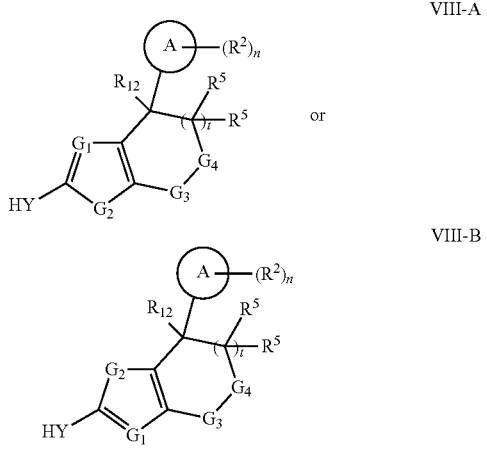

or a pharmaceutically acceptable salt thereof, wherein:

$G_1$ is N or CR$^1$, wherein R$^1$ is H, —CN, halogen, or an optionally substituted group selected from $C_{1-6}$ aliphatic, 3-10-membered cycloaliphatic, or —Z—R$^{11}$, wherein:

Z is selected from an optionally substituted $C_{1-3}$ alkylene chain, —O—, —N(R$^{1a}$)—, —S—, —S(O)—, S(O)$_2$—, —C(O)—, —CO$_2$—, —C(O)NR$^{1a}$—, —N(R$^{1a}$)C(O)—, —N(R$^{1a}$)CO$_2$—, —S(O)$_2$NR$^{1a}$—, —N(R$^{1a}$)S(O)$_2$—, —OC(O)N(R$^{1a}$)—, —N(R$^{1a}$)C(O)NR$^{1a}$—, —N(R$^{1a}$)S(O)$_2$N(R$^{1a}$)—, or —OC(O)—;

R$^{1a}$ is hydrogen or an optionally substituted $C_{1-4}$ aliphatic, and

R$^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, Se, O, or NR$^3$, where R$^3$ is hydrogen or optionally substituted $C_{1-6}$ aliphatic;

$G_3$ is C=O or SO$_2$;

$G_4$ is O or NR$^{4a}$, wherein R$^{4a}$ is hydrogen or optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

each occurrence of R$^2$ is independently —R$^{12a}$, -T$_2$-R$^{12d}$, or —V$_2$-T$_2$-R$^{12d}$, and:

each occurrence of R$^{12a}$ is independently halogen, —CN, —NO$_2$, —R$^{12c}$, —N(R$^{12b}$)$_2$, —OR$^{12b}$, —SR$^{12c}$, —S(O)$_2$R$^{12c}$, —C(O)R$^{12b}$, —C(O)OR$^{12b}$, —C(O)N(R$^{12}$)$_2$, —S(O)$_2$N(R$^{12b}$)$_2$, —OC(O)N(R$^{12b}$)$_2$, —N(R$^{12e}$)C(O)R$^{12b}$, —N(R$^{12e}$)SO$_2$R$^{12c}$, —N(R$^{12e}$)C(O)OR$^{12b}$, —N(R$^{12e}$)C(O)N(R$^{12b}$)$_2$, or —N(R$^{12e}$)SO$_2$N(R$^{12b}$)$_2$, or two occurrences of R$^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{12e}$ is independently hydrogen or an optionally substituted $C_{1-6}$ aliphatic group;

each occurrence of $V_2$ is independently —N(R$^{12e}$)—, —O—, —S—, —S(O)—, —S(O)$_2$—, —C(O)—, —C(O)O—, —C(O)N(R$^{12e}$)—, —S(O)$_2$N(R$^{12e}$)—, —OC(O)N(R$^{12e}$)—, —N(R$^{12e}$)C(O)—, —N(R$^{12e}$)SO$_2$—, —N(R$^{12e}$)C(O)O—, —N(R$^{12e}$)C(O)N(R$^{12e}$)—, —N(R$^{12e}$)SO$_2$N(R$^{12e}$)—, —OC(O)—, or —C(O)N(R$^{12e}$)—O—; and $T_2$ is an optionally substituted $C_1$-$C_6$ alkylene chain wherein the alkylene chain optionally is interrupted by —N(R$^{13}$)—, —O—, —S—, —S(O)—, —S(O)$_2$—, —C(O)—, —C(O)O—, —C(O)N(R$^{13}$)—, —S(O)$_2$N(R$^{13}$)—, —OC(O)N(R$^{13}$)—, —N(R$^{13}$)C(O)—, —N(R$^{13}$)SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein $T_2$ or a portion thereof optionally forms part of an optionally substituted 3-7 membered cycloaliphatic or heterocyclyl ring, wherein R$^{13}$ is hydrogen or an optionally substituted $C_{1-4}$ aliphatic group;

n is 0 to 4;

$R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —O$R^{4a}$, or —S$R^{4a}$;

or $R^2$ and $R^{12}$ form an optionally substituted 3-10-membered cycloaliphatic;

HY is an optionally substituted group selected from:

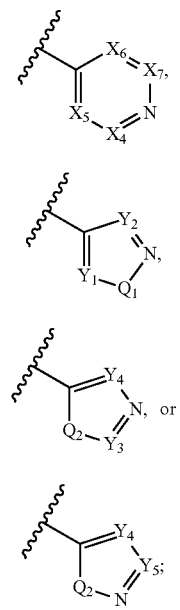

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7$C(O)O$R^{10a}$—, —$NR^7$C(O)$NR^7$—, —$NR^7$C(O)S$R^{10a}$—, —$NR^7$C(S)O$R^{10a}$—, —$NR^7$C(S)$NR^7$—, —$NR^7$C(S)S$R^{10a}$—, —$NR^7$C($NR^7$)O$R^{10a}$—, —$NR^7$C($NR^7$)$NR^7$—, —$NR^7$S(O)$_2$—, —$NR^7$S(O)$_2NR^7$—, —C(O)—, —CO$_2$—, —C(O)$NR^7$—, —C(O)$NR^7$O—, —SO$_2$—, or —SO$_2NR^7$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N($R^7$)—, —OC(O)N($R^7$)—, —N($R^7$)C(O)—, —N($R^7$)SO$_2$—, —N($R^{10a}$)C(O)O—, —N$R^{10a}$C(O)N($R^{10a}$)—, —N($R^{10a}$)S(O)$_2$N($R^{10a}$)—, —OC(O)—, or —C(O)N($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^7$)$_2$, —O$R^{10a}$, —S$R^{10a}$, —S(O)$_2R^{10a}$, —C(O)$R^{10a}$, —C(O)O$R^{10a}$, —C(O)N($R^7$)$_2$, —S(O)$_2$N($R^7$)$_2$, —OC(O)N($R^7$)$_2$, —N($R^7$)C(O)$R^{10a}$, —N($R^7$)SO$_2R^{10a}$, —N($R^7$)C(O)O$R^{10a}$, —N($R^7$)C(O)N($R^7$)$_2$, or —N($R^7$)SO$_2$N($R^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O)$R^{7a}$, —CO$_2R^{7a}$, —C(O)N($R^{7a}$)$_2$, —C(O)N($R^{7a}$)—O$R^{7a}$, —SO$_2R^{7a}$, —SO$_2$N($R^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O)$R^{6a}$, —CO$_2R^{6a}$, —C(O)N($R^{6b}$)$_2$, —SO$_2R^{6a}$, —SO$_2$N($R^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or HY is

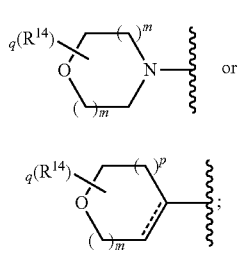

wherein each occurrence of $R^{14}$ is independently —$R^{14a}$ or -$T_1$-$R^{14d}$, wherein:
  each occurrence of $R^{14a}$, as valency and stability permit, is independently fluorine, =O, =S, —CN, —$NO_2$, —$R^{14c}$, —$N(R^{14b})_2$, —$OR^{14b}$, —$SR^{14c}$, —$S(O)_2R^{14c}$, —$C(O)R^{14b}$, —$C(O)OR^{14b}$, —$C(O)N(R^{14b})_2$, —$S(O)_2N(R^{14b})_2$, —$OC(O)N(R^{14b})_2$, —$N(R^{14e})C(O)R^{14b}$, —$N(R^{14e})SO_2R^{14e}$, —$N(R^{14e})C(O)OR^{14b}$, —$N(R^{14e})C(O)N(R^{14b})_2$, or —$N(R^{14e})SO_2N(R^{14b})_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{14e}$ is independently hydrogen or optionally substituted $C_{1-6}$ aliphatic group; and $T_1$ is an optionally substituted $C_1$-$C_6$alkylene chain wherein the alkylene chain optionally is interrupted by —$N(R^{14b})$—, —O—, —S—, —S(O)—, —$S(O)_2$—, —C(O)—, —C(O)O—, —$C(O)N(R^{14b})$—, —$S(O)_2N(R^{14b})$—, —$OC(O)N(R^{14b})$—, —$N(R^{14b})C(O)$—, —$N(R^{14b})SO_2$—, —$N(R^{14b})C(O)O$—, —$NR^{14b}C(O)N(R^{14b})$—, —$N(R^{14b})S(O)_2N(R^{14b})$—, —OC(O)—, or —$C(O)N(R^{14b})$—O— or wherein $T_1$ or a portion thereof optionally forms part of an optionally substituted 3-7 membered cycloaliphatic or heterocyclyl ring;
q is 0-6;
m is 1 or 2;
p is 0, 1, or 2;
t is 1 or 2;
each occurrence of $R^5$ is independently —$R^{15a}$ or -$T_5$-$R^{15d}$, wherein:
  each occurrence of $R^{15a}$, as valency and stability permit, is independently hydrogen, fluorine, =O, =S, —CN, —$NO_2$, —$R^{15c}$, —$N(R^{15b})_2$, —$OR^{15}$, —$SR^{15c}$, —$S(O)_2R^{15c}$, —$C(O)R^{15b}$, —$C(O)OR^{15b}$, —$C(O)N(R^{15b})_2$, —$S(O)_2N(R^{15b})_2$, —$OC(O)N(R^{15b})_2$, —$N(R^{15e})C(O)R^{15b}$, —$N(R^{15e})SO_2R^{15c}$, —$N(R^{15e})C(O)OR^{15b}$, —$N(R^{15e})C(O)N(R^{15b})_2$, or —$N(R^{15e})SO_2N(R^{15b})_2$, or two occurrences of $R^{15b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{15b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{15c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{15d}$ is independently hydrogen, —$N(R^{15b})_2$, —$OR^{15b}$, —$SR^{15c}$, —$S(O)_2R^{15c}$, —$C(O)R^{15b}$, —$C(O)OR^{15b}$, —$C(O)N(R^{15b})_2$, —$S(O)_2N(R^{15b})_2$, —$OC(O)N(R^{15b})_2$, —$N(R^{15e})C(O)R^{15b}$, —$N(R^{15e})SO_2R^{15c}$, —$N(R^{15e})C(O)OR^{15b}$, —$N(R^{15e})C(O)N(R^{15b})_2$, —$N(R^{15e})SO_2N(R^{15b})_2$, or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{15e}$ is independently hydrogen or an optionally substituted $C_{1-6}$ aliphatic group; and
  $T_5$ is an optionally substituted $C_1$-$C_6$alkylene chain wherein the alkylene chain optionally is interrupted by —$N(R^{15b})$—, —O—, —S—, —S(O)—, —$S(O)_2$—, —C(O)—, —C(O)O—, —$C(O)N(R^{15b})$—, —$S(O)_2N(R^{15b})$—, —$OC(O)N(R^{15b})$—, —$N(R^{15b})C(O)$—, —$N(R^{15b})SO_2$—, —$N(R^{15b})C(O)O$—, —$NR^{15b}C(O)N(R^{15b})$—, —$N(R^{15b})S(O)_2N(R^{15b})$—, —OC(O)—, or —$C(O)N(R^{15b})$—O— or wherein $T_5$ or a portion thereof optionally forms part of an optionally substituted 3-7 membered cycloaliphatic or heterocyclyl ring.

DETAILED DESCRIPTION OF THE INVENTION

2. Compounds and Definitions

Compounds of this invention include those described generally for formula I-A, I-B, I-C, II-A, II-B, III-A, III-B, VI-A, VI-B, VII-A, VII-B, VIII-A and VII-B above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1, 2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-C\equiv C-R^+$, $-OR^+$, $-SR^\circ$, $-S(O)R^\circ$, $-SO_2R^\circ$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^\circ$, $-NR^+CO_2R^+$, $-NR^+SO_2R^\circ$, $-NR^+SO_2N(R^+)_2$, $-O-C(O)R^+$, $-O-CO_2R^+$, $-OC(O)N(R^+)_2$, $-C(O)R^+$, $-C(S)R^\circ$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^\circ)=N-OR^+$, $-P(O)(R^+)_2$, $-P(O)(OR^+)_2$, $-O-P(O)-OR^+$, and $-P(O)(NR^+)-N(R^+)_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^\circ$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N (R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

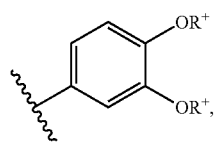

these two occurrences of R$^+$ are taken together with the oxygen atoms to which they are bound to form a fused 6-membered oxygen containing ring:

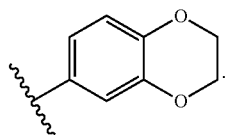

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s)

and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of general formula I-A, I-B, I-C, II-A, II-B, III-B, VI-A, VI-B, VII-A and VII-B, HY is

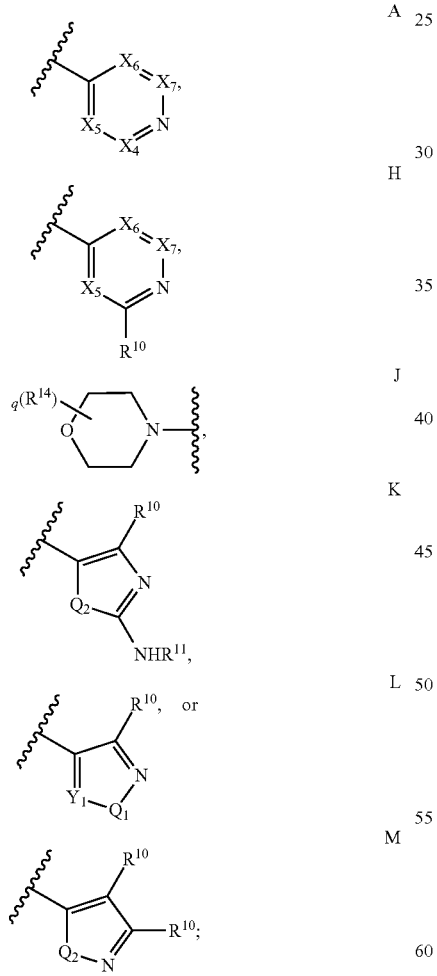

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of $R^{14}$ is independently an optionally substituted $C_{1-6}$ aliphatic group; and wherein $R^{10}$ and $R^{11}$ are as defined above.

In certain embodiments, for compounds of general formula I-A, I-B, I-C, II-A, II-B, III-A, III-B, VI-A, VI-B, VII-A and VII-B, HY is:

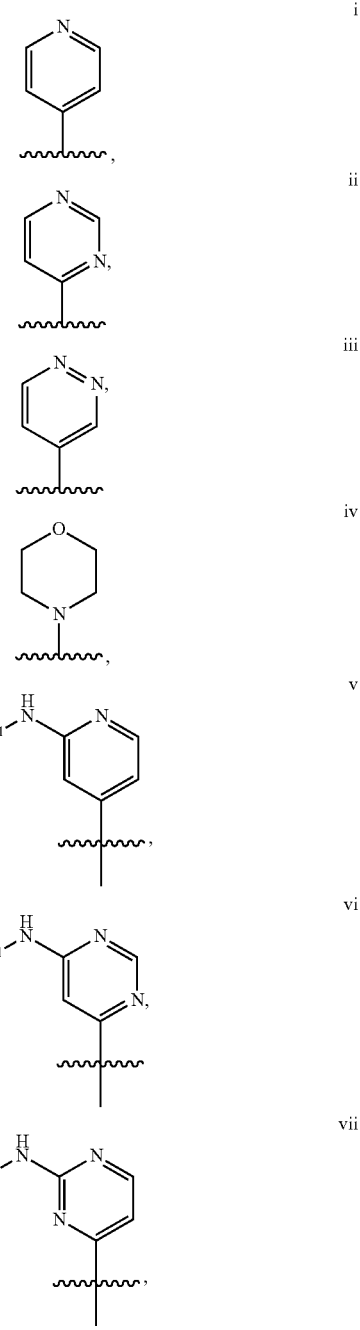

-continued

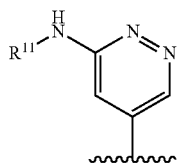 or viii

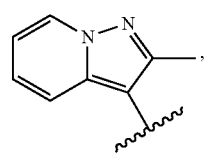, ix wherein each HY group is optionally additionally substituted with one or more occurrences of $R^{10}$ or $R^{14}$, wherein $R^{10}$, $R^{14}$, and $R^{11}$ are as defined above.

In certain embodiments, for compounds of general formula I-A, I-B, I-C, II-A, II-B, VI-A, VI-B, VII-A and VII-B, $G_1$ is N.

In certain embodiments, for compounds of general formula I-A, I-B, I-C, II-A, II-B, VI-A, VI-B, VII-A and VII-B, $G_1$ is $CR^1$.

In certain embodiments, for compounds of general formula I-A, I-B, I-C, II-A, II-B, III-B, VI-A, VI-B, VII-A and VII-B, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

In certain embodiments, for compounds of general formula I-A, I-B, I-C, II-A, II-B, III-A, III-B, VI-A, VI-B, VII-A and VII-B, Ring A is a phenyl group, $R^2$ is halogen and n is 1 or 2.

In certain embodiments, for compounds of general formula I-A, I-B, I-C, II-A, II-B, III-A, III-B, VI-A, VI-B, VII-A and VII-B, $R^{12}$ is OH.

In still other embodiments, a compound having the structure of formula IV is provided:

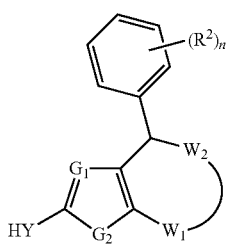

IV wherein HY, $G_1$, $G_2$, $R^2$, $R^{12}$, $W_1$, $W_2$, and n are as defined above.

In some embodiments, for compounds of formula IV, $G_2$ is S.

In still other embodiments, for compounds of formula IV, HY is

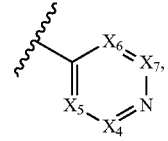

A

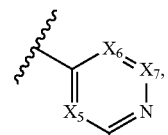

H

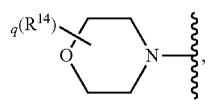

J

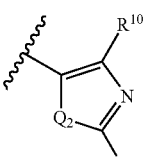

K

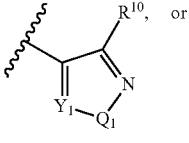

L

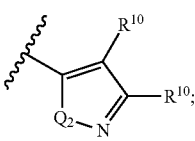

M wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of $R^{14}$ is independently an optionally substituted $C_{1-6}$ aliphatic group; and wherein $R^{10}$ and $R^{11}$ are as defined above.

In some embodiments, for compounds of formula IV, HY is:

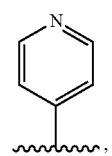

i

-continued ii
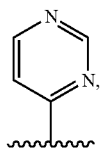

iii
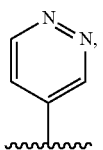

iv
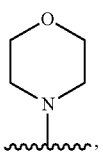

v
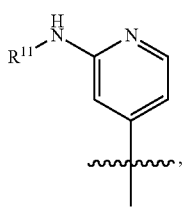

vi
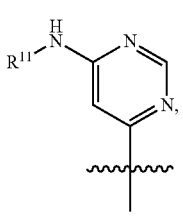

vii
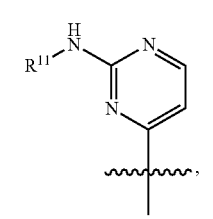

viii
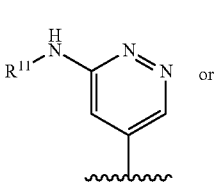

ix
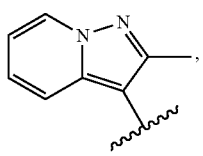

wherein each HY group is optionally additionally substituted with one or more occurrences of $R^{10}$ or $R^{14}$,
wherein $R^{10}$, $R^{14}$, and $R^{11}$ are as defined above.

In some embodiments, for compounds of formula IV, $G_1$ is N.

In some embodiments, for compounds of formula IV, $G_1$ is $CR^1$,

In some embodiments, for compounds of formula IV, each occurrence of $R^2$ is independently halogen, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NHC$_{1-3}$alkyl, —NHS(O)$_2C_{1-3}$ alkyl, or —C(O)H; and n is 0 to 3.

In some embodiments, for compounds of formula IV, $R^2$ is halogen and n is 1 or 2.

In still other embodiments, a compound having the structure of formula V is provided:

V
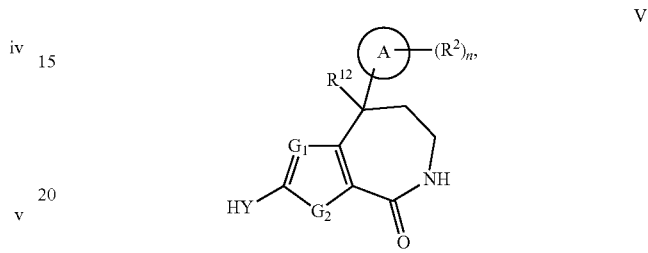

wherein HY, $G_1$, $G_2$, $R^2$, $R^{12}$, Ring A, and n are as defined above.

In some embodiments, for compounds of formula V, $G_2$ is S.

In still other embodiments, for compounds of formula V, HY is

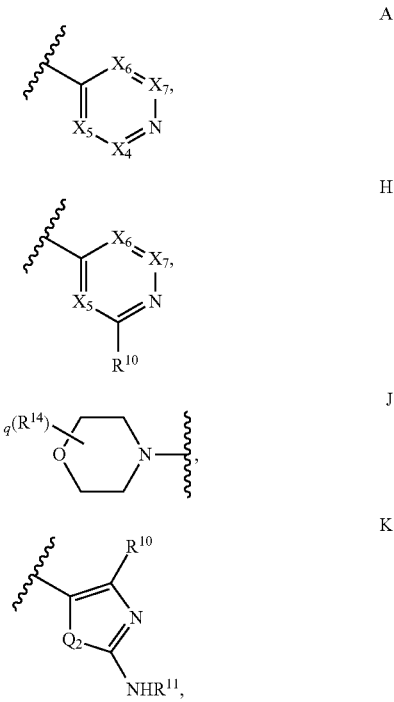

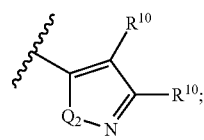

M wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of $R^{14}$ is independently an optionally substituted $C_{1-6}$ aliphatic group; and wherein $R^{10}$ and $R^{11}$ are as defined above.

In some embodiments, for compounds of formula V, HY is:

i
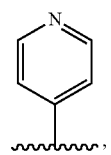

ii
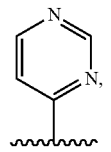

iii
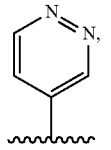

iv
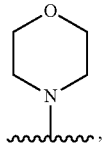

v
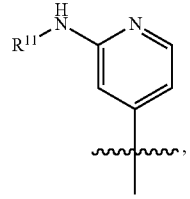

vi
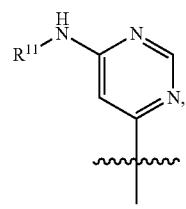

vii
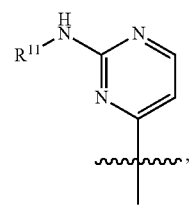

viii
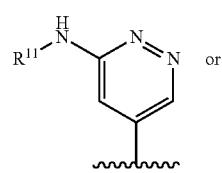

or ix
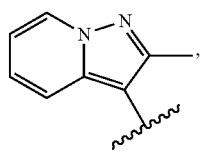

wherein each HY group is optionally additionally substituted with one or more occurrences of $R^{10}$ or $R^{14}$, wherein $R^{10}$, $R^{14}$, and $R^{11}$ are as defined above.

In some embodiments, for compounds of formula V, $G_1$ is N.

In some embodiments, for compounds of formula V, $G_1$ is $CR^1$.

In some embodiments, for compounds of formula V, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3.

In some embodiments, for compounds of formula V, Ring A is a phenyl group, $R^2$ is halogen and n is 1 or 2.

In some embodiments, for compounds of formula V, $R^{12}$ is OH.

In still other embodiments, compounds of A compound having the structure VIII-A or VIII-B:

VIII-A
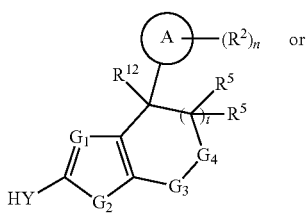

or

-continued

VIII-B

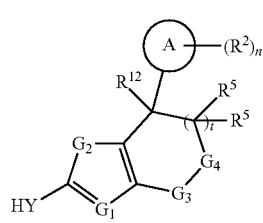

or a pharmaceutically acceptable salt thereof, wherein:

$G_1$ is N or $CR^1$, wherein $R^1$ is H, —CN, halogen, or an optionally substituted group selected from $C_{1-6}$ aliphatic, 3-10-membered cycloaliphatic, or —Z—$R^{11}$, wherein:

Z is selected from an optionally substituted $C_{1-3}$ alkylene chain, —O—, —N($R^{1a}$)—, —S—, —S(O)—, S(O)$_2$—, —C(O)—, —CO$_2$—, —C(O)N$R^{1a}$—, —N($R^{1a}$)C(O)—, —N($R^{1a}$)CO$_2$—, —S(O)$_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, or —OC(O)—;

$R^{1a}$ is hydrogen or an optionally substituted $C_{1-4}$ aliphatic, and $R^{11}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and $G_2$ is S, Se, O, or $NR^3$, where $R^3$ is hydrogen or optionally substituted $C_{1-6}$ aliphatic;

$G_3$ is C=O or SO$_2$;

$G_4$ is O or $NR^{4a}$, wherein $R^{4a}$ is hydrogen or optionally substituted $C_{1-6}$ aliphatic;

Ring A is an optionally substituted group selected from 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

$R^{12}$ is hydrogen, halo, or an optionally substituted group selected from $C_{1-6}$ aliphatic, —C(O)N($R^{5a}$)$_2$, 3-10-membered cycloaliphatic, —N($R^{4b}$)$_2$, —O$R^{4a}$, or —S$R^{4a}$;

or $R^2$ and $R^{12}$ form an optionally substituted 3-10-membered cycloaliphatic;

HY is an optionally substituted group selected from:

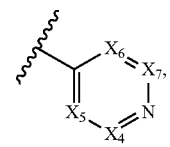

A

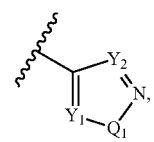

B

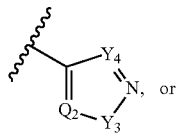

C or

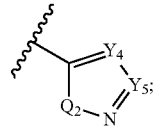

D wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7$C(O)$OR^{10a}$—, —$NR^7$C(O)$NR^7$—, —$NR^7$C(O)$SR^{10a}$—, —$NR^7$C(S)$OR^{10a}$—, —$NR^7$C(S)$NR^7$—, —$NR^7$C(S)$SR^{10a}$—, —$NR^7$C($NR^7$)$OR^{10a}$—, —$NR^7$C($NR^7$)$NR^7$—, —$NR^7$S(O)$_2$—, —$NR^7$S(O)$_2$$NR^7$—, —C(O)—, —CO$_2$—, —C(O)$NR^7$—, —C(O)$NR^7$O—, —SO$_2$—, or —SO$_2$$NR^7$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N ($R^7$)—, —OC(O)N($R^7$)—, —N($R^7$)C(O)—, —N($R^7$)SO$_2$—, —N($R^{10a}$)C(O)O—, —$NR^{10a}$C(O)N($R^{10a}$)—, —N($R^{10a}$)S(O)$_2$N($R^{10a}$)—, —OC(O)—, or —C(O)N ($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^7$)$_2$, —$OR^{10a}$, —$SR^{10a}$, —S(O)$_2$$R^{10a}$, —C(O)$R^{10a}$, —C(O)$OR^{10a}$, —C(O)N ($R^7$)$_2$, —S(O)$_2$N($R^7$)$_2$, —OC(O)N($R^7$)$_2$, —N($R^7$)C(O) $R^{10a}$, —N($R^7$)SO$_2$$R^{10a}$, —N($R^7$)C(O)$OR^{10a}$, —N($R^7$) C(O)N($R^7$)$_2$, or —N($R^7$)SO$_2$N($R^7$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^7$ is independently hydrogen, —C(O) $R^{7a}$, —CO$_2$$R^{7a}$, —C(O)N($R^{7a}$)$_2$, —C(O)N($R^{7a}$)—$OR^{7a}$, —SO$_2$$R^{7a}$, —SO$_2$N($R^{7a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{7a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^6$ is independently hydrogen, —C(O) $R^{6a}$, —CO$_2$$R^{6a}$, —C(O)N($R^{6b}$)$_2$, —SO$_2$$R^{6a}$, —SO$_2$N($R^{6b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{6a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and wherein each occurrence of $R^{6b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or HY is

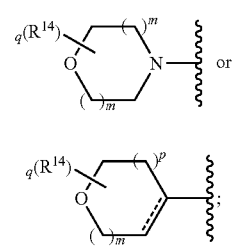

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —$OR^{14b}$, —$SR^{14c}$, —S(O)$_2$ $R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2$$R^{14c}$, —N($R^{14e}$)C(O)O$R^{14b}$, —N($R^{14c}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)—, —N($R^{14b}$)SO$_2$—, —N($R^{14b}$)C(O)O—, —N$R^{14b}$C(O)N($R^{14}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;
m is 1 or 2;
p is 0, 1, or 2;
t is 1 or 2;
each occurrence of $R^5$ is independently —$R^{15a}$ or -$T_5$-$R^{15d}$, wherein:

each occurrence of $R^{15a}$, as valency and stability permit, is independently hydrogen, fluorine, =O, =S, —CN, —NO$_2$, —$R^{15c}$, —N($R^{15b}$)$_2$, —O$R^{15b}$, —S$R^{15c}$, —S(O)$_2$$R^{15c}$, —C(O)$R^{15b}$, —C(O)O$R^{15b}$, —C(O)N($R^{15b}$)$_2$, —S(O)$_2$N($R^{15b}$)$_2$, —OC(O)N($R^{15b}$)$_2$, —N($R^{15e}$)C(O)$R^{15b}$, —N($R^{15e}$)SO$_2$$R^{15c}$, —N($R^{15e}$)C(O)O$R^{15b}$, —N($R^{15e}$)C(O)N($R^{15b}$)$_2$, or —N($R^{15e}$)SO$_2$N($R^{15b}$)$_2$, or two occurrences of $R^{15b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{15b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{15c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{15d}$ is independently hydrogen, —N($R^{15b}$)$_2$, —O$R^{15b}$, —S$R^{15c}$, —S(O)$_2$$R^{15c}$, —C(O)$R^{15b}$, —C(O)O$R^{15b}$, C(O)N($R^{15b}$)$_2$, —S(O)$_2$N($R^{15b}$)$_2$, —OC(O)N($R^{15b}$)$_2$, —N($R^{15e}$)C(O)$R^{15b}$, —N($R^{15e}$)SO$_2$$R^{15c}$, —N($R^{15e}$)C(O)O$R^{15b}$, —N($R^{15e}$)C(O)N($R^{15b}$)$_2$, —N($R^{15e}$)SO$_2$N($R^{15b}$)$_2$, or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{15e}$ is independently hydrogen or an optionally substituted $C_{1-6}$ aliphatic group; and $T_5$ is an optionally substituted $C_1$-$C_6$ alkylene chain wherein the alkylene chain optionally is interrupted by —N($R^{15b}$)—, —O—, —S—, —S(O)—, —S(O)$_2$—, —C(O)—, —C(O)O—, —C(O)N($R^{15b}$)—, —S(O)$_2$N($R^{15b}$)—, —OC(O)N($R^{15b}$)—, —N($R^{15b}$)C(O)—, —N($R^{15b}$)SO$_2$—, —N($R^{15b}$)C(O)O—, —N$R^{15b}$C(O)N($R^{15b}$)—, —N($R^{15b}$)S(O)$_2$N($R^{15}$)—, —OC(O)—, or —C(O)N($R^{15b}$)—O— or wherein $T_5$ or a portion thereof optionally forms part of an optionally substituted 3-7 membered cycloaliphatic or heterocyclyl ring.

In still other embodiments, for compounds having the structure VIII-A or VIII-B, $G_1$ is $CR^1$ or N and $G_2$ is S. In yet other embodiments, $G_1$ is $CR^1$ or N and $G_2$ is S. In still other embodiments, $G_1$ is $CR^1$ or N, and $G_2$ is Se. In yet other embodiments, $G_1$ is $CR^1$ or N, and $G_2$ is O. In still further embodiments, $G_1$ is $CR^1$ or N, and $G_2$ is $NR^3$. In still other embodiments, $G_1$ is $CR^1$ and $G_2$ is S. In yet other embodiments, $G_1$ is N and $G_2$ is S.

In still further embodiments, for compounds having the structure VIII-A or VIII-B, when $G_1$ is $CR_1$, $R^1$ is hydrogen, CN, optionally substituted $C_{1-6}$aliphatic or $C_{3-6}$cycloaliphatic, or optionally substituted alkyne.

In yet other embodiments, compounds have the structure VIII-A.

In still other embodiments, compounds have the structure VIII-A-i or VIII-B-i

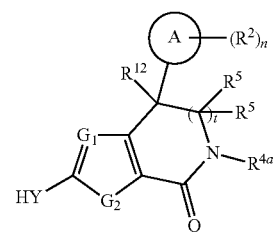

VIII-A-i

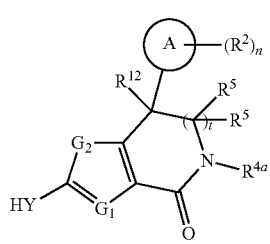

VIII-B-i

In yet other embodiments, compounds have the structure VIII-A-ii or VIII-B-ii

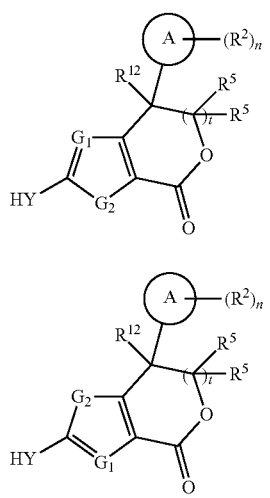

VIII-A-ii

VIII-B-ii

In yet other embodiments, compounds have the structure VIII-A-iii or VIII-B-iii

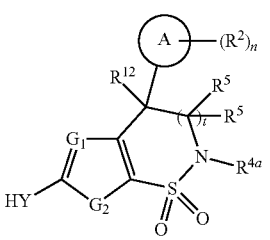

VIII-A-iii

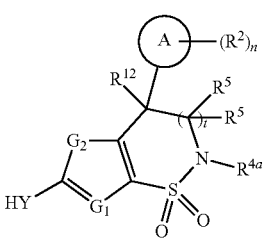

VIII-B-iii

In still other embodiments for compounds having the structure VIII-A, VIII-B, VIII-A-i, VIII-B-i, VIII-A-ii, VIII-B-ii, VIII-A-iii, or HY is selected from:

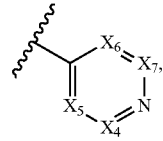
A

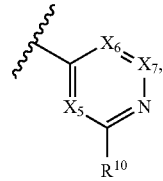
H

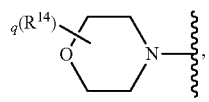
J

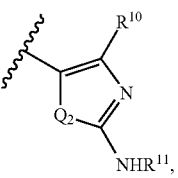
K

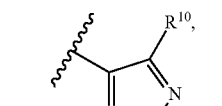
L

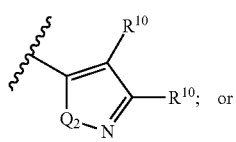
M

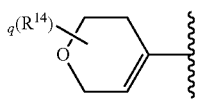
F-i wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of $R^{14}$ is independently an optionally substituted $C_{1-6}$ aliphatic group.

In yet other embodiments, for compounds having structures VIII-A-i, VIII-B-i, VIII-A-ii, VIII-B-ii, VIII-A-iii, or VIII-B-iii, HY is selected from:

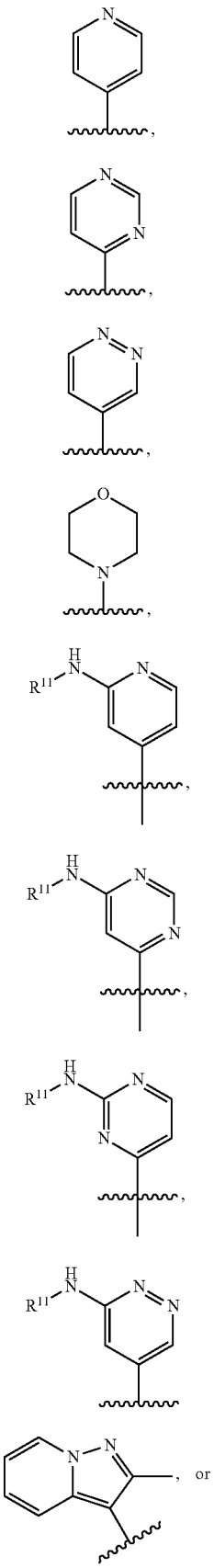

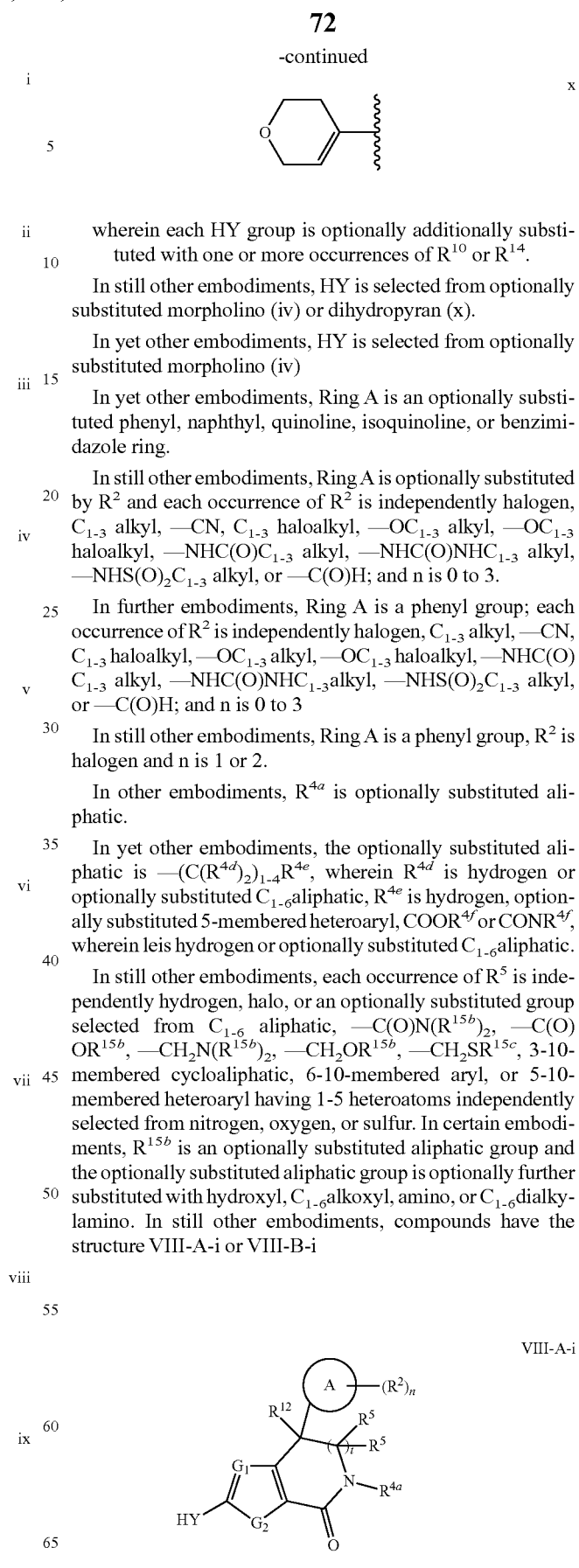

wherein each HY group is optionally additionally substituted with one or more occurrences of $R^{10}$ or $R^{14}$.

In still other embodiments, HY is selected from optionally substituted morpholino (iv) or dihydropyran (x).

In yet other embodiments, HY is selected from optionally substituted morpholino (iv)

In yet other embodiments, Ring A is an optionally substituted phenyl, naphthyl, quinoline, isoquinoline, or benzimidazole ring.

In still other embodiments, Ring A is optionally substituted by $R^2$ and each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3.

In further embodiments, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O) $C_{1-3}$ alkyl, —NHC(O)NHC$_{1-3}$alkyl, —NHS(O)$_2$C$_{1-3}$ alkyl, or —C(O)H; and n is 0 to 3

In still other embodiments, Ring A is a phenyl group, $R^2$ is halogen and n is 1 or 2.

In other embodiments, $R^{4a}$ is optionally substituted aliphatic.

In yet other embodiments, the optionally substituted aliphatic is —(C(R$^{4d}$)$_2$)$_{1-4}$R$^{4e}$, wherein $R^{4d}$ is hydrogen or optionally substituted $C_{1-6}$aliphatic, $R^{4e}$ is hydrogen, optionally substituted 5-membered heteroaryl, COOR$^{4f}$ or CONR$^{4f}$, wherein le is hydrogen or optionally substituted $C_{1-6}$aliphatic.

In still other embodiments, each occurrence of $R^5$ is independently hydrogen, halo, or an optionally substituted group selected from $C_{1-6}$ aliphatic, —C(O)N(R$^{15b}$)$_2$, —C(O)OR$^{15b}$, —CH$_2$N(R$^{15b}$)$_2$, —CH$_2$OR$^{15b}$, —CH$_2$SR$^{15c}$, 3-10-membered cycloaliphatic, 6-10-membered aryl, or 5-10-membered heteroaryl having 1-5 heteroatoms independently selected from nitrogen, oxygen, or sulfur. In certain embodiments, $R^{15b}$ is an optionally substituted aliphatic group and the optionally substituted aliphatic group is optionally further substituted with hydroxyl, $C_{1-6}$alkoxyl, amino, or $C_{1-6}$dialkylamino. In still other embodiments, compounds have the structure VIII-A-i or VIII-B-i VIII-B-i

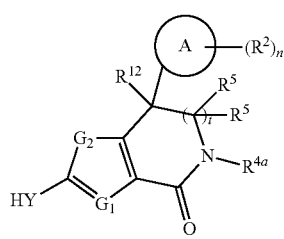

wherein G₁ is N or CR¹ and G₂ is S or Se. In certain embodiments, G₁ is N or CR¹ and G₂ is S. In still other embodiments, G₁ is CR¹, wherein R¹ is hydrogen, CN, optionally substituted C$_{1-6}$aliphatic or C$_{3-6}$cycloaliphatic, or optionally substituted alkyne and G₂ is S. In yet other embodiments, G₁ is N and G₂ is S. Other embodiments and subsets where HY, R¹², ring A, R², n, R⁵, t, and R$^{4a}$ are described above and herein are also encompassed within the scope of the invention for compounds VII-A-i and VIII-B-i.

For example, in still other embodiments for compounds having the structure VIII-A-i and VIII-B-i HY is selected from:

F-i

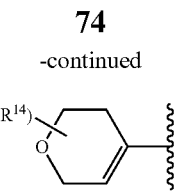

wherein each occurrence of X₄, X₅, X₆, and X₇ is independently —CR¹⁰ or N, provided no more than two occurrences of X₄, X₅, X₆, and X₇ are N;

each occurrence of Q₁ and Q₂ is independently S, O or —NR⁶;

each occurrence of Y₁ is independently —CR¹⁰ or N;

or wherein two adjacent occurrences of X₆ and X₇, or Y₁ and Q₁, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of R¹⁴ is independently an optionally substituted C$_{1-6}$ aliphatic group.

In yet other embodiments, for compounds having structures VIII-A-i and VIII-B-i, HY is selected from:

A

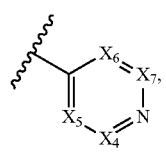

H

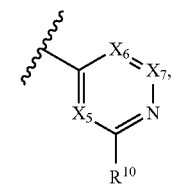

J

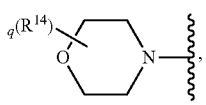

K

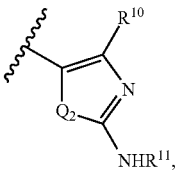

L

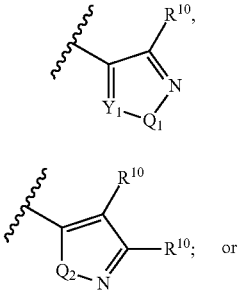

M i

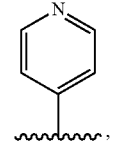

ii

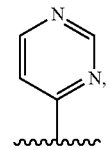

iii

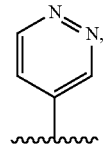

iv

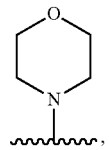

v

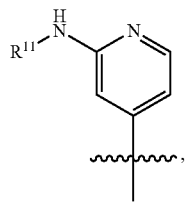

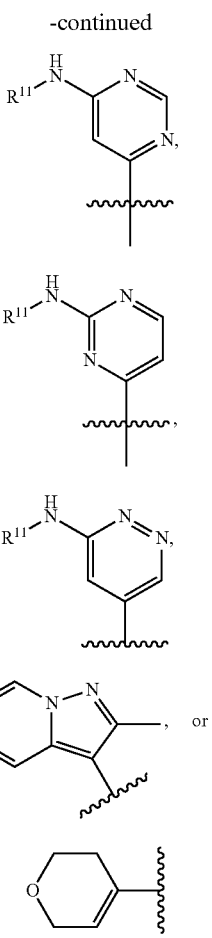

wherein each HY group is optionally additionally substituted with one or more occurrences of $R^{10}$ or $R^{14}$.

In still other embodiments, HY is selected from optionally substituted morpholino (iv) or dihydropyran (x).

In yet other embodiments, HY is selected from optionally substituted morpholino (iv)

In yet other embodiments, Ring A is an optionally substituted phenyl, naphthyl, quinoline, isoquinoline, or benzimidazole ring.

In still other embodiments, Ring A is optionally substituted by $R^2$ and each occurrence of $R^2$ is independently halogen, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NHC$_{1-3}$alkyl, —NHS(O)$_2$C$_{1-3}$ alkyl, or —C(O)H; and n is 0 to 3.

In further embodiments, Ring A is a phenyl group; each occurrence of $R^2$ is independently halogen, $C_{1-3}$ alkyl, —CN, $C_{1-3}$haloalkyl, —$OC_{1-3}$haloalkyl, —NHC(O)$C_{1-3}$alkyl, —NHC(O)NHC$_{1-3}$alkyl, —NHS(O)$_2$C$_{1-3}$ alkyl, or —C(O)H; and n is 0 to 3

In still other embodiments, Ring A is a phenyl group, $R^2$ is halogen and n is 1 or 2.

In other embodiments, $R^{4a}$ is optionally substituted aliphatic.

In yet other embodiments, the optionally substituted aliphatic is —(C($R^{4d}$)$_2$)$_{1-4}$$R^{4e}$, wherein $R^{4d}$ is hydrogen or optionally substituted $C_{1-6}$aliphatic, $R^{4e}$ is hydrogen, optionally substituted 5-membered heteroaryl, COOR$^{4f}$ or CONR$^{4f}$, wherein $R^{4f}$ is hydrogen or optionally substituted $C_{1-6}$aliphatic.

In still other embodiments, each occurrence of $R^5$ is independently hydrogen, halo, or an optionally substituted group selected from $C_{1-6}$ aliphatic, —C(O)N($R^{15b}$)$_2$, —C(O)OR$^{15b}$, —CH$_2$N($R^{15}$)$_2$, —CH$_2$OR$^{15b}$, —CH$_2$SR$^{15c}$, 3-10-membered cycloaliphatic, 6-10-membered aryl, or 5-10-membered heteroaryl having 1-5 heteroatoms independently selected from nitrogen, oxygen, or sulfur. In certain embodiments, $R^{15b}$ is an optionally substituted aliphatic group and the optionally substituted aliphatic group is optionally further substituted with hydroxyl, $C_{1-6}$alkoxyl, amino, or $C_{1-6}$dialkylamino.

4. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and rectum, thyroid, liver and intrahepatic bile duct, hepatocellular, gastric, glioma/glioblastoma, endometrial, melanoma, kidney, and renal pelvis, urinary bladder, uttering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PI3K kinase plays a role.

Experimental Procedures

I-A. Preparation of certain exemplary compounds compounds 1 through 214 (Shown in Table 1 below) were prepared using the general methods and specific examples described directly below.

5. General Synthetic Methods and Intermediates

The compounds of the present invention can be prepared by methods known to one of ordinary skill in the art and/or by reference to the schemes shown below and the synthetic examples that follow. Exemplary synthetic routes are set forth in Schemes 1-29 below, and in the Examples.

In methods defined below X represents halogen (Br, I or Cl), P is Hy itself or a substituent convertible to Hy by applying a generally known method, $W^R$ is a part of a cyclic ring, either $W_1$, $W_2$, or —C($R^{12}$)(A)-, or groups convertible to $W_1$, $W_2$, or —C($R^{12}$)(A)- by applying a generally known method, $W^A$ is a group that can be cyclized to become a part of a ring system, either $W_1$, $W_2$, or —C($R^{12}$)(A)-, or groups convertible to $W_1$, $W_2$, or —C($R^{12}$)(A)- by applying a generally known method, $A^R$ is either ring A itself, or a substituent convertible to ring A by applying a generally known method, $R^A$ is either $R^{12}$ itself, or a substituent convertible to $R^{12}$ by applying a generally known method. R' and R" refer to any substituents defined within the claims compatible with performed reactions. For example, in some embodiments, R" is equivalent to $R^5$ as described in the claims and specification here. PG is a protective group that can be installed or removed using generally known methods, and EWG stands for an electron-withdrawing group.

Examples of the solvent for the below-mentioned reactions include, but are not limited to halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane, DME and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

One of ordinary skill in the art will recognise that numerous variations in reaction conditions including variations in solvent, reagents, catalysts, reaction temperatures and times are possible for each of the reactions described. Variation of order of synthetic steps and alternative synthetic routes are also possible.

In many cases, synthesis can be started from commercially available analogs to prepare target compounds. In some cases, specific methods can be used to build bicyclic scaffolds as described in Schemes 1-29.

Scheme 1: General method for the synthesis of bicyclic analogs via Friedel-Craft cyclization

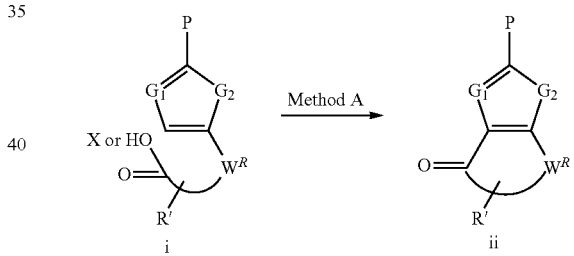

Bicyclic ketones ii can be purchased from commercial sources, or obtained by the well known Friedel-Craft type cyclization (Method A) of carboxylic acids or carboxylic acid halides i in the presence of acid, such as sulfuric acid, polyphospholic acid (PPA), AlCl$_3$, other Lewis acids, etc. at elevated temperature.

Scheme 2: Alternative method for the synthesis of bicyclic analogs via Sonogashira coupling reaction

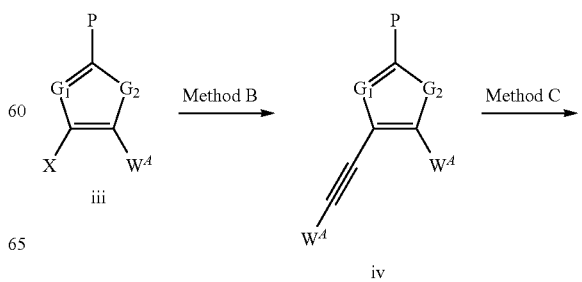

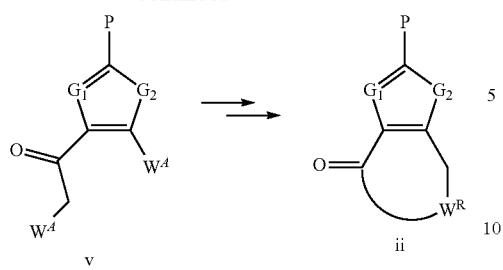

v → ii

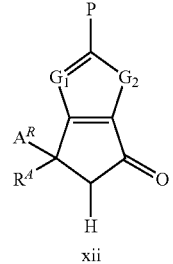

xii

Scheme 2 shows an alternative method for building bicyclic ketones ii. Halides iii can be treated with alkynes using generally known Sonogashira conditions (Method B), for example Pd(PPh$_3$)$_2$Cl$_2$, CuI as catalysts, triethylamine as a base in a suitable solvent, like DMF to give alkynes iv, that can be subsequently hydrated using water, an acid, for example TFA in a suitable solvent, such as DCM (Method C) to afford ketones v. If needed, a mercury salt such as HgSO$_4$ can be added to facilitate the process. Functional groups W$^A$ can be then connected using generally known methods, for example amide coupling in the case where one W$^A$ contains a carboxylic acid, and the other W$^A$ contains an amine to afford ketones ii.

Scheme 3: Alternate route for the synethsis of bicyclic analogs

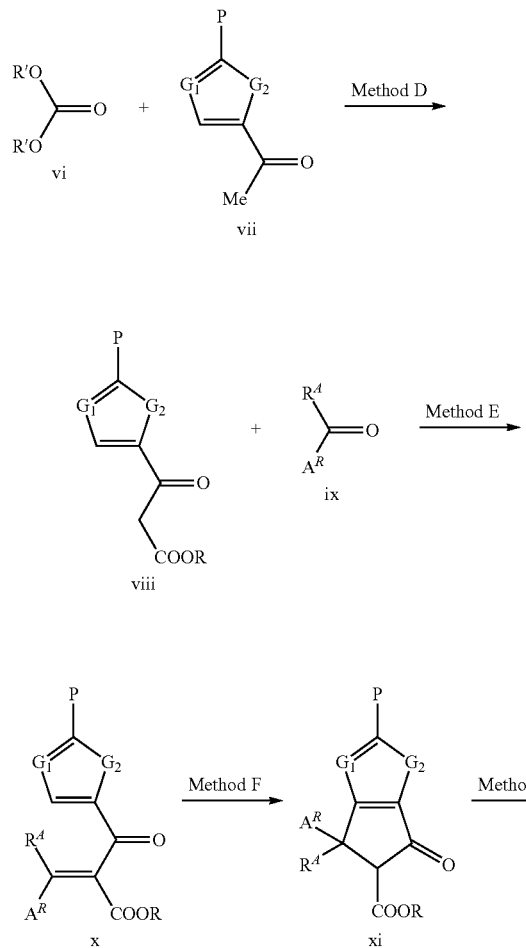

Scheme 3 shows an alternate method for the synthesis of 5-membered bicyclic analogs xii. As shown in scheme 3, ketones vii can be treated with dialkyl carbonates vi in a presence of a suitable base, such as sodium hydride in an appropriate solvent, for example THF at elevated temperature (Method D). The formed keto esters viii can be then subjected to Knoevenagel condensation with an aldehyde or ketone, using an appropriate base, for example piperidine, and an appropriate acid, for example acetic acid (Method E). Benzene or other appropriate solvent can be used, and the reaction can be run at elevated temperature using a suitable method for azeotropic removal of water, such as Dean-Stark trap. The formed α,β unsaturated keto esters x can be then cyclized using a Nazarov reaction, with a Lewis acid such as AlCl3, in a suitable solvent like dichloroethane at elevated temperature (Method F) to afford cyclic b-ketoesters xi. Decarboxylation can then be carried out thermally in a suitable solvent, for example DMSO and water at elevated temperature (Method G) to afford ketones xii.

Scheme 4: General method for the synthesis of bicyclic lactams

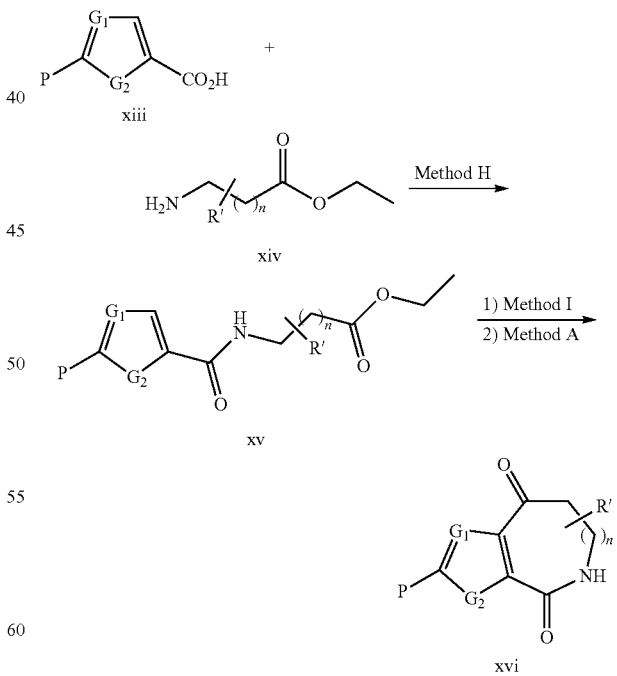

Scheme 4 shows a general route for the synthesis of bicyclic lactams. Carboxylic acids xiii can be coupled with amino esters xiv under standard conditions, for example EDCI, HOBt, in an appropriate solvent like DCM (Method H) to afford amides xv. Carboxylic ester group can be then hydrolyzed using standard conditions, for example NaOH in THF-water mixture (Method I) and the acids xv can be subjected to intramolecular Friedel-Crafts cyclization as described in Scheme 1 (Method A) to afford compounds of formula xvi.

Scheme 5: General method for the synthesis of bicyclic thiazoles

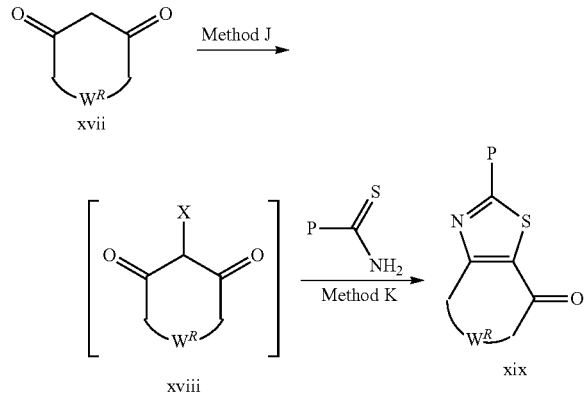

Scheme 5 shows a general route for the synthesis of bicyclic thiazoles. 1,3-diketones xvii can be treated with halogen, for example bromine in a suitable solvent, such as acetic acid (Method J). The formed halides xviii are then treated with thioamides or thiourea (P=NH$_2$) in a suitable solvent, for example acetic acid at elevated temperature (Method K) to afford bicyclic thiazoles xix.

Scheme 6: Alternate method for the synthesis of bicyclic thiazoles

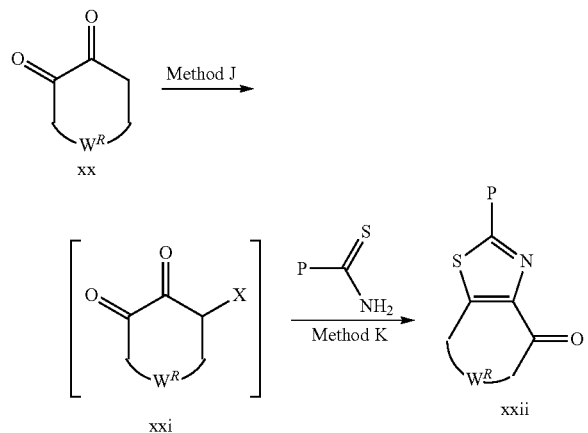

Scheme 6 shows a general route for the synthesis of bicyclic thiazoles xxii. 1,2-diketones xx can be treated with halogen, for example bromine in a suitable solvent, such as acetic acid (Method J). The formed halides xxi are then treated with thioamides or thiourea (P=NH$_2$) in a suitable solvent, for example acetic acid at elevated temperature (Method K) to afford bicyclic thiazoles xxii.

Schemes 7-13 describe specific methods for further transformations of scaffolds obtained from commercial sources, prepared based on literature examples or by methods described in schemes 1-6.

Scheme 7: General method for addition of aryl group to bicyclic ketones

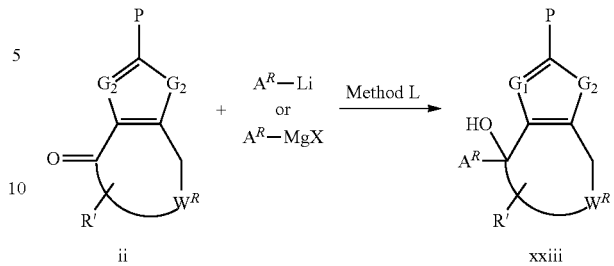

Scheme 7 shows a general route for the addition of an organometallic agent to a cyclic ketone ii. Ketones ii can be treated with aryllithium or aryl Grignard reagents, such as 4-chlorophenylmagnesium bromide in a suitable solvent, such as THF at room temperature, or with cooling (Method L) to afford tertiary alcohols xxiii.

Scheme 8: General method for elimination/deoxygenation of benzylic carbinols

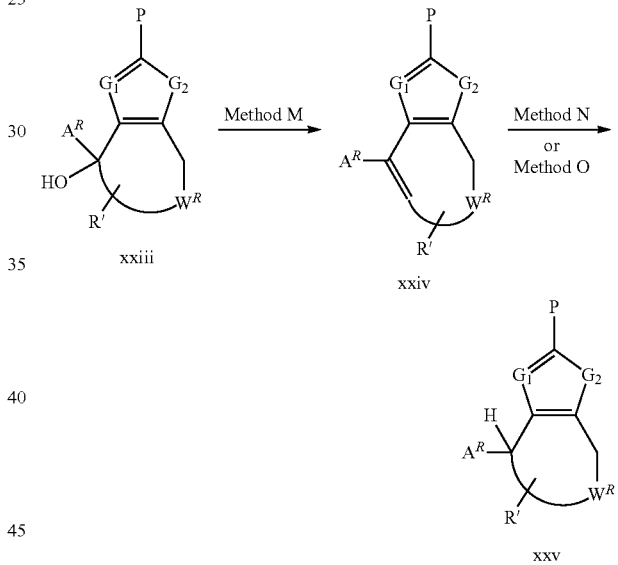

Scheme 8 shows a general method for obtaining saturated analogs from hydroxyl compounds xxiii by the reductive removal of the hydroxyl functional group. In this case, olefin intermediate xxiv can be isolated if necessary. For example, treatment of hydroxyl compound xxiii with acid such as TFA, sulfuric acid, TfOH, etc (Method M) affords olefin compound xxiv. This reaction is usually carried out in the usual organic solvent such as dichloromethane, 1,2-dichloroethane, toluene etc., but can be also performed without any organic solvent. The reaction is usually carried out at rt to reflux temperature. The olefin intermediate xxiv can be then converted to compound xxv by the well known hydrogenation reaction, like pressurized hydrogen, Pd/C as a catalyst and a suitable solvent, for example ethanol. (Method N). Also, the olefin intermediate xxvi can be converted to the compound xxv by acid mediated hydride reduction, using a suitable acid, such as sulfuric acid, TFA, TfOH, BF$_3$-ether complex, or other Lewis acids and a hydride agent, for example Et$_3$SiH, NaBH$_4$, Red-Al etc in a suitable solvent, such as dichloromethane, dichloroethane or toluene at rt or at elevated temperature (Method O). Compound xxv can be also directly prepared without isolation of the olefin intermediate xxiv. In this case, well known hydrogenation condition such as H$_2$—Pd/C system and a suitable solvent, such as ethyl acetate, ethanol etc (Method N) can be applied. If necessary, acids such as acetic acid, hydrochloric acid etc can be added. Direct acid mediated hydride reduction reaction without isolation of the olefin intermediate xxiv can be also applied, for example using preferred conditions with TfOH as an acid and Et3SiH as a hydride agent in a suitable solvent, such as dichloroethane at elevated temperature (Method O) to afford compounds of formula xxv.

Scheme 9: General method for oxidation of alkylenes to alcohols and ketones

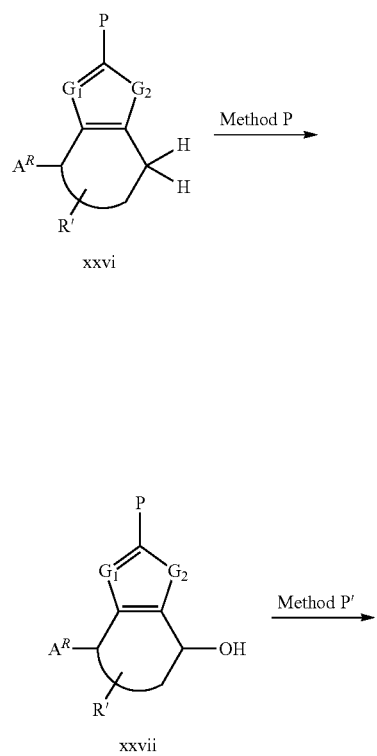

Scheme 10: General method for preparation of lactams from ketones

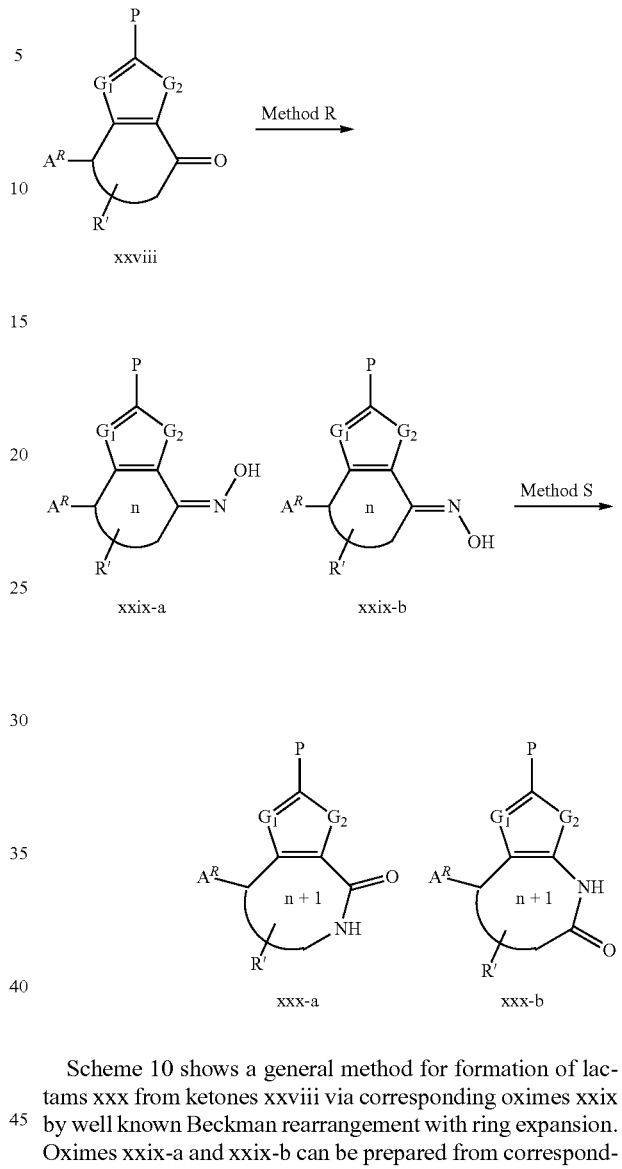

Scheme 9 shows a general method for oxidation of methylene group in xxvi to ketones xxviii. As an oxidant, K$_2$Cr$_2$O$_7$, KMnO$_4$, SeO2, the combination of TBHP and NaClO$_3$, the combination of copper sulfate and potassium persulfate etc can be used (Method P). Among them, the copper sulfate-potassium persulfate system is preferable. In this reaction, organic base such as 2,4,6-trimethylpyridine can be added as a base, if needed. The reaction is usually carried out in solvent such as dioxane, acetonitrile and water or their mixture. The reaction is usually carried out at rt to reflux temperature. In some cases, the reaction may afford hydroxyl compounds xxvii exclusively, or in addition to ketones xxviii. In this case, hydroxyl compounds xxvii can be converted to target keto-compounds xxviii by the further oxidation using Dess-Martin reagent, MnO$_2$, Swern oxidation systems etc (Method P'). The second oxidation can also be performed using a mixture of hydroxyl compounds xxvii and keto-compounds xxviii.

Scheme 10 shows a general method for formation of lactams xxx from ketones xxviii via corresponding oximes xxix by well known Beckman rearrangement with ring expansion. Oximes xxix-a and xxix-b can be prepared from corresponding ketones ii using standard conditions, for example by treatment of with hydroxylamine hydrochloride and sodium acetate in appropriate solvent, such as THF, acetonitrile, ethanol, DMF, dioxane etc (Method R). Usually, the reaction affords a stereo isomeric mixture of oximes xxix-a and xxix-b, however, in some cases, xxix-a or xxix-b are produced stereoselectively. The Beckman rearrangement reaction can be performed using a stereo isomeric mixture of oximes xxix-a and xxix-b to afford a regio isomeric mixture of lactams xxx-a and xxx-b. Usually, a mixture of lactam xxx-a and xxx-b can be separated by chromatographic purification method. For this reaction, strong Bronsted acid, such as sulfuric acid, polyphosphoric acid (PPA), methansulfonic acid etc can be used. The reaction can be run at room temperature to 200° C. (Method S). Alternatively, Beckman reaction can be performed in the presence of Lewis acid such as AlCl$_3$ etc in an appropriate solvent at rt to 200° C. In cases when single isomers of oximes are used, a single isomer of lactam can be formed, depending on stereochemistry of the starting material.

Scheme 11: General method for halogenation of 5-membered heteroaromates

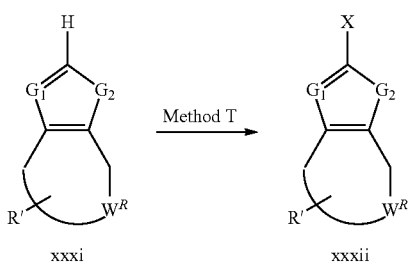

Scheme 11 shows a general method for halogenation non-substituted 5-membered heteroaromates xxxi. Non-substituted heteroaromates xxxi can be treated with a halogenation agent, such as Br$_2$, NBS, etc in a suitable solvent, such as acetic acid, DCM or others (Method T) to afford compounds of formula xxxii. As a halogen, Br is the most preferable, however, in some cases, Cl or I can be also chosen.

Scheme 12: General method for C—C or C—N bond formation on 5-membered heteroaromates

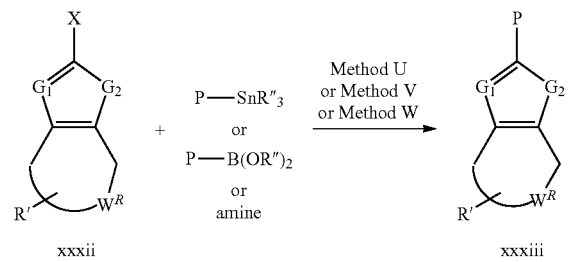

Scheme 12 shows a general method for C—C or C—N bond formation on 5-membered heteroaromatics xxxii. Halides xxxii can be treated with stannanes using standard Stille conditions, for example Pd(PPh$_3$)$_4$, CuI, LiCl, in a suitable solvent, like dioxane at elevated temperature (Method U) to afford compounds xxxiii. Alternatively, boronic acids or esters can be used in Suzuki reaction, for example using Pd catalyst such as Pd(dppf)$_2$Cl$_2$, base, such as Cs$_2$CO$_3$ and a suitable solvent, for example dioxane-water at elevated temperature (Method V). For C—N bond forming reactions with an amine, such as morpholine, Buchwald-Hartwig conditions can be employed. In such cases Pd catalysts like Pd(dba)$_2$ with a suitable ligand, such as XantPhos, as well as a base, for example Cs$_2$CO$_3$ can be used in a suitable solvent, like dioxane at elevated temperature (Method W).

Scheme 13: General method for the formation of annulated pyrazoles

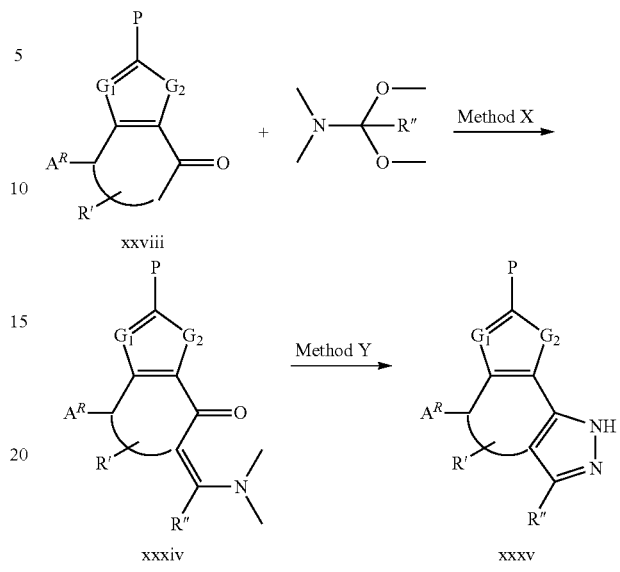

Scheme 13 shows a general method for formation of annulated azoles xxxv from corresponding ketones xxviii. Ketones xxviii can be transformed to appropriate keto-enamines xxxiv using suitable conditions, such as Dimethylformamide-dimethyl acetal, either neat, or with a co-solvent, such as toluene at elevated temperature (Method X). Keto-enamines xxxiv can be then treated with hydrazine in a suitable solvent, such as AcOH at elevated temperature (Method Y) to afford annulated pyrroles xxxv.

Scheme 14: General method for ring expansion towards lactams

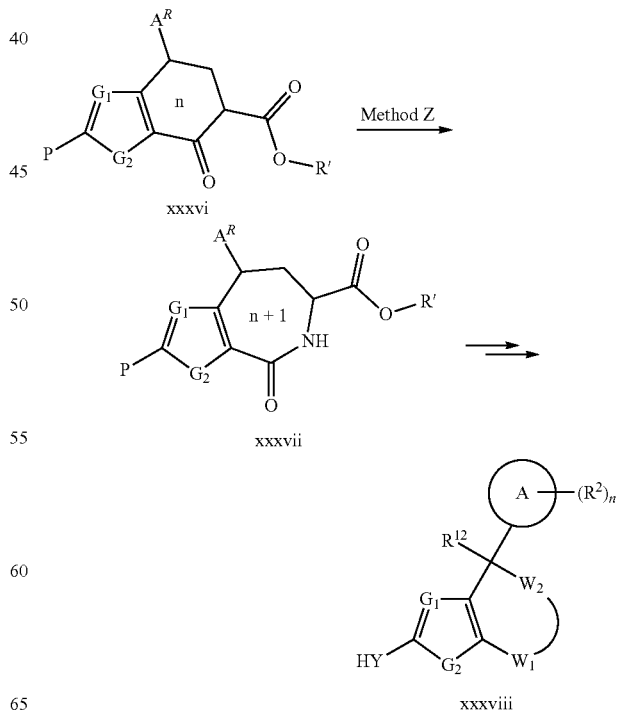

Scheme 14 shows a general method for ring expansion of keto esters xxxvi towards lactams xxxvii. Keto esters xxxvi are treated with a suitable azide source, such as NaN$_3$ in acidic conditions, such as sulfuric acid in an appropriate solvent, for example benzene, toluene or chloroform to afford lactams xxxvii (Method Z). Compounds of formula xxxvii can be then subsequently transformed to xxxviii using well known synthetic methods, including those described in this document.

Scheme 15: General method for benzylic alkylation followed by cyclization

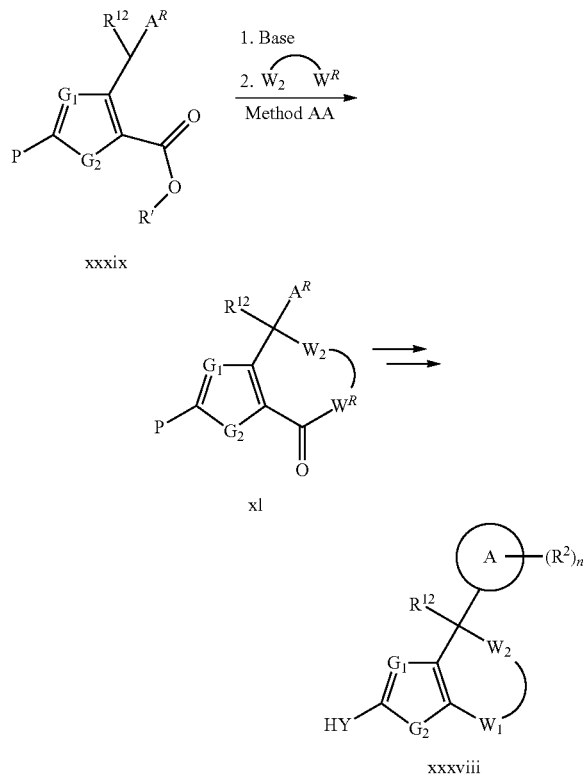

Scheme 15 shows a general method for benzylic alkylation followed by cyclization towards bicyclic ring systems. Substrate xxxix, where $A^R$ is an aryl group can be deprotonated with a suitable base, such as KOtBu, KHMDS, LiHMDS, and NaHMDS, in a suitable solvent, for example THF, DMF, or a combination of solvents. Deprotonation can be carried out at a range of temperatures, preferably between –78 C and room temperature. The formed benzylic ion can be then treated with an electrophile bearing a suitable group for subsequent cyclization with the ester group in xxxix (Method AA). This sequence may be a one-pot process, or carried out in separate steps. Examples of electrophiles include, but are not limited to protected aminoalkylene halides, protected hydroxyalkylene halides, substituted 1,2,3-oxathiazolidine 2,2-dioxides. Overall reaction conditions may differ based on the choice of substrate and electrophile, including temperature, solvents, reagent stochiometry and substrate concentration. Cyclization to close the bicyclic ring (xl) is usually achieved after protective group removal. The process may require elevated temperature and additives based on the nature of the reacting functionality. Compounds of formula xl can be then subsequently transformed to xxxviii using well known synthetic methods, including those described in this document.

Scheme 16: Specific method for benzylic alkylation followed by cyclization towards 6-membered lactams

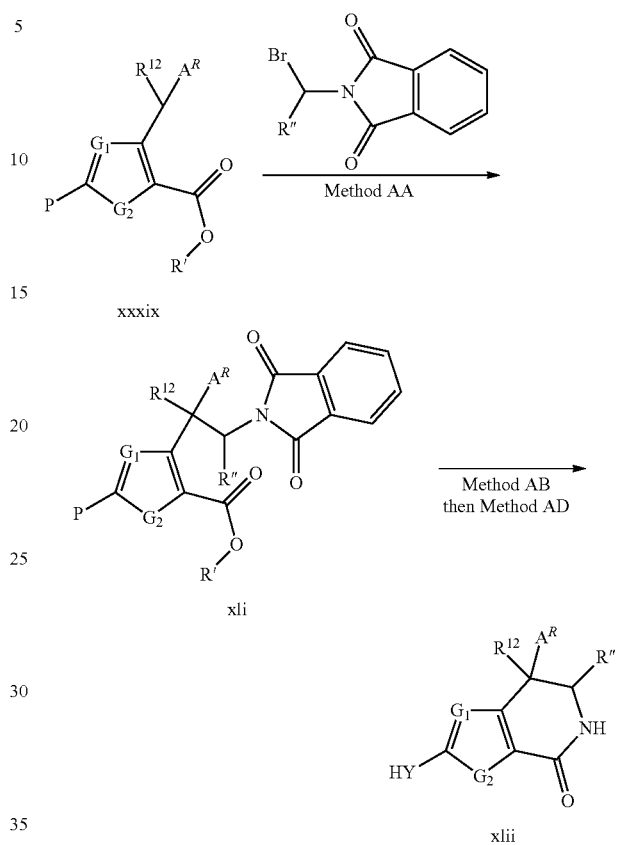

Scheme 16 shows a specific method for benzylic alkylation followed by cyclization towards 6-membered bicyclic lactam rings. Substrate xxxix, where $A^R$ is an aryl group can be deprotonated with a suitable base, such as KOtBu, KHMDS, LiHMDS, LDA, NaH in a suitable solvent, for example THF, DMF, or a combination of solvents. Preferably, potassium t-butoxide is used as a base and the reaction is carried out in a mixture of THF and DMF at –20° C., with or without the addition of a coordinating salt such as lithium chloride or tetrabutylammonium iodide. The formed benzylic ion can be then treated with a protected, optionally substituted aminomethylene halide, for example phthalimide protected 1-bromomethylamine to give compounds of formula xli (Method AA). Reaction temperature, reagent stochiometry and substrate concentration may vary based on the combination of reacting partners. Preferably, the anion is formed with 3 eq of potassium t-butoxide in a 2:3 ratio of THF:DMF at –20° C. and at a concentration of 0.03M. A solution of the electrophile in THF is added at 0° C. and the reaction is allowed to warm to room temperature before workup. The protecting group can be subsequently deprotected using generally known methods. For example, phthalimide can be removed using hydrazine in a suitable solvent, such as ethanol at rt or elevated temperature (Method AB). The subsequent cyclization (Method AD) may proceed spontaneously, or at elevated temperature to form compounds of formula xlii.

Scheme 17: Specific method for benzylic alkylation followed by cyclization towards 7-membered lactams

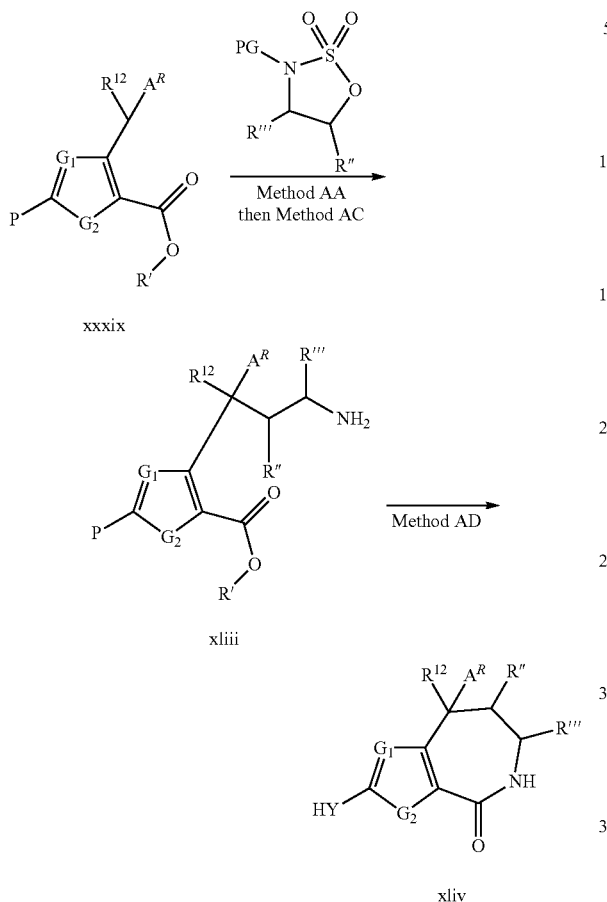

xxxix xliii xliv

Scheme 18: General method for benzylic alkylation followed by cyclization towards 6 and 7-membered lactones

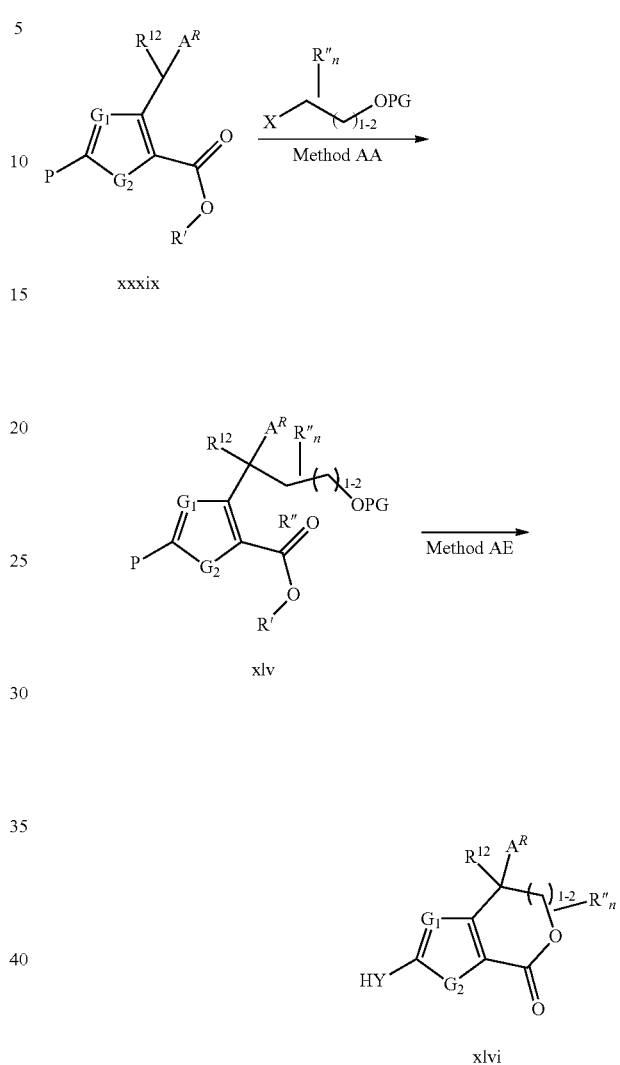

xxxix xlv xlvi

Scheme 17 shows a specific method for benzylic alkylation followed by cyclization towards 7-membered bicyclic lactam rings. Substrate xxxix, where $A^R$ is an aryl group can be deprotonated with a suitable base, such as KOtBu, KHMDS, LiHMDS, LDA, NaH, (others), in a suitable solvent, for example THF, DMF, or a combination of solvents. The formed benzylic ion can be then treated with a protected, optionally substituted ethylamine with a suitable leaving group in 2-position, such as substituted N-Boc-1,2,3-oxathiazolidine 2,2-dioxide to provide compounds of formula xliii (Method AA). Reaction temperature, reagent stochiometry and substrate concentration may vary based on the combination of reacting partners. Examples of preferred conditions include KOtBu (1.2 eq), 3.5 eq of electrophile, 0° C. to room temp in DMF or NaHMDS (1.2 eq), 2.0 eq of electrophile, −78° C. to 0° C. in DMF/THF (4:1). The protecting group can be subsequently deprotected using generally known methods. For example, Boc can be removed using an acid, such as TFA in a suitable solvent, such as DCM at rt or elevated temperature to give compounds of formula xliii (Method AC). The subsequent cyclization is achieved using a suitable base, for example KOMe in an appropriate solvent, such as MeOH, preferably at elevated temperature to provide compounds of formula xliv (Method AD).

Scheme 18 shows a general method for benzylic alkylation followed by cyclization towards 6 or 7-membered bicyclic lactone rings. Substrate xxxix, where $A^R$ is an aryl group can be deprotonated with a suitable base, such as KOtBu, KHMDS, LiHMDS, NaHMDS, in a suitable solvent, for example THF, DMF, or a combination of solvents. Preferably, KOtBu is used as a base and the reaction is carried out in THF and DMF at −20-0 C. The formed benzylic ion can be then treated with a protected, optionally substituted halomethanol, such as SEMCl, 2-halo-ethanol, or 3-halo-propanol, such as TBS-protected 2-bromoethanol to provide compounds of formula xlv (Method AA). Reaction temperature, reagent stochiometry and substrate concentration may vary based on the combination of reacting partners. Preferably, 4 equivalents of electrophile and 1.1 equivalent of KOtBu are used with the substrate concentration 0.1M. The protecting group can be subsequently deprotected using generally known methods. For example, TBS can be removed using an acid, such as HCl in a suitable solvent, such as dioxane at rt or elevated temperature, resulting in subsequent cyclization to compounds of formula xlvi (Method AE).

Scheme 19: General method for metal-catalyzed addition to alkenes followed by cyclization

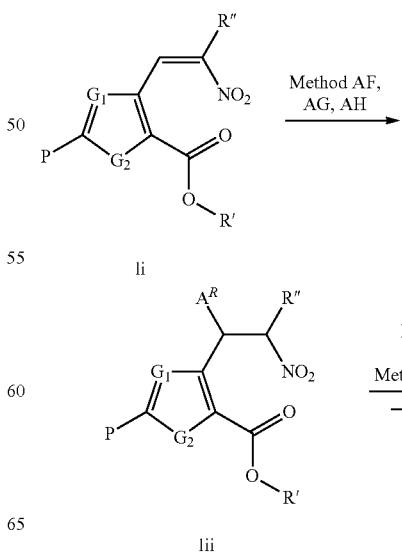

Scheme 19 shows a general method for preparation of bicyclic systems xxxviii. Alkenes xlvii that can be prepared by generally known transformations, such as Heck coupling of an alkene with aryl halide, or Knovenaegel condensation of an aryl carbaldehyde, can be subjected to addition reactions to form compounds xlviii. Addition reactions include, but are not limited to Michael addition (Huy, P. *Org. Lett.* 2011, 13, 216-219) of a nucleophile to alkene xlvii (Method AF) (R", $W^R$, or both are electron withdrawing groups); metal-catalyzed additions to alkenes, such as Rh(I)-catalyzed addition of an organometallic species (Method AG) (Hayashi, T. et al, *Org. Lett.* 2008, 10, 589), such as arylboronic acid or ester; radical additions, for example Rh-catalyzed (Method AH) (Padova, A. and Wang, Q. *J. Org. Chem.* 2006, 71, 7391-7402). Compounds xlviii are subsequently cyclized by connecting $W^R$ and $W^{R'}$ using generally known methods to provide compounds of formula xxxviii.

Scheme 20: General method for metal-catalyzed addition to alkenes followed by cyclization

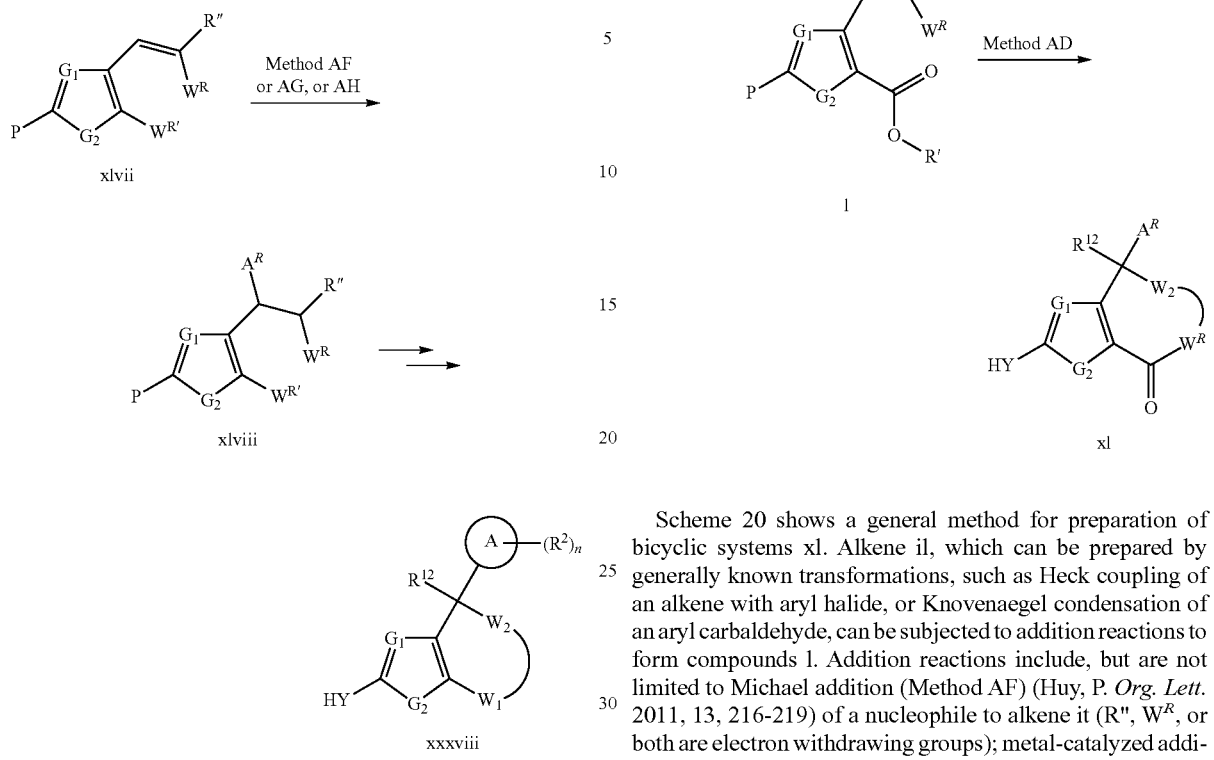

Scheme 20 shows a general method for preparation of bicyclic systems xl. Alkene il, which can be prepared by generally known transformations, such as Heck coupling of an alkene with aryl halide, or Knovenaegel condensation of an aryl carbaldehyde, can be subjected to addition reactions to form compounds l. Addition reactions include, but are not limited to Michael addition (Method AF) (Huy, P. *Org. Lett.* 2011, 13, 216-219) of a nucleophile to alkene it (R", $W^R$, or both are electron withdrawing groups); metal-catalyzed additions to alkenes, such as Rh(I)-catalyzed addition of an organometallic species (Method AG) (Hayashi, T. et al, *Org. Lett.* 2008, 10, 589), such as arylboronic acid or ester; radical additions, for example Rh-catalyzed (Method AH) (Padwa, A. and Wang, Q. *J. Org. Chem.* 2006, 71, 7391-7402). Compounds l are subsequently cyclized by connecting $W^R$ and an ester or carboxylic acid group using generally known methods, some of which are described in this document towards compounds of formula xl.

Scheme 21: Specific method for metal-catalyzed addition to alkenes followed by cyclization towards 6-membered lactams

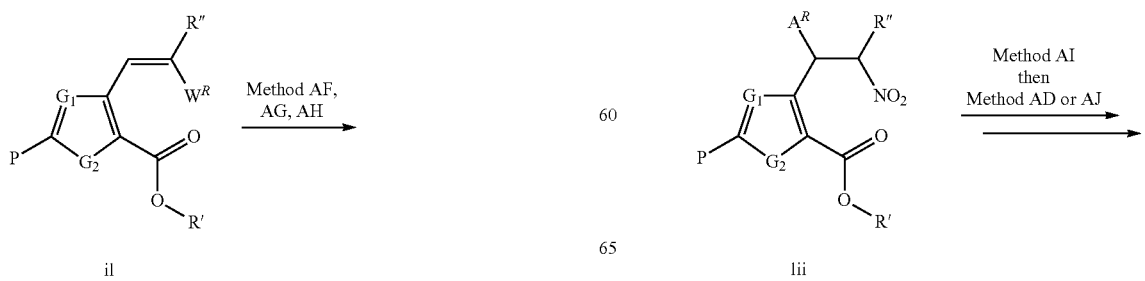

-continued

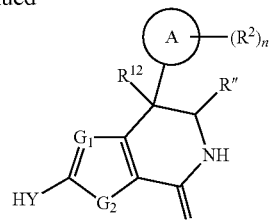

xlii

-continued

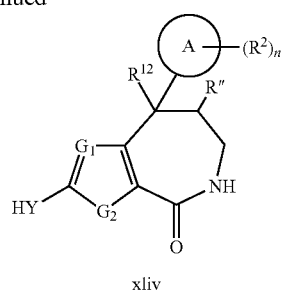

xliv

Scheme 21 shows a general method for preparation of 6-membered bicyclic lactams xlii. Alkenes li, which can be prepared by generally known transformations, such as Henry reaction with aryl carboxaldehyde and nitroalkane followed by dehydration, can be used as starting materials towards bicyclic lactams xlii. Addition of nucleophiles, such as arylmagnesium halides to alkenes li under standard Michael addition conditions (Method AF) can provide compounds lii. The reaction can be carried out as described in Huy, P. *Org. Lett.* 2011, 13, 216-219. Alternatively, a metal-catalyzed addition can be used, for example Rh(I)-catalyzed addition of organometallic reagents, such as boronic acids or esters (Method AG). Reaction can be carried out using a suitable Rh(I) catalyst, such as $[RhCl(CH_2CH_2)_2]_2$ and (3,5-Dioxa-4-phosphacyclohepta[2,1-a:3,4-a']dinaphthalen-4-yl)dimethylamine, in a suitable solvent, for example dioxane, at elevated temperature to form compounds of formula lii. The reaction can also be run under radical conditions, for example Padwa, A. and Wang, Q. *J. Org. Chem.* 2006, 71, 7391-7402 (Method AH). The nitro group in compounds lii can be subsequently reduced to amino group using standard conditions, such as Zn/AcOH, catalytic hydrogenation etc (Method AI). The formed amines can react with ester groups spontaneously, or at elevated temperature to form lactams of formula xlii (Method AD). When amino acids are formed, their cyclization can be achieved using standard coupling conditions, such as EDCI/HOBt in a suitable solvent, for example DCM (Method AJ).

Scheme 22: Specific method for metal-catalyzed addition to alkenes followed by cyclization towards 7-membered lactams

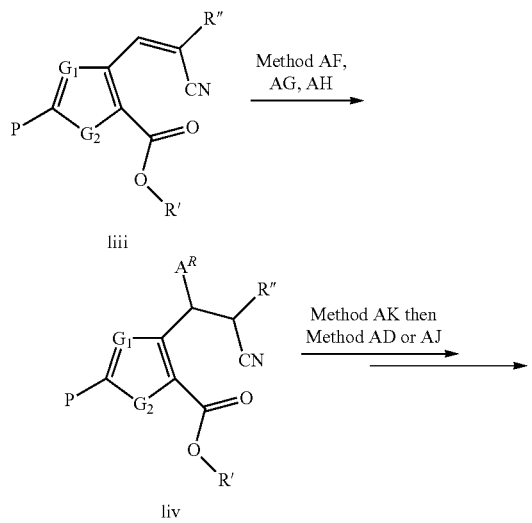

Scheme 22 shows a general method for preparation of 6-membered bicyclic lactams xx. Alkenes liii, which can be prepared by generally known transformations, such as Heck coupling of a nitroalkene with aryl halide, or Knovenaegel condensation of an aryl carbaldehyde, can be used as starting materials towards bicyclic lactams xliv. Addition of nucleophiles, such as arylmagnesium halides to alkenes liii under standard Michael addition conditions (Method AF) can provide compounds liv. Alternatively, a metal-catalyzed addition can be used, for example Rh(I)-catalyzed addition of organometallic reagents, such as boronic acids or esters (Method AG). Reaction can be carried out using a suitable Rh(I) catalyst, such as $[RhCl(CH_2CH_2)_2]_2$ and (1R,4R)-2,5-diphenyl-bicyclo[2.2.2]octa-2,5-diene, in a suitable solvent, for example dioxane/water, at elevated temperature to form compounds of formula liv. The reaction can also be run under radical conditions (Method AH). The cyano group in compounds liv can be subsequently reduced to amino group using standard conditions, such as $NaBH_4$, catalytic hydrogenation etc (Method AK). The formed amines can react with ester groups spontaneously, or at elevated temperature to form lactams of formula xliv (Method AD). When amino acids are formed, their cyclization can be achieved using standard coupling conditions, such as EDCI/HOBt in a suitable solvent, for example DCM (Method AJ).

Scheme 23: General method for metal-catalyzed addition to cyclic alkenes

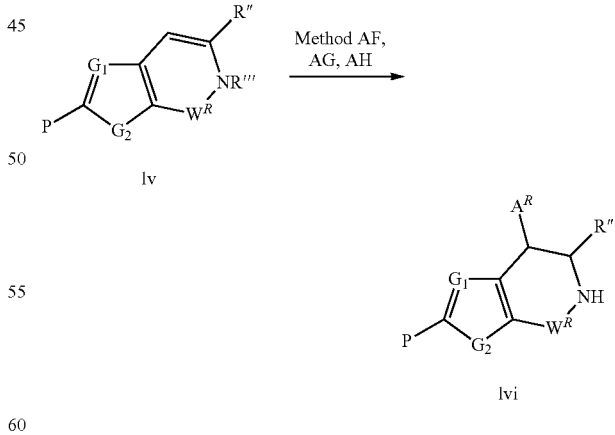

Scheme 23 shows an alternative method for preparation of bicyclic analogs lvi. Cyclic enamines lv that can be prepared from corresponding acyclic compounds in a similar manner as described in schemes 19-22 can be subsequently transformed to compounds lvi using methods analogous to those described in schemes 19-22.

Scheme 24: General method for benzylic alkylation followed by cyclization

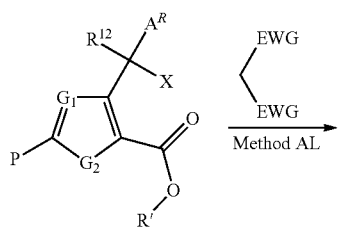

lvii

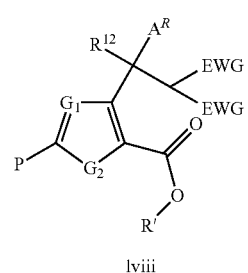

lviii

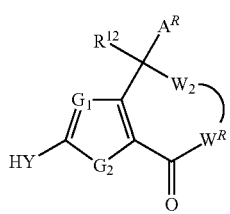

xl

Scheme 24 shows a general method for preparation of bicyclic analogs xl. Halides lvii, which can be prepared by halogenations of corresponding alcohols using generally known methods, such as PBr$_3$ in DCM, can be treated with nucleophiles to form compounds of formula lviii. The conditions can include treatment with a base, such as NaH in a suitable solvent, for example DMSO, as described in Kogan, N. A. *Khimiya Geterotsiklicheskikh Soedinenii*, 1980, 1, 59-62 (Method AL). The formed acyclic compounds lviii can be subsequently cyclized by connecting EWG with an ester or carboxylic acid group using generally known conditions.

Scheme 25: Specific method for benzylic alkylation followed by cyclization towards 6-membered lactams

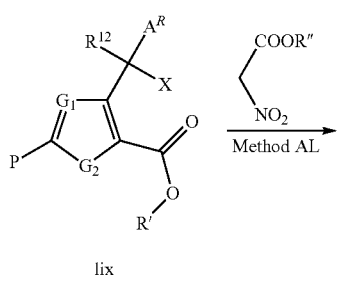

lix

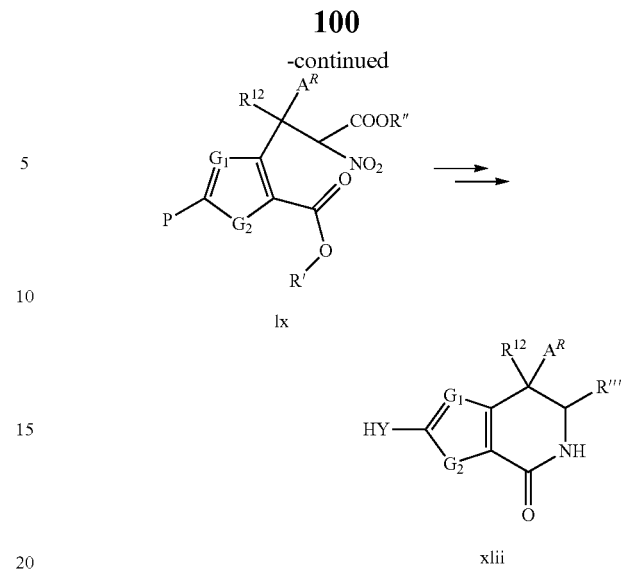

Scheme 25 shows a general method for preparation of bicyclic 6-membered lactams xlii. Halides lix, which can be prepared by halogenations of corresponding alcohols using generally known methods, such as PBr$_3$ in DCM, can be substituted with optionally substituted nitroacetic esters to form compounds of formula lx. The conditions can include treatment with a base, such as NaH in a suitable solvent, for example DMSO, as described in Kogan, N. A. *Khimiya Geterotsiklicheskikh Soedinenii*, 1980, 1, 59-62 (Method AL). The formed nitro esters can be reduced to amino esters using generally known methods, such as Zn/AcOH or catalytic hydrogenation (Method AI) followed by cyclization to provide lactams of formula xlii (Method AD).

Scheme 26: General method for cyclization towards 6-membered lactams

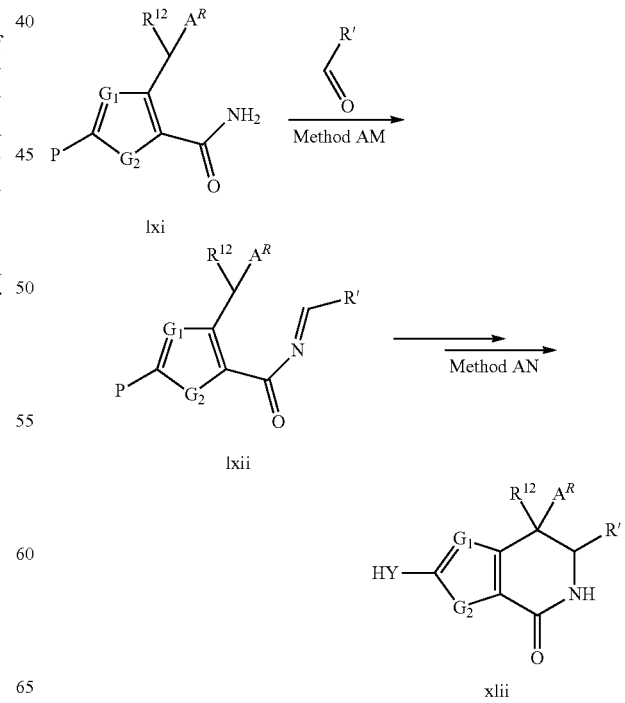

Scheme 26 shows a general method for cyclization of N-alkylidene carboxamides to lactams. Amides lxi are treated with aldehydes under suitable conditions, such as heating in toluene in the presence of molecular sieves to give N-alkylidene carboxamides lxii (Method AM), or stepwise using the condition described in reference: Prashant Singh et al, E-Journal of Chemistry, 2009, 6(1), 99-105. Compounds lxii can be subsequently transformed to lactams xlii using a suitable basic treatment, for example KotBu in THF (Method AN) (references for inter molecular addition of acyl Schiff base: Dziedzic, Pawel et al, Chemistry—A European Journal (2009), 15, (16), 4044-4048; Dobrev, A. et al, Liebigs Annalen der Chemie, (8), 863-5, 1992; Kaiser, A. and Wiegrebe, W., Monatshefte fuer Chemie, 127(4), 397-415; 1996)

Scheme 27: General method for condensation of ketones with halomalonate esters towards 6-membered lactones with subsequent transformation to 6-membered lactams

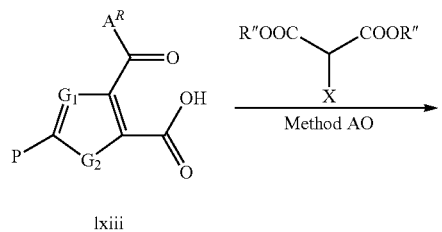

lxiii

Scheme 28: General method for metal-catalyzed oxidative cycloaddition towards 6-membered lactams

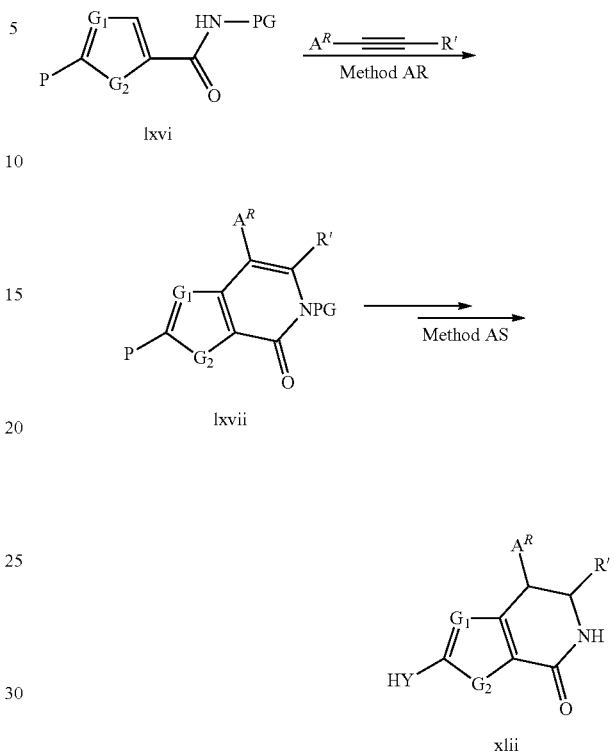

Scheme 28 describes a general method for preparation of 6-membered lactams xlii. N-substituted amides lxvi are reacted with alkynes using a suitable metal catalyst, such as Rh(CpCl2), oxidant, for example Cu(OAc)$_2$ in a suitable solvent, for example amyl alcohol (Method AR, procedure similar to described in J. Am. Chem. Soc 2010, 132, 10565). When N-substituent is a protecting group, such as N-benzyl, it can de subsequently deprotected using standard conditions, such as catalytic hydrogenation using Pd/C with simultaneous saturation of the lactam ring (Method AS) to afford compounds of formula xlii.

Scheme 29: General method for metal-catalyzed coupling of vinyl stannanes towards 7-membered lactams

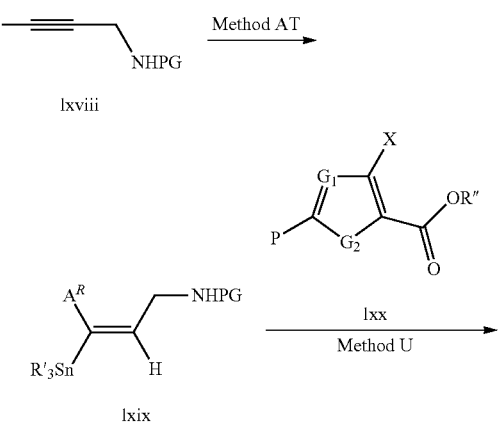

Scheme 27 describes a general method for synthesis of lactones and lactams. Keto acids lxiii can be treated with halomalonate esters under basic conditions, for example using K$_2$CO$_3$ in a suitable solvent, such as DMF, followed by acidic workup, for example using HCl in AcOH to give lactones lxiv (Method AO, procedure similar to described in Tetrahedron Lett. 2009, 50, 2057). Subsequent treatment with a suitable amine source, such as amines or ammonia at elevated temperatures (Method AP) can lead to lactams lxv.

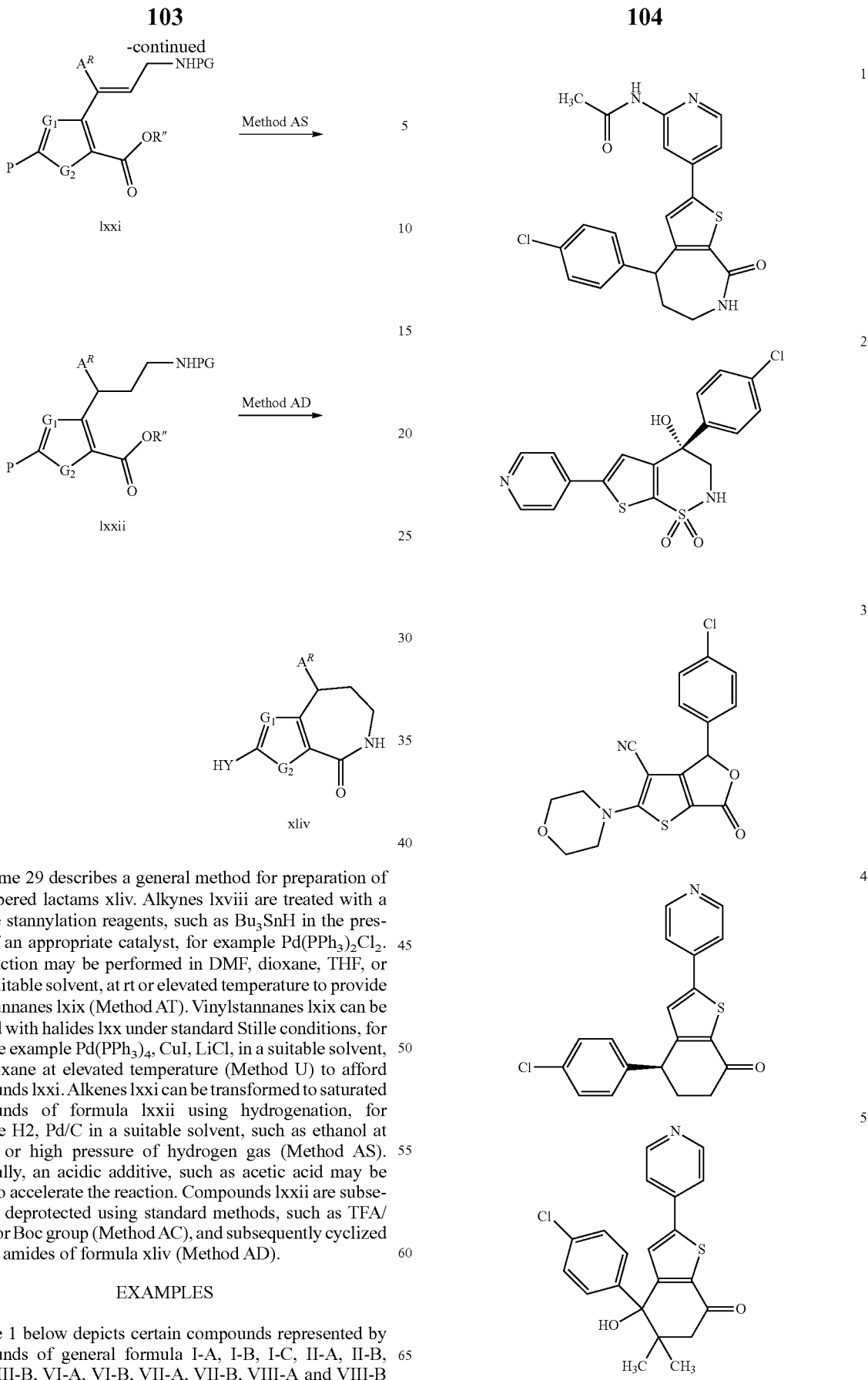

Scheme 29 describes a general method for preparation of 7-membered lactams xliv. Alkynes lxviii are treated with a suitable stannylation reagents, such as Bu₃SnH in the presence of an appropriate catalyst, for example Pd(PPh₃)₂Cl₂. The reaction may be performed in DMF, dioxane, THF, or other suitable solvent, at rt or elevated temperature to provide vinylstannanes lxix (Method AT). Vinylstannanes lxix can be coupled with halides lxx under standard Stille conditions, for example example Pd(PPh₃)₄, CuI, LiCl, in a suitable solvent, like dioxane at elevated temperature (Method U) to afford compounds lxxi. Alkenes lxxi can be transformed to saturated compounds of formula lxxii using hydrogenation, for example H2, Pd/C in a suitable solvent, such as ethanol at normal or high pressure of hydrogen gas (Method AS). Optionally, an acidic additive, such as acetic acid may be added to accelerate the reaction. Compounds lxxii are subsequently deprotected using standard methods, such as TFA/DCM for Boc group (Method AC), and subsequently cyclized to form amides of formula xliv (Method AD).

EXAMPLES

Table 1 below depicts certain compounds represented by compounds of general formula I-A, I-B, I-C, II-A, II-B, 1H-A, III-B, VI-A, VI-B, VII-A, VII-B, VIII-A and VIII-B and subsets thereof.

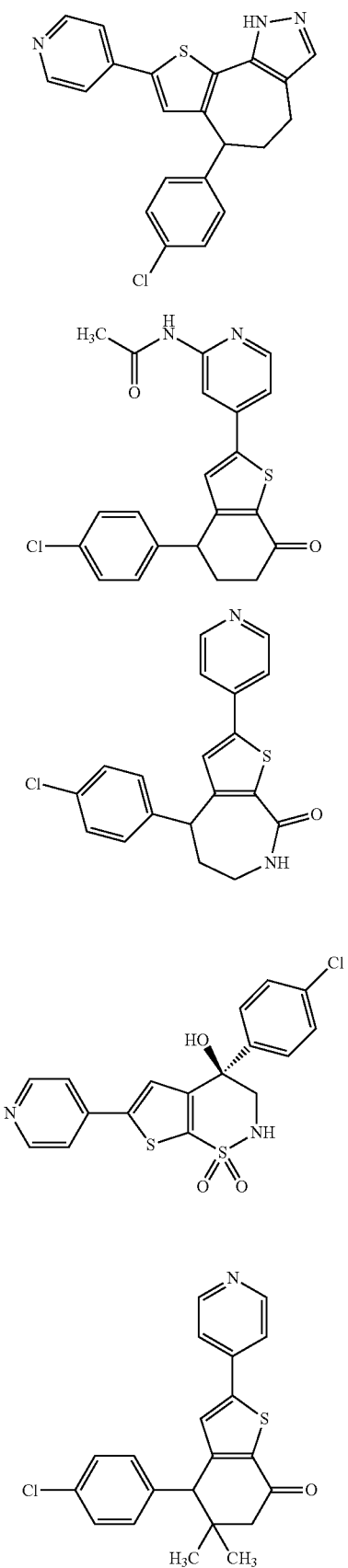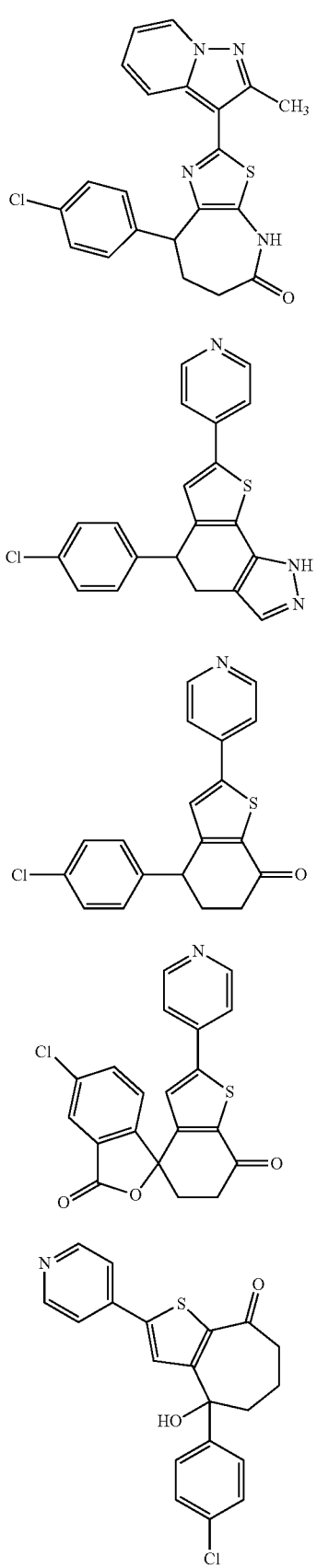

-continued
16
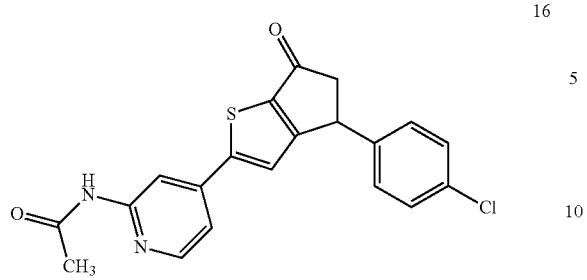
17
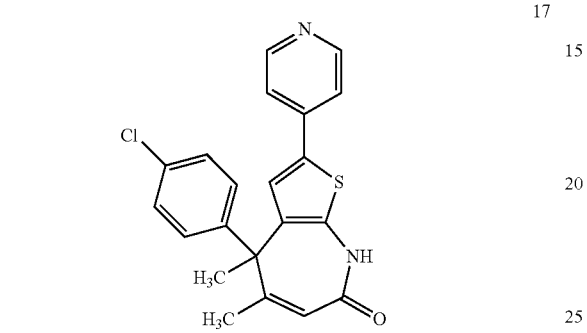
18
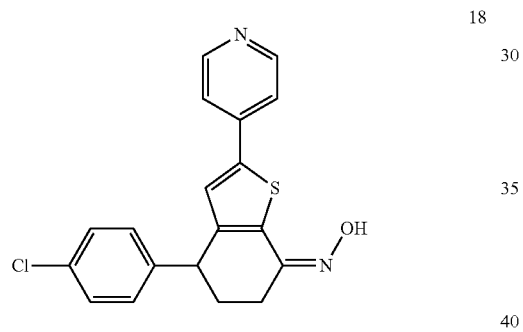
19
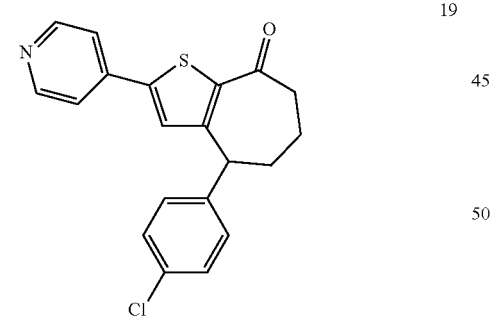
20
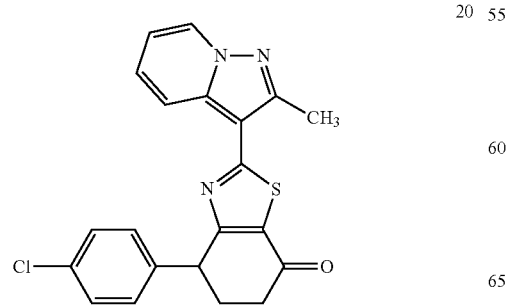
-continued
21
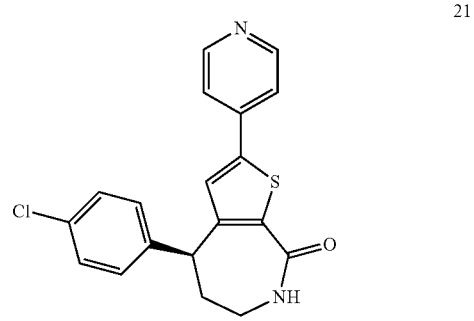
22
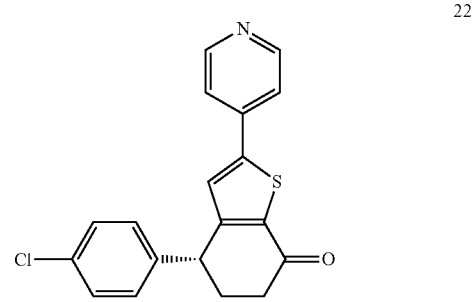
23
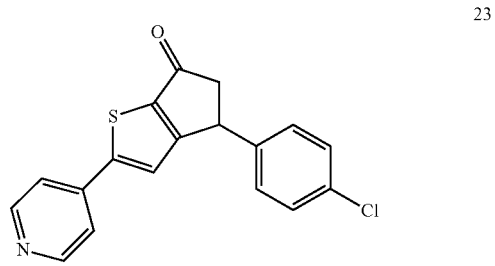
24
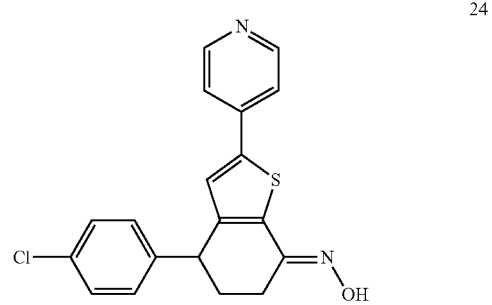
25
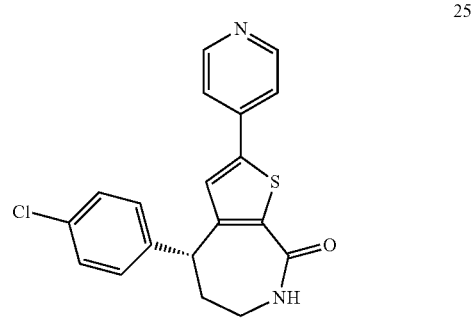

26 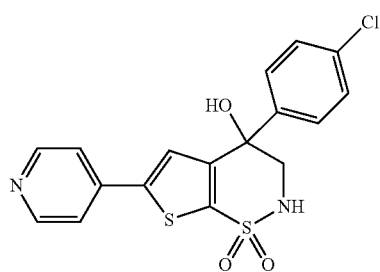
27 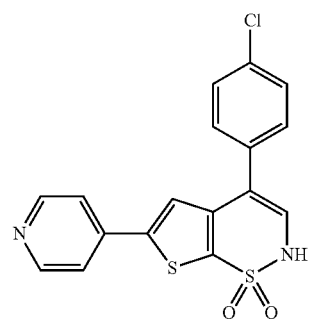
28 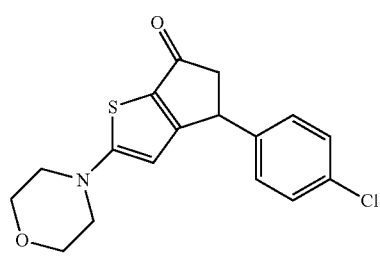
29 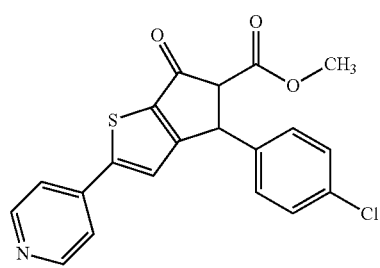
30 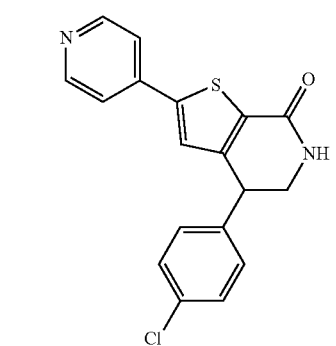
31 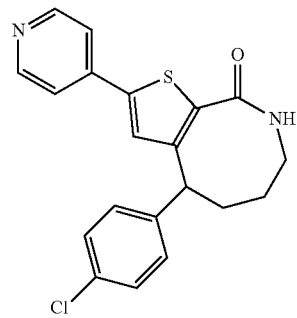
32 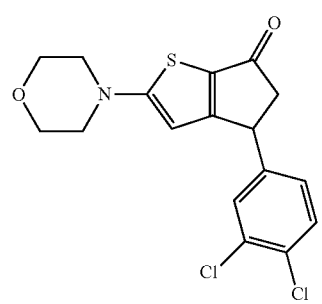
33 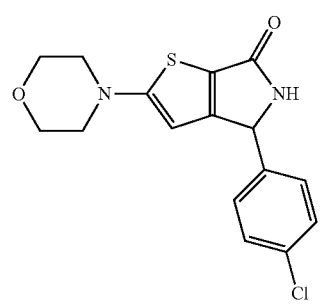
34 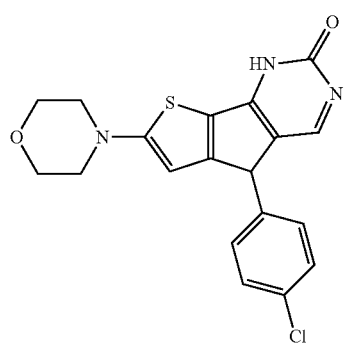
35 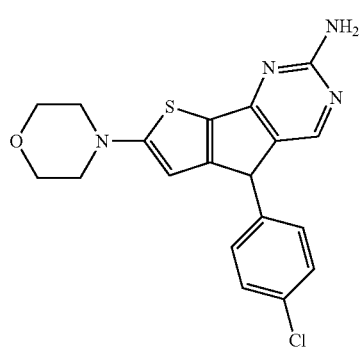

36
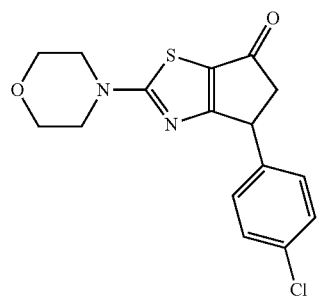
37
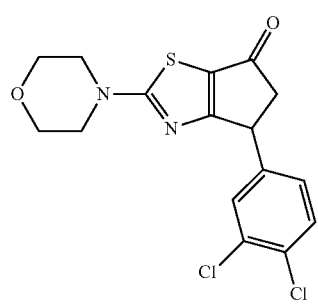
38
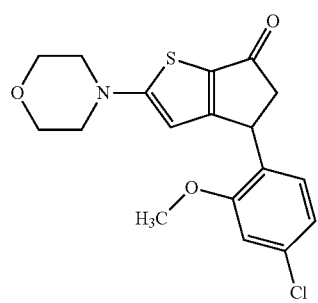
39
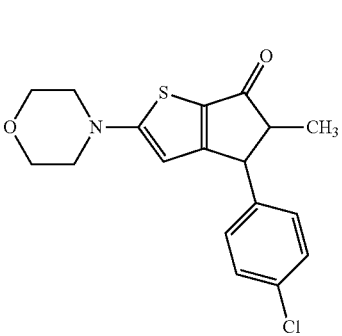
40
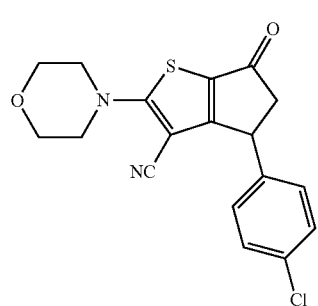
41
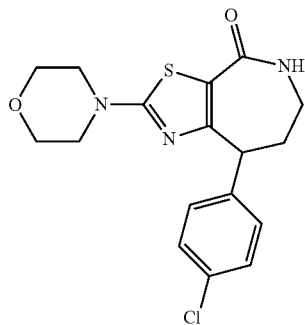
42
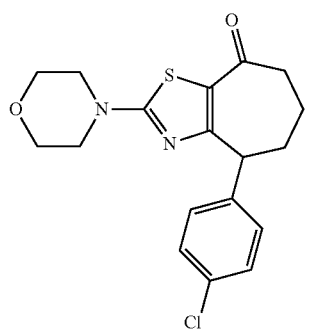
43
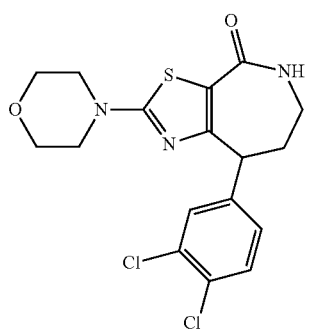
44
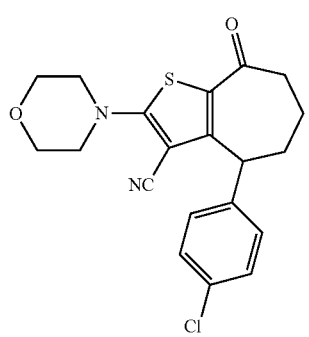
45
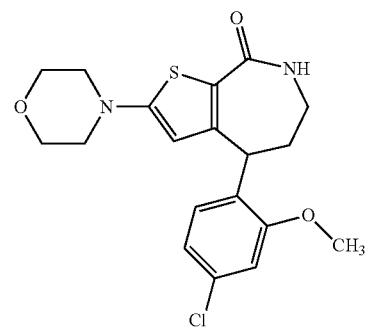

46
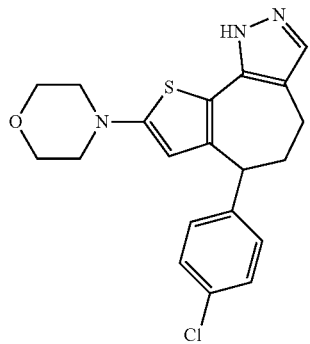
47
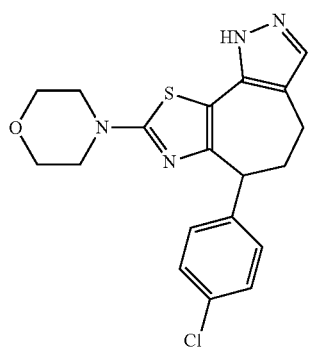
48
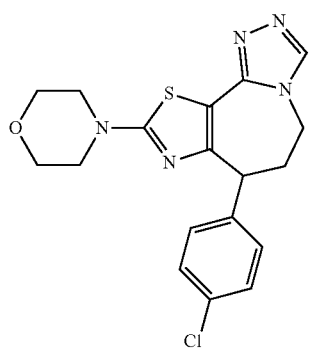
49
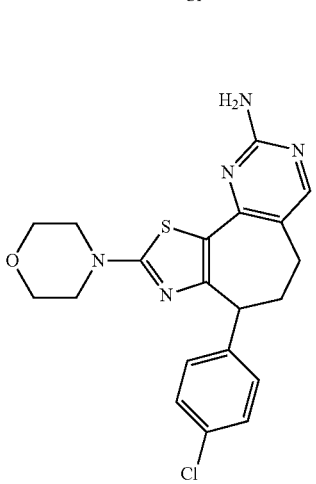
50
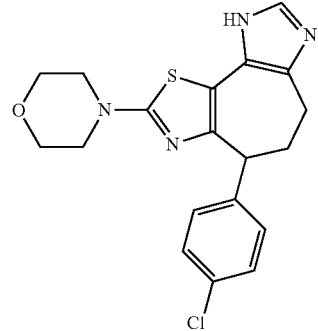
51
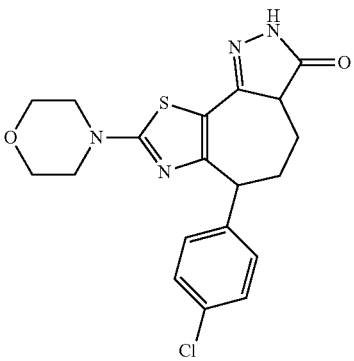
52
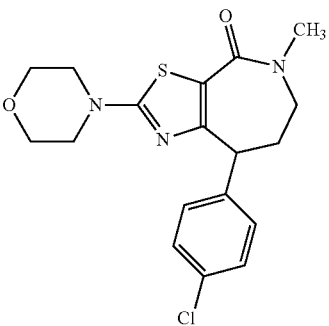
53
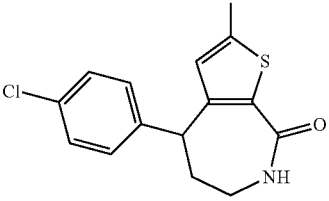
54
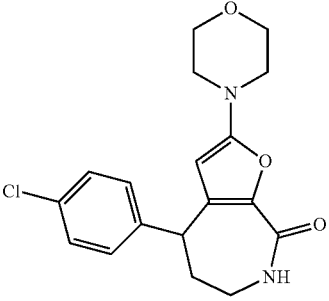

55 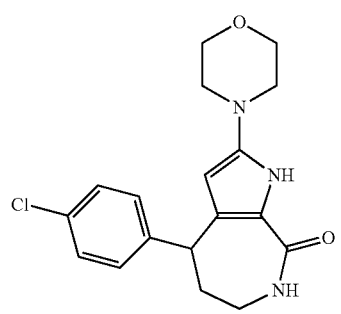
56 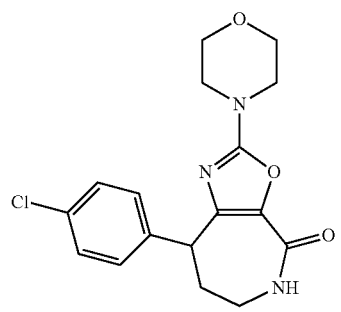
57 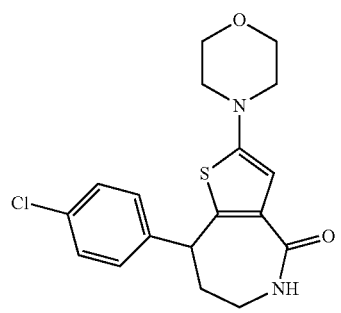
58 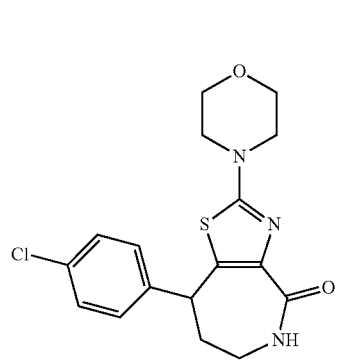
59 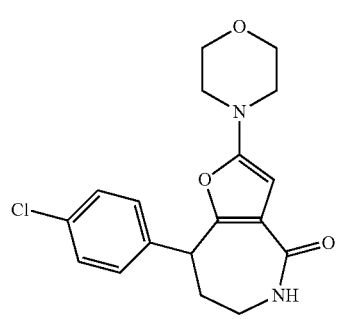
60 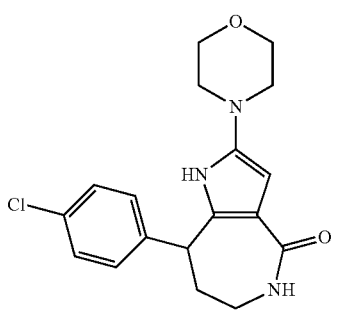
61 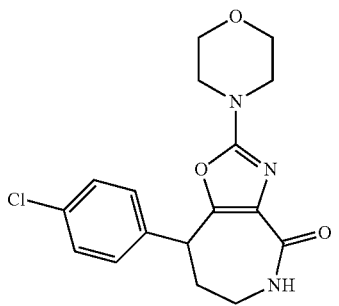
62 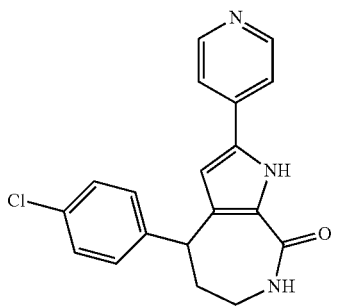
63 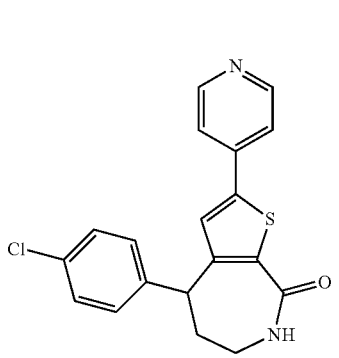
64 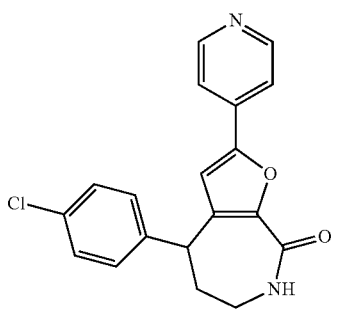

| 117 | 118 |
|---|---|
| 65 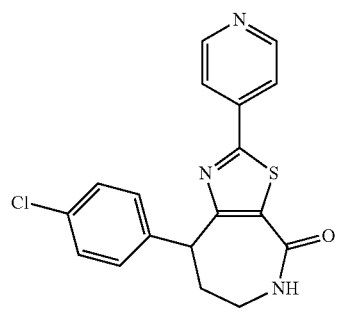 | 70 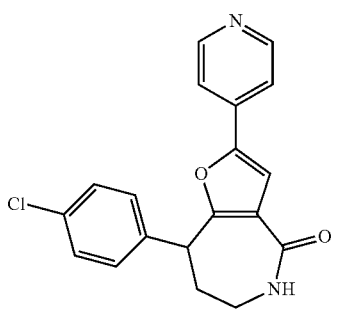 |
| 66 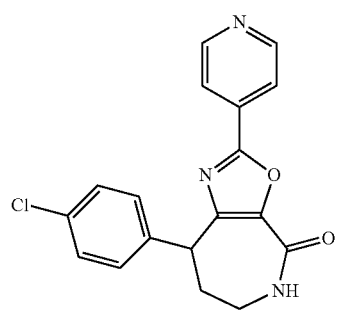 | 71 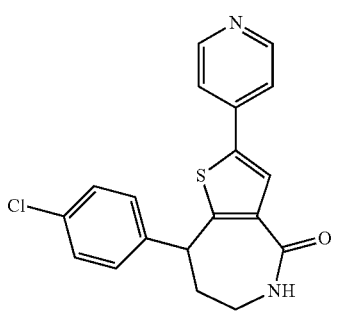 |
| 67 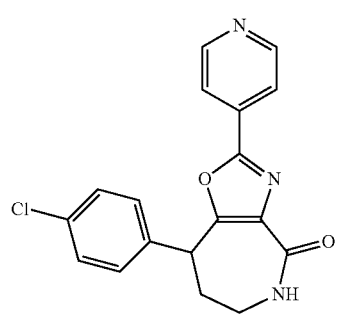 | 72 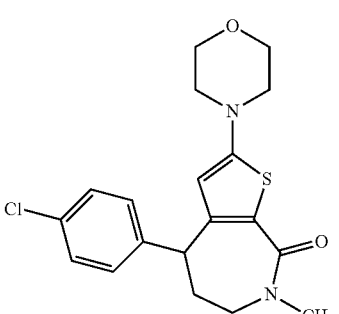 |
| 68 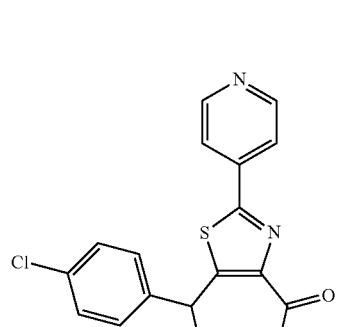 | 73 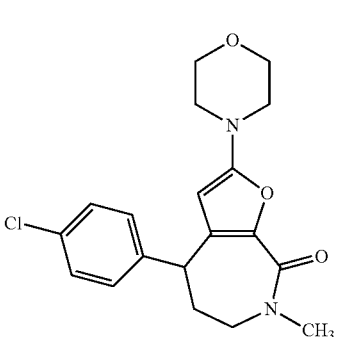 |
| 69 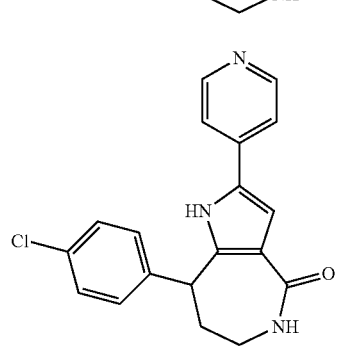 | 74 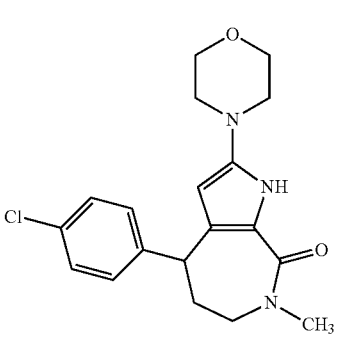 |

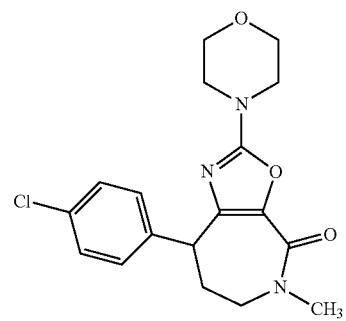
75
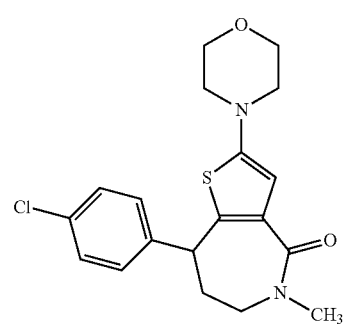
76
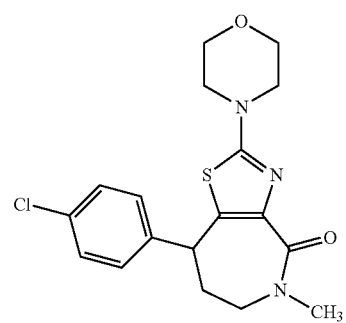
77
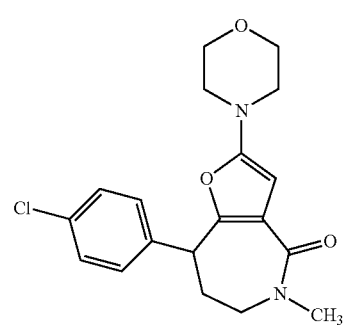
78
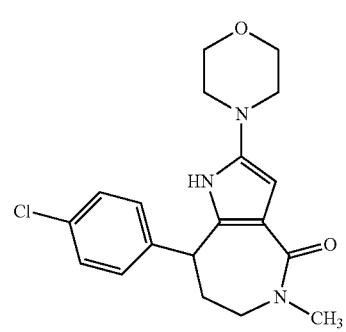
79
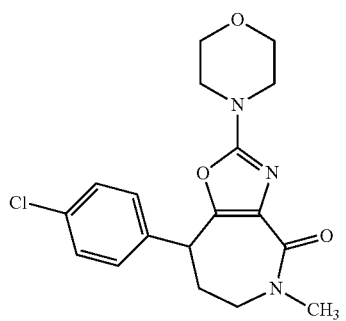
80
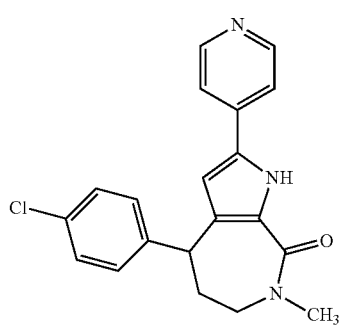
81
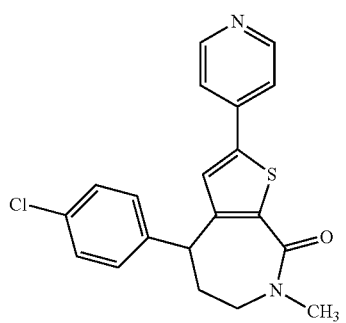
82
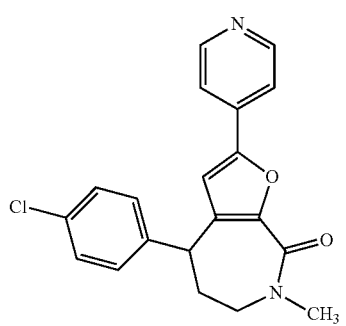
83
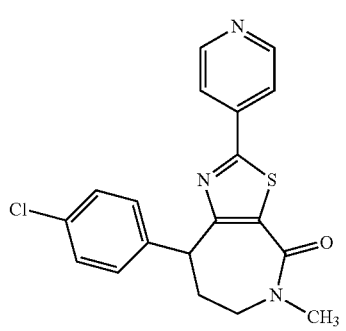
84

85 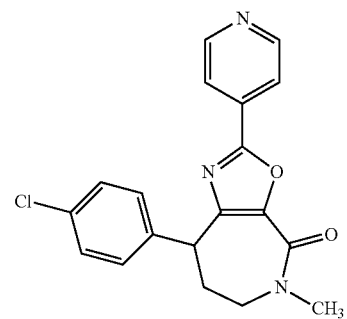
86 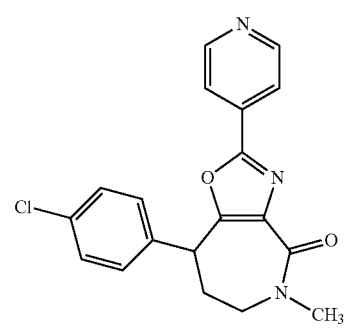
87 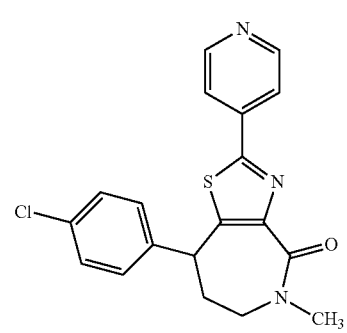
88 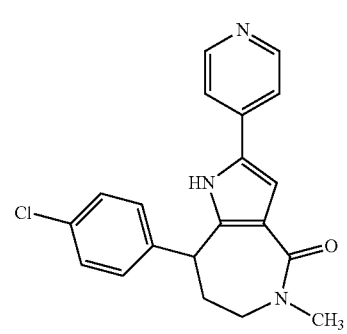
89 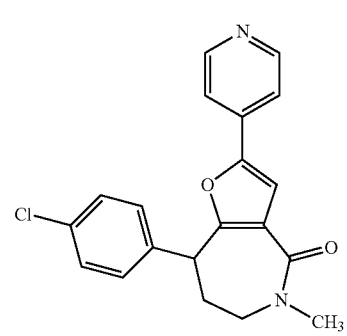
90 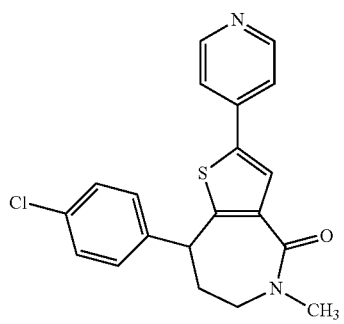
91 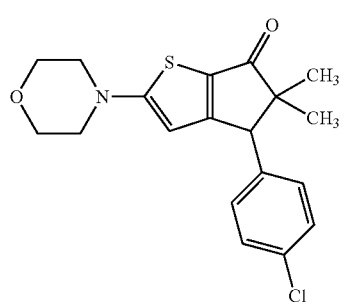
92 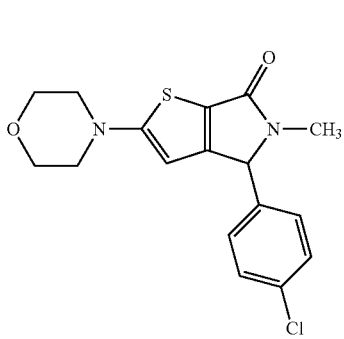
93 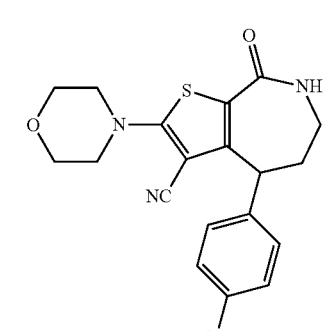
94 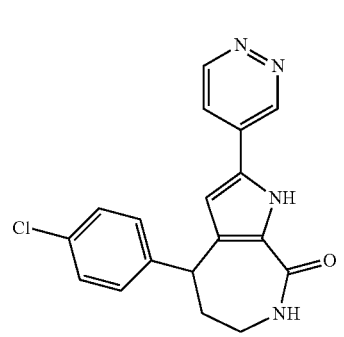

123
-continued
95
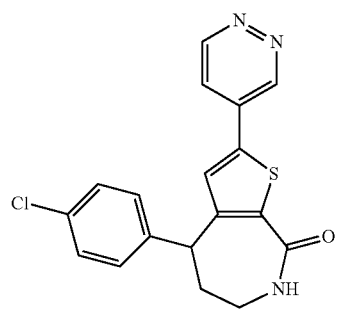
96
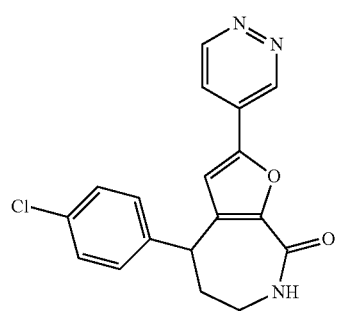
97
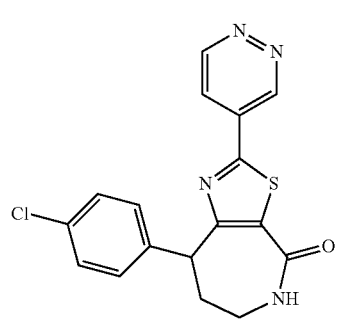
98
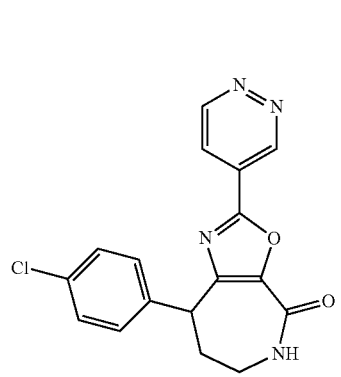
99
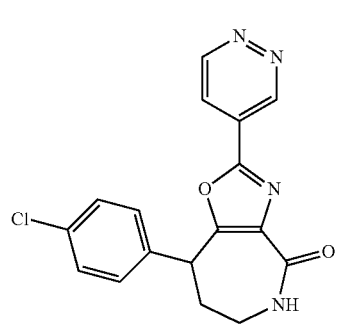
124
-continued
100
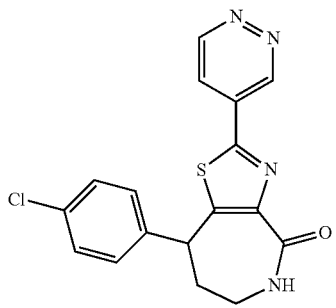
101
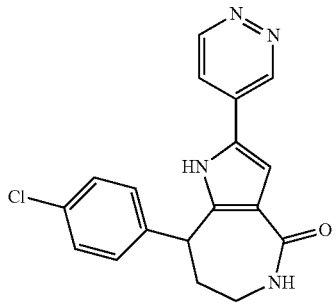
102
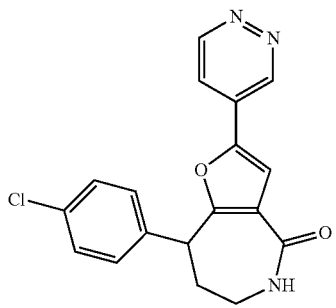
103
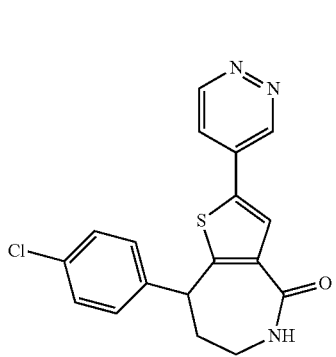
104
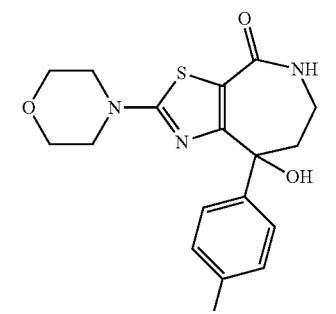

| | |
|---|---|
| 105 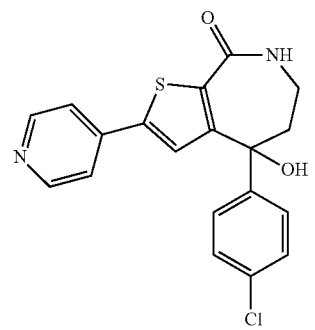 | 110 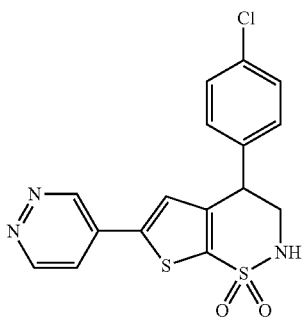 |
| 106 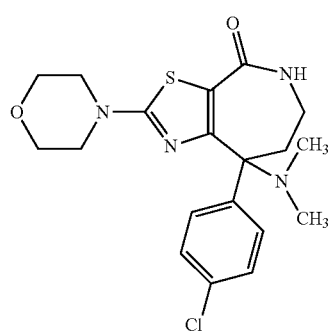 | 111 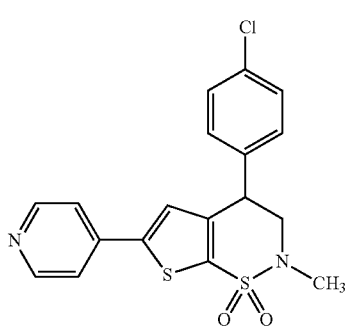 |
| 107 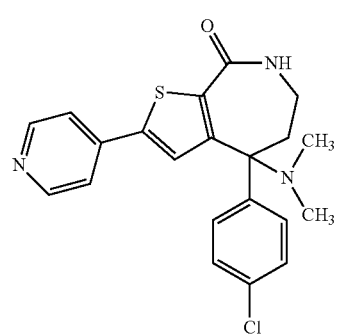 | 112 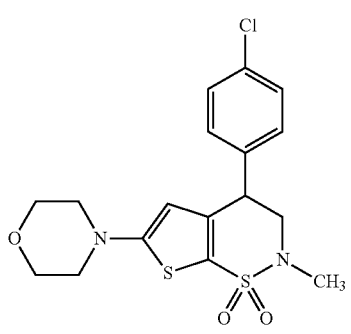 |
| 108 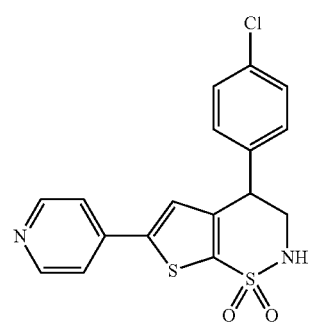 | 113 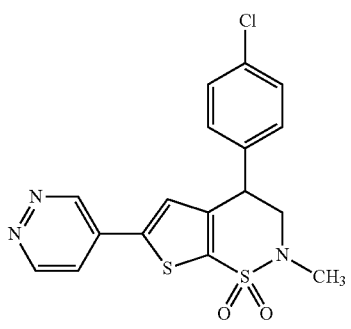 |
| 109 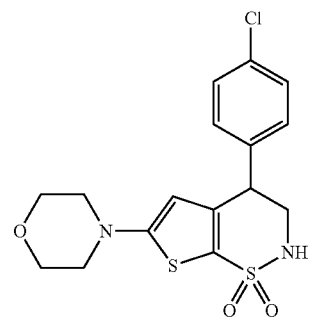 | 114 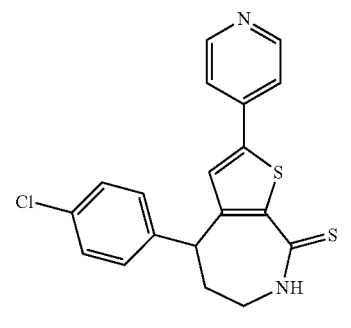 |

| 115 | 120 |
|---|---|
| 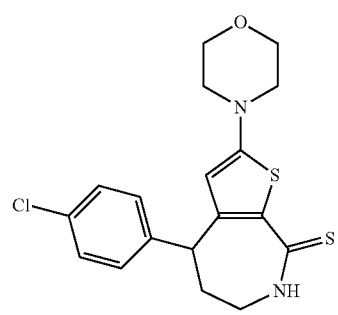 | 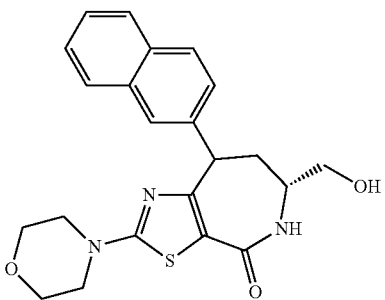 |
| 116 | 121 |
| 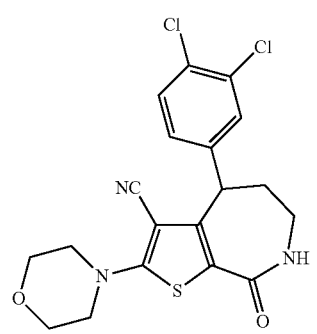 | 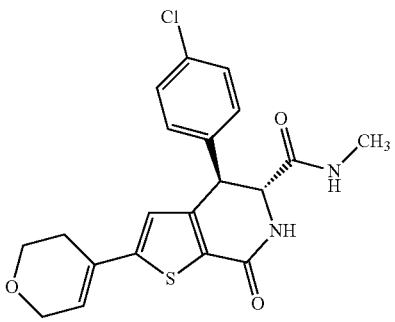 |
| 117 | 122 |
| 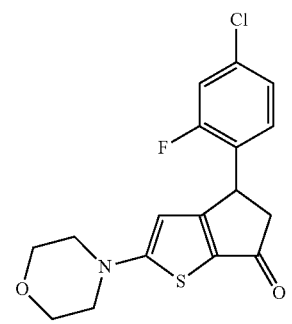 | 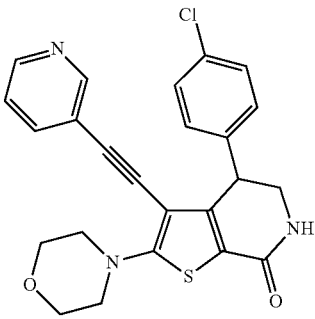 |
| 118 | 123 |
| 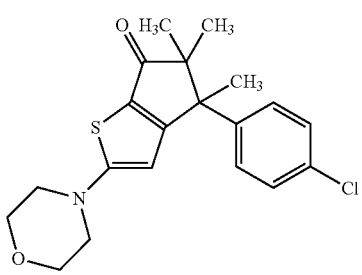 | 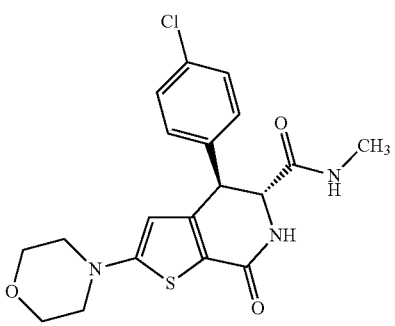 |
| 119 | 124 |
| 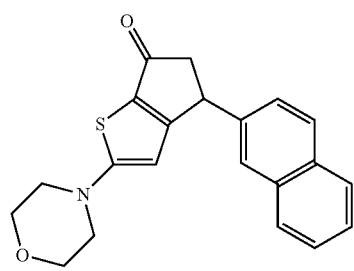 | 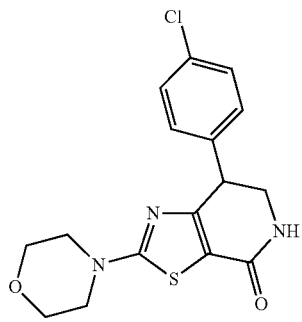 |

| 125 | 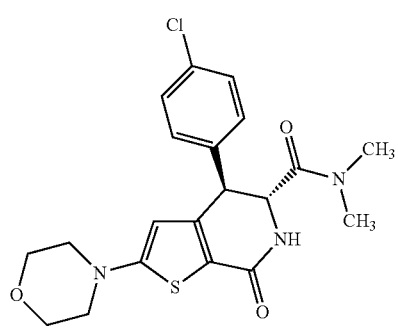 | 130 | 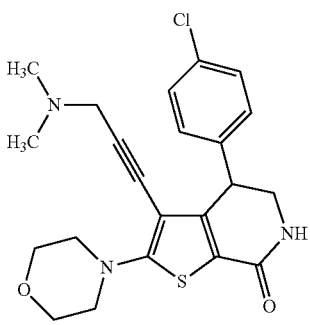 |
| 126 | 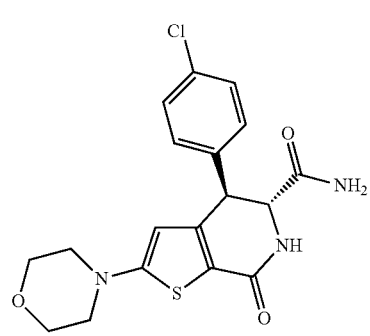 | 131 | 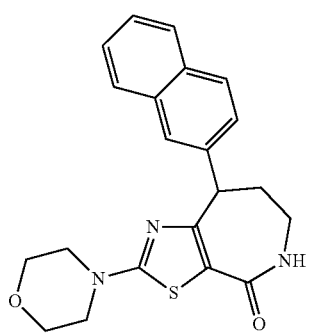 |
| 127 | 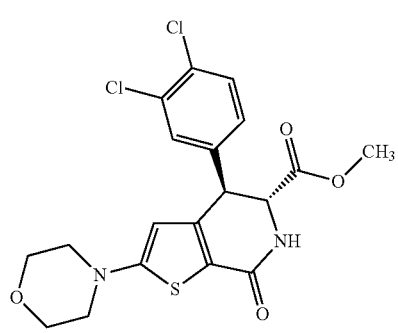 | 132 | 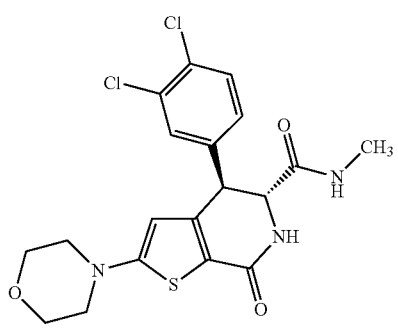 |
| 128 | 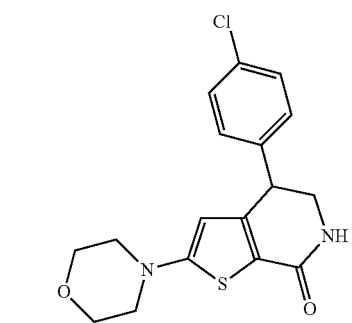 | 133 | 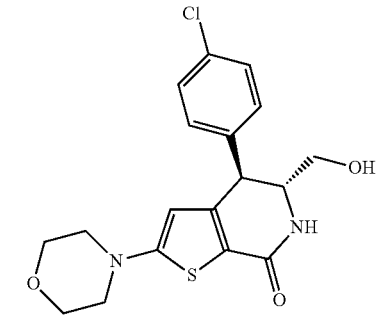 |
| 129 | 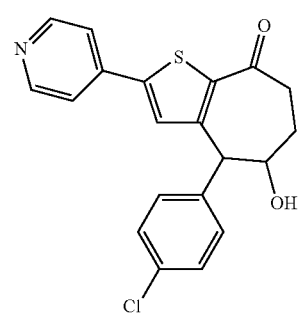 | 134 | 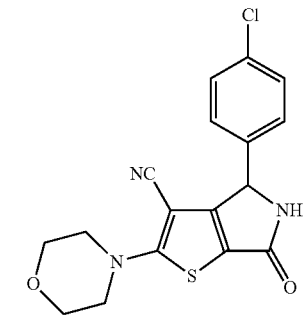 |

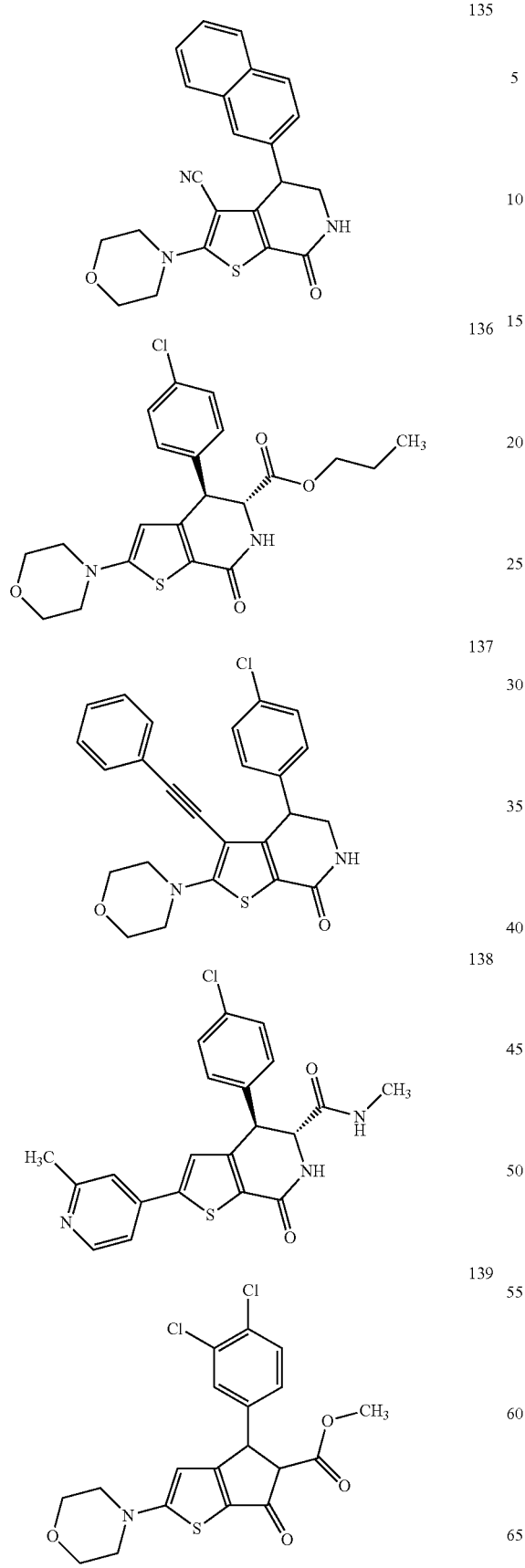
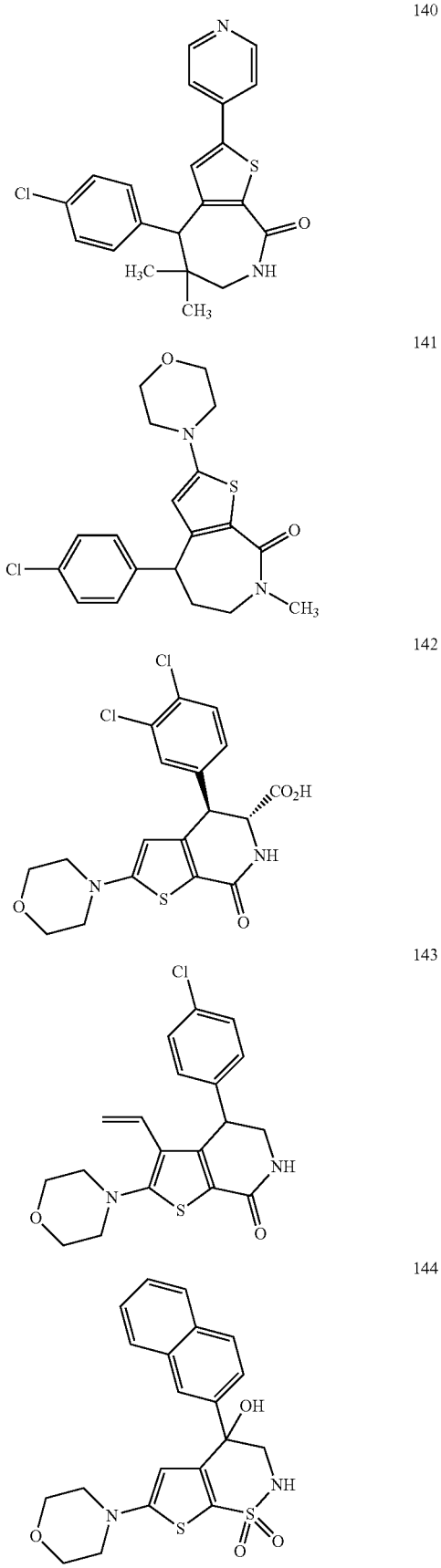

145
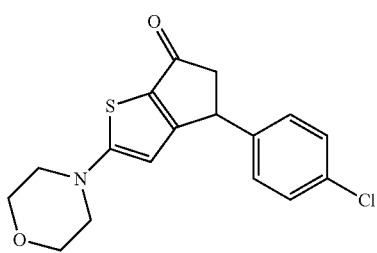
146
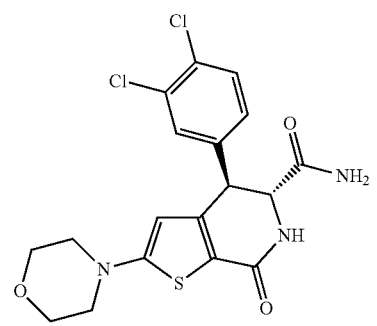
147
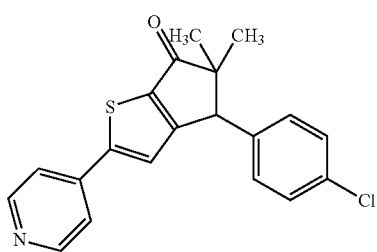
148
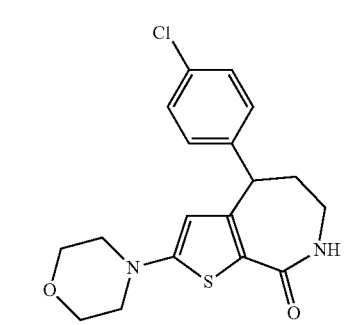
149
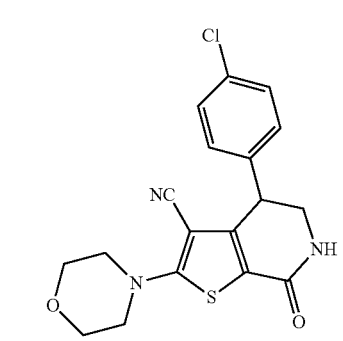
150
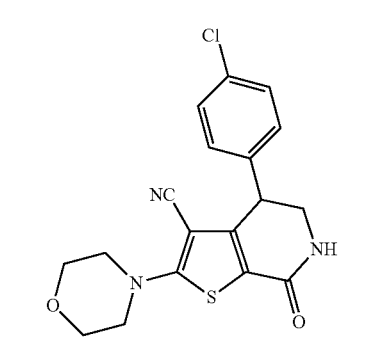
151
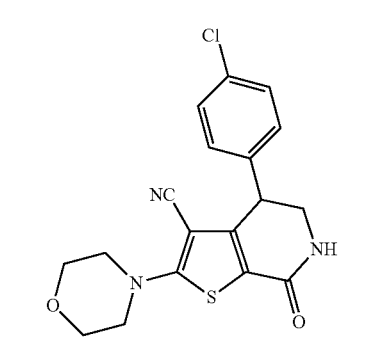
152
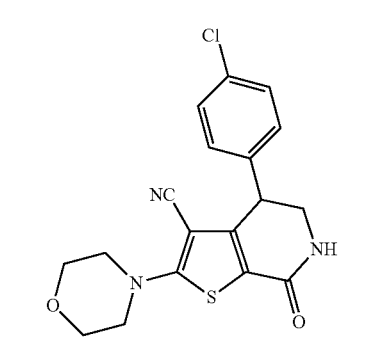
153
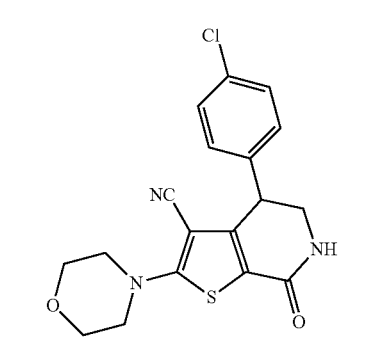
154
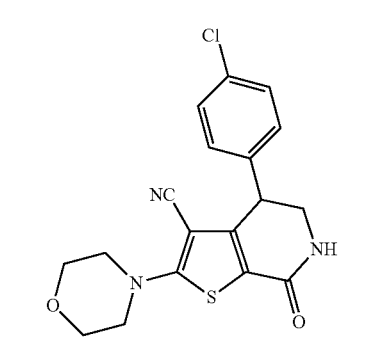

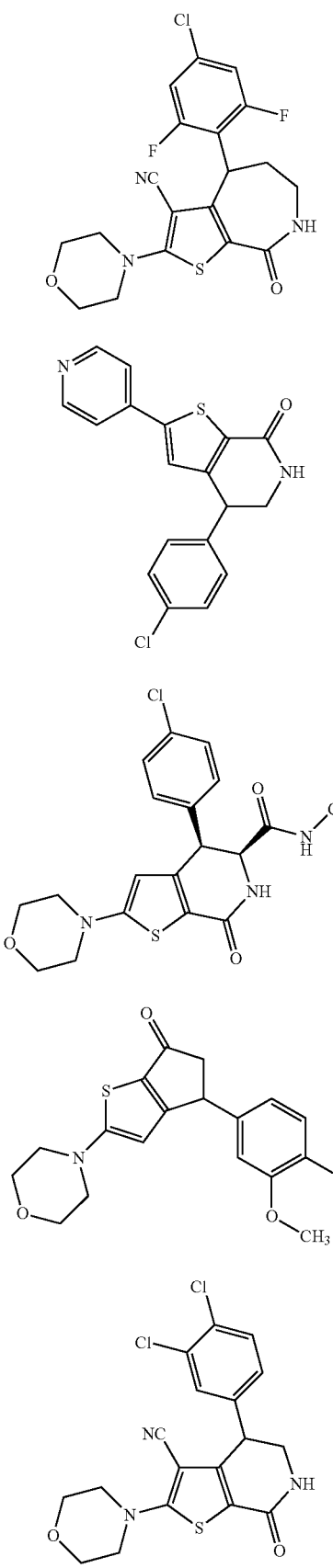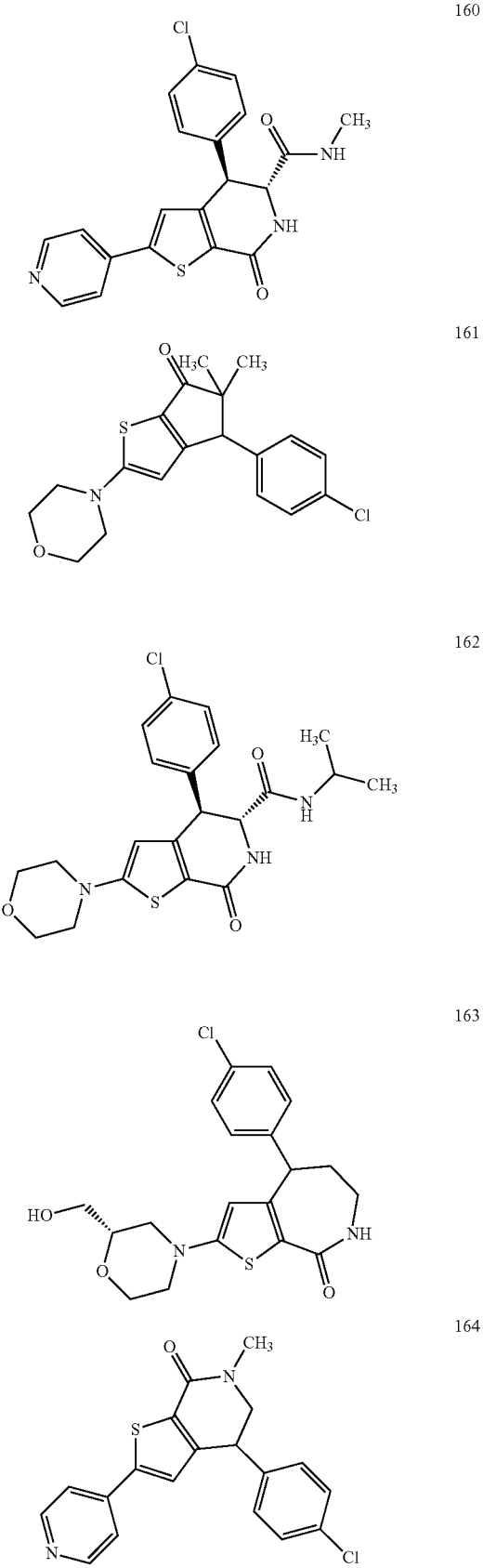

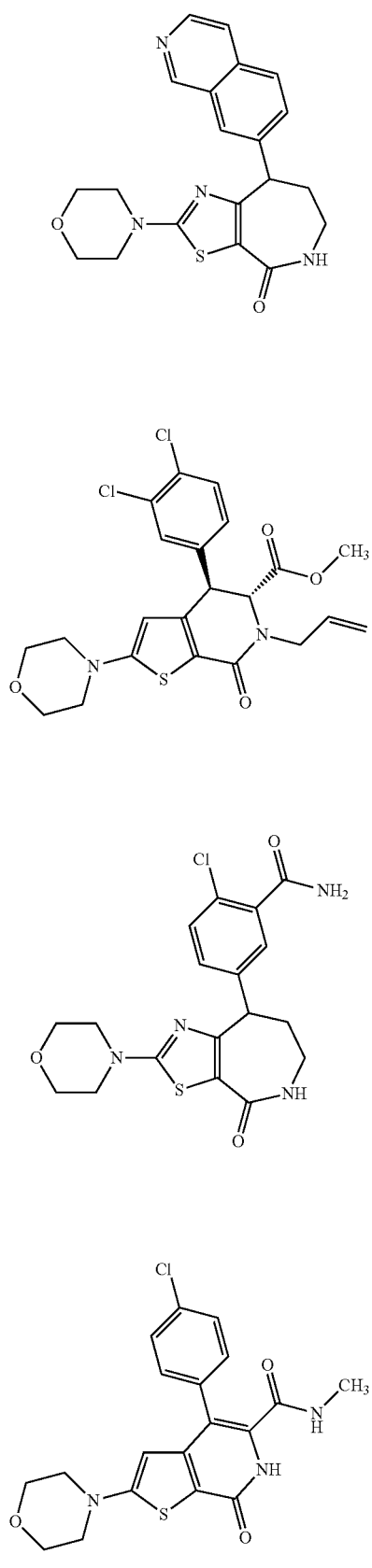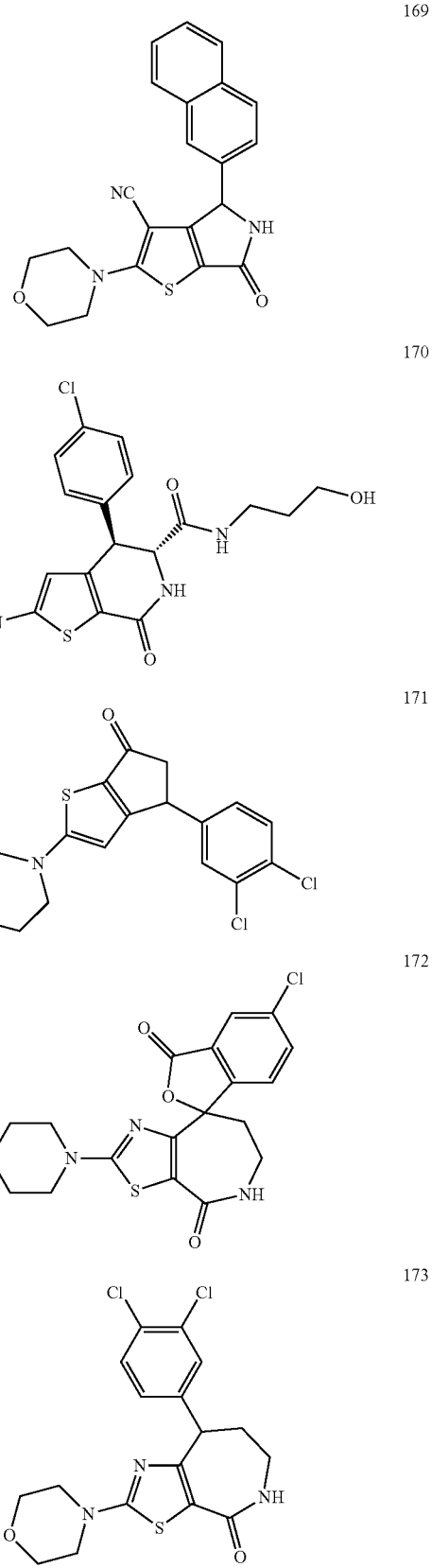

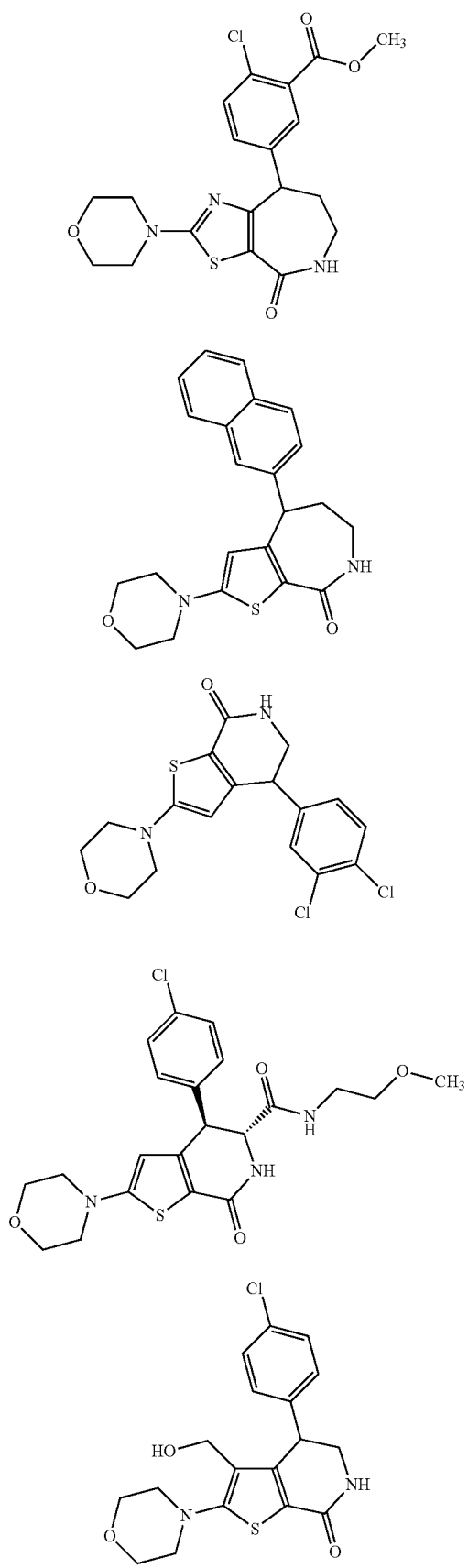

184
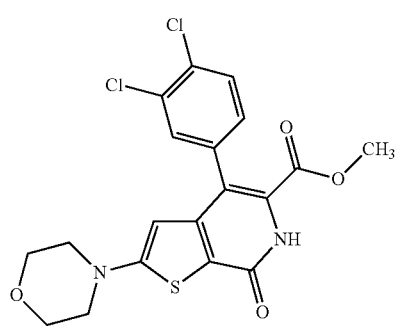
185
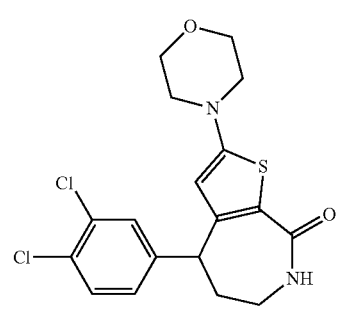
186
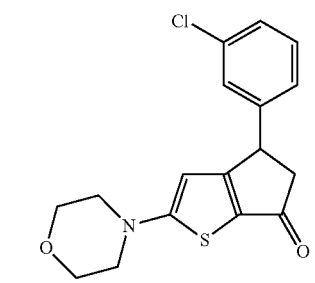
187
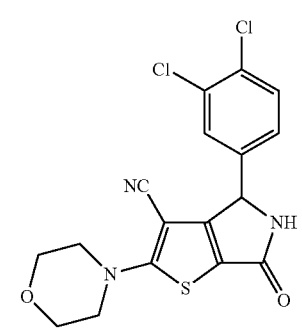
188
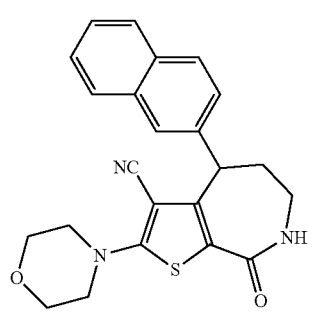
189
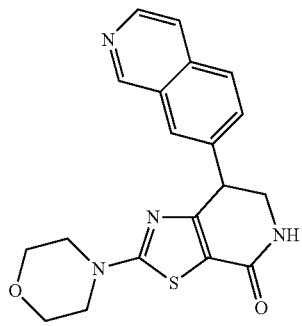
190
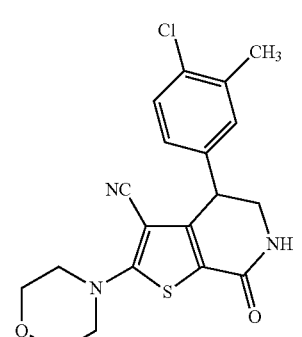
191
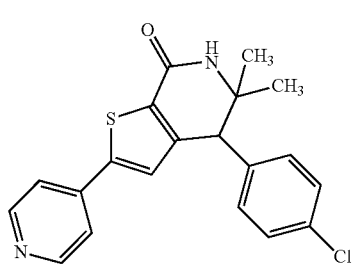
192
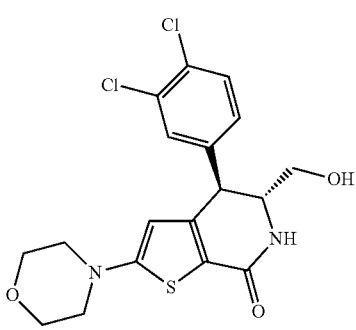
193
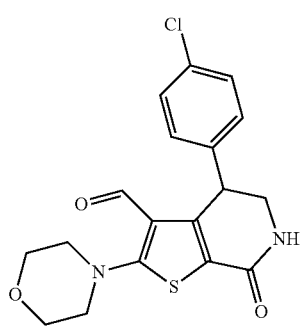

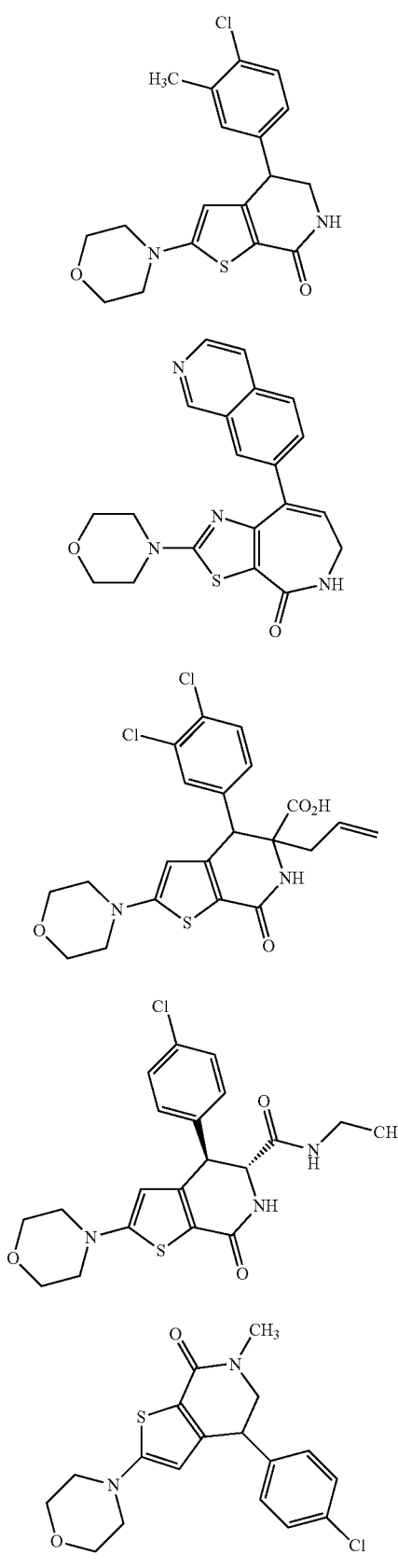
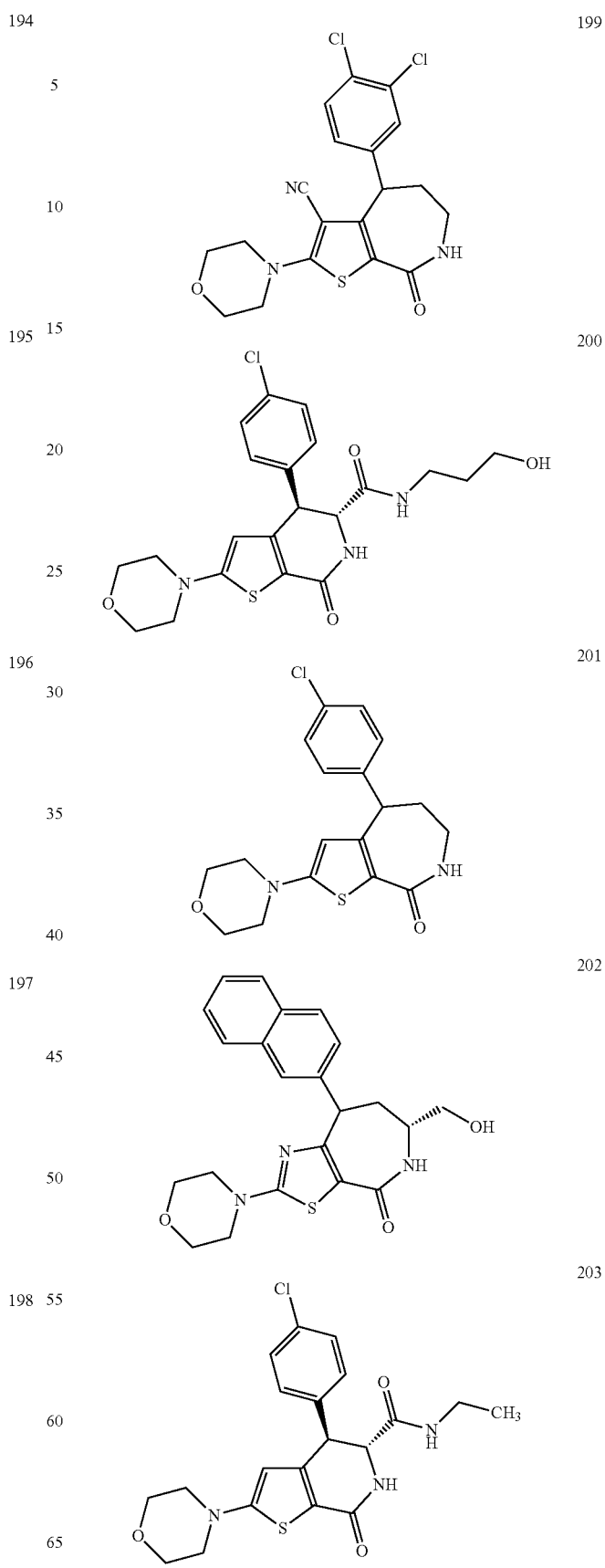

204 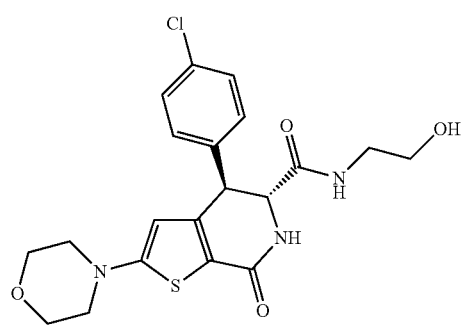
205 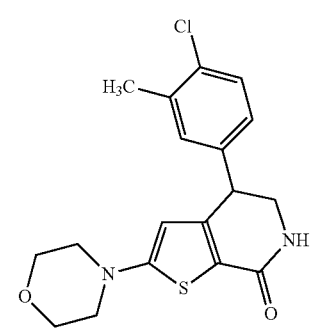
206 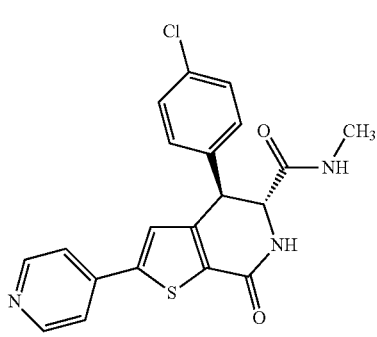
207 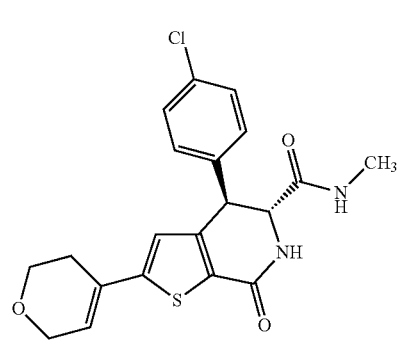
208 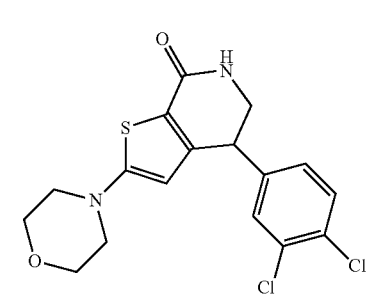
209 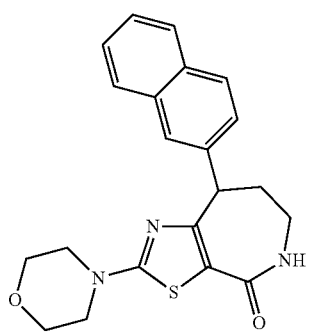
210 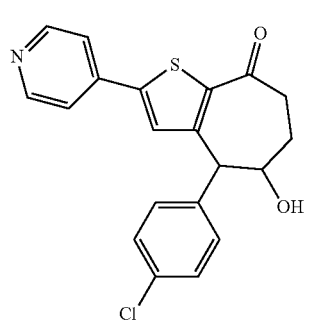
211 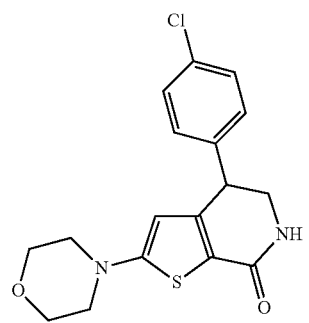
212 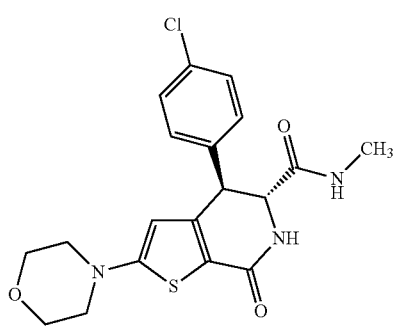
213 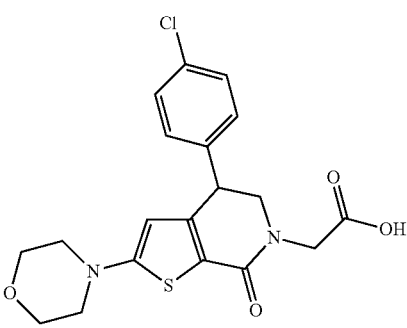

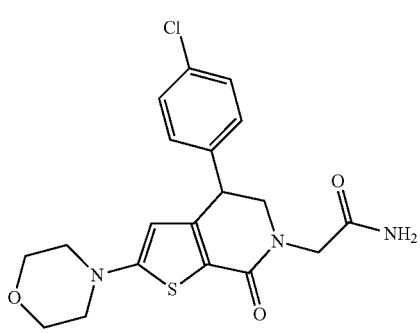

| | Definitions |
|---|---|
| AcOH | acetic acid |
| ACN | acetonitrile |
| ATP | adenosine triphosphate |
| br | broad |
| BCA | bicinchoninic acid |
| BSA | bovine serum albumin |
| BOC | tert-butoxycarbonyl |
| BuLi | butyllithium |
| m-CPBA | m-chloroperbenzoic acid |
| d | doublet |
| dd | doublet of doublets |
| DCE | dichloroethane |
| DCM | dichloromethane |
| DDQ | 2,3-dichloro-5,6-dicyano-1,4-benzoquinone |
| DIPEA | diisopropylethyl amine |
| DMAP | N,N-dimethylaminopyridine |
| DME | 1,2-Dimethoxyethane |
| DMEM | Dulbecco's Modified Eagle's Medium |
| DMF | N,N-dimethylformamide |
| DMFDMA | N,N-dimethylformamide dimethyl acetal |
| DMSO | dimethylsulfoxide |
| DPPA | diphenylphosphoryl azide |
| DTT | dithiothreitol |
| dppf | diphenylphosphinoferrocene |
| EDCI | N-(3-dimethylaminopropyl)-N'-ethylcarbodiimide hydrochloride |
| EDTA | ethylenediaminetetraacetic acid |
| EtOAc | ethyl acetate |
| EtOH | ethanol |
| FA | formic acid |
| FBS | fetal bovine serum |
| J | coupling constant |
| h | hours |
| Hz: | hertz |
| HATU | N,N,N',N'-tetramethyl-o-(7-azabenzotriazole-1-yl)uronium hexafluorophosphate |
| HBTU | o-benzotriazol-1-yl-N,N,N',N'-tetramethyluronium hexafluorophosphate |
| HEPES | N-(2-Hydroxyethyl)piperazine-N'-(2-ethanesulfonic acid) |
| HOBT | 1-hydroxybenztriazole hydrate |
| HRMS | high resolution mass spectrum |
| LAH | lithium aluminum hydride |
| LCMS | liquid chromatography mass spectrum |
| LDA | lithium diisopropylamide |
| LiHMDS | Lithium bis(trimethylsilyl)amide |
| m | multiplet |
| m/z | mass to charge |
| Me | methyl |
| MeOH | methanol |
| min | minutes |
| MS | mass spectrum |
| MTT | methylthiazoletetrazolium |
| MWI | microwave irradiation |
| NBS | N-bromosuccinimide |
| PBS | phosphate buffered saline |
| PKA | cAMP-dependent protein kinase |
| PPA | polyphosphoric acid |
| rt | room temperature |

| | Definitions |
|---|---|
| s | singlet |
| t | triplet |
| TEA | triethylamine |
| TFA: | trifluoroacetic acid |
| TFFA | trifluoroacetic anhydride |
| THF | tetrahydrofuran |
| TMB | 3,3',5,5'-Tetramethylbenzidine |
| TMEDA | Tetramethylethylenediamine |
| q | quartet |
| WST | (4-[3-(4-iodophenyl)-2-(4-nitrophenyl)-2H-5-tetrazolio]-1,3-benzene disulfonate sodium salt) |

The following analytical methods were used:

LCMS sectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

Chiral isomers were separated using chiral HPLC on a Chiralpak IC 250×25 mm 5 micron column using hexane/ethanol/diethylamine or hexane/isopropylalcohol/ethanol/diethylamine as mobile phase. Absolute configurations of the separated isomers were unknown, structures were assigned arbitrarily.

NMR spectrum is shown by proton NMR, with tetramethylsilane as the internal standard and using 300 MHz Bruker Avance spectrometer equipped with a 5 mm QNP probe and 400 MHz Bruker Avance II spectrometer equipped with a 5 mm QNP probe for the measurement; δ values are expressed in ppm.

Example 1

Synthesis of 4-(4-chlorophenyl)-2-pyridin-4-yl-5,6-dihydro-1-benzothiophen-7(4H)-one (Compound 13)

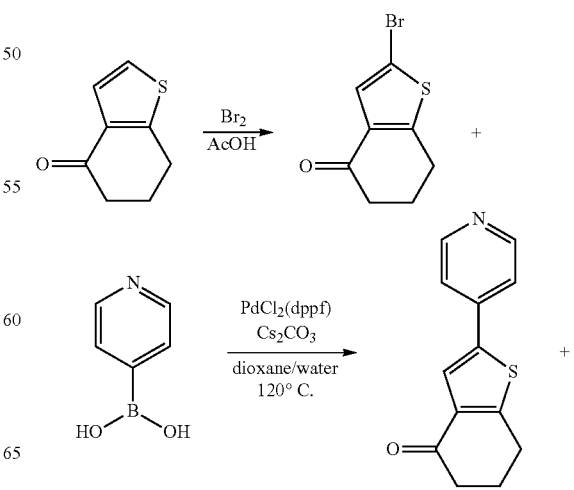

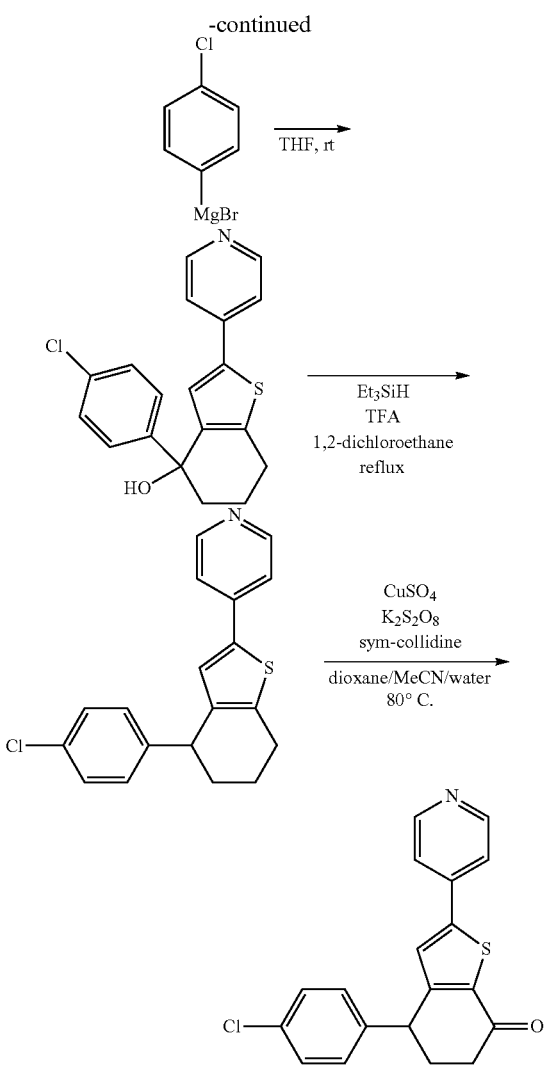

Step 1: 2-bromo-6,7-dihydro-1-benzothiophen-4(5H)-one

In a 500 mL round bottomed flask was placed 6,7-dihydro-4-benzo[b]thiophenone (8.3 g, 54 mmol) and then dissolved in acetic acid (30 mL). To the mixture was added water (30 mL) and the solution was stirred for 30 min at rt. To the mixture was dropwise added freshly prepared solution of bromine (9.4 g, 59 mmol) in acetic acid (50 mL) over 10 min. After addition of the Br$_2$, the mixture was stirred for 1.5 h at the same temperature. The mixture was concentrated under reduced pressure and the residue was diluted with ether (150 mL), which was washed with 1N NaOH aq (100 mL). The aqueous phase was extracted with ether (100 mL) and the combined organic phase was washed with brine (100 mL), dried over anhydrous MgSO$_4$ and then decolorized with activated carbon. Insoluble materials were removed by filtration through Celite pad and the filtrate was concentrated under reduced pressure. The residue was suspended in 50 mL of MeOH and then stirred for 15 min for washing. The precipitate was collected by filtration to obtain the title compound (5.65 g; 45%) as a yellowish crystalline solid. From the mother liquid, 2nd crop of the title compound (6.66 g; 53%) has been obtained. LCMS: (FA) ES+ 231, 233. $^1$H NMR (300 MHz, d$_1$-chloroform) δ: 7.35 (s, 1H), 2.95 (t, 2H), 2.52-2.56 (m, 2H), 2.17-2.25 (m, 2H).

Step 2: 2-pyridin-4-yl-6,7-dihydro-1-benzothiophen-4(5H)-one

In a 250 mL round bottomed flask were placed 2-bromo-6,7-dihydro-1-benzothiophen-4(5H)-one (3.69 g, 16.0 mmol), pyridine-4-boronic acid (3.0 g, 24.5 mmol), and then suspended in 1,4-dioxane (50 mL). To the mixture were added cesium carbonate (18.7 g, 57.3 mmol), [1,1'-bis(diphenylphosphino)ferrocene]dichloropalladium(II), complex with dichloromethane (1:1) (910 mg, 1.1 mmol) and water (50 mL). The mixture was refluxed for 16 h with vigorous stirring. The mixture was allowed to cool to rt and was then diluted with EtOAc (100 mL), which was washed with water (50 mL) and brine (50 mL). Insoluble materials were removed by filtration through Celite pad. The combined aqueous phase was extracted with EtOAc (50 mL). The combined organic phase was dried over anhydrous MgSO$_4$ and insoluble materials were removed by filtration. The filtrate was concentrated under reduced pressure and the residue was purified by prepacked silica gel (120 g) column chromatography eluted with a 50% to 100% EtOAc/hexane. Concentration of appropriate fractions afforded colorless crystalline solid which was suspended in ether (50 mL) and then stirred for 15 min and then ultra-sonicated. The remaining crystalline materials were collected by filtration to obtain the title compound (2.6 g; 71%). From mother liquid, 2nd crop of the title compound (760 mg; 21%) has been obtained. LCMS: (FA) ES+ 230. $^1$H NMR (300 MHz, d$_6$-DMSO) δ: 8.57 (dd, 2H), 7.95 (s, 1H), 7.67 (dd, 2H), 3.08 (2H, t), 2.50-2.54 (m, 2H), 2.10-2.19 (m, 2H).

Step 3: 4-[4-(4-chlorophenyl)-4,5,6,7-tetrahydro-1-benzothien-2-yl]pyridine

In a 250 mL round bottomed flask was placed 2-pyridin-4-yl-6,7-dihydro-1-benzothiophen-4(5H)-one (1400 mg, 6.1 mmol) and then dissolved in tetrahydrofuran (50 mL). To the mixture was added 1 M of 4-chlorophenylmagnesium bromide in ether (10 mL, 10 mmol) and the mixture was stirred for 1.5 h at rt. To the mixture were added a 5% aqueous solution of NH$_4$Cl (100 mL) and EtOAc (100 mL). The resulting bi-phasic mixture was vigorously stirred for 15 min and then the aqueous phase was discarded. The organic phase was washed with brine (50 mL), and then dried over anhydrous MgSO$_4$. Insoluble materials were removed by filtration and the filtrate was concentrated under reduced pressure. The residue was purified by pre-packed silica gel (40 g) column chromatography eluted with a 20% to 80% EtOAc/hexane to obtain 4-(4-chlorophenyl)-2-pyridin-4-yl-4,5,6,7-tetrahydro-1-benzothiophene-4-ol (2.9 g) as a colorless foam.

In a 250 mL round bottomed flask was placed 4-(4-chlorophenyl)-2-pyridin-4-yl-4,5,6,7-tetrahydro-1-benzothiophene-4-ol prepared above, and then dissolved in 1,2-dichloroethane (30 mL, 400 mmol). To the stirred mixture was added triethylsilane (3.5 mL, 22 mmol) and the mixture was stirred for 15 min at rt. To the mixture was added trifluoroacetic Acid (10 mL, 100 mmol) and the mixture was stirred for 16 h at rt. The mixture was concentrated under reduced pressure and then the residue was diluted with CH$_2$Cl$_2$ (100 mL), which was washed with saturated aqueous solution of NaHCO$_3$ (150 mL). The aqueous phase was extracted with CH$_2$Cl$_2$ (50 mL). The combined organic phase was dried over anhydrous MgSO₄. Insoluble materials were removed by filtration and the filtrate was concentrated under reduced pressure.

The resulting brown syrup has been dissolved in 10 mL of MeOH and then diluted with ether (100 mL). To the solution 2N HCl in ether (5 mL) was slowly added with vigorous stirring. Yellowish precipitate appeared. The mixture was stirred for 15 min at rt. and then ether (200 mL) was added. The resulting suspension was stirred for additional 30 min. The resulting precipitate was collected by filtration and then well washed with ether to obtain 4-[4-(4-chlorophenyl)-4,5, 6,7-tetrahydro-1-benzothien-2-yl]pyridine hydrochloride (2.1 g, 95%) as an yellowish off-white crystalline solid.

In a 250 mL round bottomed flask was placed 4-[4-(4-chlorophenyl)-4,5,6,7-tetrahydro-1-benzothien-2-yl]pyridine hydrochloride (2.1 g, 5.8 mmol) and then suspended in 1 M of Sodium hydroxide in water (50 mL, 50 mmol). To the mixture was added ethyl acetate (50 mL) and the mixture was vigorously stirred for 30 min at rt. The aqueous phase was extracted with EtOAc (50 mL×2) and the combined organic phase was dried over anhydrous MgSO₄. Insoluble materials were removed by filtration and the filtrate was concentrated under reduced pressure to obtain the title compound (1.85 g; 98%) as a brown syrup, which was spontaneously solidified by keeping on standing at rt for 3 h. ¹H NMR (300 MHz, d₁-chloroform) δ: 8.51 (d, 2H), 7.26-7.35 (m, 4H), 7.09 (d, 2H), 6.91 (s, 1H), 3.98 (t, 1H), 2.90 (t, 2H), 1.71-2.21 (m, 6H).

Step 4: 4-(4-chlorophenyl)-2-pyridin-4-yl-5,6-dihydro-1-benzothiophen-7(4H)-one (Compound 13)

In a 100 mL round bottomed flask was placed 4-[4-(4-chlorophenyl)-4,5,6,7-tetrahydro-1-benzothien-2-yl]pyridine (821 mg, 2.52 mmol) and then dissolved in acetonitrile (10 mL) and 1,4-dioxane (10 mL). Then γ-Collidine (1.5 mL, 11 mmol) was added. To the mixture were added freshly prepared suspension of potassium persulfate (2.96 g, 10.9 mmol) and Copper(II) sulfate pentahydrate (278 mg, 1.11 mmol) in water (20 mL). The resulting mixture was stirred 6 h at 80° C. After stirring was continued for additional 1.5 h at the same temperature no increase in product formation was observed. The mixture was allowed to cool to rt and then was diluted with water (50 mL) and then extracted with EtOAc (50 mL×2). The combined organic phase was washed with freshly prepared 10% aqueous NaHSO₃ (50 mL), saturated aqueous solution of NaHCO₃ (50 mL), brine (50 mL), dried over anhydrous MgSO₄. Insoluble materials were removed by filtration and the filtrate was concentrated under reduced pressure. The residue was purified by pre-packed silica gel (24 g) column chromatography eluted with a 30% to 100% EtOAc/hexane to yield title compound (568 mg; 66.3%) as a colorless crystalline solid.

Step 5: Enantiomeric Separation to Compounds 4 and 22

Racemic 4-(4-chlorophenyl)-2-pyridin-4-yl-5,6-dihydro-1-benzothiophen-7(4H)-one (Compound 13) was separated into each enantiomer on a Chiralpak IC 20×250 column using 85/15/0.1 Hexane-EtOH-TEA mixture (Flow rate: 20 mL/min). The faster moving enantiomer (27.9 min) was arbitrarily assigned as (S), while the slower moving enantiomer (31.0 min) was arbitrarily assigned as (R).

Absolute configuration of the separated isomers was unknown, the structures were assigned arbitrarily.

LCMS: (FA) ES⁺, 340, 342. ¹H NMR (400 MHz, d₁-chloroform) δ: 8.63 (dd, 2H), 7.43 (dd, 2H), 7.35 (d, 2H), 7.15 (d, 2H), 6.99 (s, 1H), 4.20 (dd, 1H), 2.64-2.80 (m, 2H), 2.45-2.52 (m, 1H), 2.24-2.34 (m, 1H).

Example 2

Synthesis of 4-(4-chlorophenyl)-2-pyridin-4-yl-4,5,6, 7-tetrahydro-8H-thieno[2,3-c]azepin-8-one (Compound 8)

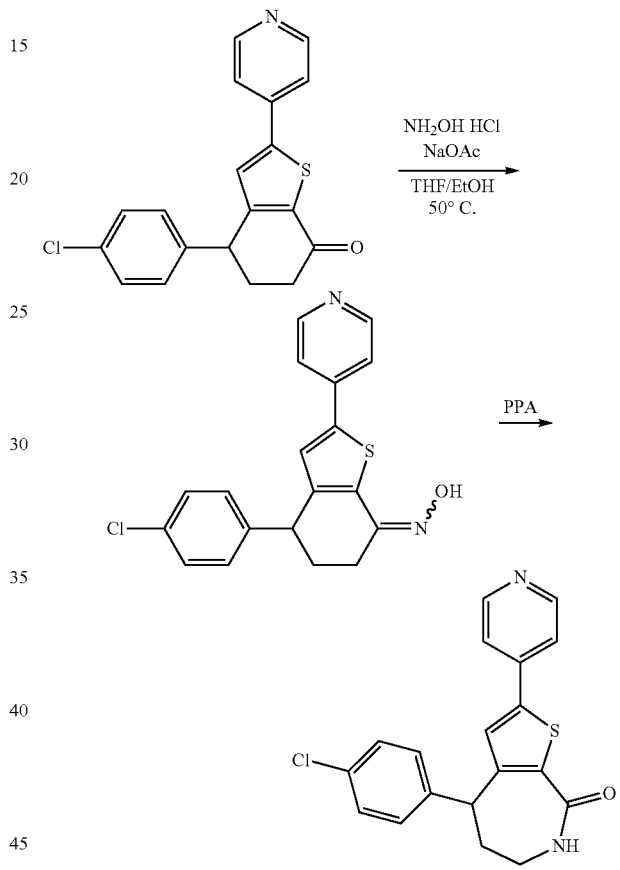

In a 100 mL round bottomed flask was placed 4-(4-chlorophenyl)-2-pyridin-4-yl-5,6-dihydro-1-benzothiophen-7 (4H)-one (325 mg, 0.956 mmol) and then dissolved in tetrahydrofuran (3 mL) and ethanol (3 mL). To the solution were added sodium acetate (402 mg, 4.90 mmol) and hydroxylamine hydrochloride (333.6 mg, 4.801 mmol). The resulting suspension was stirred for 16 h at 50° C. The mixture was concentrated under reduced pressure and the residue was suspended in water (50 mL), which was extracted with CH₂Cl₂-THF (1:1; 50 mL×2). The combined organic phase was dried over anhydrous MgSO₄. Insoluble materials were removed by filtration and the filtrate was concentrated under reduced pressure. The residue was a stereo isomeric mixture (E/Z) of 4-(4-chlorophenyl)-2-pyridin-4-yl-5,6-dihydro-1-benzothiophen-7(4H)-one oxime (260 mg; 77%) and was used in the next step without further purification. LCMS: (FA) ES+ 355, 357

In a 100 mL round bottomed flask was placed stereo isomeric mixture of 4-(4-chlorophenyl)-2-pyridin-4-yl-5,6-dihydro-1-benzothiophen-7(4H)-one oxime prepared above and then was added polyphosphoric acid (11 g, 46 mmol) and the mixture was stirred for 6 h at 130° C. During this period, the mixture was occasionally mixed by hand. The mixture was allowed to cool to ambient temperature and then was added crushed ice (ca 20 ml) while the reaction mixture is hot. The mixture was stirred for 30 min at rt. A dark brown suspension was obtained, which was basicified by the addition of 5N NaOH (30 mL, pH ca 12). The mixture was extracted with a 1:1 mixture of CH$_2$Cl$_2$ and THF (30 mL×3). The combined organic phase was dried over anhydrous MgSO$_4$. Insoluble materials were removed by filtration and the filtrate was concentrated under reduced pressure to obtain title compound (230 mg; 68%) as a yellowish off-white powder, which was only one isomer.

Enantiomeric Separation to Compounds 21 and 25.

Racemic 4-(4-chlorophenyl)-2-pyridin-4-yl-4,5,6,7-tetrahydro-8H-thieno[2,3-c]azepin-8-one (Compound 8) was separated into each enantiomers on a Chiralpak AS 20×250 column (10 micron) using 80/20/0.1 Hexane-EtOH-DEA mixture (Flow rate: 20 mL/min).

The faster moving enantiomer was re-purified on a Chiralpak AS 20×250 column (10 micron) using 85/15/0.1 Hexane-EtOH-DEA mixture (Flow rate: 20 mL/min).

The faster moving enantiomer (16.1 min) arbitrarily assigned as (S), while the slower moving enantiomer (29.6 min) arbitrarily assigned as (R).

Absolute configurations of the separated isomers were unknown, structures were assigned arbitrarily.

LCMS: (FA) ES+ 355, 357, $^1$H NMR (400 MHz, d$_6$-DMSO) δ ppm 8.54 (dd, 2H), 8.34 (br t, 1H), 7.58 (dd, 2H), 7.37 (d, 2H), 7.25 (s, 1H), 7.17 (d, 2H), 4.53 (dd, 1H), 3.15-3.22 (m, 2H), 2.25-2.35 (m, 1H), 2.02-2.07 (m, 1H).

Compounds in the following table were prepared from the appropriate starting materials in a method analogous to that of Example 2:

| 30 | LCMS: (AA) ES+ 341, 343 |
| 31 | LCMS: (AA) ES+ 369, 371. |

Example 3

Synthesis of 5-(4-chlorophenyl)-7-pyridin-4-yl-4,5-dihydro-1H-thieno[3,2-g]indazole (Compound 12)

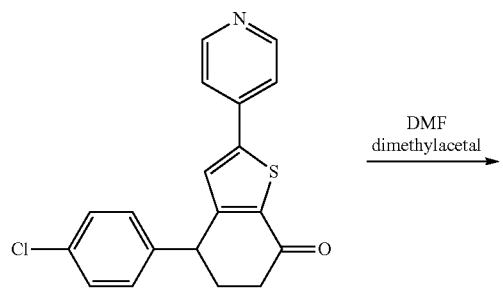

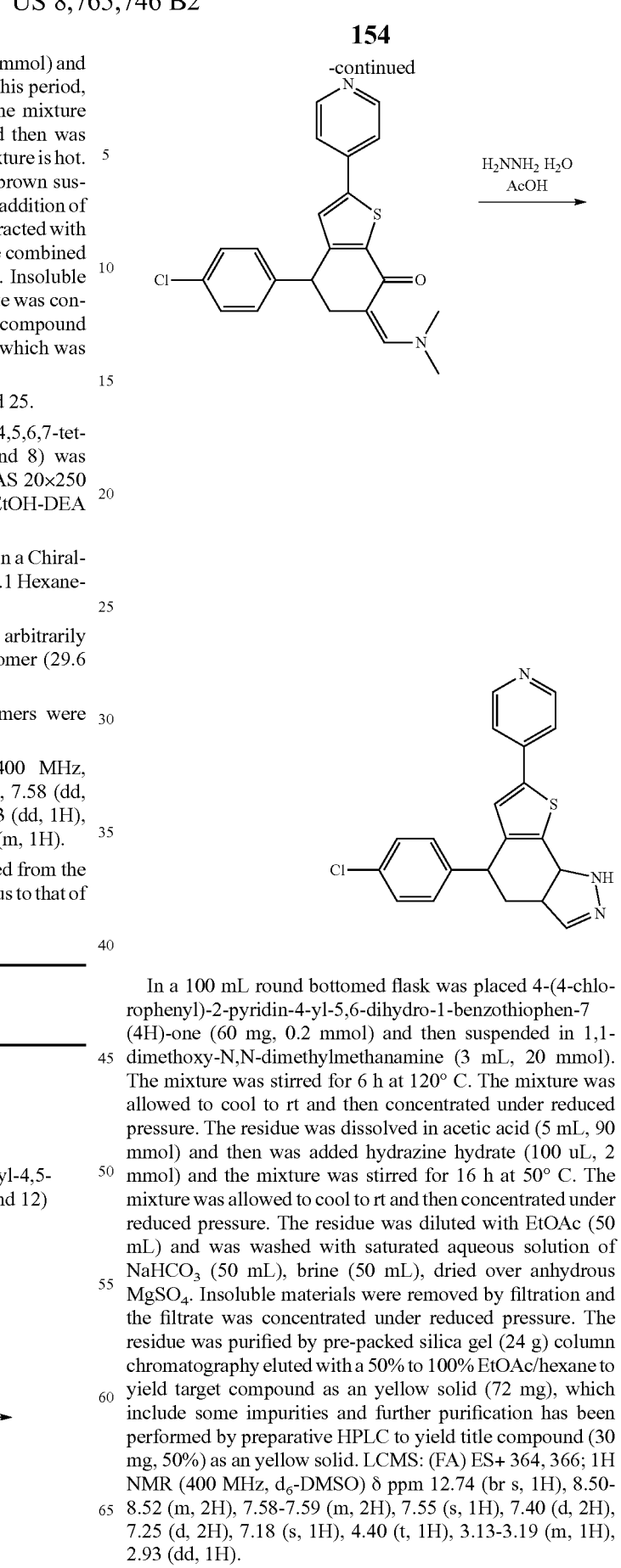

In a 100 mL round bottomed flask was placed 4-(4-chlorophenyl)-2-pyridin-4-yl-5,6-dihydro-1-benzothiophen-7 (4H)-one (60 mg, 0.2 mmol) and then suspended in 1,1-dimethoxy-N,N-dimethylmethanamine (3 mL, 20 mmol). The mixture was stirred for 6 h at 120° C. The mixture was allowed to cool to rt and then concentrated under reduced pressure. The residue was dissolved in acetic acid (5 mL, 90 mmol) and then was added hydrazine hydrate (100 uL, 2 mmol) and the mixture was stirred for 16 h at 50° C. The mixture was allowed to cool to rt and then concentrated under reduced pressure. The residue was diluted with EtOAc (50 mL) and was washed with saturated aqueous solution of NaHCO$_3$ (50 mL), brine (50 mL), dried over anhydrous MgSO$_4$. Insoluble materials were removed by filtration and the filtrate was concentrated under reduced pressure. The residue was purified by pre-packed silica gel (24 g) column chromatography eluted with a 50% to 100% EtOAc/hexane to yield target compound as an yellow solid (72 mg), which include some impurities and further purification has been performed by preparative HPLC to yield title compound (30 mg, 50%) as an yellow solid. LCMS: (FA) ES+ 364, 366; 1H NMR (400 MHz, d$_6$-DMSO) δ ppm 12.74 (br s, 1H), 8.50-8.52 (m, 2H), 7.58-7.59 (m, 2H), 7.55 (s, 1H), 7.40 (d, 2H), 7.25 (d, 2H), 7.18 (s, 1H), 4.40 (t, 1H), 3.13-3.19 (m, 1H), 2.93 (dd, 1H).

Example 4

Synthesis of (7Z)-4-(4-chlorophenyl)-2-pyridin-4-yl-5,6-dihydro-1-benzothiophen-7(4H)-one oxime (Compound 18) (major isomer) and (7E)-4-(4-chlorophenyl)-2-pyridin-4-yl-5,6-dihydro-1-benzothiophen-7(4H)-one oxime (Compound 30) (minor isomer)

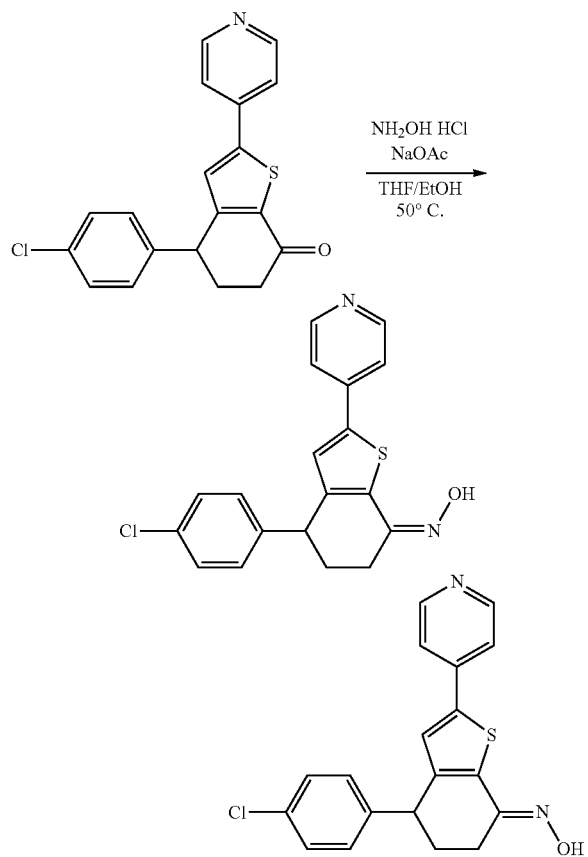

In a 20 mL vial was placed 4-(4-chlorophenyl)-2-pyridin-4-yl-5,6-dihydro-1-benzothiophen-7(4H)-one (82 mg, 0.24 mmol) and then dissolved in ethanol (2 mL) and THF (1 mL). To the mixture were added hydroxylamine hydrochloride (51.5 mg, 0.741 mmol) and sodium acetate (66 mg, 0.80 mmol). The mixture was stirred for 16 h at 50° C. The mixture was allowed to cool to rt and then diluted with EtOAc (50 mL), which was washed with saturated aqueous solution of NaHCO$_3$ (50 mL). The aqueous phase was extracted with EtOAc (50 mL).

The combined organic phase was dried over anhydrous MgSO$_4$. Insoluble materials were removed by filtration and the filtrate was concentrated under reduced pressure. The residual off-white crystalline solid was a ca 8:1 mixture of E/Z stereo isomers. Those mixtures were purified by preparative HPLC (FA). The stereochemistry of these separated isomers was not determined.

The faster eluting major isomer; tentatively assigned as 7Z (18): (24 mg; 28%), yellowish off-white crystalline material. LCMS: (FA) ES+ 355, 357; 1H NMR (400 MHz, d$_6$-DMSO) δ ppm 11.82 (br s, 1H), 8.51 (dd, 2H), 7.61 (dd, 2H), 7.37-7.40 (m, 2H), 7.26 (s, 1H), 7.17-7.20 (m, 2H), 7.30 (dd, 1H), 2.53-2.65 (m, 2H), 2.19-2.26 (m, 1H), 1.92-2.00 (m, 1H).

The slower eluting minor isomer; tentatively assigned as 7E (30): (2.4 mg; 2.8%), colorless crystalline material. LCMS: (FA) ES+ 355, 357; 1H NMR (400 MHz, d$_6$-DMSO) δ ppm 11.31 (br s, 1H), 8.50-8.55 (m, 2H), 7.56-7.61 (m, 2H), 7.38-7.44 (m, 2H), 7.18-7.30 (m, 3H), 4.20-1.24 (m, 1H), 2.62-2.70 (m, 1H), 2.11-2.21 (m, 2H), 1.84-2.00 (m, 1H).

Example 5

Synthesis of 4-(4-chlorophenyl)-4-hydroxy-5,5-dimethyl-2-pyridin-4-yl-5,6-dihydro-1-benzothiophen-7(4H)-one (Compound 5)

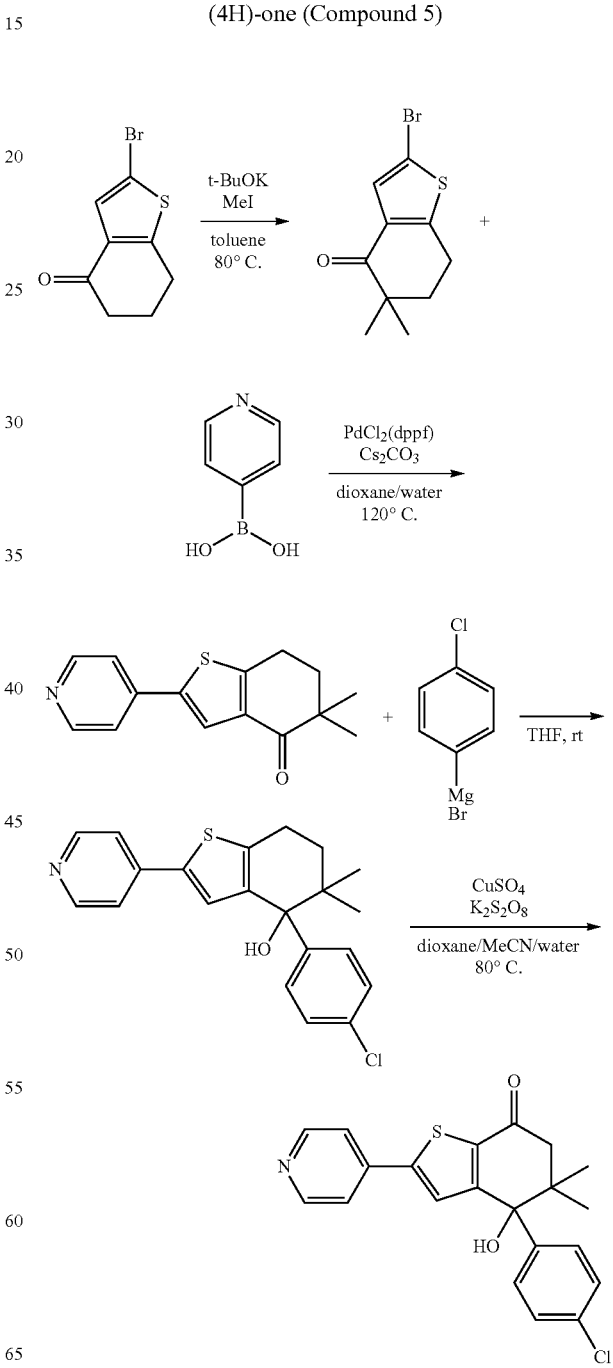

Step 1: 2-bromo-5,5-dimethyl-6,7-dihydro-1-benzothiophen-4(5H)-one

In a 100 mL round bottomed flask was placed 2-bromo-6,7-dihydro-1-benzothiophen-4(5H)-one (1.21 g, 5.24 mmol) and then dissolved in toluene (30 mL). To the mixture was added potassium tert-butoxide (1.29 g, 11.5 mmol) and the mixture was stirred for 30 min at 80° C. To the mixture, was added methyl iodide (3 mL, 50 mmol) while hot and the mixture was stirred for 16 at rt. The reaction was quenched by the addition of saturated aqueous solution of $NH_4Cl$ (30 mL) and then extracted with EtOAc (50 mL×2). The combined organic phase was dried over anhydrous $MgSO_4$ and then insoluble materials were removed by filtration. The filtrate was concentrated and the residue was purified by pre-packed silica gel (40 g) column chromatography eluted with a 0% to 30% EtOAc/hexane to obtain title compound (550 mg; 40%) as a yellow oil. LCMS: (FA) ES+ 259, 261; $^1$H NMR (400 MHz, d-chloroform) δ ppm 7.32 (s, 1H), 2.95 (t, 2H), 2.04 (t, 2H), 1.19 (s, 6H).

Step 2: 5,5-dimethyl-2-pyridin-4-yl-6,7-dihydro-1-benzothiophen-4(5H)-one

In a 100 ml round bottomed flask, were placed 2-bromo-5,5-dimethyl-6,7-dihydro-1-benzothiophen-4(5H)-one (550 mg, 2.1 mmol), pyridine-4-boronic acid (326 mg, 2.65 mmol) and 1,1'-bis(diphenylphosphino)ferrocenepalladium(II) dichloride, dichloromethane (96 mg, 0.12 mmol) and then suspended in 1,4-dioxane (30 mL, 400 mmol). To the mixture were added cesium carbonate (3.08 g, 9.45 mmol) and water (20 mL). The mixture was stirred for 16 h at 120° C. The mixture was allowed to cool to rt and then diluted with EtOAc (100 mL), which was washed with water (50 mL×2). The combined aqueous phase was extracted with EtOAc (50 mL×2). The combined organic phase was dried over anhydrous MgSO4. Insoluble materials were removed by filtration and the filtrate was concentrated under reduced pressure. The residue was purified by pre-packed silica gel (40 g) column chromatography eluted with a 30% to 100% EtOAc/hexane to obtain title compound (420 mg, 77%) as a colorless crystalline solid. LCMS: (FA) ES+ 258; $^1$H NMR (400 MHz, d-chloroform) δ ppm 8.60 (dd, 2H), 7.77 (s, 1H), 7.43 (dd, 2H), 3.09 (t, 2H), 2.10 (t, 2H), 1.24 (s, 6H).

Step 3: 4-(4-chlorophenyl)-5,5-dimethyl-2-pyridin-4-yl-4,5,6,7-tetrahydro-1-benzothiophene-4-ol In a 100 mL round bottomed flask was placed 5,5-dimethyl-2-pyridin-4-yl-6,7-dihydro-1-benzothiophen-4(5H)-one (380 mg, 1.5 mmol) and then dissolved in tetrahydrofuran (30 mL). To the mixture was added 1 M of 4-chlorophenyl magnesiumbromide in ether (3.5 mL, 3.5 mmol) and then stirred for 3 h at rt. To the mixture was added 1 M of 4-chlorophenyl magnesiumbromide in ether (2.5 mL, 2.5 mmol) and then stirred for 16 h at rt. The mixture was stirred for 10 h at 70° C. The mixture was allowed to cool to rt and then 1 M of 4-chlorophenyl magnesiumbromide in ether (5 mL, 5 mmol) was added and the mixture was stirred for 16 h at rt. The mixture was diluted with saturated aqueous solution of $NH_4Cl$ (50 mL), which was extracted with EtOAc (50 mL×2). The combined organic phase was dried over anhydrous $MgSO_4$. Insoluble materials were removed by filtration and the filtrate was concentrated under reduced pressure. The residue was purified by pre-packed silica gel (24 g) column chromatography eluted with a 30% to 100% EtOAc/hexane to obtain title compound (530 mg; 97%) as a colorless foam. LCMS: (FA) ES+ 370, 372; $^1$H NMR (400 MHz, d6-DMSO) δ ppm 8.48 (dd, 2H), 7.45 (dd, 2H), 7.33 (d, 2H), 7.23-7.25 (m, 2H), 5.55 (s, 1H), 2.87-2.91 (m, 2H), 1.84-1.90 (m, 1H), 1.57-1.63 (m, 1H, 0.95 (s, 3H), 0.62 (s, 3H).

Step 4: 4-(4-chlorophenyl)-4-hydroxy-5,5-dimethyl-2-pyridin-4-yl-5,6-dihydro-1-benzothiophen-7(4H)-one (Compound 5)

In a 100 mL round bottomed flask was placed 4-(4-chlorophenyl)-5,5-dimethyl-2-pyridin-4-yl-4,5,6,7-tetrahydro-1-benzothiophene-4-ol (238 mg, 0.643 mmol) and then dissolved in 1,4-dioxane (7 mL) and acetonitrile (7 mL). To the mixture were added freshly prepared suspension of potassium persulfate (715 mg, 2.64 mmol) in water (7 mL) and freshly prepared solution of copper(II) sulfate pentahydrate (675 mg, 2.70 mmol) in water (5 mL). The mixture was stirred for 2 days at 90° C. The reaction mixture was allowed to cool to rt and then diluted with water (50 mL), and extracted with EtOAc (50 mL). The aqueous phase was bacisified by the addition of saturated aqueous solution of $NaHCO_3$ (ca 20 mL) to adjust pH ca 10 and then, to the resulting bluish white suspension, was added a saturated aqueous solution of $NH_4Cl$ (ca 10 mL). The resulting deep blue clear aqueous solution was extracted with EtOAc (50 mL).

The combined organic phase was washed with a saturated aqueous solution of $NH_4Cl$ (50 mL), brine (50 mL), dried over anhydrous $MgSO_4$. Insoluble materials were removed by filtration and the filtrate was concentrated under reduced pressure. The residual yellow crystalline solid was used in the next step without further purification.

In a 100 mL round bottomed flask was placed the solid prepared above and then dissolved in methylene chloride (15 mL, 230 mmol). To the mixture was added Dess-Martin periodinane (294.4 mg, 0.6941 mmol) and the mixture was stirred for 16 h at rt. The reaction mixture was suspension. The mixture was diluted with $CH_2Cl_2$ (50 mL), which was washed with saturated aqueous solution of $NaHCO_3$ (50 mL) and then washed with freshly prepared 10% aqueous solution of $NaHSO_3$ (50 mL). The each aqueous phase was extracted with $CH_2Cl_2$ (50 mL) and the combined organic phase was dried over anhydrous $MgSO_4$. Insoluble materials were removed by filtration and the filtrate was concentrated under reduced pressure. The residue was treated with $CH_2Cl_2$ to afford crystalline solid, which was collected by filtration to obtain title compound (110 mg; 44%) as a yellowish off-white crystalline solid. The filtrate was purified by pre-packed silica gel (24 g) column chromatography eluted with a 30% to 100% EtOAc/hexane. The appropriate fractions were concentrated and then the residue was recrystallized from $CH_2Cl_2$ to yield a 2nd crop of title compound (35 mg; 14%) as a colorless crystalline solid. LCMS: (FA) ES+ 384, 386; $^1$H NMR (400 MHz, d6-DMSO) δ ppm 8.61 (dd, 2H), 7.69 (dd, 2H), 7.56 (s, 1H), 7.33-7.42 (m, 4H), 6.24 (s, 1H), 2.43 (br s, 1H), 2.39 (br s, 1H), 1.02 (s, 3H), 0.77 (s, 3H).

Example 6

Synthesis of 4-(4-chlorophenyl)-4,5-dimethyl-2-pyridin-4-yl-4,8-dihydro-7H-thieno[2,3-b]azepin-7-one (Compound 17)

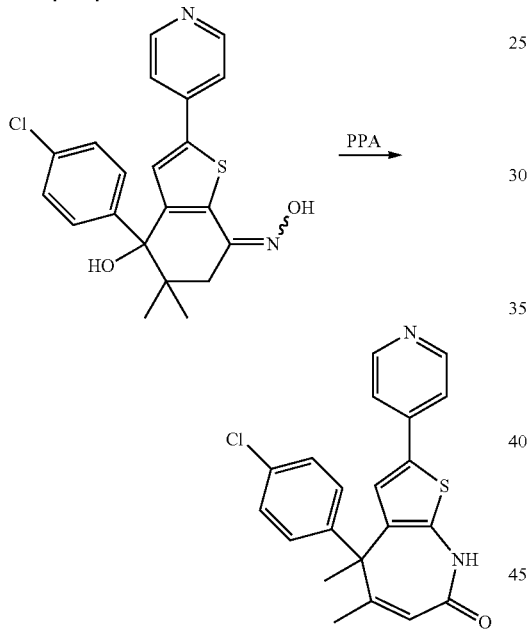

In a 100 mL round bottomed flask was placed 4-(4-chlorophenyl)-4-hydroxy-5,5-dimethyl-2-pyridin-4-yl-5,6-dihydro-1-benzothiophen-7(4H)-one (170 mg, 0.44 mmol) and then suspended in tetrahydrofuran (5 mL) and ethanol (5 mL). The suspension was stirred for 30 min at 60° C. To the resulting solution were added sodium acetate (188 mg, 2.29 mmol) and hydroxylamine hydrochloride (157 mg, 2.26 mmol). The mixture was stirred for 20 h at rt. The mixture was diluted with saturated aqueous solution of NaHCO$_3$ (50 mL), which was extracted with CH$_2$Cl$_2$ (50 mL×2). The combined organic phase was dried over anhydrous MgSO$_4$.

Insoluble materials were removed by filtration and the filtrate was concentrated under reduced pressure to obtain stereo isomeric mixture of 4-(4-chlorophenyl)-4-hydroxy-5,5-dimethyl-2-pyridin-4-yl-5,6-dihydro-1-benzothiophen-7(4H)-oxime (175 mg; 99%) as a colorless foam. The crude material was used in the next step without further purifications.

In a 100 mL round bottomed flask, was placed stereo isomeric mixture of 4-(4-chlorophenyl)-4-hydroxy-5,5-dimethyl-2-pyridin-4-yl-5,6-dihydro-1-benzothiophen-7(4H)-one oxime prepared above, and then was added PPA (10.5 g, 43.8 mmol). The mixture was stirred for 4 h at 130° C. During this period, the mixture was occasionally shaken by hand. To the mixture was added crushed ice (ca 30 g) while hot and then the mixture was neutralized with cold 5N NaOH (ca 20 mL) to adjust pH ca 7.0. The mixture was diluted with water (50 mL) and then extracted with CH$_2$Cl$_2$ (50 mL×3). The combined organic phase was dried over anhydrous MgSO$_4$. Insoluble materials were removed by filtration and the filtrate was concentrated under reduced pressure. The residue was purified by pre-packed silica gel (24 g) column chromatography eluted with a 10% to 80% EtOAc/hexane to yield title compound (117 mg; 69%) as a yellowish amorphous solid. LCMS: (FA) ES+ 381, 383; $^1$H NMR (400 MHz, d-chloroform) δ ppm 8.58 (dd, 2H), 7.45 (dd, 2H), 7.28 (d, 2H), 7.19 (d, 2H), 6.99 (s, 1H), 6.37 (s, 1H), 1.82 (s, 3H), 1.69 (s, 3H).

Example 7

Synthesis of 4-(4-chlorophenyl)-5,5-dimethyl-2-pyridin-4-yl-5,6-dihydro-1-benzothiophen-7(4H)-one (Compound 10)

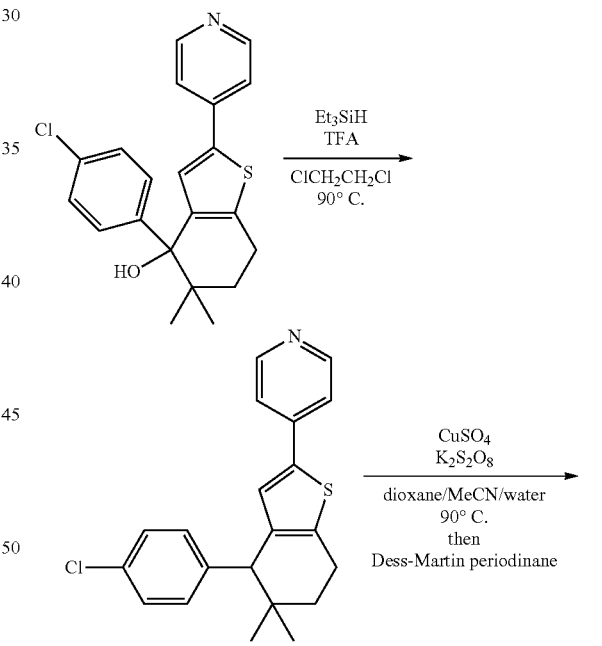

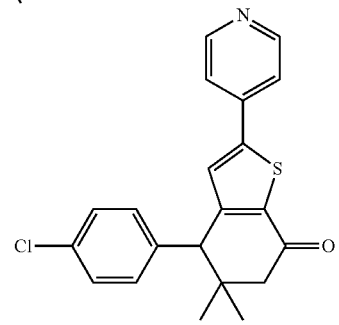

Step 1: 4-[4-(4-chlorophenyl)-5,5-dimethyl-4,5,6,7-tetrahydro-1-benzothien-2-yl]pyridine 4-(4-chlorophenyl)-5,5-dimethyl-2-pyridin-4-yl-4,5,6,7-tetrahydro-1-benzothiophene-4-ol (240 mg, 0.65 mmol) was placed in a 100 mL round bottomed flask and dissolved in 1,2-dichloroethane (10 mL). To the solution were added trifluoroacetic acid (1 mL, 10 mmol) and triethylsilane (1 mL, 6 mmol). The resulting yellow solution was stirred for 16 hr at 90° C. The mixture was allowed to cool to rt and then concentrated under reduced pressure. The residue was diluted with EtOAc (50 mL) and the resulting solution was washed with a saturated aqueous solution of NaHCO₃ (50 mL). The aqueous phase was separated and extracted with EtOAc (50 mL). The combined organic phases were dried over anhydrous MgSO₄. Insoluble materials were removed by filtration and the filtrate was concentrated under reduced pressure. The residue was purified by pre-packed silica gel (24 g) column chromatography, eluting with a 30% to 100% EtOAc in hexane to obtain product as colorless syrup. LCMS: (FA) ES+ 354, 356; $^1$H NMR (400 MHz, d-chloroform) δ ppm 8.49 (dd, 2H), 7.31 (dd, 2H), 7.20 (d, 2H), 7.03 (d, 2H), 6.84 (s, 1H), 3.67 (s, 1H), 2.83-3.00 (m, 2H), 1.77-1.82 (m, 1H), 1.63-1.70 (m, 1H), 1.04 (s, 3H), 0.74 (s, 3H).

Step 2: 4-(4-chlorophenyl)-5,5-dimethyl-2-pyridin-4-yl-5,6-dihydro-1-benzothiophen-7(4H)-one (Compound 10)

4-[4-(4-chlorophenyl)-5,5-dimethyl-4,5,6,7-tetrahydro-1-benzothien-2-yl]pyridine (215 mg, 0.608 mmol), prepared above, was placed in a 100 mL round bottomed flask and dissolved in 1,4-dioxane (5 mL) and acetonitrile (5 mL). To the mixture was added a freshly prepared solution of copper (II) sulfate pentahydrate (672 mg, 2.69 mmol) and potassium persulfate (669 mg, 2.47 mmol) in water (10 mL). The resulting bluish gray suspension was stirred for 16 hr at 90° C. The mixture was allowed to cool to rt and then diluted with EtOAc (50 mL). The resulting solution was washed with water (50 mL). The aqueous phase was separated and basified by the addition of a saturated aqueous solution of NaHCO₃ (ca 50 mL, to adjust pH ca 12, then treated with a saturated aqueous solution of NH₄Cl(ca 50 mL to dissolve Cu salts). The resulting deep blue aqueous solution was extracted with EtOAc (50 mL×2). The combined organic phases were washed with a freshly prepared 10% aqueous solution of NaHSO₃(100 mL), then a saturated aqueous solution of NaHCO₃ (50 mL), and then dried over anhydrous MgSO₄. Insoluble materials were removed by filtration and the filtrate was concentrated under reduced pressure. The residue, a mixture of 4-(4-chlorophenyl)-5,5-dimethyl-2-pyridin-4-yl-4,5,6,7-tetrahydro-1-benzothiophene-7-ol (240 mg) and title compound (340 mg), was used in the next step without further purification.

The mixture of 4-(4-chlorophenyl)-5,5-dimethyl-2-pyridin-4-yl-4,5,6,7-tetrahydro-1-benzothiophene-7-ol and title compound was dissolved in dichloromethane (50 mL, 800 mmol) and then Dess-Martin periodinane (515 mg, 1.22 mmol) was added. The mixture was stirred for 3 hr at rt. The mixture was diluted with DCM (50 mL) and then washed with a 10% aqueous solution of NaHSO₃ (50 mL). The aqueous phase was separated, basified by the addition of a saturated aqueous solution of NaHCO₃ (ca 100 mL) and then extracted with DCM (50 mL×2). The combined organic phases were washed with a saturated aqueous solution of NaHCO₃ (50 mL) then dried over anhydrous MgSO₄. Insoluble materials were removed by filtration and the filtrate was concentrated under reduced pressure. The residue was purified by pre-packed silica gel (24 g) column chromatography, eluting with 30% to 100% EtOAc in hexane to yield the title compound as a colorless foam (170 mg; 76%). LCMS: (FA) ES+ 368, 370; $^1$H NMR (400 MHz, d-chloroform) δ ppm 8.62 (dd, 2H), 7.42 (dd, 2H), 7.33 (d, 2H), 7.10 (d, 2H), 7.05 (s, 1H), 4.01 (s, 1H), 2.63 (d, 1H), 2.53 (d, 1H), 1.14 (s, 3H), 0.90 (s, 3H).

Example 8

Synthesis of 5-chloro-2'-pyridin-4-yl-5',6'-dihydro-3H,7'H-spiro[2-benzofuran-1,4'-[1]benzothiophene]-3,7'-dione (Compound 14)

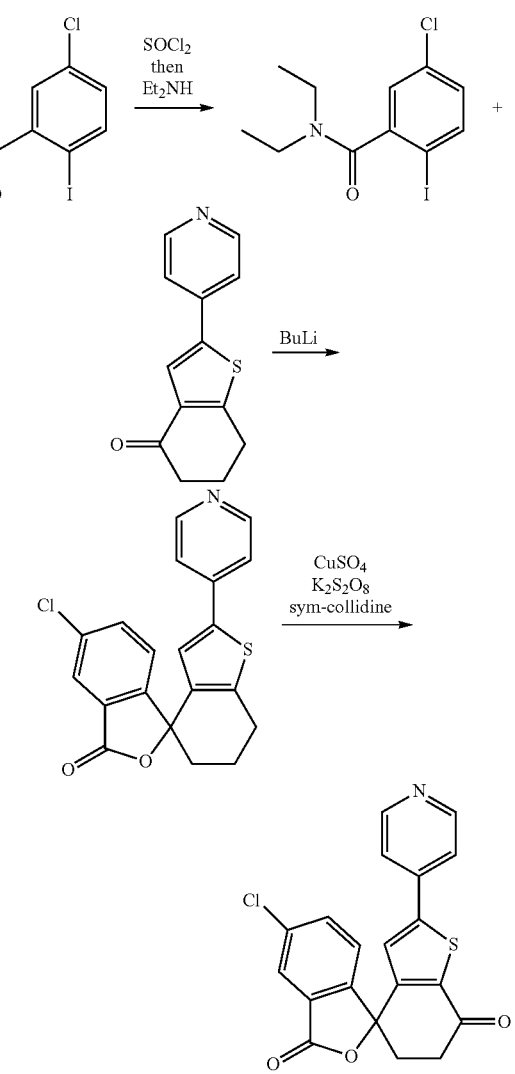

Step 1: 4-[5-chloro-N,N-diethyl-2-iodobenzamide

In a 50 mL round bottomed flask was placed 5-chloro-2-iodo-benzoic acid (2.69 g, 9.52 mmol). Toluene (30 mL) was added to give a suspension. To the mixture was added thionyl chloride (5 mL, 70 mmol) and the reaction was refluxed for 16 hr with vigorous stirring. The mixture was allowed to cool to rt and then concentrated under reduced pressure. The residual yellow oil was used in the next step without further purification.

In a 100 mL round bottomed flask was placed the 5-chloro-2-iodobenzoyl chloride prepared above. Pyridine (50 mL, 600 mmol) and tetrahydrofuran (10 mL, 100 mmol) were then added. To the reaction mixture was added diethylamine (3 mL, 30 mmol) and the mixture was stirred for 3 hr at rt. The mixture was stirred for an additional 3 hr at 50° C. The mixture was allowed to cool to rt and then concentrated under reduced pressure. The residue was dissolved in EtOAc (100 mL) and then washed with 1N HCl (50 mL×2), 1N NaOH (50 mL), brine (50 mL), and dried over anhydrous $MgSO_4$. Insoluble materials were removed by filtration and the filtrate was concentrated under reduced pressure to obtain the title compound (1.96 g, 61%) as a light yellow syrup. LCMS: (FA) ES+ 338, 340; $^1H$ NMR (300 MHz, $d_6$-DMSO) δ ppm 7.86 (d, 1H), 7.38 (d, 1H), 7.21 (dd, 1H), 3.61-3.68 (m, 1H), 2.91-3.29 (m, 3H), 1.17 (t, 3H), 1.01 (t, 3H).

Step 2: 5-chloro-2'-pyridin-4-yl-6',7'-dihydro-3H,5'H-spiro[2-benzofuran-1,4'-[1]benzothiophen]-3-one In a 100 mL round bottomed flask was placed 5-chloro-N,N-diethyl-2-iodobenzamide (840 mg, 2.5 mmol) and tetrahydrofuran (10 mL). The mixture was stirred for 5 min at −78° C. then n-butyllithium in hexane (1.6M, 1.8 mL, 2.9 mmol) was added and the mixture was stirred for an additional 30 min at the same temperature. To the mixture was added a solution of 2-pyridin-4-yl-6,7-dihydro-1-benzothiophen-4 (5H)-one (445 mg, 1.94 mmol) in tetrahydrofuran (15 mL). The mixture was stirred for an additional 16 hr during which time the reaction temperature was allowed to slowly rise from −78° C. to rt. The reaction mixture was then refluxed for 4 hr, cooled to rt and then diluted with EtOAc (50 mL). The resulting solution was washed with water (50 mL). The aqueous phase was separated and neutralized by the addition of 1N HCl (ca 1.21 mL, pH ca 7.0) and then extracted with EtOAc (50 mL). Finally, the combined organic phases were washed with brine (30 mL) then dried over anhydrous $MgSO_4$. Insoluble materials were removed by filtration and the filtrate was concentrated under reduced pressure. The residue was purified by pre-packed silica gel (40 g) column chromatography, eluting with 30% to 100% EtOAc/hexane to yield the title compound (550 mg; 77%) as an off-white foam, which included a small amount of 2-pyridin-4-yl-1-benzothiophene-4-ol as an impurity. The crude material was used in the next step without further purification. LCMS: (FA) ES+ 368, 370; $^1H$ NMR (400 MHz, $d_6$-DMSO) δ ppm 8.46 (dd, 2H), 7.98 (dd, 1H), 7.82 (dd, 1H), 7.57 (d, 1H), 7.49 (dd, 2H), 7.11 (s, 1H), 3.03-3.09 (m, 1H), 2.89-2.97 (m, 1H), 2.29-2.37 (m, 1H), 2.00-2.16 (m, 3H).

Step 3: 4 5-chloro-2'-pyridin-4-yl-5',6'-dihydro-3H,7'H-spiro[2-benzofuran-1,4'-[1]benzothiophene]-3,7'-dione (Compound 14)

In a 100 mL round bottomed flask was placed 5-chloro-2'-pyridin-4-yl-6',7'-dihydro-3H,5'H-spiro[2-benzofuran-1,4'-[1]benzothiophen]-3-one (0.714 g, 1.94 mmol) (including side product) along with 1,4-dioxane (20 mL) and acetonitrile (10 mL). To the mixture was added a suspension of potassium persulfate (1.85 g, 6.84 mmol) and copper (II) sulfate pentahydrate (180 mg, 0.72 mmol) in water (20 mL) followed by γ-collidine (0.897 mL, 6.79 mmol). The mixture was stirred for 3.5 hr at 80° C. Again, to the mixture was added a suspension of potassium persulfate (1.96 g, 7.25 mmol) and copper (II) sulfate pentahydrate (20 mg, 0.08 mmol) in water (20 mL, 1000 mmol) followed by γ-collidine (0.9 mL, 7 mmol) and 1,4-dioxane (10 mL, 100 mmol). The mixture was stirred for an additional 16 hr at 80° C. The mixture was allowed to cool to rt and then diluted with EtOAc (50 mL). Insoluble materials were removed by filtration through a celite pad and the aqueous phase was separated from the filtrate. The aqueous phase was extracted with EtOAc (50 mL). The combined organic phases were dried over anhydrous $MgSO_4$. Insoluble materials were removed by filtration and the filtrate was concentrated under reduced pressure. The residue was purified by HPLC (FA) to obtain the title compound (22.5 mg; 3%) as an off-white crystalline solid. LCMS: (FA) ES+ 382, 384; $^1H$ NMR (400 MHz, $d_6$-DMSO) δ ppm 8.59 (dd, 2H), 8.07 (d, 1H), 7.89 (dd, 1H), 7.77 (d, 1H), 7.71 (dd, 2H), 7.46 (s, 1H), 2.47-3.05 (m, 4H).

Example 9

Synthesis of N-{4-[4-(4-chlorophenyl)-7-oxo-4,5,6,7-tetrahydro-1-benzothien-2-yl]pyridin-2-yl}acetamide (Compound 7)

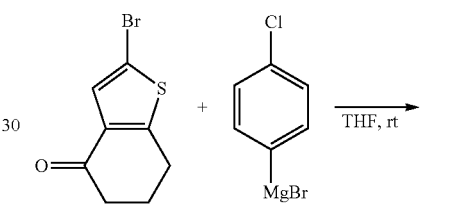

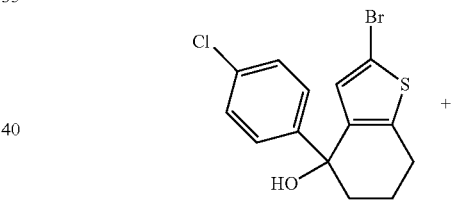

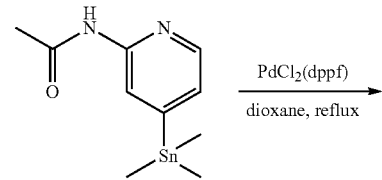

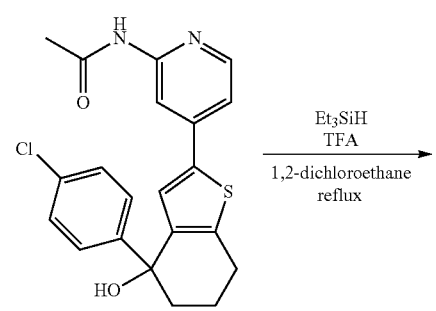

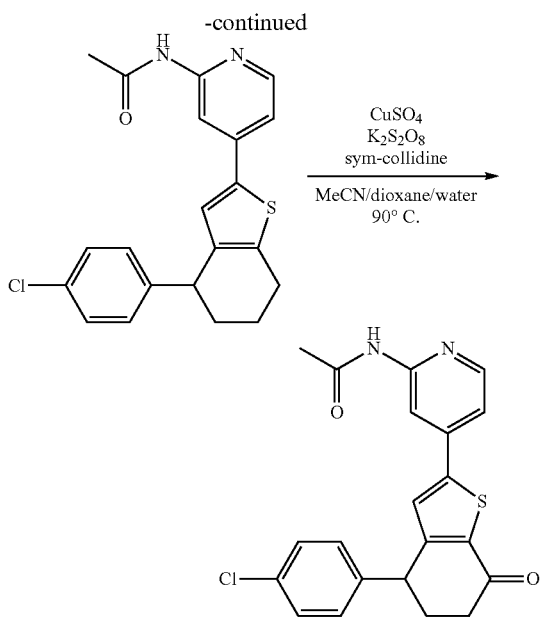

Step 1: 2-bromo-4-(4-chlorophenyl)-4,5,6,7-tetrahydro-1-benzothiophene-4-ol

In a 250 mL round bottomed flask was placed 2-bromo-6,7-dihydro-1-benzothiophen-4(5H)-one (1.9 g, 8.2 mmol) and tetrahydrofuran (30 mL). To the solution was added 4-chlorophenylmagnesium bromide in ether (1 M, 8.2 mL, 8.2 mmol) and the mixture was stirred for 30 min at rt. To the mixture were added 10% NH₄Cl aq (50 mL) and EtOAc (50 mL). The mixture was vigorously stirred for 10 min and then the aqueous phase was discarded. The organic phase was dried over anhydrous MgSO₄ and insoluble materials were removed by filtration. The filtrate was concentrated under reduced pressure and the residue was purified pre-packed silica gel (40 g) column chromatography eluted with 0% to 50% EtOAc/hexane to yield the title compound (2.4 g; 85%) as a colorless syrup. ¹H NMR (300 MHz, d-chloroform) δ ppm 7.26-7.29 (m, 4H), 6.56 (s, 1H), 2.68-2.86 (m, 2H), 1.81-2.17 (m, 5H).

Step 2: 2 N-{4-[4-(4-chlorophenyl)-4-hydroxy-4,5,6,7-tetrahydro-1-benzothien-2-yl]pyridin-2-yl}acetamide In a 100 mL round bottomed flask were placed 2-bromo-4-(4-chlorophenyl)-4,5,6,7-tetrahydro-1-benzothiophene-4-ol (640 mg, 1.9 mmol) and 1,4-dioxane (10 mL). To the mixture were added N-[4-(trimethylstannyl)pyridin-2-yl]acetamide (925 mg, 3.09 mmol) and [1,1'-bis(diphenylphosphino)ferrocene]dichloropalladium(II), complex with dichloromethane (1:1) (198 mg, 0.242 mmol). The mixture was refluxed for 16 hr with vigorous stirring. The mixture was allowed to cool to rt and then diluted with EtOAc (100 mL). The resulting solution was washed with H₂O (50 mL×2). The combined aqueous phases were extracted with EtOAc (50 mL×2). The combined organic phases were washed with brine (50 mL) and dried over MgSO4. Insoluble materials were removed by filtration and the filtrate was concentrated under reduced pressure. The residue was purified by pre-packed silica gel (40 g) column chromatography, eluting with a 30% to 100% EtOAc/hexane to obtain crude title compound (ca 500 mg). About 100 mg of this material was purified by HPLC (AA) to obtain pure title compound (74 mg; 10%). LCMS: (AA) ES+ 399, 401; ¹H NMR (400 MHz, d₆-DMSO) δ ppm 10.51 (br s, 1H), 8.23 (s, 1H), 8.20 (d, 1H), 7.36 (d, 2H), 7.30 (d, 2H), 7.19 (dd, 1H), 7.14 (s, 1H), 5.85 (s, 1H), 2.83-2.90 (m, 2H), 2.07 (s, 3H), 1.85-2.01 (m, 3H), 1.65-1.70 (m, 1H).

Step 3: N-{4-[4-(4-chlorophenyl)-4,5,6,7-tetrahydro-1-benzothien-2-yl]pyridin-2-yl}acetamide In a 100 mL round bottomed flask was placed crude N-{4-[4-(4-chlorophenyl)-4-hydroxy-4,5,6,7-tetrahydro-1-benzothien-2-yl]pyridin-2-yl}acetamide (410 mg, 1.0 mmol) prepared above and 1,2-dichloroethane (10 mL). The mixture was refluxed for 30 min to obtain a yellow solution. To the refluxing mixture were added triethylsilane (1 mL, 6 mmol) and trifluoroacetic acid (2 mL, 20 mmol), and refluxing was continued for an additional 3 hr. The mixture was allowed to cool to rt then concentrated under reduced pressure. The residue was diluted with EtOAc (50 mL) then washed with a saturated aqueous solution of NaHCO₃ (50 mL). The aqueous phase was extracted with EtOAc (50 mL). The combined organic phases were dried over anhydrous MgSO₄.

Insoluble materials were removed by filtration and the filtrate was concentrated under reduced pressure. The residue was purified by pre-packed silica gel (24 g) column chromatography, eluting with 20% to 100% EtOAc/hexane to yield the title compound (230 mg, 58%) as a colorless foam. LCMS: (FA) ES+ 383, 385; ¹H NMR (400 MHz, d₆-DMSO) δ ppm 10.49 (br s, 1H), 8.18-8.20 (m, 2H), 7.36 (d, 2H), 7.22 (dd, 1H), 7.15-7.19 (m, 2H), 7.00 (s, 1H), 4.08 (t, 1H), 2.81-2.91 (m, 2H), 2.07 (s, 3H), 1.67-1.88 (m, 4H).

Step 4: N-{4-[4-(4-chlorophenyl)-7-oxo-4,5,6,7-tetrahydro-1-benzothien-2-yl]pyridin-2-yl}acetamide (Compound 7)

In a 100 mL round bottomed flask was placed N-{4-[4-(4-chlorophenyl)-4,5,6,7-tetrahydro-1-benzothien-2-yl]pyridin-2-yl}acetamide (229.6 mg, 0.5996 mmol), 1,4-dioxane (15 mL) and acetonitrile (15 mL). To the mixture were added a solution of potassium persulfate (665.0 mg, 2.460 mmol) and copper (II) sulfate pentahydrate (68.9 mg, 0.276 mmol) in water (30 mL) and γ-collidine (320 uL, 2.4 mmol). The resulting blue-white suspension was stirred for 16 hr at 90° C. The mixture was allowed to cool to rt and then concentrated under reduced pressure to remove 1,4-dioxane and acetonitrile. The aqueous residue was extracted with EtOAc (50 mL×2). The combined organic phases were washed with 10% NaHSO₃ aq (30 mL), saturated aqueous solution of NaHCO₃ (30 mL), saturated aqueous solution of ammonium chloride (30 mL), and dried over anhydrous MgSO4. Insoluble materials were removed by filtration and the filtrate was concentrated under reduced pressure. The residue was purified by prepacked silica gel (24 g) column chromatography, eluting with 20% to 100% EtOA/hexane to yield the title compound (95 mg; 40%) as a colorless foam, which was recrystallized from EtOAc and ether to obtain a colorless crystalline solid. LCMS: (FA) ES+ 397, 399; ¹H NMR (400 MHz, d₆-DMSO) δ ppm 10.64 (br s, 1H), 8.30-8.34 (m, 2H), 7.40-7.45 (m, 3H), 7.29 (d, 2H), 7.21 (s, 1H), 4.39 (dd, 1H), 2.59-2.75 (m, 1H), 2.20-2.52 (m, 3H), 2.09 (s, 3H).

Example 10

Synthesis of N-{4-[4-(4-chlorophenyl)-8-oxo-5,6,7,8-tetrahydro-4H-thieno[2,3-c]azepin-2-yl]pyridin-2-yl}acetamide (Compound 1)

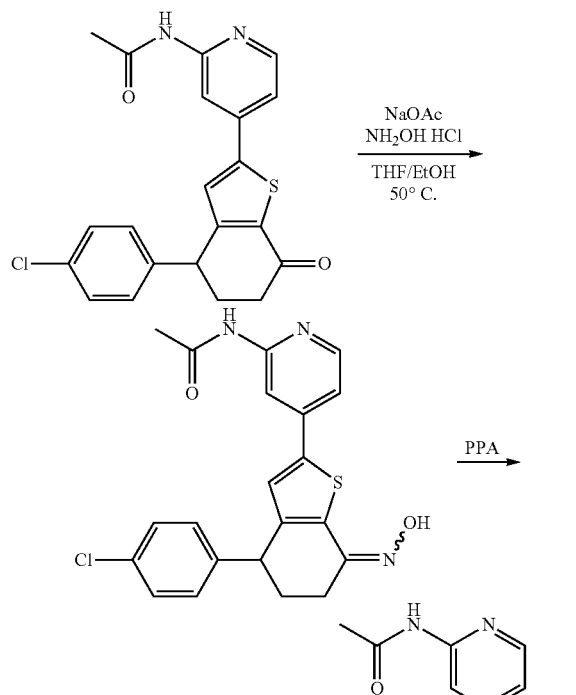

In a 100 mL round bottomed flask was placed N-{4-[4-(4-chlorophenyl)-7-oxo-4,5,6,7-tetrahydro-1-benzothien-2-yl]pyridin-2-yl}acetamide (42 mg, 0.10 mmol) along with ethanol (5 mL) and tetrahydrofuran (3 mL). To the solution were added sodium acetate (143.1 mg, 1.744 mmol) and hydroxylamine hydrochloride (111.8 mg, 1.609 mmol) and the mixture was stirred for 16 hr at 50° C. The mixture was allowed to cool to rt and then concentrated under reduced pressure. The residue was diluted with DCM (50 mL) then washed with a saturated aqueous solution of NaHCO₃ (50 mL). The aqueous phase was separated and extracted with DCM (50 mL).

The combined organic phases were dried over anhydrous MgSO₄. Insoluble materials were removed by filtration and the filtrate was concentrated under reduced pressure to yield an isomeric mixture of N-{4-[4-(4-chlorophenyl)-7-(hydroxyimino)-4,5,6,7-tetrahydro-1-benzothien-2-yl]pyridin-2-yl}acetamide (48 mg; 110%) as an off-white crystalline solid. The crude product was used in the next step without further purification.

In a 100 mL round bottomed flask was placed the N-{4-[(4-(4-chlorophenyl)-7-(hydroxyimino)-4,5,6,7-tetrahydro-1-benzothien-2-yl]pyridin-2-yl}acetamide prepared above. To this was added PPA (8.5 g, 35 mmol). The mixture was stirred for 16 hr at 130° C. The mixture was allowed to cool to ca 50° C. and then 1N NaOH aq (120 mL) was added (pH was ca 10). The mixture was stirred for 2 hr at rt and then the aqueous mixture was extracted with DCM (50 mL×3). The combined organic phases were dried over anhydrous MgSO₄ and then insoluble materials were removed by filtration. The filtrate was concentrated under reduced pressure.

The resulting solid was placed in a 100 mL round bottomed flask then acetic anhydride (5 mL, 50 mmol) and sulfuric acid (100 uL, 2 mmol) were added. The mixture was stirred for 2 hr at 100° C. then was allowed to cool to rt and then concentrated under reduced pressure.

The residue was dissolved in THF (10 mL) then treated with a saturated aqueous solution of NaHCO₃ (10 mL). The mixture was stirred for 16 hr at rt. To the mixture was added water (30 mL) and the mixture was extracted with DCM (30 mL×3). The combined organic phases were dried over anhydrous MgSO₄. Insoluble materials were removed by filtration and the filtrate was concentrated under reduced pressure. The crude material (20 mg) was purified by HPLC (AA) to obtain title compound (4.7 mg, 11%) as an off-white solid. LCMS: (FA) ES+ 412, 414; ¹H NMR (400 MHz, d₆-DMSO) δ ppm 10.59 (br s, 1H), 8.34 (t, 1H), 8.26-8.27 (m, 2H), 7.38 (d, 2H), 7.16-7.31 (m, 3H), 7.12 (s, 1H), 4.54 (dd, 1H), 3.15-3.22 (m, 2H), 2.24-2.33 (m, 1H), 2.01-2.09 (m, 4H).

Example 11

Synthesis of 4-(4-chlorophenyl)-2-(2-methylpyrazolo[1,5-a]pyridin-3-yl)-5,6-dihydro-1,3-benzothiazol-7(4H)-one (Compound 20)

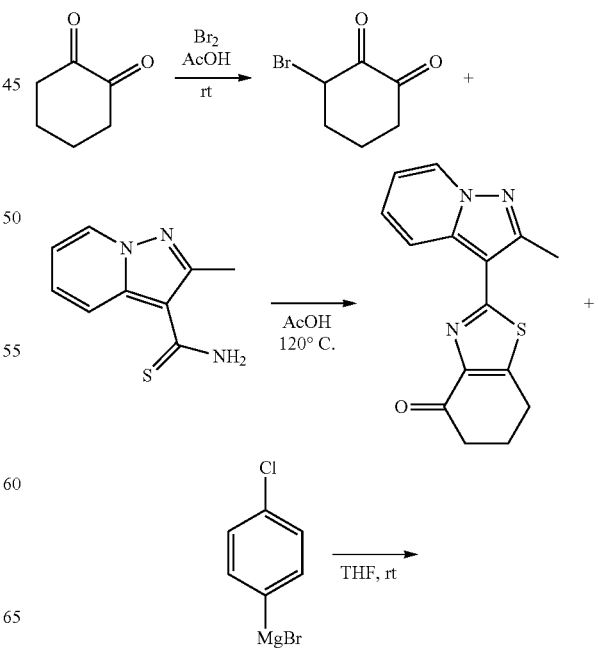

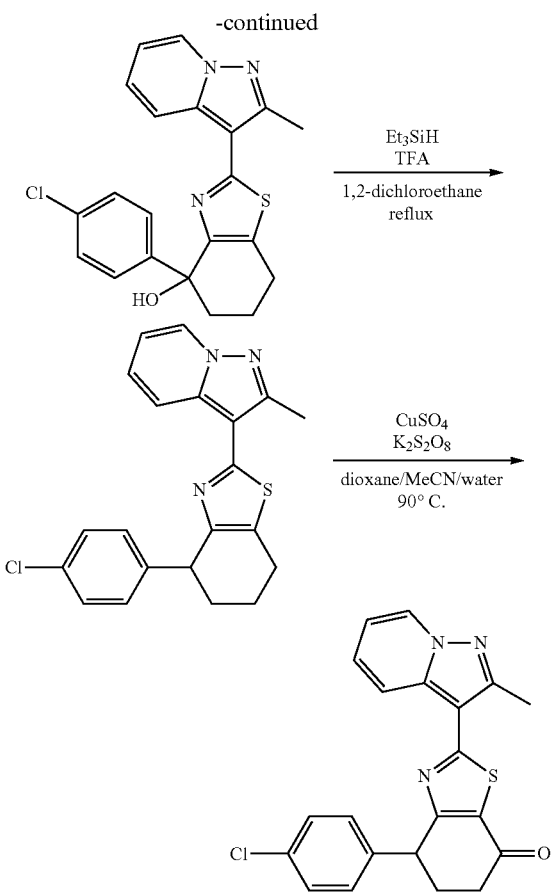

Step 1: 2-(2-methylpyrazolo[1,5-a]pyridin-3-yl)-6,7-dihydro-1,3-benzothiazol-4(5H)-one In a 250 mL round bottomed flask were placed 1,2-cyclohexanedione (1.32 g, 11.8 mmol) and acetic acid (30 mL). To the solution was added dropwise a solution of bromine (1.67 g, 10.4 mmol) in acetic acid (20 mL). The mixture was stirred for 30 min at rt. To the mixture was added 2-methylpyrazolo[1,5-a]pyridine-3-carbothioamide (1.92 g, 10.0 mmol) and the resulting suspension was stirred for 1 hr at 120° C. After 30 min the suspension turned into a clear brown solution. After 1 hour the mixture was allowed to cool to rt during which time an off-white solid precipitated. The mixture was concentrated under reduced pressure and the residue was diluted with EtOAc (100 mL) and a saturated aqueous solution of NaHCO$_3$ (100 mL). The resulting bi-phasic mixture was vigorously stirred for 30 min at rt. The aqueous phase was separated and the organic phase was washed with a 10% aqueous solution of NaHSO$_3$ (50 mL), then a saturated aqueous solution of NaHCO$_3$ (50 mL). The organic phase was dried over anhydrous MgSO$_4$. Insoluble materials were removed by filtration and the filtrate was concentrated under reduced pressure. The residue was recrystallized from EtOAc and ether to yield the title compound (1.0 g; 35%) as a yellowish off-white crystalline solid. From the mother liquor, a 2nd crop of title compound (1.5 g; 53%) was obtained. LCMS: (FA) ES+ 284; $^1$H NMR (400 MHz, d$_6$-DMSO) δ ppm 8.75 (dt, 1H), 8.29 (dt, 1H), 7.54 (dd, 1H), 7.07 (td, 1H), 3.16 (t, 2H), 2.65 (s, 3H), 2.60 (dd, 2H), 2.14-2.21 (m, 2H).

Step 2: 4-(4-chlorophenyl)-2-(2-methylpyrazolo[1,5-a]pyridin-3-yl)-4,5,6,7-tetrahydro-1,3-benzothiazole In a 250 mL round bottomed flask was placed 2-(2-methylpyrazolo[1,5-a]pyridin-3-yl)-6,7-dihydro-1,3-benzothiazol-4(5H)-one (505.1 mg, 1.783 mmol) and tetrahydrofuran (50 mL). To the mixture was added a solution of 4-chlorophenylmagnesium bromide in ether (1M, 3.0 mL, 3.0 mmol) and the mixture was stirred for 4 hr at rt. To the mixture were added a saturated aqueous solution of NH$_4$Cl (50 mL) and water (50 mL) and the resulting mixture was extracted with EtOAc (50 mL×2). The combined organic phases were dried over anhydrous MgSO$_4$. Insoluble materials were removed by filtration and the filtrate was concentrated under reduced pressure to obtain crude 4-(4-chlorophenyl)-2-(2-methylpyrazolo[1,5-a]pyridin-3-yl)-4,5,6,7-tetrahydro-1,3-benzothiazol-4-ol as a yellowish off-white crystalline solid which was used in the next step without further purification.

In a 500 mL round bottomed flask was placed 4-(4-chlorophenyl)-2-(2-methylpyrazolo[1,5-a]pyridin-3-yl)-4,5,6,7-tetrahydro-1,3-benzothiazol-4-ol prepared above. The material was suspended in 1,2-dichloroethane (50 mL) and the suspension was stirred for 60 min at 90° C. To the hot solution were added triethylsilane (2 mL, 10 mmol) and trifluoroacetic acid (3 mL, 40 mmol). The mixture Was stirred for 2 days at the same temperature. The mixture was allowed to cool to rt and then concentrated under reduced pressure. The residue was diluted with EtOAc (100 mL) and then washed with a saturated aqueous solution of NaHCO$_3$ (50 mL). The aqueous phase was extracted with EtOAc (50 mL). The combined organic phases were dried over anhydrous MgSO$_4$. Insoluble materials were removed by filtration and the filtrate was concentrated under reduced pressure. The residue was purified by pre-packed silica gel (40 g) column chromatography, eluting with 30% to 100% EtOAc/hexane to yield the title compound (622 mg; 91.8%) as a yellow crystalline solid. $^1$H NMR (400 MHz, d$_6$-DMSO) δ ppm 8.66 (dt, 1H), 7.95 (dt, 1H), 7.33-7.37 (m, 3H), 7.16 (d, 2H), 6.96 (td, 1H), 4.27 (t, 1H), 2.84-2.93 (m, 2H), 2.56 (s, 3H), 2.15-2.21 (m, 1H), 1.77-1.88 (m, 3H).

Step 3: 4-(4-chlorophenyl)-2-(2-methylpyrazolo[1,5-a]pyridin-3-yl)-5,6-dihydro-1,3-benzothiazol-7(4H)-one (Compound 20)

In a 100 mL round bottomed flask was placed 4-(4-chlorophenyl)-2-(2-methylpyrazolo[1,5-a]pyridin-3-yl)-4,5,6,7-tetrahydro-1,3-benzothiazole (250 mg, 0.66 mmol) along with 1,4-dioxane (15 mL) and acetonitrile (15 mL). To the mixture were added a solution of copper (II) sulfate pentahydrate (670 mg, 2.7 mmol) in water (10 mL) and a solution of potassium persulfate (770 mg, 2.8 mmol) in water (10 mL). The mixture was stirred for 6 hr at 90° C. The mixture was allowed to cool to rt and then insoluble materials were removed by filtration through a celite pad. The celite pad was washed with water and EtOAc. The aqueous phase was separated from the filtrate and then extracted with EtOAc (50 mL×2). The combined organic phases were washed with a 10% aqueous solution of NaHSO$_3$ (50 mL), then a saturated aqueous solution of NaHCO$_3$ (50 mL), then a saturated aqueous solution of NH$_4$Cl (50 mL), and then dried over anhydrous MgSO$_4$. Insoluble materials were removed by filtration and the filtrate was concentrated under reduced pressure. The residue was purified by pre-packed silica gel (12 g) column chromatography, eluting with 0% to 50% EtOAc/hexane to yield the title compound (100 mg; 40%) as a yellow crystalline solid. LCMS: (FA) ES+ 394, 396; $^1$H NMR (400 MHz, d$_6$-DMSO) δ ppm 8.42 (dt, 1H), 8.15 (dt, 1H), 7.32-7.35 (m, 3H), 7.17 (d, 2H), 6.90 (td, 1H), 4.45 (dd, 1H), 2.57-2.75 (m, 5H), 2.29-2.37 (m, 1H), 2.00-2.15 (m, 1H).

Example 12

Synthesis of 8-(4-chlorophenyl)-2-(2-methylpyrazolo[1,5-a]pyridin-3-yl)-4,6,7,8-tetrahydro-5H-[1,3]thiazolo[5,4-b]azepin-5-one (Compound 11)

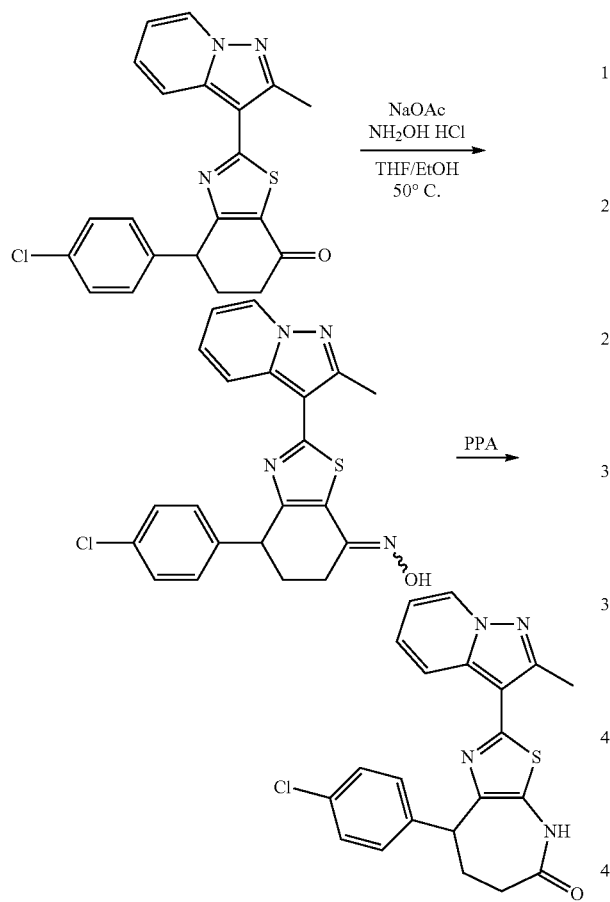

Into a 100 mL round bottomed flask was placed 4-(4-chlorophenyl)-2-(2-methylpyrazolo[1,5-a]pyridin-3-yl)-5,6-dihydro-1,3-benzothiazol-7(4H)-one (150 mg, 0.38 mmol) followed by tetrahydrofuran (5 mL) and ethanol (5 mL). To the mixture were added sodium acetate (132.7 mg, 1.618 mmol) and hydroxylamine hydrochloride (120.1 mg, 1.728 mmol) and the mixture was stirred for 16 hr at 50° C. The reaction mixture was allowed to cool to rt and then concentrated under reduced pressure. The residue was diluted with DCM (50 mL) then was washed with a saturated aqueous solution of NaHCO$_3$ (50 mL). The aqueous phase was extracted with DCM (50 mL). The combined organic phases were dried over anhydrous MgSO$_4$. Insoluble materials were removed by filtration and the filtrate was concentrated under reduced pressure to obtain an isomeric mixture of 4-(4-chlorophenyl)-2-(2-methylpyrazolo[1,5-a]pyridin-3-yl)-5,6-dihydro-1,3-benzothiazol-7(4H)-one oxime (150 mg; 96%) as a yellow solid. The crude product was essentially pure and was used in the next step without further purification.

In a 100 mL round bottomed flask was placed the crude 4-(4-chlorophenyl)-2-(2-methylpyrazolo[1,5-a]pyridin-3-yl)-5,6-dihydro-1,3-benzothiazol-7(4H)-one oxime prepared above and then PPA (10 g, 40 mmol) was added. The mixture was stirred for 2 hr at 130° C. During this period, the mixture was occasionally mixed manually. After 2 hours crushed ice (ca 30 mL) was added to the hot mixture which was stirred for 10 min.

The color of the mixture changed to yellow from brown. To the mixture were added 1N NaOH aq (ca 200 mL) and crushed ice (ca 50 mL) and the mixture was stirred for 10 min at rt. The aqueous mixture was extracted with DCM (50 mL×3). The combined organic phases were dried over anhydrous MgSO$_4$. Insoluble materials were removed by filtration and the filtrate was concentrated to obtain a yellow foam, which was purified by HPLC to obtain the title compound (123 mg; 79%) as a yellowish off-white solid. LCMS: (FA) ES+ 409, 411; $^1$H NMR (400 MHz, d$_6$-DMSO) δ ppm 11.60 (s, 1H), 8.71 (d, 1H), 8.02 (d, 1H), 7.37-7.43 (m, 3H), 7.19 (d, 2H), 7.00 (td, 1H), 4.50 (t, 1H), 2.53-2.66 (m, 5H), 2.30-2.37 (m, 1H), 2.03-2.11 (m, 1H).

Example 13

Synthesis of 4-(4-chlorophenyl)-2-(pyridin-4-yl)-4H-cyclopenta[b]thiophen-6(5H)-one (Compound 23)

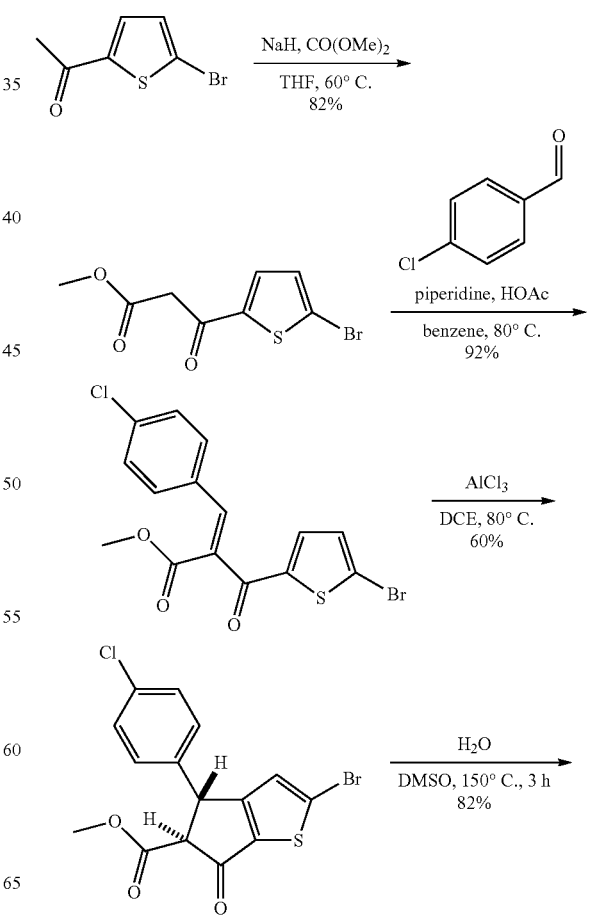

-continued

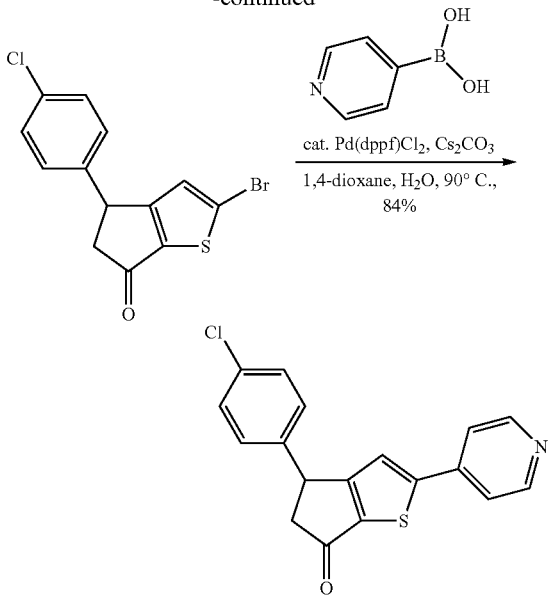

Step 1: Preparation methyl 3-(5-bromothiophen-2-yl)-3-oxopropanoate

To a 500 mL round bottom flask was added a suspension of sodium hydride (1.950 g, 48.76 mmol) in tetrahydrofuran (250.00 mL, 3082.3 mmol). Dimethyl carbonate (8.218 mL, 97.53 mmol) was added followed by 2-bromo-5-acetylthiophene (5.000 g, 24.382 mmol) which was added in portions. The reaction mixture was heated to 60° C. and allowed to stir for 18 hours. The reaction was cooled to ambient temperature and quenched by the dropwise addition of water (100.0 mL). The mixture was acidified to pH 2 with 6N HCl (8.00 mL) and extracted with diethyl ether (150.00 mL×3). The combined organic layers were dried over anhydrous MgSO4, filtered and concentrated under reduced pressure. The crude material was split in half and dry loaded onto silica gel and then purified using a ISCO (40 g cartridge, gradient hexanes to 25% EtOAc over 30 min) to afford the title compound (5.547 g, 82%) as a brown oil. LC/MS (AA) ES+ 263, 265. 1H NMR (dmso-d6, 400 MHz): δ 7.87 (d, 1H), 7.45 (d, 1H), 4.13 (s, 2H), 3.65 (s, 3H).

Step 2: Preparation of (Z)-methyl 2-(5-bromothiophene-2-carbonyl)-3-(4-chlorophenyl)acrylate To a 500 mL round bottom flask was added a solution of methyl 3-(5-bromo-2-thienyl)-3-oxopropanoate (4.402 g, 16.73 mmol), 4-chlorobenzaldehyde (2.822 g, 20.08 mmol) and piperidine (0.165 mL, 1.673 mmol) in anhydrous benzene (200.0 mL, 2238 mmol). Acetic acid (0.665 mL, 11.712 mmol) was added and the reaction mixture was fitted with a Dean-Stark trap and the bath was heated to 92° C. and allowed to reflux for 18 hours. The reaction was cooled to ambient temperature and concentrated under reduced pressure. The crude material was split in half and dry loaded onto silica gel and then purified using a ISCO (40 g cartridge, gradient hexanes to 40% EtOAc over 30 min) to afford the title compound (6.26 g, 92%) as a yellow solid. LC/MS (AA) ES− 385, 387, 389(dmso-d6, 400 MHz): δ 7.89 (s, 1H), 7.34-7.24 (m, 5H), 7.00 (d, 1H), 3.71 (s, 3H).

Step 3: Preparation of trans-methyl 2-bromo-4-(4-chlorophenyl)-6-oxo-5,6-dihydro-4H-cyclopenta[b]thiophene-5-carboxylate To a 500 mL round bottom flask was added a solution of methyl (2Z)-2-[(5-bromo-2-thienyl)carbonyl]-3-(4-chlorophenyl)acrylate (6.26 g, 16.2 mmol), in 1,2-dichloroethane (210.0 mL, 2665.4 mmol). Aluminum trichloride (2.164 g, 16.23 mmol) was added and the reaction mixture was heated to 80° C. and allowed to stir for 18 hours. The reaction was cooled to ambient temperature and concentrated under reduced pressure. The crude material was dry loaded onto silica gel and then purified using a ISCO (40 g cartridge, gradient hexanes to 30% EtOAc over 30 min) to afford the title compound (3.96 g, 60%) as a brown oil. LC/MS (AA) ES− 385, 387, 389. 1H NMR (dmso-d6, 400 MHz): δ 7.43-7.29 (m, 5H), 4.91 (d, 1H), 4.04 (d, 1H), 3.71 (s, 3H).

Step 4: Preparation of 2-bromo-4-(4-chlorophenyl)-4H-cyclopenta[b]thiophen-6(5H)-one To a 500 mL round bottom flask was added a solution of methyl 2-bromo-4-(4-chlorophenyl)-6-oxo-5,6-dihydro-4H-cyclopenta[b]thiophene-5-carboxylate (3.96 g, 10.3 mmol) in dimethyl sulfoxide (88.393 mL, 1245.6 mmol). Water (4.420 mL, 245.3 mmol) was added and the reaction mixture was heated to 150° C. and allowed to stir for 3 hours. The reaction was cooled to ambient temperature and quenched by the addition of a saturated aqueous solution of sodium bicarbonate (500 mL) and extracted with EtOAc (300 mL×3). The combined organic layers were dried over anhydrous Na2SO4, filtered and concentrated under reduced pressure. The crude material was dry loaded onto silica gel and then purified using a ISCO (40 g cartridge, gradient hexanes to 100% EtOAc over 30 min) to afford the title compound (2.91 g, 82%) as a brown oil. LC/MS (AA) ES− 327, 329, 331. 1H NMR (dmso-d6, 400 MHz): δ 7.40-7.38 (m, 2H), 7.31 (s, 1H). 7.24-7.22 (m, 2H), 4.67 (dd, 1H), 3.40 (dd, 1H), 2.72 (dd, 1H).

Step 5: Preparation of 4-(4-chlorophenyl)-2-(pyridin-4-yl)-4H-cyclopenta[b]thiophen-6(5H)-one (Compound 23)

To a 40 mL vial was added a solution of 2-bromo-4-(4-chlorophenyl)-4,5-dihydro-6H-cyclopenta[b]thiophen-6-one (0.150 g, 0.458 mmol) and pyridine-4-boronic acid (0.105 g, 0.855 mmol) in a solution of 1,4-dioxane (8.000 mL, 102.5 mmol) and water (0.800 mL, 44.4 mmol). Cesium carbonate (0.448 g, 1.374 mmol) was added followed by [1,1′-bis(diphenylphosphino)ferrocene]palladium(II)dichloride (0.045 g, 0.055 mmol). The reaction mixture was heated to 90° C. and allowed to stir for 18 h. The reaction was cooled to ambient temperature and quenched by the addition of a saturated aqueous solution of sodium bicarbonate (10.0 mL) and extracted with EtOAc (10.0 mL×3). The combined organic layers were dried over anhydrous Na2SO4, filtered and concentrated under reduced pressure. The crude material was dry loaded onto silica gel and then purified using ISCO (12 g cartridge, gradient hexanes to 100% EtOAc over 30 min) to afford the title compound (0.132 g, 84%) as a white solid. LC/MS (AA) ES+ 326, 328. 1H NMR (dmso-d6, 400

MHz): δ 8.65-8.63 (m, 2H), 7.79 (s, 1H). 7.77-7.76 (m, 2H), 7.42-7.40 (m, 2H), 7.30-7.28 (m, 2H), 4.72 (dd, 1H), 3.49 (dd, 1H), 2.81 (dd, 1H).

Example 14

Synthesis of 4-(4-chlorophenyl)-2-morpholino-4H-cyclopenta[b]thiophen-6(5H)-one (Compound 28)

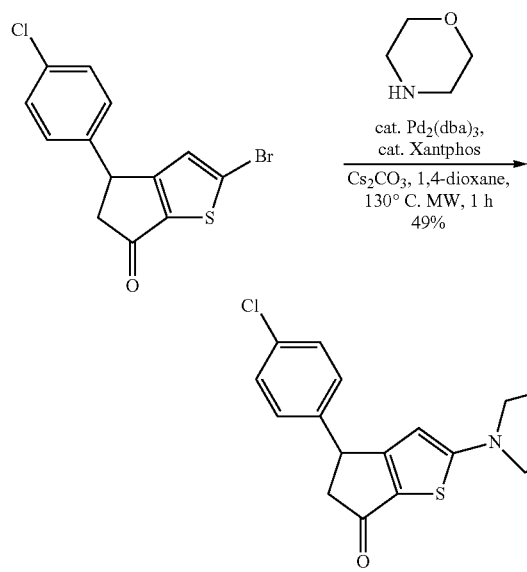

To a 10-20 mL microwave vial was added a solution of 2-bromo-4-(4-chlorophenyl)-4,5-dihydro-6H-cyclopenta[b]thiophen-6-one (0.150 g, 0.458 mmol) and morpholine (0.120 mL, 1.374 mmol) in anhydrous 1,4-dioxane (8.00 mL, 102.5 mmol) and degassed under nitrogen for 10 min. Cesium carbonate (0.694 g, 2.130 mmol) and 4,5-bis(diphenylphosphino)-9,9-dimethylxanthene (0.080 g, 0.137 mmol) was added followed by tris(dibenzylideneacetone)dipalladium(0) (0.042 g, 0.046 mmol). The reaction mixture was sealed and heated via microwave to 140° C. and allowed to stir for 1 hour. The reaction was cooled to ambient temperature and quenched by the addition of a solution of saturated aqueous solution of sodium bicarbonate (10.0 mL) and extracted with EtOAc (10.0 mL×3). The combined organic layers were dried over anhydrous $Na_2SO_4$, filtered and concentrated under reduced pressure. The crude material was dry loaded onto silica gel and then purified using an ISCO (12 g cartridge, gradient hexanes to 100% EtOAc over 30 min) to afford the title compound (0.088 g, 49%) as a brown oil. LC/MS (AA) ES+ 334, 336. $^1$H NMR (dmso-d6, 400 MHz): δ 7.38 (d, 2H), 7.19 (d, 2H), 6.04 (s, 1H), 4.48 (dd, 1H), 3.69-3.68 (m, 4H), 3.27-3.19 (m, 6H).

Compounds in the following table are prepared from appropriate starting materials in a method analogous to that of Examples 13 and 14.

| | |
|---|---|
| 117 | LC/MS: (AA) ES+ 352, 354 |
| 119 | LC/MS: (AA) ES+ 350 |
| 145 | LC/MS: (AA) ES+ 334, 336 |
| 158 | LC/MS: (AA) ES+ 364, 366 |

-continued

| | |
|---|---|
| 171 | LC/MS: (AA) ES+ 368, 370, 372 |
| 183 | LC/MS: (AA) ES+ 351 |
| 186 | LC/MS: (FA) ES+ 334, 336 |

Example 15

Synthesis of N-(4-(4-(4-chlorophenyl)-6-oxo-5,6-dihydro-4H-cyclopenta[b]thiophen-2-yl)pyridin-2-yl)acetamide (Compound 16)

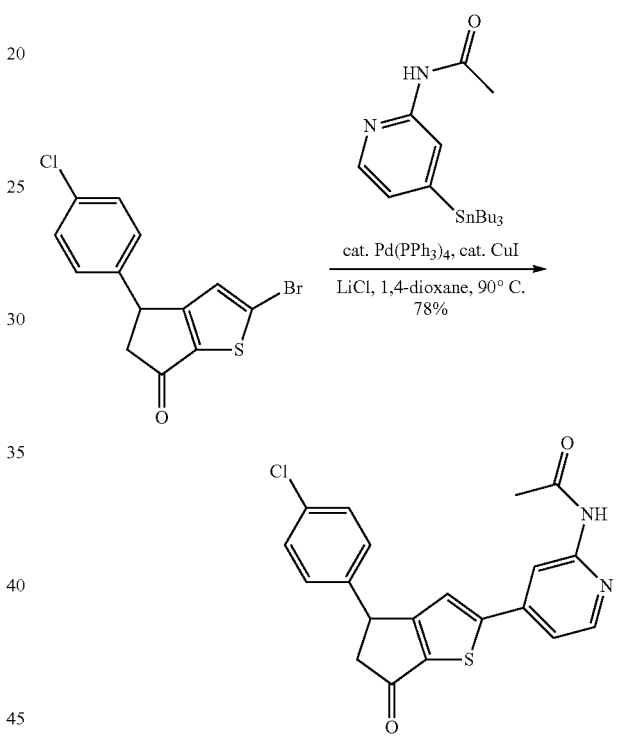

To a 20 mL vial was added a solution of 2-bromo-4-(4-chlorophenyl)-4,5-dihydro-6H-cyclopenta[b]thiophen-6-one (0.046 g, 0.141 mmol) and N-[4-(trimethylstannyl)pyridin-2-yl]acetamide (0.063 g, 0.211 mmol) in anhydrous 1,4-dioxane (2.00 mL, 25.63 mmol) was degassed for 10 minutes. Lithium chloride (0.018 g, 0.42 mmol) and copper(I) iodide (0.008 g, 0.043 mmol) was added followed by tetrakis(triphenylphosphine)palladium(0) (0.008 g, 0.007 mmol). The reaction mixture was heated to 90° C. and allowed to stir for 18 h. The reaction was cooled to ambient temperature and quenched by the addition of a saturated aqueous solution of sodium bicarbonate (2.00 mL) and extracted with EtOAc (2.00 mL×3). The combined organic layers were dried over anhydrous $Na_2SO_4$, filtered and concentrated under reduced pressure. The crude material was dry loaded onto silica gel and then purified using an ISCO (12 g cartridge, gradient hexanes to 100% EtOAc over 30 min) to afford the title compound (0.044 g, 78%) as a yellow oil. LC/MS (AA) ES+ 383, 385. 1H NMR (dmso-d6, 400 MHz): δ 10.68 (s, 1H), 8.40 (s, 1H), 8.36 (d, 1H), 7.66 (s, 1H), 7.50 (dd, 1H), 7.42-7.40 (m, 2H), 7.30-7.28 (m, 2H), 4.72 (dd, 1H), 3.48 (dd, 1H), 2.82 (dd, 1H), 2.11 (s, 3H).

Example 16

Synthesis of trans-methyl 4-(4-chlorophenyl)-6-oxo-2-(pyridin-4-yl)-5,6-dihydro-4H-cyclopenta[b]thiophene-5-carboxylate (Compound 29)

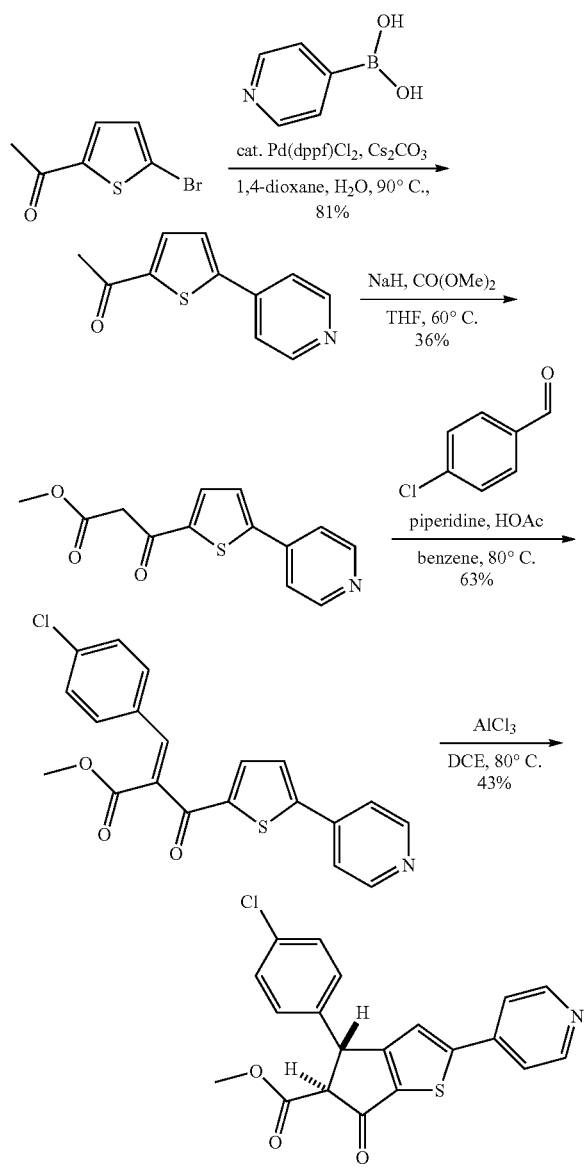

Step 1: Preparation of 1-(5-(pyridin-4-yl)thiophen-2-yl)ethanone

To a 100 mL round bottom flask was added a solution of 2-bromo-5-acetylthiophene (0.500 g, 2.438 mmol) and pyridine-4-boronic acid (0.560 g, 4.555 mmol) in a solution of 1,4-dioxane (20.00 mL, 256.3 mmol) and water (4.00 mL, 222 mmol). Cesium carbonate (2.383 g, 7.314 mmol) was added followed by [1,1'-bis(diphenylphosphino)ferrocene] palladium(II)dichloride (0.2407 g, 0.293 mmol). The reaction mixture was fitted with an air condenser and heated to 90° C. and allowed to stir for 18 h. The reaction was cooled to ambient temperature and quenched by the addition of a saturated aqueous solution of sodium bicarbonate (10.00 mL) and extracted with EtOAc (10.00 mL×3). The combined organic layers were dried over anhydrous Na2SO4, filtered and concentrated under reduced pressure The crude material was dry loaded onto silica gel and then purified using a ISCO (24 g cartridge, gradient hexanes to 100% EtOAc over 30 min) to afford the title compound (0.423 g, 81%) as a yellow solid. LC/MS (AA) ES+ 204. 1H NMR (dmso-d6, 400 MHz): δ 8.65-8.64 (m, 2H), 8.02 (d, 1H), 7.92 (d, 1H), 7.76-7.75 (m, 2H), 2.58 (s, 3H).

Step 2: Preparation of methyl 3-oxo-3-(5-(pyridin-4-yl)thiophen-2-yl)propanoate

To a 100 mL round bottom flask was added a suspension of sodium hydride (0.1574 g, 3.936 mmol) in tetrahydrofuran (16.000 mL, 197.26 mmol). Dimethyl carbonate (0.663 mL, 7.872 mmol) was added followed by 1-(5-pyridin-4-yl-2-thienyl)ethanone (0.400 g, 1.968 mmol) which was added in portions. The red reaction mixture was heated to 60° C. and allowed to stir for 18 hours. The reaction was cooled to ambient temperature and quenched by the dropwise addition of water (5.00 mL). The mixture was neutralized to pH 7 by the addition of a saturated aqueous solution of ammonium chloride (10.00 mL) and extracted with EtOAc (70.00 mL×3). The combined organic layers were dried over anhydrous Na2SO4, filtered and concentrated under reduced pressure. The crude material was dry loaded onto silica gel and then purified using ISCO (12 g cartridge, gradient hexanes to 100% EtOH over 30 min) to afford the title compound (0.197 g, 36%) as a yellow oil. LC/MS (AA) ES+ 262. 1H NMR (dmso-d6, 400 MHz): δ 8.67-8.65 (m, 2H), 8.08 (d, 1H), 7.94 (d, 1H), 7.78-7.77 (m, 2H), 4.20 (s, 2H), 3.67 (s, 3H).

Step 3: Preparation of (Z)-methyl 3-(4-chlorophenyl)-2-(5-(pyridin-4-yl)thiophene-2-carbonyl)acrylate To a 100 mL round bottom flask was added a solution of methyl 3-oxo-3-(5-pyridin-4-yl-2-thienyl)propanoate (0.150 g, 0.574 mmol), 4-chlorobenzaldehyde (0.097 g, 0.689 mmol) and piperidine (0.006 mL, 0.057 mmol) in anhydrous benzene (10.00 mL, 111.9 mmol). Acetic acid (0.023 mL, 0.401 mmol) was added and the reaction mixture was fitted with a Dean-Stark trap and the bath was heated to 92° C. and allowed to reflux for 18 hours. The reaction was cooled to ambient temperature and concentrated under reduced pressure. The crude material was dry loaded onto silica gel and then purified using ISCO (12 g cartridge, gradient hexanes to 100% EtOAc over 30 min) to afford the title compound (0.145 g, 63%) as a white solid. LC/MS (AA) ES+ 384, 386. 1H NMR (dmso-d6, 400 MHz): δ 8.66-8.65 (m, 2H), 8.00 (d, 1H), 7.84-7.75 (m, 4H), 7.47-7.46 (m, 4H), 3.76 (s, 3H).

Step 4: Preparation of trans-methyl 4-(4-chlorophenyl)-6-oxo-2-(pyridin-4-yl)-5,6-dihydro-4H-cyclopenta[b]thiophene-5-carboxylate (Compound 29)

To a 20 mL vial was added a solution of methyl (2Z)-3-(4-chlorophenyl)-2-[(5-pyridin-4-yl-2-thienyl)carbonyl]acrylate (0.049 g, 0.128 mmol), in 1,2-dichloroethane (4.000 mL, 50.77 mmol). Aluminum trichloride (0.0340 g, 0.255 mmol) was added and the reaction mixture was heated to 80° C. and allowed to stir for 2 days. The reaction was cooled to ambient temperature and quenched by the addition of a saturated aqueous solution of sodium bicarbonate (5.00 mL) and extracted with EtOAc (10.00 mL×3). The combined organic layers were dried over anhydrous Na2SO4, filtered and concentrated under reduced pressure. The crude material was dry loaded onto silica gel and then purified using ISCO (12 g cartridge, gradient hexanes to 100% EtOAc over 30 min) to afford the title compound (0.022 g, 43%) as a yellow oil. LC/MS (AA) ES+ 384, 386. 1H NMR (dmso-d6, 400 MHz): δ 8.66-8.65 (m, 2H), 7.81-7.78 (m, 3H), 7.45-7.34 (m, 4H), 4.96 (d, 1H), 4.13 (d, 1H), 3.72 (s, 3H).

Example 17

Synthesis of 4-(4-chlorophenyl)-2-morpholin-4-yl-6-oxo-4,6-dihydrothieno[2,3-c]furan-3-carbonitrile (Compound 3)

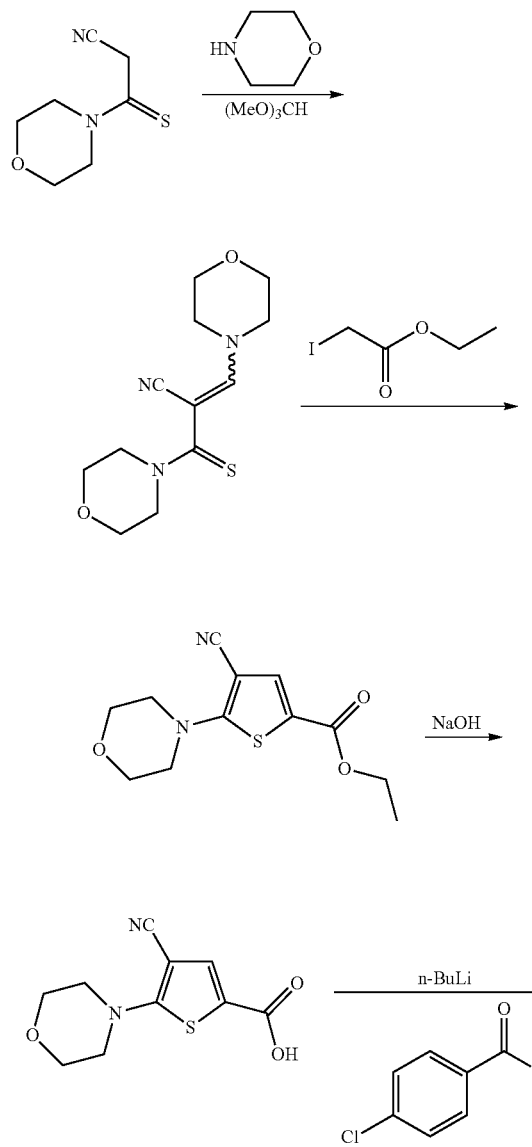

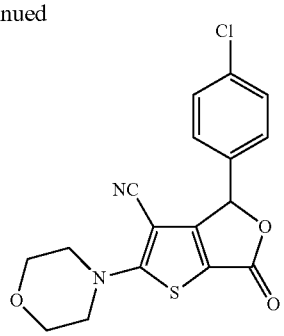

Step 1: 3-morpholin-4-yl-2-(morpholin-4-ylcarbonothioyl)acrylonitrile

To a solution of 3-morpholin-4-yl-3-thioxopropanenitrile (0.1 g, 0.59 mmol) in triethylorthoformate (0.245 mL, 1.48 mmol) was added morpholine (0.064 mL, 0.73 mmol). The reaction mixture was subjected to microwave irradiation at 150° C. for 10 min. The reaction mixture was concentrated to small volume until the product precipitated. The precipitate was filtered off, washed with MeOH and hexane to give the title compound (0.13 g, 83%). LCMS: (AA) ES+ 268.2. $^1$H NMR (400 MHz, $d_6$-DMSO) δ: 3.96 (m, 4H) and 3.67-3.78 (m, 12H).

Step 2: ethyl 4-cyano-5-morpholin-4-ylthiophene-2-carboxylate

A mixture of 3-morpholin-4-yl-2-(morpholin-4-ylcarbonothioyl)acrylonitrile (0.07 g, 0.26 mmol), ethyl iodoacetate (0.034 mL, 0.29 mmol) and DIPEA (0.091 mL, 0.52 mmol) in ACN (0.55 mL) was subjected to microwave irradiation at 120° C. for 10 min. The crystals formed upon cooling were filtered, washed with cold MeOH and diethyl ether to give the title compound (0.06 g, 87%). LCMS: (AA) ES+ 267.1. $^1$H NMR (400 MHz, CDCl$_3$) δ: 7.62 (s, 1H), 4.30 (q, 2H), 3.85-3.87 (m, 4H), 3.58-3.60 (m, 4H) and 1.34 (t, 3H).

Step 3: 4-cyano-5-morpholin-4-ylthiophene-2-carboxylic acid

To a solution of ethyl 4-cyano-5-morpholin-4-ylthiophene-2-carboxylate (0.06 g, 0.23 mmol) in THF/MeOH/water (3:1:1) (5 mL) was added sodium hydroxide (0.095 g, 2.3 mmol). The reaction mixture was allowed to stir at rt for 20 h and was concentrated. The residue was acidified to pH 1-2 with 1N HCl and was extracted with EtOAc. The organic solutions were combined, washed with brine, dried over MgSO$_4$, filtered and concentrated to give the title compound (0.048 g, 88%). LCMS: (FA) ES+ 239.1. $^1$H NMR (400 MHz, $d_6$-DMSO) δ:7.67 (s, 1H), 3.72-3.75 (m, 4H) and 3.52-3.55 (m, 4H).

Step 4: 4-(4-chlorophenyl)-2-morpholin-4-yl-6-oxo-4,6-dihydrothieno[2,3-c]furan-3-carbonitrile (Compound 3)

A solution of 4-cyano-5-morpholin-4-ylthiophene-2-carboxylic acid (0.1 g, 0.42 mmol) in anhydrous THF (1.5 mL) was cooled down to −70° C. To this cooled solution was added a 2.5 M solution of n-butyl lithium in hexanes (0.672 mL, 1.68 mmol) dropwise under nitrogen. The resulting solution was stirred at −70° C. for 2 h and 4-chlorobenzaldehyde (0.142 mL, 1.26 mmol) was added. The reaction mixture was stirred at −70° C. for a further 2 h and was quenched with water. The mixture was concentrated to a small volume and the aqueous residue was washed with EtOAc. The aqueous solution was separated, acidified with 1N HCl and extracted with EtOAc. The organic solutions were combined, washed with brine, dried over MgSO$_4$, filtered and concentrated. The crude material was purified by column chromatography to give the title compound (0.020 g, 13%), LCMS: (FA) ES+ 361, 363. $^1$H NMR (400 MHz, d$_6$-DMSO) δ: 7.54 (d, J=8.48 Hz, 2H), 7.38 (d, J=8.48 Hz, 2H), 6.72 (s, 1H), 3.77-3.73 (m, 4H), 3.65-3.60 (m, 4H)

Example 18

Synthesis of 4-(4-chlorophenyl)-6-pyridin-4-yl-3,4-dihydro-2H-thieno[3,2-e][1,2]thiazin-4-ol 1,1-dioxide (Compound 26)

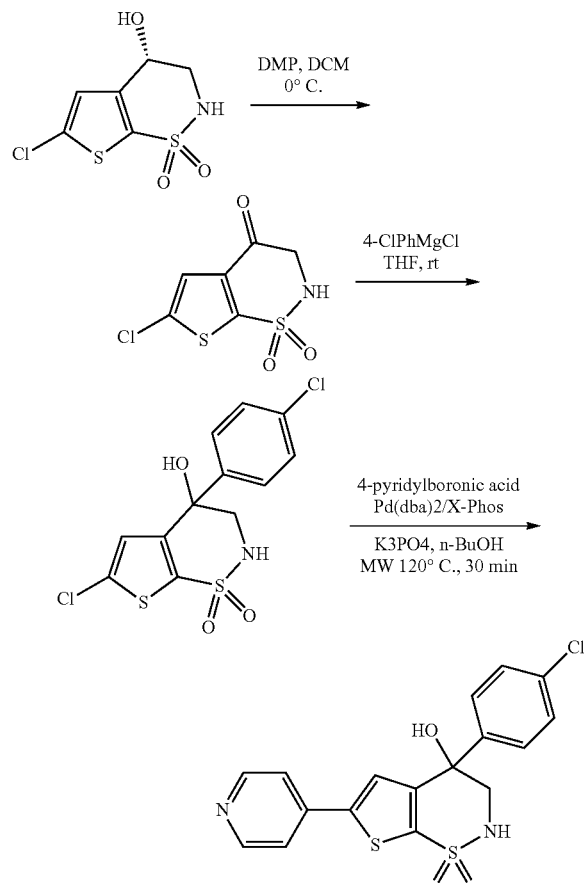

Step 1: 6-chloro-2,3-dihydro-4H-thieno[3,2-e][1,2]thiazin-4-one 1,1-dioxide (4-S)-6-chloro-3,4-dihydro-2H-thieno[3,2-e][1,2]thiazin-4-ol 1,1-dioxide (1.50 g, 6.26 mmol; purchased from Waterstone Technology) was suspended in DCM (100 mL) and the suspension was cooled at 0° C. Dess-Martin periodinane (3.54 g, 8.34 mmol) was added and the mixture was stirred at 0° C. for 1 hour. At that time, TLC indicated nearly complete conversion. Mixture was quenched with satd. NaHCO$_3$ (50 mL) and extracted with DCM (3×50 mL). DCM layer was dried with MgSO$_4$, filtered and evaporated. The residue was purified using column chromatography on silica gel (80 g Analogix column, gradient 5% EA in hexane to 50% EA in hexane over 20 minutes) to give the title compound (0.82 g, 53%). LCMS: (FA) ES 236, 238. $^1$H NMR (400 MHz, d$_6$-DMSO) δ: 9.06 (t, J=7.05, 1H), 7.57 (s, 1H), 4.27 (d, J=7.05 Hz, 2H).

Step 2: 6-chloro-4-(4-chlorophenyl)-3,4-dihydro-2H-thieno[3,2-e][1,2]thiazin-4-ol 1,1-dioxide 6-chloro-2,3-dihydro-4H-thieno[3,2-e][1,2]thiazin-4-one 1,1-dioxide (0.820 g, 3.45 mmol) was dissolved in THF (31 mL) and 1 M of 4-Chlorophenylmagnesium bromide in ether (8.2 mL, 8.2 mmol) was added. The solution was stirred at room temperature overnight. At that time, TLC indicated good conversion. Reaction was quenched by addition of satd NaHCO$_3$ (20 mL) and extracted with EA (3×50 mL). The combined organic extracts were washed with brine (20 mL), dried with MgSO4, filtered and evaporated. The residue was purified using column chromatography on silica gel (80 g Analogix column, gradient 10% EA in hexane to 40% EA in hexane over 20 minutes) to give the product (0.34 g, 26%). LCMS: (FA) ES-348, 350, 352. $^1$H NMR (400 MHz, d$_6$-DMSO) δ: 8.41 (dd, J=8.75, 5.76 Hz, 1H), 7.49-7.42 (m, 2H), 7.33-7.25 (m, 2H), 6.74 (s, 1H), 6.57 (s, 1H), 3.70-3.60 (m, 2H).

Step 3: 4-(4-chlorophenyl)-6-pyridin-4-yl-3,4-dihydro-2H-thieno[3,2-e][1,2]thiazin-4-ol 1,1-dioxide (Compound 26)

6-chloro-4-(4-chlorophenyl)-3,4-dihydro-2H-thieno[3,2-e][1,2]thiazin-4-ol 1,1-dioxide (0.180 g, 0.514 mmol), pyridine-4-boronic acid (0.126 g, 1.03 mmol), Bis(dibenzylideneacetone)palladium(0) (0.0296 g, 0.0514 mmol), 2-dicyclohexylphosphino-2',4',6'-tri-i-propyl-1,1'-biphenyl (0.0980 g, 0.206 mmol) and Potassium phosphate (0.327 g, 1.54 mmol) were combined in microwave vial and flushed with argon. 1-Butanol (10 mL) was added and the reaction was microwaved on 150 watts, 120° C. for 30 minutes. LCMS indicated the product of coupling. The solvent was evaporated and the residue was purified using column chromatography on silica gel (40 g Analogix column, gradient 10% EA in hexane to 100% EA in hexane over 25 minutes) to give the title compound (110 mg, 52%). LCMS: (FA) ES+ 393, 395. $^1$H NMR (400 MHz, d$_6$-DMSO) δ: 8.59 (dd, J=4.54, 1.64 Hz, 2H), 8.36 (d, J=0.94 Hz, 1H), 7.68 (dd, J=4.52, 1.68 Hz, 2H), 7.50-7.41 (m, 3H), 6.57 (s, 1H), 7.39-7.27 (m, 2H), 3.75-3.59 (m, 2H).

Step 4: Enantiomeric Separation to Compounds 2 and 9

Racemic 4-(4-chlorophenyl)-6-pyridin-4-yl-3,4-dihydro-2H-thieno[3,2-e][1,2]thiazin-4-ol 1,1-dioxide was separated into enantiomers on a Chiralpak OJ 4.6×250 column using 75/25/0.1 Hexane-EtOH-DEA mixture. The faster moving enantiomer (21.8 min) was arbitrarily assigned as (R), while the slower moving enantiomer (30.2 min) was arbitrarily assigned as (S).

Example 19

Synthesis of 4-(4-chlorophenyl)-6-pyridin-4-yl-2H-thieno[3,2-e][1,2]thiazine 1,1-dioxide (Compound 27)

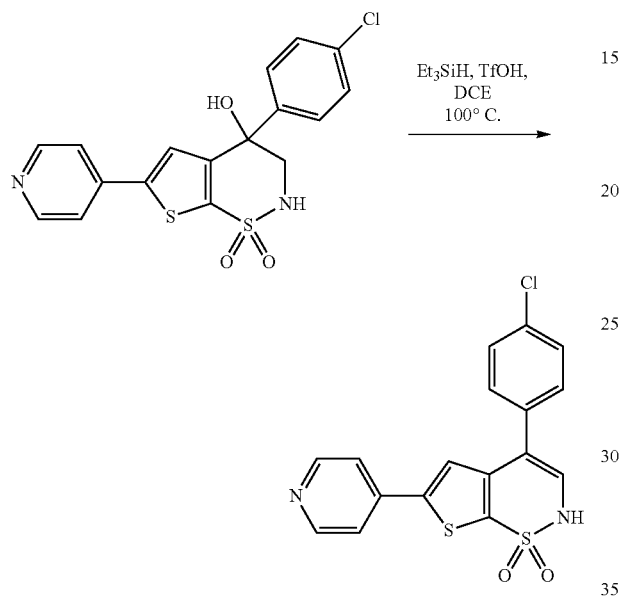

4-(4-chlorophenyl)-6-pyridin-4-yl-3,4-dihydro-2H-thieno[3,2-e][1,2]thiazin-4-ol 1,1-dioxide (25 mg, 0.064 mmol) was suspended in 1,2-Dichloroethane (1.0 mL) and triethylsilane (0.1016 mL, 0.6363 mmol) and Trifluoromethanesulfonic acid (0.02815 mL, 0.3182 mmol) were added to a pressure tube and the resulting yellowish solution was heated at 90° C. overnight. At that time, LCMS indicated mainly the product of elimination. Mixture was cooled to room temperature, solid NaHCO$_3$ (20 mg) was added, mixture was filtered and the filtrate was absorbed on silica gel (1 g). The material was purified by ISCO using DCM to 10% MeOH in DCM over 10 minutes to afford the title compound (10 mg, 42%). LCMS: (FA) ES+ 375, 377. $^1$H NMR (400 MHz, d$_6$-DMSO) δ: 8.63 (dd, J=4.60, 1.62 Hz, 2H), 7.79 (dd, J=4.58, 1.63 Hz, 2H), 7.64 (s, 1H), 7.51 (s, 4H), 7.06 (s, 1H).

Example 20

Synthesis of 4-(4-chlorophenyl)-2-pyridin-4-yl-4,5,6,7-tetrahydro-8H-cyclohepta[b]thiophen-8-one (Compound 19)

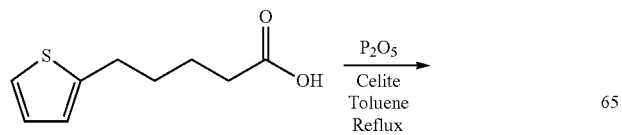

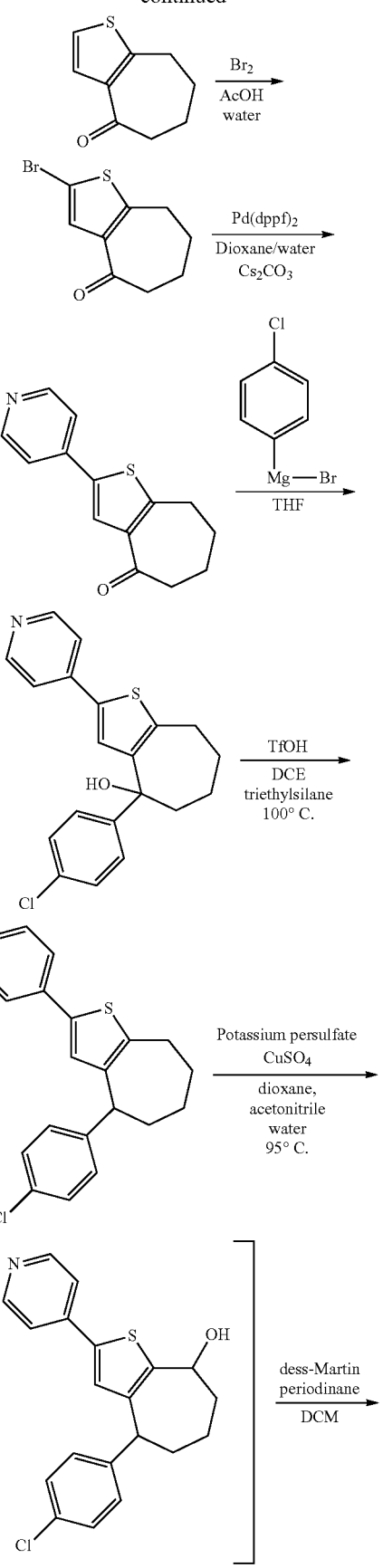

Step 1: Preparation of 5,6,7,8-tetrahydro-4H-cyclohepta[b]thiophen-4-one

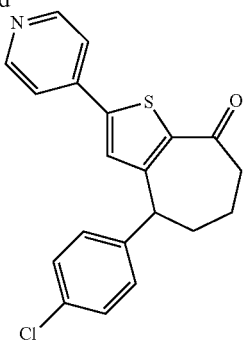

A mixture of 5-(2-thienyl)pentanoic acid (8.9 g, 48.0 mmol), phosphorus pentoxide (24.7 g, 86.9 mmol) and celite (16.0 g) in toluene (338 mL, 3170 mmol) was heated to reflux for 2 hr. The resulting black mixture was allowed to cool to rt and filtered. The solid cake was washed thoroughly with ethyl acetate then the filtrate was washed with saturated NaHCO3, dried over MgSO4, concentrated and dried under high vacuum to afford 6.0 g product as a brown oil (74.0% yield). LCMS: (FA) ES$^+$, 167. $^1$H NMR (400 MHz, CDCl$_3$) δ: 7.40-7.42 (d, J=5.3, 2H), 6.98-7.00 (d, J=5.3, 2H), 3.0-3.12 (m, 2H), 2.72-2.76 (m, 2H), 1.85-2.0 (m, 4H).

Step 2: Preparation of 2-bromo-5,6,7,8-tetrahydro-4H-cyclohepta[b]thiophen-4-one To a solution of 5,6,7,8-tetrahydro-4H-cyclohepta[b]thiophen-4-one (4.96 g, 29.8 mmol) in water (23.0 mL, 1200 mmol) and acetic acid (23.0 mL, 4000 mmol) at −5° C. was added a solution of bromine (1.6 mL, 31 mmol) in acetic acid (3.2 mL, 56 mmol) dropwise and the reaction mixture was stirred at −5° C. for 1 hr. The reaction mixture was quenched into aqueous sodium acetate, ethyl acetate (30 mL) was added, the organic layer was separated, and the aqueous layer was extracted with ethyl acetate (3×10 mL). The combined organic layers were washed with brine, dried over MgSO4, filtered, concentrated and dried under high vacuum to afford 7.3 g product as a brownish solid (99.0% yield). LCMS: (FA) ES$^+$, 246. $^1$H NMR (300 MHz, CDCl$_3$) δ: 7.35-7.36 (br s, 1H), 2.98-3.0 (m, 2H), 2.68-2.73 (m, 2H), 1.85-2.0 (m, 4H).

Step 3: Preparation of [2-pyridin-4-yl-5,6,7,8-tetrahydro-4H-cyclohepta[b]thiophen-4-one To a pressure tube were added 2-bromo-5,6,7,8-tetrahydro-4H-cyclohepta[b]thiophen-4-one (2.15 g, 8.77 mmol), 1,4-dioxane (54.8 mL, 702 mmol), pyridine-4-boronic acid (1.40 g, 11.4 mmol), cesium carbonate (8.50 g, 26.0 mmol), [1,1'-bis(diphenylphosphino)ferrocene]dichloropalladium (II), complex with dichloromethane (1:1) (380 mg, 0.460 mmol) and water (7.90 mL, 439 mmol). The tube was sealed and the mixture was heated at 110° C. for 16 hr. The reaction mixture was allowed to cool to rt then diluted with ethyl acetate (15 mL) and water (10 mL) and transferred to a separatory funnel. The organic layer was separated and the aqueous phase was extracted with ethyl acetate (3×10 mL). The combined organic phases were washed with brine (10 mL) then dried over anhydrous MgSO4. Insoluble materials were removed by filtration, the filtrate was concentrated and the obtained residue was purified by column chromatography (SiO$_2$, elution with 0-100% EA/DCM) to give the title compound as a yellow foam (1.44 g, 68% yield). LCMS: (FA) ES$^+$, 244. $^1$H NMR (300 MHz, DMSO-d6) δ: 8.55-8.57 (dd, J=1.7 Hz, J=4.9 Hz, 2H), 7.91-7.92 (br s, 1H), 7.62-7.64 (dd, J=1.5 Hz, J=4.9 Hz, 2H), 3.15-3.20 (m, 2H), 2.69-2.73 (m, 2H), 1.80-1.90 (m, 4H).

Step 4: Preparation of 4-(4-chlorophenyl)-2-pyridin-4-yl-5,6,7,8-tetrahydro-4H-cyclohepta[b]thiophene-4-ol To a solution of [2-pyridin-4-yl-5,6,7,8-tetrahydro-4H-cyclohepta[b]thiophen-4-one (1.44 g, 5.92 mmol) in tetrahydrofuran (30.0 mL, 400 mmol), 4-chlorophenyl magnesium bromide in ether (1M, 8.00 mL, 8.00 mmol) was added and the mixture was stirred for 40 min at rt. To the mixture were added a saturated aqueous solution of NH4Cl (10 mL) and ethyl acetate (10 mL). The resulting biphasic mixture was vigorously stirred for 15 min then the organic layer was separated. The organic phase was washed with brine (10 mL) then dried over anhydrous MgSO4. Insoluble materials were removed by filtration and the filtrate was concentrated under reduced pressure. The obtained residue was purified by column chromatography (SiO$_2$, elution with 0-100% ethyl acetate/dichloromethane) to give the title compound as a yellow foam (1.76 g, 83.6% yield). LCMS: (FA) ES$^+$, 356. $^1$H NMR (400 MHz, DMSO-d6) δ: 8.47-8.57 (dd, J=1.7 Hz, J=4.5 Hz, 2H), 7.43-7.46 (m, 3H), 7.34-7.40 (m, 2H), 7.21-7.28 (m, 2H), 5.88-5.90 (br s, 1H), 2.86-3.0 (m, 1H), 2.65-2.80 (m, 1H), 2.20-2.35 (m, 1H), 1.95-2.10 (m, 1H), 1.55-1.80 (m, 3H), 1.20-1.40 (m, 1H).

Step 5: Preparation of 4-[4-(4-chlorophenyl)-5,6,7,8-tetrahydro-4H-cyclohepta[b]thien-2-yl]pyridine To a solution of 4-(4-chlorophenyl)-2-pyridin-4-yl-5,6,7,8-tetrahydro-4H-cyclohepta[b]thiophene-4-ol (745.8 mg, 2.10 mmol) in 1,2-dichloroethane (11.0 mL, 140 mmol) were added triethylsilane (3.35 mL, 20.9 mmol) and trifluoromethanesulfonic acid (0.927 mL, 10.5 mmol) and the resulting reddish solution was heated at 100° C. for 16 hr. The reaction mixture was allowed to cool to rt then was neutralized to pH 7 by the addition of a saturated NaHCO3 solution. The organic layer was separated and the aqueous layer was extracted with ethyl acetate (3×10 mL). The organic layers were combined, washed with brine, dried over MgSO4, filtered, concentrated and the obtained residue was purified by column chromatography (SiO$_2$, elution with 0-100% EA/DCM) to give the title compound as a white foam (587.4 mg, 95% yield). LCMS: (FA) ES$^+$, 354. $^1$H NMR (400 MHz, DMSO-d6) δ: 8.45-8.49 (dd, J=1.5 Hz, J=4.7 Hz, 2H), 7.36-7.44 (m, 4H), 7.16-7.20 (dd, J=8.2 Hz, 2H), 7.10-7.12 (br s, 1H), 4.28-4.33 (m, 1H), 2.75-3.0 (m, 2H), 2.10-2.20 (m, 1H), 1.88-1.95 (m, 1H), 1.60-1.80 (m, 4H).

Step 6: Preparation of 4-(4-chlorophenyl)-2-pyridin-4-yl-4,5,6,7-tetrahydro-8H-cyclohepta[b]thiophen-8-one (Compound 19)

To a solution of 4-[4-(4-chlorophenyl)-5,6,7,8-tetrahydro-4H-cyclohepta[b]thien-2-yl]pyridine (2.20 g, 6.50 mmol) in 1,4-dioxane (52.0 mL, 670 mmol), acetonitrile (52.0 mL, 1000.0 mmol) and water (56.0 mL, 3120 mmol) were added copper(II) sulfate pentahydrate (6.46 g, 25.9 mmol) and potassium persulfate (6.99 g, 25.9 mmol). The reaction mixture was stirred for 16 h at 95° C. during which time a yellow-greenish suspension was obtained and the blue color of the reaction disappeared.

The reaction mixture was quenched with saturated sodium bisulfite then was cooled to rt and insoluble materials were removed by filtration. The pH of the filtrate was adjusted to 9 by the addition of a saturated NaHCO3 solution and the organic layer was separated. To the aqueous layer was added saturated NH4Cl solution (5 mL) and it was then extracted with DCM (3×20 mL). The combined organic layers were dried over anhydrous MgSO4, filtered, and concentrated. The obtained residue, 4-(4-chlorophenyl)-2-pyridin-4-yl-5,6,7,8-tetrahydro-4H-cyclohepta[b]thiophene-8-ol (3.17 g, 8.30 mmol), was dissolved in methylene chloride (1217 mL, 580 mmol) and Dess-Martin periodinane (3.9 g, 9.20 mmol) was added. The reaction mixture was stirred for 16 h at rt. The reaction mixture was neutralized to pH ~7 by the addition of NaHCO3, the organic layer was separated, and the aqueous layer was extracted with DCM (3×20 mL). The combined organic layers were dried over anhydrous MgSO4, filtered, and concentrated. The obtained residue was purified by column chromatography (SiO$_2$, elution with 0-100% EA/hexane) to give the title compound as a white solid (1.34 g, 50% yield). LCMS: (AA) ES$^+$, 354. $^1$H NMR (400 MHz, DMSO-d6) δ: 8.51-8.54 (dd, J=1.5 Hz, J=4.5 Hz, 2H), 8.12-8.18 (m, 1H), 7.51-7.54 (dd, J=1.5 Hz, J=4.5 Hz, 2H), 7.34-7.38 (m, 2H), 7.15-7.17 (br s, 2H), 7.13-7.14 (br s, 1H), 4.26-4.31 (m, 1H), 3.10-3.28 (m, 1H), 2.05-2.15 (m, 1H), 1.80-1.90 (m, 2H), 1.50-1.72 (m, 2H).

Example 21

Synthesis of 6-(4-chlorophenyl)-8-pyridin-4-yl-1,4,5,6-tetrahydrothieno[3',2':6,7]cyclohepta[1,2-c]pyrazole (Compound 6)

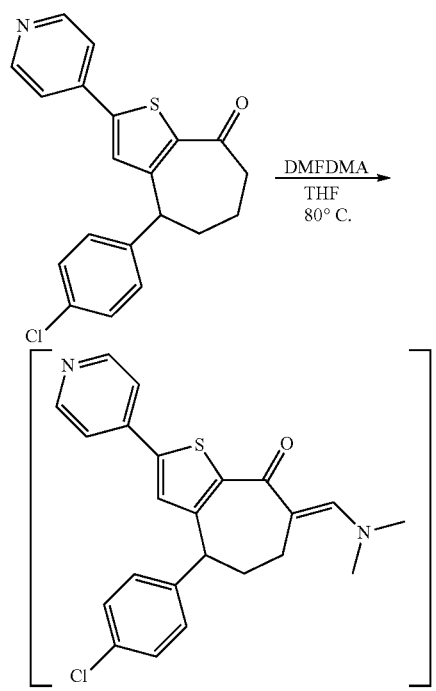

A solution of 4-(4-chlorophenyl)-2-pyridin-4-yl-4,5,6,7-tetrahydro-8H-cyclohepta[b]thiophen-8-one (81.5 mg, 0.230 mmol) and 1,1-dimethoxy-N,N-dimethylmethanamine (0.514 mL, 3.87 mmol) in tetrahydrofuran (9.27 mL, 114 mmol) was refluxed under argon for 6 hr. The reaction was cooled to room temperature and concentrated under reduced pressure. The obtained residue (81.0 mg, 0.212 mmol), (7E)-4-(4-chlorophenyl)-7-[(dimethylamino)methylene]-2-pyridin-4-yl-4,5,6,7-tetrahydro-8H-cyclohepta thiophen-8-one, was dissolved in acetic acid (6.55 mL, 115 mmol) then hydrazine hydrate (0.112 mL, 2.30 mmol) was added and the reaction mixture was heated at 50° C. for 16 h. The mixture was allowed to cool to rt and concentrated under reduced pressure. The residue was diluted with ethyl acetate (5 mL) then washed with a saturated aqueous solution of NaHCO3 (5 mL), then brine (5 mL), then dried over anhydrous MgSO4, filtered, and concentrated. The obtained residue was purified by preparative HPLC to yield 7.4 mg product as a white solid (9.0% yield). LCMS: (AA) ES$^+$, 378. $^1$H NMR (400 MHz, DMSO-d6) δ: 12.8 (br s, 1H), 8.49-8.52 (dd, J=1.7 Hz, J=4.7 Hz, 2H), 7.53-7.55 (dd, J=1.7 Hz, J=4.7 Hz, 2H), 7.34-7.39 (m, 3H), 7.04-7.08 (m, 2H), 4.65-4.70 (m, 1H), 2.63-2.75 (m, 1H), 2.20-2.32 (m, 2H), 2.0-2.10 (m, 1H).

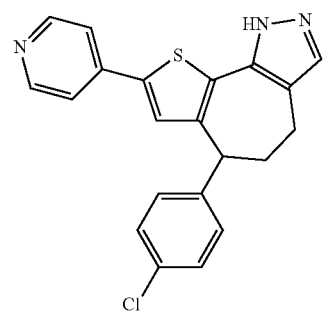

Example 22

Synthesis of 4-(4-chlorophenyl)-4-hydroxy-2-pyridin-4-yl-4,5,6,7-tetrahydro-8H-cyclohepta[b]thiophen-8-one (Compound 15)

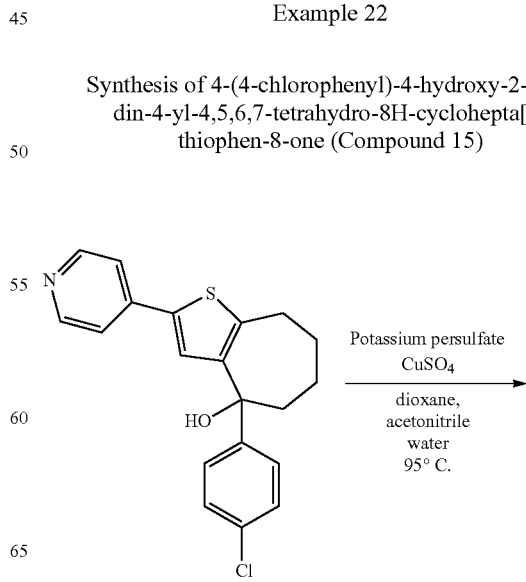

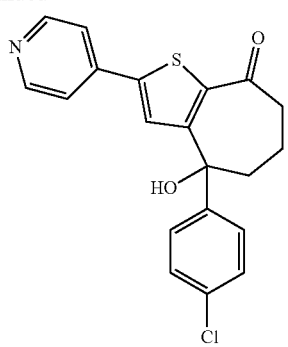

To a solution of 4-(4-chlorophenyl)-2-pyridin-4-yl-5,6,7,8-tetrahydro-4H-cyclohepta[b]thiophene-4-ol (46.3 mg, 0.130 mmol) in 1,4-dioxane (3.0 mL, 38.0 mmol), acetonitrile (3.0 mL, 57 mmol) and water (2 mL, 100 mmol) were added copper(II) sulfate pentahydrate (145.0 mg, 0.580 mmol) and potassium persulfate (180.0 mg, 0.666 mmol). The reaction mixture was stirred for 16 hr at 90° C. during which time a yellow-greenish suspension was obtained and the blue color of the reaction disappeared.

The reaction was quenched with saturated sodium bisulfite, cooled to rt, and insoluble materials were removed by filtration. The pH of the filtrate was adjusted to 9 by the addition of saturated NaHCO3. The organic layer was separated. To the aqueous layer was added saturated NH4Cl then it was extracted with DCM (10 mL). The combined organic layers were dried over anhydrous MgSO4, filtered, and concentrated. The obtained residue was purified by preparative HPLC to yield 4.5 mg product as a white solid (8.0% yield). LCMS: (AA) ES+, 370. $^1$H NMR (400 MHz, DMSO-d6) δ: 8.55-8.65 (m, 2H), 7.59-7.62 (m, 2H), 7.40-7.44 (br s, 1H), 7.30-7.40 (m, 4H), 6.36-6.38 (br s, 1H), 2.75-2.85 (m, 2H), 2.19-2.30 (m, 2H), 1.90-2.0 (m, 1H), 1.50-1.62 (m, 1H).

Example 23

Synthesis of 4-(4-chlorophenyl)-2-(pyridin-4-yl)-5,6-dihydrothieno[2,3-c]pyridin-7(4H)-one (Compound 156) and 4-(4-chlorophenyl)-2-(pyridin-4-yl)-4,5-dihydrothieno[2,3-b]pyridin-6(7H)-one (Compound 182)

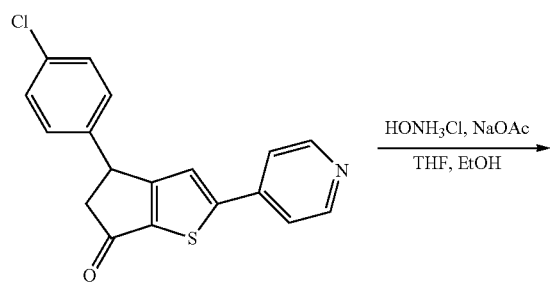

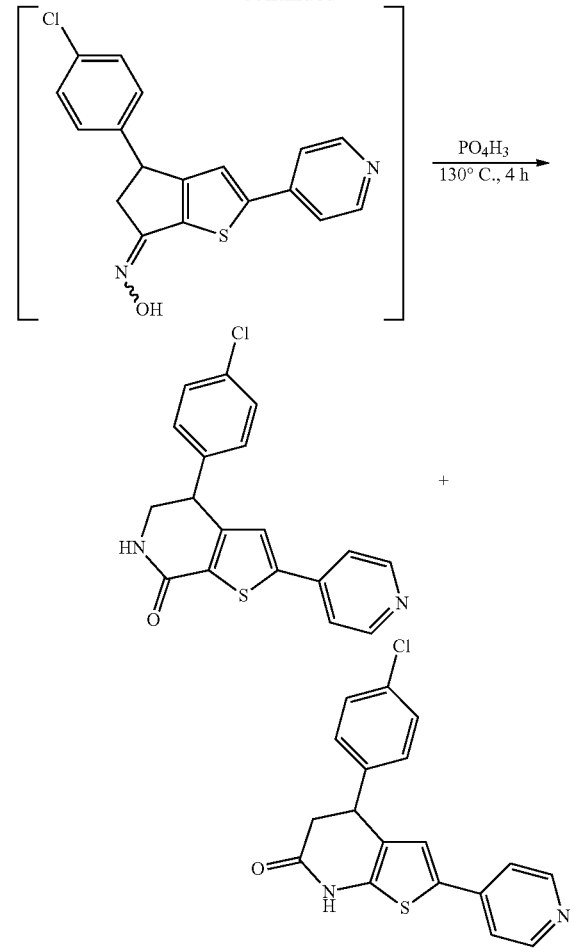

Step 1, Preparation of 4-(4-chlorophenyl)-2-(pyridin-4-yl)-5,6-dihydrothieno[2,3-c]pyridin-7(4H)-one and 4-(4-chlorophenyl)-2-(pyridin-4-yl)-4,5-dihydrothieno[2,3-b]pyridin-6(7H)-one To a 20 mL vial was added a solution of 4-(4-chlorophenyl)-2-pyridin-4-yl-4,5-dihydro-6H-cyclopenta[b]thiophen-6-one (0.0200 g, 0.0614 mmol) in tetrahydrofuran (1.00 mL, 12.3 mmol) and ethanol (1.00 mL, 17.1 mmol). Hydroxylamine hydrochloride (0.0214 g, 0.308 mmol) and sodium acetate (0.0246 g, 0.300 mmol) was added and the resulting yellow suspension was allowed to stir for 18 hours. The reaction was quenched by the addition of a saturated aqueous solution of sodium bicarbonate (1.00 mL). EtOAc (1.00 mL) was added and the mixture was vigorously stirred for 30 minutes. The organic layer was separated and the aqueous phase was extracted with EtOAc (10.00 mL×3). The combined organic layers were dried over anhydrous Na2SO4, filtered and concentrated under reduced pressure. The crude material was used without further purification. To a 20 mL vial was charged with crude (6Z)-4-(4-chlorophenyl)-2-pyridin-4-yl-4,5-dihydro-6H-cyclopenta[b]thiophen-6-one oxime. Polyphosphoric acid (0.8600 g, 3.584 mmol) was added and the mixture was heated to 130° C. and allowed to stir for 4 hours. The black reaction was cooled to ambient temperature and diluted with water (20.0 mL). The mixture was basified to pH 9 by the addition of K2CO3 (8.0 g) which was added in portions. The mixture was extracted with EtOAc (10.00 mL×3) and the combined organic layers were dried over anhydrous Na$_2$SO$_4$, filtered and concentrated under reduced pressure. The crude material was purified using preparative HPLC to afford the products. Peak 1, RT 7.73 minutes=4-(4-chlorophenyl)-2-(pyridin-4-yl)-5,6-dihydrothieno[2,3-c]pyridin-7(4H)-one (0.0040 g, 18.0%) as a white solid. LC/MS (AA) ES+ 341, 343. 1H NMR (DMSO, 400 MHz): δ 8.60-8.58 (2H, m), 7.94 (1H, br s), 7.69-7.68 (2H, m), 7.55 (1H, s), 7.43-7.41 (2H, m), 7.28-7.26 (2H, m), 4.42 (1H, J=4.00 Hz, t), 3.80-3.75 (1H, m), 3.53-3.48 (1H, m). Peak 2, RT 7.90 minutes=4-(4-chlorophenyl)-2-(pyridin-4-yl)-4,5-dihydrothieno[2,3-b]pyridin-6(7H)-one (0.0030 g, 14.0%) as a white solid. LC/MS (AA) ES+ 341, 343, 344. 1H NMR (DMSO, 400 MHz): δ 8.62-8.61 (2H, m), 8.31 (1H, br s), 7.71 (1H, s), 7.68-7.67 (2H, m), 7.42-7.41 (4H, m), 4.95 (1H, J=6.40, 2.40 Hz, dt), 3.30-3.27 (1H, m), 3.06-3.00 (1H, m).

ate (10.00 mL) and extracted with EtOAc (10.00 mL×3). The combined organic layers were dried over anhydrous Na$_2$SO$_4$, filtered and concentrated under reduced pressure. The crude material was purified using preparative HPLC to afford the product (0.0080 g, 19.0%) as a white solid. LC/MS (AA) ES+ 355, 357, 358, 359. 1H NMR (DMSO, 400 MHz): δ 8.59-8.58 (2H, m), 7.69-7.67 (2H, m), 7.51 (1H, s), 7.44-7.42 (2H, m), 7.31-7.29 (2H, m), 5.00 (1H, J=6.40, Hz, t), 3.95-3.91 (1H, m), 3.71-3.66 (1H, m), 2.50 (3H, s).

Example 25

Synthesis of 4-(4-chlorophenyl)-5-hydroxy-2-pyridin-4-yl-4,5,6,7-tetrahydro-8H-cyclohepta[b]thiophen-8-one (Compound 210)

Example 24

Synthesis of 4-(4-chlorophenyl)-6-methyl-2-(pyridin-4-yl)-5,6-dihydrothieno[2,3-c]pyridin-7(4H)-one (Compound 163)

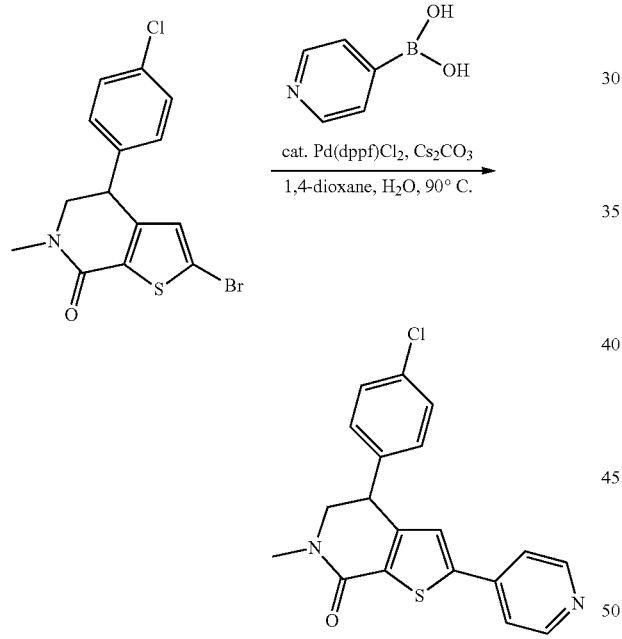

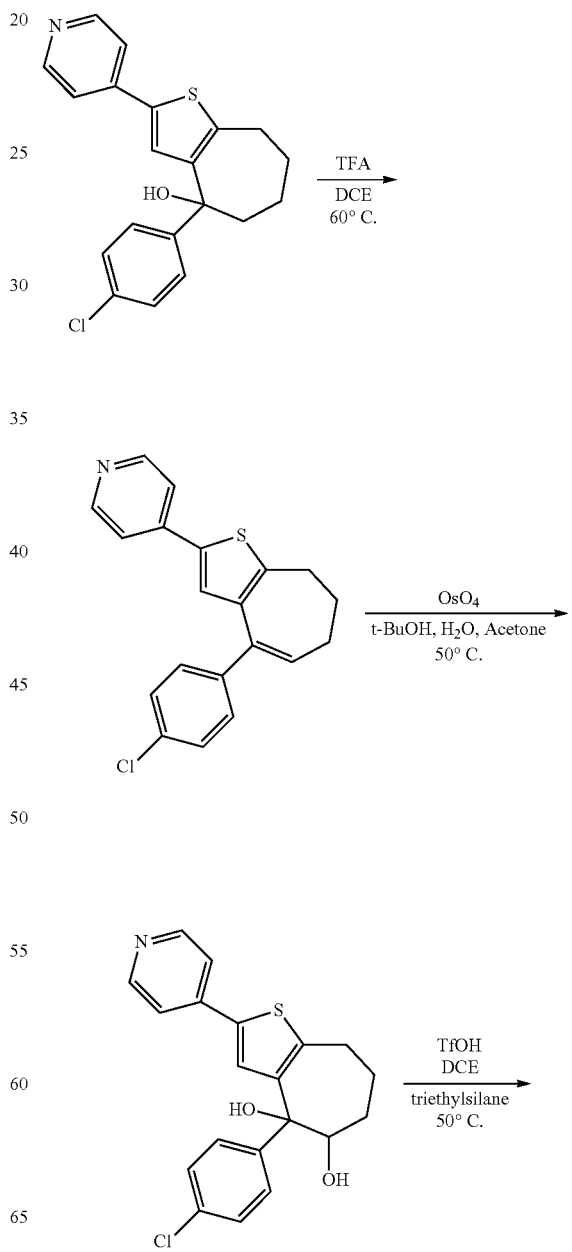

Step 1, Preparation of 4-(4-chlorophenyl)-6-methyl-2-(pyridin-4-yl)-5,6-dihydrothieno[2,3-c]pyridin-7(4H)-one 2-bromo-4-(4-chlorophenyl)-6-methyl-5,6-dihydrothieno[2,3-c]pyridin-7(4H)-one (0.0400 g, 0.112 mmol) and pyridine-4-boronic acid (0.02575 g, 0.2095 mmol) were dissolved in a mixture of 1,4-dioxane (2 mL) and water (0.2 mL). Cesium carbonate (0.1096 g, 0.3364 mmol) was added followed by [1,1'-bis(diphenylphosphino)ferrocene]palladium(II)dichloride (0.0111 g, 0.0134 mmol). The reaction mixture was heated to 90° C. and allowed to stir for 18 h. The reaction was cooled to ambient temperature and quenched by the addition of a saturated aqueous solution of sodium bicarbon-

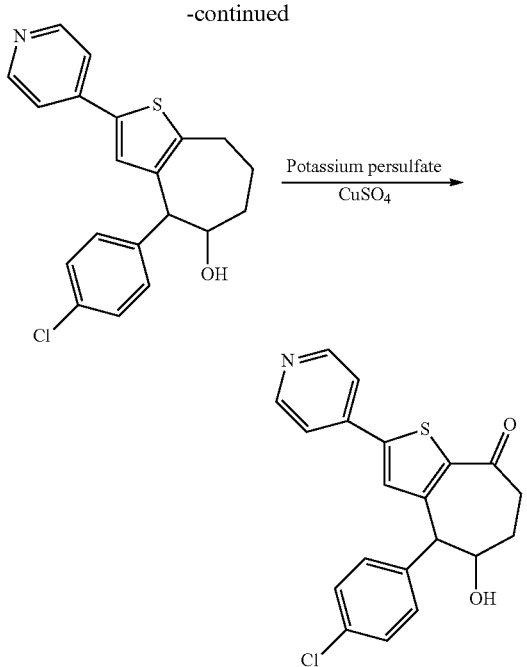

Step 1, Preparation of 4-[4-(4-chlorophenyl)-7,8-dihydro-6H-cyclohepta[b]thien-2-yl]pyridine To a solution of 4-(4-chlorophenyl)-2-pyridin-4-yl-5,6,7,8-tetrahydro-4H-cyclohepta thiophene-4-ol (500.0 mg, 1.405 mmol) in 1,2-dichloroethane (6.0 mL, 76 mmol) trifluoroacetic acid (1.082 mL, 14.05 mmol) was added at 0° C., and the resulting brownish solution was heated at 60° C. for 16 hr. The reaction mixture was allowed to cool to rt, the solvent was evaporated, saturated NaHCO$_3$ (5 mL) and ethyl acetate (5 mL) were added, and the mixture was stirred for 30 min, the organic layer was separated, the aqueous layer was extracted with ethyl acetate (3×5 mL), the combined organic layers were dried over MgSO$_4$, filtered, concentrated and the obtained residue was purified by column chromatography (SiO$_2$, elution with 0-100% EA/DCM) to give the title compound as a yellow solid (428.7 mg, 91.2% yield). LCMS: (FA) ES$^+$, 338/340. $^1$H NMR (300 MHz, DMSO) E. 8.64 (d, J=6.7 Hz, 2H), 7.92 (d, J=6.6 Hz, 2H), 7.63 (s, 1H), 7.47-7.37 (m, 2H), 7.37-7.21 (m, 2H), 6.49 (t, J=6.5 Hz, 1H), 2.91 (t, J=6.4 Hz, 2H), 2.31-2.07 (m, 4H).

Step 2, Preparation of 4-(4-chlorophenyl)-2-pyridin-4-yl-5,6,7,8-tetrahydro-4H-cycloheptathiophene-4,5-diol To a solution of 4-[4-(4-chlorophenyl)-7,8-dihydro-6H-cyclohepta[b]thien-2-yl]pyridine (304.0 mg, 0.899 mmol) in tert-butyl alcohol (2.06 mL, 21.5 mmol) were added water (3.43 mL) and acetone (20.56 mL). N-methylmorpholine N-oxide (210.8 mg, 1.79 mmol) and 4% osmium tetroxide in water (0.164 mL, 0.0269 mmol) were added and the resulting pinkish suspension was heated at 50° C. for 3 hr. The reaction mixture was allowed to cool to rt and then diluted with ethyl acetate (15 mL) and water (10 mL), the organic layer was separated and the aqueous phase was extracted with ethyl acetate (3×10 mL). The combined organic phases were washed with brine (10 mL) then dried over anhydrous MgSO$_4$, Insoluble materials were removed by filtration and then the filtrate was concentrated and the obtained residue was purified by column chromatography (SiO$_2$, elution with 0-20% MeOH/DCM) to give the title compound as a yellow foam (241.8 mg, 72% yield). LCMS: (FA) ES$^+$, 372/374. $^1$H NMR (400 MHz, DMSO) δ 8.50 (dd, J=4.6, 1.6 Hz, 2H), 7.49 (d, J=13.4 Hz, 1H), 7.44 (dd, J=4.6, 1.6 Hz, 2H), 7.38 (d, J=8.6 Hz, 2H), 7.25 (d, J=8.6 Hz, 2H), 5.75 (s, 1H), 5.71 (s, 1H), 4.83 (d, J=4.8 Hz, 1H), 4.14 (t, J=5.1 Hz, 1H), 2.93 (dd, J=15.7, 3.9 Hz, 1H), 2.75-2.55 (m, 1H), 2.05-1.73 (m, 2H), 1.52 (d, J=3.7 Hz, 1H), 1.38 (t, J=12.9 Hz, 1H).

Step 3, Preparation of 4-(4-chlorophenyl)-2-pyridin-4-yl-5,6,7,8-tetrahydro-4H-cyclohepta[b]thiophene-5-ol To a solution of 4-(4-chlorophenyl)-2-pyridin-4-yl-5,6,7,8-tetrahydro-4H-cyclohepta thiophene-4,5-diol (197.5 mg, 0.531 mmol) in 1,2-dichloroethane (2.9 mL, 37 mmol) were added triethylsilane (0.848 mL, 5.31 mmol) and trifluoromethanesulfonic acid (47.00 uL, 0.531 mmol). The resulting reddish solution was heated at 50° C. for 16 hr. Then the reaction mixture was allowed to cool to rt, and neutralized to pH 7 by the addition of saturated NaHCO$_3$. The organic layer was separated and the aqueous phase was extracted with ethyl acetate (3×10 mL). The combined organic phases were washed with brine (10 mL) then dried over anhydrous MgSO$_4$. Insoluble materials were removed by filtration and then the filtrate was concentrated and the obtained residue was purified by column chromatography (SiO$_2$, elution with 0-100% EA/hexane) to give the title compound as a yellow solid (145.6 mg, 77% yield). LCMS: (AA) ES$^+$, 356/358. $^1$H NMR (300 MHz, DMSO) δ, 8.48 (dd, J=4.5, 1.6 Hz, 2H), 7.45 (td, 4.4, 1.7 Hz, 2H), 7.42-7.20 (m, 4H), 5.75 (d, J=1.8 Hz, 1H), 5.03 (d, J=3.6 Hz, 1H), 4.45 (d, J=2.5 Hz, 1H), 4.01 (s, 1H), 3.05-2.61 (m, 2H), 2.02-1.43 (m, 4H).

Step 4, Preparation of 4-(4-chlorophenyl)-5-hydroxy-2-pyridin-4-yl-4,5,6,7-tetrahydro-8H-cyclohepta[b]thiophen-8-one To a solution of 4-(4-chlorophenyl)-2-pyridin-4-yl-5,6,7,8-tetrahydro-4H-cyclohepta thiophene-5-ol (120.0 mg, 0.337 mmol) in 1,4-dioxane (7.7 mL, 98 mmol) and acetonitrile (7.7 mL, 150 mmol) were added a solution of copper(II) sulfate pentahydrate (375.8 mg, 1.505 mmol) in water (5 mL, 300 mmol) and a solution of potassium persulfate (466.5 mg, 1.73 mmol) in water (5 mL, 300 mmol). The reaction mixture was stirred for 16 hr at 95° C. during which time a yellow-greenish suspension was obtained and the blue color of the reaction disappeared. The reaction was quenched with saturated sodium bisulfite, cooled to rt, and insoluble materials were removed by filtration. The pH of the filtrate was adjusted to 9 by the addition of saturated NaHCO3. The organic layer was separated. To the aqueous layer was added saturated NH4Cl then it was extracted with DCM (10 mL). The combined organic layers were dried over anhydrous MgSO4, filtered, and concentrated. The obtained residue was purified by preparative HPLC to give two sets of isomers, compound A as a white solid (2.3 mg, 1.8% yield). LCMS: (AA) ES$^+$, 369.9/371.9, Rt 7.7 min. $^1$H NMR (300 MHz, DMSO) δ 8.57 (d, J=6.1 Hz, 2H), 7.59 (d, J=6.1 Hz, 2H), 7.48-7.33 (m, 2H), 7.32-7.14 (m, 2H), 5.27 (d, J=4.1 Hz, 1H), 4.56 (d, J=5.9 Hz, 1H), 4.24 (s, 1H), 2.99 (m, 2H), 1.91 (m, 2H), and compound B as a white solid (2.3 mg, 1.8% yield). LCMS: (AA) ES$^+$, 369.9/371.9, Rt, 8.1 min, $^1$H NMR (300 MHz, DMSO) δ 8.58 (d, J=4.6 Hz, 2H), 7.72-7.56 (m, 2H), 7.32 (dd, J=36.3, 7.6

Hz, 4H), 5.24 (s, 1H), 4.64 (s, 1H), 4.26 (s, 1H), 2.76 (dt, J=44.4, 18.5 Hz, 2H), 2.08-1.65 (m, 2H).

Compounds in the following table are prepared from appropriate starting materials in a method analogous to that of Example 25.

| 129 | LC/MS: (FA) ES+ 370, 372 |
| --- | --- |

Example 26

Synthesis of 4-(4-chlorophenyl)-6-methyl-2-morpholino-5,6-dihydrothieno[2,3-c]pyridin-7(4H)-one (Compound 198)

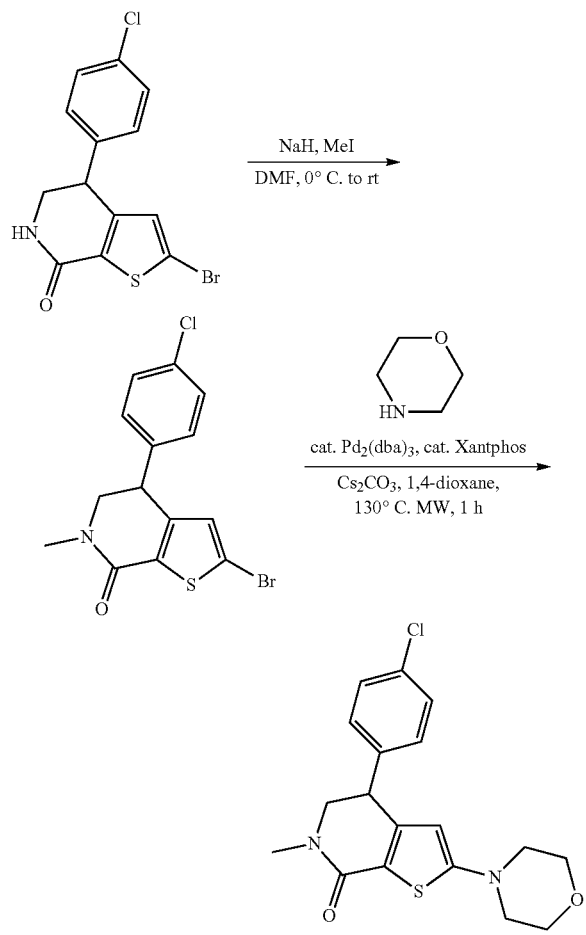

Step 1, Preparation of 2-bromo-4-(4-chlorophenyl)-6-methyl-5,6-dihydrothieno[2,3-c]pyridin-7(4H)-one To a 20 mL vial was added a solution of 2-bromo-4-(4-chlorophenyl)-5,6-dihydrothieno[2,3-c]pyridin-7(4H)-one (0.0800 g, 0.233 mmol) in anhydrous N,N-dimethylformamide (3.00 mL, 38.7 mmol) and cooled to 0° C. NaH 60% in mineral oil (60:40, sodium hydride:Mineral Oil, 0.0500 g, 1.25 mmol) was added in portions and stirred for 10 minutes. Methyl iodide (0.0876 mL, 1.41 mmol) was added and the reaction mixture was slowly warmed to room temperature and allowed to stir for 1 hour. The reaction was quenched by the addition of a saturated aqueous solution of ammonium chloride (5.00 mL) and diluted with EtOAc (10.00 mL). The mixture was successively washed with water (10.0 mL×2) and brine (10.0 mL). The organic layer was dried over anhydrous Na2SO4, filtered and concentrated under reduced pressure. The crude material was wet loaded onto silica gel and then purified using a ISCO (4 g cartridge, gradient hexanes to 75% EtOAc over 30 min) to afford the product (0.0812 g, 78%) as a yellow oil. LC/MS (AA) ES+ 356, 358, 360. 1H NMR (dmso-d6, 400 MHz): d 7.43-7.37 (2H, m), 7.25-7.19 (2H, m), 6.98 (1H, s), 3.81-3.73 (1H, m), 3.66-3.58 (1H, m), 2.85 (3H, s).

Step 2, Preparation of 4-(4-chlorophenyl)-6-methyl-2-morpholino-5,6-dihydrothieno[2,3-c]pyridin-7(4H)-one To a 2.0-5.0 mL microwave vial was added a solution of 2-bromo-4-(4-chlorophenyl)-6-methyl-5,6-dihydrothieno[2,3-c]pyridin-7(4H)-one (0.0400 g, 0.112 mmol) and morpholine (0.02934 mL, 0.3364 mmol) in anhydrous 1,4-dioxane (1.500 mL, 19.22 mmol) and degassed under nitrogen for 10 min. Cesium carbonate (0.1700 g, 0.5216 mmol) and 4,5-bis(diphenylphosphino)-9,9-dimethylxanthene (0.0195 g, 0.0336 mmol) were added followed by tris(dibenzylideneacetone)dipalladium(0) (0.0103 g, 0.0112 mmol). The reaction mixture was sealed and heated via microwave to 140° C. and allowed to stir for 40 minutes. The reaction was cooled to ambient temperature and quenched by the addition of a solution of saturated aqueous solution of sodium bicarbonate (10.0 mL) and extracted with EtOAc (10.0 mL×3). The combined organic layers were dried over anhydrous Na2SO4, filtered and concentrated under reduced pressure. The crude material was submitted for HPLC purification to afford the product (0.0080 g, 19.0%) as a white solid. LC/MS (AA) ES+ 361, 363, 365. 1H NMR (dmso-d6, 400 MHz): d 7.51 (1H, s), 7.41-7.39 (2H, m), 7.25-7.23 (2H, m), 5.03 (1H, J=4.80, Hz, t), 3.80-3.66 (5H, m), 3.46-3.40 (1H, m), 3.11-3.09 (4H, m), 2.84 (3H, s).

Example 27

Synthesis of 4-(4-chlorophenyl)-5,5-dimethyl-2-(pyridin-4-yl)-4H-cyclopenta[b]thiophen-6(5H)-one (Compound 147)

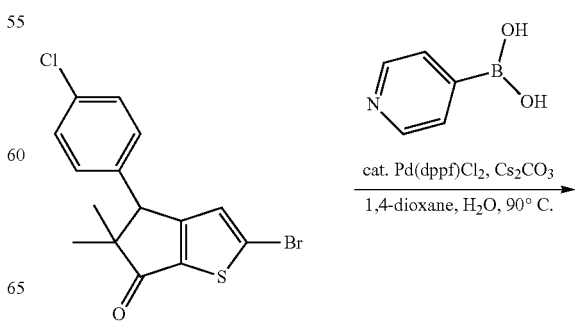

-continued

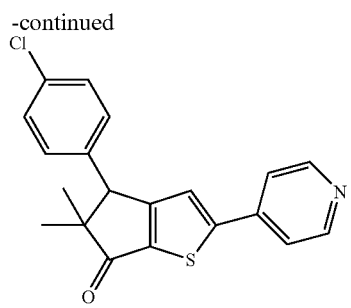

Step 1: Preparation of 4-(4-chlorophenyl)-5,5-dimethyl-2-(pyridin-4-yl)-4H-cyclopenta[b]thiophen-6(5H)-one To a 20 mL vial was added a solution of 2-bromo-4-(4-chlorophenyl)-5,5-dimethyl-4,5-dihydro-6H-cyclopenta[b]thiophen-6-one (0.0434 g, 0.122 mmol) and pyridine-4-boronic acid (0.02802 g, 0.2280 mmol) in 1,4-dioxane (2 mL) and water (0.200 mL). Cesium carbonate (0.1193 g, 0.3661 mmol) was added followed by [1,1'-bis(diphenylphosphino)ferrocene]palladium(II)dichloride (0.0120 g, 0.0146 mmol). The reaction mixture was heated to 90° C. and allowed to stir for 18 hr. The reaction was cooled to ambient temperature and quenched by the addition of a saturated aqueous solution of sodium bicarbonate (10 mL) and extracted with EtOAc (10 mL×3). The combined organic layers were dried over anhydrous $Na_2SO_4$, filtered and concentrated under reduced pressure. The crude material was purified and the enantiomers were separated on a Chiralpak IC 20×250 column using 90/10/01% Hexane/EtOH/DEA, 1.0 mL/minute for 40 minutes. Peak 1 RT=23.9 minutes (0.0050 g, 11%) and Peak 2 RT=39.4 minutes (0.0048 g, 11%) were both isolated as white solids. Absolute configuration of the obtained enantiomers is unknown. LC/MS (AA) ES+ 354, 356, 357, 358. 1H NMR (DMSO-d6, 400 MHz): δ 8.67-8.65 (2H, m), 7.88 (1H, s), 7.80-7.79 (2H, m), 7.43-7.42 (2H, m), 7.16-7.14 (2H, m), 4.48 (1H, s), 1.34 (3H, s), 0.63 (3H, s).

Example 28

Synthesis of 4-(4-chlorophenyl)-5,5-dimethyl-2-pyridin-4-yl-4,5,6,7-tetrahydro-8H-thieno[2,3-c]azepin-8-one (Compound 140)

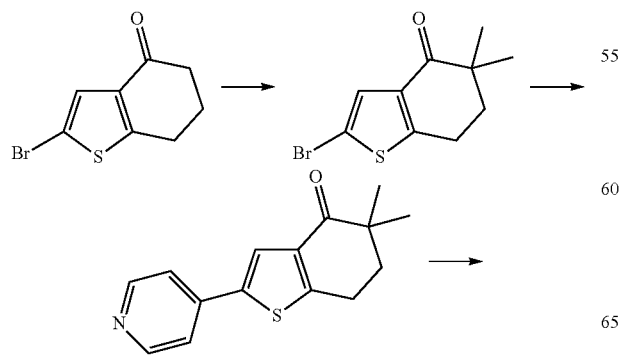

-continued

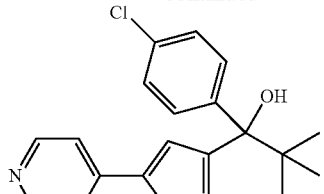

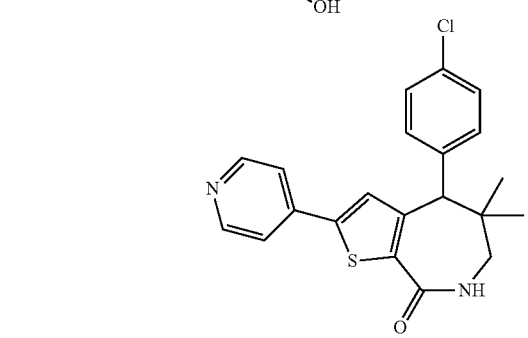

Step 1: 2-bromo-5,5-dimethyl-6,7-dihydro-1-benzothiophen-4(5H)-one

In a 100 mL round bottomed flask was placed 2-bromo-6,7-dihydro-1-benzothiophen-4(5H)-one (1.21 g, 5.24 mmol) and toluene (30 mL). To the mixture was added potassium tert-butoxide (1.29 g, 11.5 mmol) and the mixture was stirred for 30 min at 80° C. Methyl iodide (3 mL, 50 mmol) was added to mixture then the mixture was stirred for 16 at rt. The reaction was quenched by the addition of saturated aqueous solution of $NH_4Cl$ (30 mL) and then extracted with EtOAc (50 mL×2). The combined organic phases were dried over anhydrous $MgSO_4$ then the insoluble materials were removed by filtration. The filtrate was concentrated and the residue was purified using column chromatography on silica gel (40 g RediSep column, gradient 0% EA in hexane to 30% EA in hexane) to give the product (550 mg; 40%) as a yellow oil: $^1H$ NMR (400 MHz, $CDCl_3$) δ: 7.32 (s, 1H), 2.95 (t, 2H), 2.04 (t, 2H), 1.19 (s, 6H).

Step 2: 5,5-dimethyl-2-pyridin-4-yl-6,7-dihydro-1-benzothiophen-4(5H)-one

In a 100 ml round bottomed flask were placed 2-bromo-5,5-dimethyl-6,7-dihydro-1-benzothiophen-4(5H)-one (550 mg, 2.1 mmol), pyridine-4-boronic acid (326 mg, 2.65 mmol), 1,1'-bis(diphenylphosphino)ferrocenepalladium(II) dichloride, dichloromethane (96 mg, 0.12 mmol) and 1,4-dioxane (30 mL). To the mixture were added cesium carbonate (3.08 g, 9.45 mmol) and water (20 mL). The mixture was stirred for 16 h at 120° C. The mixture was allowed to cool to rt then diluted with EtOAc (100 mL). The mixture was transferred to a separatory funnel and washed with water (50 mL×2). The combined aqueous phases were extracted with EtOAc (50 mL×2). The combined organic phases were dried over anhydrous $MgSO_4$. Insoluble materials were removed by filtration and the filtrate was concentrated under reduced pressure. The residue was purified using column chromatography on silica gel (40 g RediSep column, gradient 30% EA in hexane to 100% EA in hexane) to give the product (420 mg; 77%) as a colorless crystalline solid: $^1H$ NMR (400 MHz, $CDCl_3$) δ 8.60 (dd, 2H), 7.77 (s, 1H), 7.43 (dd, 2H), 3.09 (t, 2H), 2.10 (t, 2H), 1.24 (s, 6H).

Step 3: 4-(4-chlorophenyl)-5,5-dimethyl-2-pyridin-4-yl-4,5,6,7-tetrahydro-1-benzothiophene-4-ol In a 100 mL round bottomed flask were placed 5,5-dimethyl-2-pyridin-4-yl-6,7-dihydro-1-benzothiophen-4(5H)-one (380 mg, 1.5 mmol) and THF (30 mL). To the mixture was added a solution of 4-chlorophenylmagnesium bromide in ether (1.0 M, 3.5 mL, 3.5 mmol) then the reaction was stirred for 3 hr at rt. LCMS indicated that starting material still remained, so additional 4-chlorophenylmagnesium bromide in ether (1.0M, 2.5 mL, 2.5 mmol) was added and the reaction was stirred for 16 hr at rt then for 10 hr at 70° C. The mixture was allowed to cool to rt then additional 4-chlorophenylmagnesium bromide in ether (1.0M, 5 mL, 5 mmol) was added and the mixture was stirred for 16 hr at rt. The mixture was then diluted with a saturated aqueous solution of $NH_4Cl$ (50 mL) and was extracted with EtOAc (50 mL×2). The combined organic phases were dried over anhydrous $MgSO_4$. The insoluble materials were removed by filtration and the filtrate was concentrated under reduced pressure. The residue was purified using column chromatography on silica gel (24 g RediSep column, gradient 30% EA in hexane to 100% EA in hexane) to give the product (530 mg; 97%) as a colorless foam: $^1H$ NMR (400 MHz, DMSO-$d_6$) δ: 8.48 (dd, 2H), 7.45 (dd, 2H), 7.32-7.35 (m, 2H), 7.23-7.25 (m, 3H), 5.55 (s, 1H), 2.87-2.91 (m, 2H), 1.84-1.90 (m, 1H), 1.57-1.63 (m, 1H), 0.91 (s, 3H), 0.63 (s, 3H).

Step 4: 4-[4-(4-chlorophenyl)-5,5-dimethyl-4,5,6,7-tetrahydro-1-benzothien-2-yl]pyridine In a 100 mL round bottomed flask was placed 4-(4-chlorophenyl)-5,5-dimethyl-2-pyridin-4-yl-4,5,6,7-tetrahydro-1-benzothiophene-4-ol (240 mg, 0.65 mmol) and 1,2-dichloroethane (10 mL). To the solution were added trifluoroacetic acid (1 mL, 10 mmol) and triethylsilane (1 mL, 6 mmol). The resulting yellow solution was stirred for 16 hr at 90° C. The mixture was allowed to cool to rt then was concentrated under reduced pressure. The residue was diluted with EtOAc, then was washed with a saturated aqueous solution of NaHCO3 (50 mL). The aqueous phase was extracted with EtOAc (50 mL). The combined organic phases were dried over anhydrous $MgSO_4$. Insoluble materials were removed by filtration and the filtrate was concentrated under reduced pressure. The residue was purified using column chromatography on silica gel (24 g RediSep column, gradient 30% EA in hexane to 100% EA in hexane) to give the product (215 mg, 94%) as a colorless syrup: $^1H$ NMR (400 MHz, $CDCl_3$) δ: 8.49 (dd, 2H), 7.31 (dd, 2H), 7.25-7.27 (m, 2H), 7.03 (br d, 2H), 6.84 (s, 1H), 3.67 (s, 1H), 1.77-1.83 (m, 1H), 1.63-1.70 (m, 1H), 1.03 (s, 3H), 0.74 (s, 3H).

Step 5: 4-(4-chlorophenyl)-5,5-dimethyl-2-pyridin-4-yl-5,6-dihydro-1-benzothiophen-7(4H)-one In a 100 mL round bottomed flask were placed 4-[4-(4-chlorophenyl)-5,5-dimethyl-4,5,6,7-tetrahydro-1-benzothien-2-yl]pyridine (215 mg, 0.608 mmol), 1,4-dioxane (5 mL) and acetonitrile (5 mL). To the mixture was added a freshly prepared solution of copper(II) sulfate pentahydrate (672 mg, 2.69 mmol) and potassium persulfate (669 mg, 2.47 mmol) in water (10 mL). The resulting bluish gray suspension was stirred for 16 hr at 90° C. The mixture was allowed to cool to rt, diluted with EtOAc (50 mL), then washed with water (50 mL). The aqueous phase was basified by the addition of a saturated aqueous solution of $NaHCO_3$ (ca 50 mL, to adjust pH to ca 12), then saturated aqueous solution of $NH_4Cl$ was added (ca 50 mL to dissolve Cu salts). The resulting deep blue aqueous solution was extracted with EtOAc (50 mL×2). The combined organic phases were washed with a freshly prepared 10% aqueous solution of $NaHSO_3$ (100 mL), then a saturated aqueous solution of $NaHCO_3$ (50 mL), then were dried over anhydrous $MgSO_4$. Insoluble materials were removed by filtration and the filtrate was concentrated under reduced pressure. The residue was used in the next step without further purifications.

The residue prepared above was dissolved in methylene chloride (50 mL) and then Dess-Martin periodinane (515 mg, 1.22 mmol) was added. The mixture was stirred for 3 hr at rt, then was diluted with $CH_2Cl_2$ (50 mL) and then washed with a 10% aqueous solution of $NaHSO_3$ (50 mL). The aqueous phase was basified by the addition of saturated aqueous solution of $NaHCO_3$ (ca 100 mL) and then extracted with $CH_2Cl_2$ (50 mL×2). The combined organic phases were washed with a saturated aqueous solution of $NaHCO_3$ (50 mL) then dried over anhydrous $MgSO_4$. Insoluble materials were removed by filtration and the filtrate was concentrated under reduced pressure. The residue was purified using column chromatography on silica gel (24 g RediSep column, gradient 30% EA in hexane to 100% EA in hexane) to give the product (170 mg; 76%) as a colorless foam: $^1H$ NMR (300 MHz, DMSO-$d_6$) δ: 8.62 (dd, 2H), 7.42 (dd, 2H), 7.32-7.35 (m, 2H), 7.08-7.10 (m, 2H), 7.05 (s, 1H), 4.01 (s, 1H), 2.63 (d, 1H), 2.53 (d, 1H), 1.14 (s, 3H), 0.90 (d, 3H).

Step 6: 4-(4-chlorophenyl)-5,5-dimethyl-2-pyridin-4-yl-4,5,6,7-tetrahydro-8H-thieno[2,3-c]azepin-8-one In a 100 mL round bottomed flask were placed 4-(4-chlorophenyl)-5,5-dimethyl-2-pyridin-4-yl-5,6-dihydro-1-benzothiophen-7(4H)-one (160 mg, 0.43 mmol), THF (5 mL) and ethanol (5 mL). To the mixture were added sodium acetate (183.4 mg, 2.236 mmol) and hydroxylamine hydrochloride (160.3 mg, 2.307 mmol).

The mixture was stirred for 16 hr at 50° C. The mixture was allowed to cool to rt and then concentrated under reduced pressure. The residue was suspended in a saturated aqueous solution of $NaHCO_3$ (50 mL), then extracted with $CH_2Cl_2$ (50 mL×2). The extracts were combined and dried over anhydrous $MgSO_4$. Insoluble materials were removed by filtration and the filtrate was concentrated under reduced pressure. The oxime intermediate was used in the next step (150 mg; 90%) without further purification.

In a 100 mL round bottomed flask were placed the oxime intermediate prepared above and polyphosphoric acid (7.60 g, 31.7 mmol). The mixture was stirred for 4 hr at 130° C. during which time the mixture was occasionally mixed by hand. Crushed ice (ca 30 g) was then added while the reaction was hot. After the ice had melted, the mixture was neutralized by the addition of 5N aq NaOH and was then extracted with $CH_2Cl_2$ (50 mL×2). The combined organic phases were dried over anhydrous $MgSO_4$. Insoluble materials were removed by filtration and the filtrate was concentrated under reduced pressure. The residue (144 mg) was purified by HPLC to yield title compound (70 mg; 40%) as an yellowish off-white solid: $^1$H NMR (400 MHz, DMSO-$d_6$) δ 8.54 (dd, 2H), 8.24 (t, 1H), 7.55 (dd, 2H), 7.37 (d, 2H), 7.20 (s, 1H), 7.14 (d, 2H), 4.23 (s, 1H), 3.12 (dd, 1H), 2.85 (dd, 1H), 1.05 (s, 3H), 0.75 (s, 3H).

Example 29

Synthesis of 4-(4-chlorophenyl)-5,5-dimethyl-2-morpholino-4H-cyclopenta[b]thiophen-6(5H)-one (Compound 161) and 4-(4-chlorophenyl)-4,5,5-trimethyl-2-morpholino-4H-cyclopenta[b]thiophen-6(5H)-one (Compound 118)

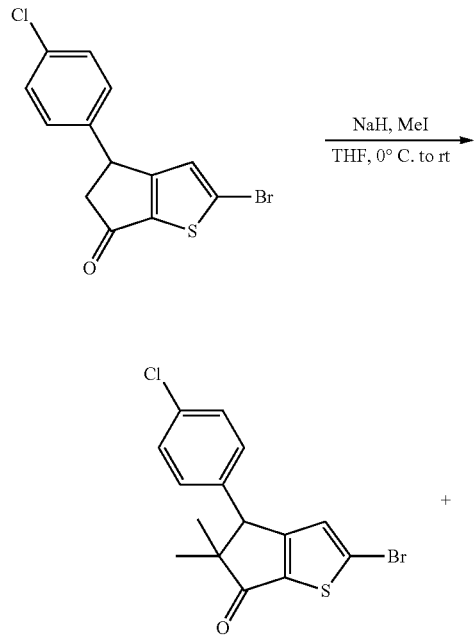

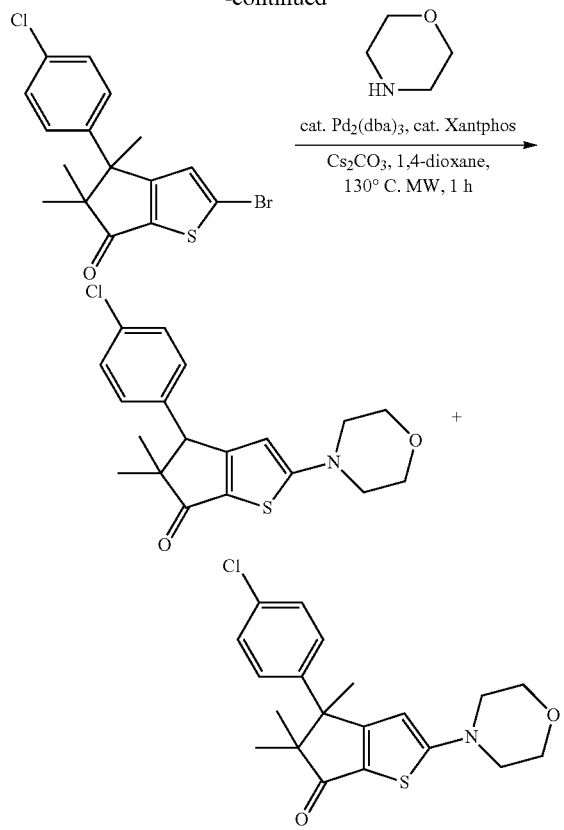

Step 1: Preparation of 2-bromo-4-(4-chlorophenyl)-5,5-dimethyl-4H-cyclopenta[b]thiophen-6(5H)-one and 2-bromo-4-(4-chlorophenyl)-4,5,5-trimethyl-4H-cyclopenta[b]thiophen-6(5H)-one To a 20 mL vial was added a solution of 2-bromo-4-(4-chlorophenyl)-4,5-dihydro-6H-cyclopenta[b]thiophen-6-one (0.1350 g, 0.4120 mmol) in tetrahydrofuran (4.00 mL, 49.3 mmol) and cooled to 0° C. NaH 60% in mineral oil (60:40, sodium hydride:mineral oil, 0.09888 g, 2.472 mmol) was added and the orange suspension was slowly warmed to ambient temperature over a period of 30 minutes. Methyl iodide (0.2565 mL, 4.120 mmol) was added and the reaction mixture was continued to stir for 4 hours. The reaction was quenched by the dropwise addition of a saturated aqueous solution of ammonium chloride (5.0 mL) and diluted with EtOAc (10.00 mL). The organic layer was washed with brine (10.0 mL), dried over anhydrous Na2SO4, filtered and concentrated under reduced pressure. The crude material was dry loaded onto silica gel and then purified using a ISCO (12 g cartridge, gradient hexanes to 30% EtOAc over 30 min) to afford the products as an inseparable mixture (1:2 product:side-product) (0.0780 g, 53%) as a yellow oil and used without further separation. LC/MS (AA) ES+ 355, 357, 359 and 369, 371, 373. $^1$H NMR (400 MHz, DMSO-$d_6$) δ: d 7.55 (1H, s), 7.42-7.38 (2H, m), 7.15-7.07 (2H, m), 4.42 (0.5H, s), 1.61 (2H, s), 1.30 (1H, s), 0.52 (1H, s).

Step 2: Preparation of 4-(4-chlorophenyl)-5,5-dimethyl-2-morpholino-4H-cyclopenta[b]thiophen-6(5H)-one and 4-(4-chlorophenyl)-4,5,5-trimethyl-2-morpholino-4H-cyclopenta[b]thiophen-6(5H)-one To a 10-20 mL microwave vial was added a solution of 2-bromo-4-(4-chlorophenyl)-5,5-dimethyl-4,5-dihydro-6H- cyclopenta[b]thiophen-6-one (1.2610 g, 3.5453 mmol) and morpholine (1.546 mL, 17.73 mmol) in anhydrous 1,4-dioxane (20.00 mL, 256.3 mmol) and the resulting solution was degassed under nitrogen for 10 min. Cesium carbonate (4.100 g, 12.58 mmol) and 4,5-bis(diphenylphosphino)-9,9-dimethylxanthene (0.615 g, 1.06 mmol) were added followed by tris(dibenzylideneacetone)dipalladium(0) (0.325 g, 0.354 mmol). The reaction mixture was sealed and heated via microwave to 140° C. and allowed to stir for 45 minutes. The reaction was cooled to ambient temperature and quenched by the addition of a solution of saturated aqueous solution of sodium bicarbonate (50.00 mL) and extracted with EtOAc (50.00 mL×3). The combined organic layers were dried over anhydrous Na2SO4, filtered and concentrated under reduced pressure. The crude material was submitted for purification to afford racemic trimethyl product (0.0300 g, 6%) as a white powder and separation of the dimethyl product to afford the enantiomers on a Chiralpak IC 20×250 column using 90/10/01% Hexane/EtOH/DEA, 1.0 mL/minute for 60 minutes. Peak 1 RT=13.84 minutes (0.0600 g, 4%) and Peak 2 RT=14.28 minutes (0.0300 g, 2%) both as a white solid. Absolute configuration of the obtained enantiomers is unknown. Dimethyl product: LC/MS (AA) ES+ 362, 364, 365, 366. 1H NMR (dmso-d6, 400 MHz): d 7.40-7.38 (2H, m), 7.09-7.07 (2H, m), 6.11 (1H, s), 4.22 (1H, s), 3.72-3.70 (4H, m), 3.33-3.29 (4H, m), 1.24 (3H, s), 0.53 (3H, s). Trimethyl product: LC/MS (AA) ES+ 376, 378, 379. $^1$H NMR (400 MHz, DMSO-d$_6$) δ: d 7.38-7.36 (2H, m), 7.17-7.15 (2H, m), 6.25 (1H, s), 3.74-3.72 (4H, m), 3.33-3.30 (4H, m), 1.58 (3H, s), 1.14 (3H, s), 0.47 (3H, s).

Example 30

Synthesis of methyl 2-chloro-5-[2-(morpholin-4-yl)-4-oxo-5,6,7,8-tetrahydro-4H-[1,3]thiazolo[5,4-c]azepin-8-yl]benzoate (Compound 174)

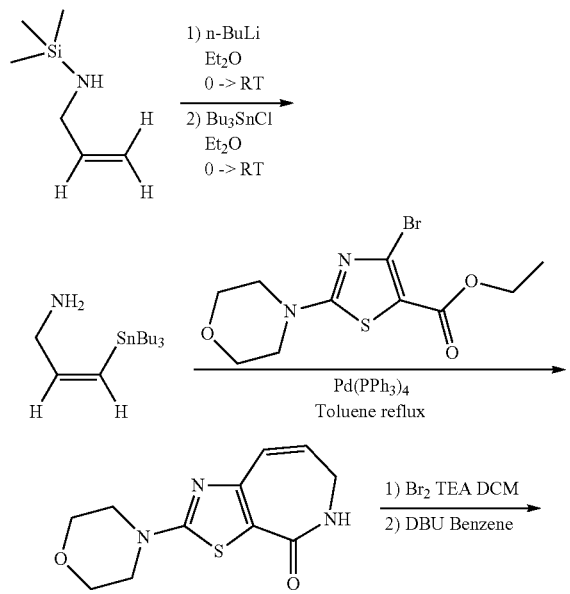

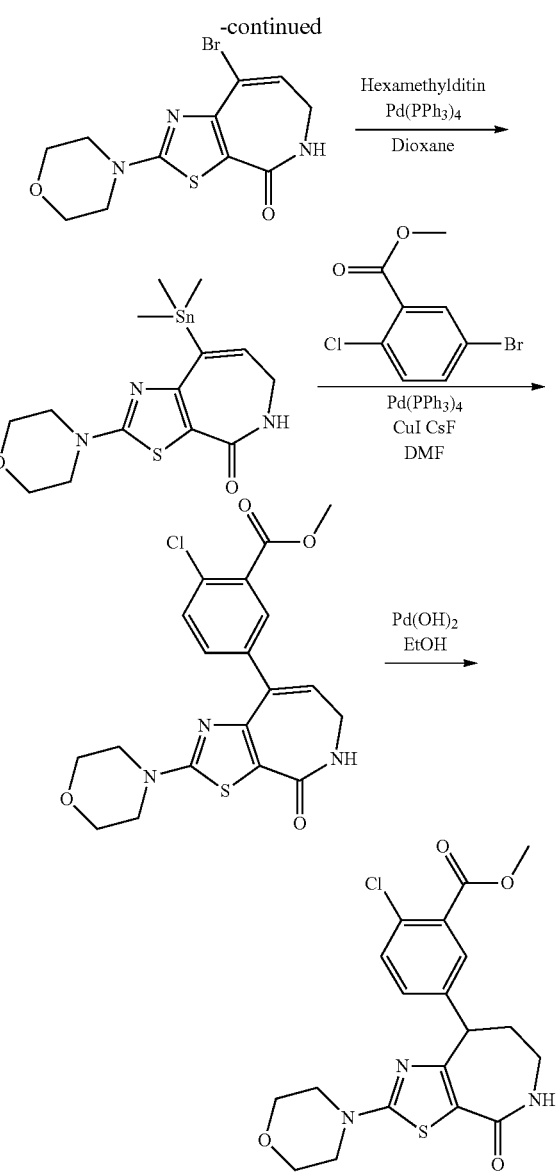

Step 1: Z-3-(Tributylstannyl)-2-propen-1-amine

To a solution of N-trimethylsilylallylamine (21.0 mL, 125. mmol) in diethyl ether (323 mL) at 0° C. under an atmosphere of nitrogen was added 2.5M n-butyllithium in hexanes (100. mL, 250. mmol). The solution was stirred at 0° C. for 15 minutes then the reaction was allowed to warm to room temperature and stirred for 16 hours. To the reaction mixture was added a solution of tributyltin chloride (33.6 mL, 124. mmol) in diethyl ether (158 mL) slowly at 0° C., then the reaction was allowed to warm to room temperature and stirred for 16 hours. The reaction mixture was quenched with saturated ammonium chloride solution then extracted twice with diethyl ether. The organic layer was dried over anhydrous sodium sulfate and then concentrated. The residue was purified using column chromatography on silica gel (400 gr Analogix column, gradient DCM to 10% MeOH in DCM over 30 minutes) to give the product (30.6 g, 71%). $^1$H NMR (400 MHz, CDCl$_3$) δ: 6.81-6.37 (m, 1H), 6.03-5.76 (m, 1H), 3.31-3.17 (m, 2H), 1.60-1.22 (m, 12H), 1.00-0.79 (m, 15H).

Step 2: 2-(morpholin-4-yl)-5,6-dihydro-4H-[1,3] thiazolo[5,4-c]azepin-4-one

A solution of Z-3-(tributylstannyl)-2-propen-1-amine (30.0 g, 86.7 mmol) and 4-bromo-2-morpholin-4-yl-1,3-thiazole-5-carboxylate (27.8 g, 86.7 mmol) in toluene (136 mL) was purged with argon, and then tetrakis(triphenylphosphine-palladium(0) (5.01 g, 4.33 mmol) was added. The reaction mixture was stirred at 120° C. under an atmosphere of argon for 5 days. The solvent was evaporated, then the residue was adsorbed onto silica gel then purified using column chromatography on silica gel (600 gr Analogix column, gradient DCM to 5% MeOH in DCM over 40 minutes) to give the product (3.44 g, 16%). LCMS: (AA) ES+ 252. $^1$H NMR (400 MHz, d$_6$-DMSO) δ: 7.73 (s, 1H), 6.63 (d, J=10.3 Hz, 1H), 6.24 (dt, J=10.3, 6.6 Hz, 1H), 3.74-3.63 (m, 4H), 3.54-3.47 (m, 2H), 3.47-3.40 (m, 4H).

Step 3: 8-bromo-2-(morpholin-4-yl)-5,6-dihydro-4H-[1,3]thiazolo[5,4-c]azepin-4-one To a solution of 2-(morpholin-4-yl)-5,6-dihydro-4H-[1,3]thiazolo[5,4-c]azepin-4-one (3.41 g, 13.6 mmol) in DCM (42.0 mL) at 0° C. was added triethylamine (1.02 mL, 7.33 mmol), then a solution of bromine (1.15 mL, 22.4 mmol) in DCM (21.0 mL) was added dropwise and the reaction mixture was stirred at 0° C. for 3 hours. The solvent was evaporated and the residue was dissolved in benzene (80.0 mL) then added 1,8-diazabicyclo[5.4.0]undec-7-ene (6.09 mL, 40.7 mmol) and the solution was stirred at room temperature for 16 hours. The reaction mixture was diluted with EA and water, and a precipitate formed which was filtered and dried to give the product (2.90 g). In order to obtain additional product the layers were separated and the aqueous layer was extracted twice more with EA. The combined organic layer was then washed with brine then dried over anhydrous sodium sulfate and concentrated. The residue was adsorbed onto silica gel then purified using column chromatography on silica gel (40 gr Analogix column, gradient DCM to 5% MeOH in DCM over 15 minutes) to give 0.223 g additional product (total product: 3.02 g, 67%). LCMS: (AA) ES+ 331, 333. $^1$H NMR (300 MHz, d$_6$-DMSO) δ: 8.14-7.89 (m, 1H), 6.69 (t, J=7.3 Hz, 1H), 3.81-3.62 (m, 4H), 3.55-3.38 (m, 6H).

Step 4: 2-(morpholin-4-yl)-8-(trimethylstannyl)-5,6-dihydro-4H-[1,3]thiazolo[5,4-c]azepin-4-one To a solution of 8-bromo-2-(morpholin-4-yl)-5,6-dihydro-4H-[1,3]thiazolo[5,4-c]azepin-4-one (2.02 g, 6.12 mmol) in 1,4-dioxane (46 mL) under an atmosphere of argon was added hexamethylditin (1.52 mL, 7.34 mmol) and tetrakis(triphenylphosphinepalladium(0) (0.353 g, 0.306 mmol) and stirred at 95° C. for 3 hours. The reaction mixture was cooled to room temperature and the solvent was evaporated. The residue was adsorbed onto silica gel then purified using column chromatography on silica gel (120 gr Analogix column, gradient DCM to 5% MeOH in DCM over 25 minutes) to give the product (1.90 g, 75%). LCMS: (AA) ES+ 415. $^1$H NMR (400 MHz, d$_6$-DMSO) δ: 7.79-7.64 (m, 1H), 6.43-6.17 (m, 1H), 3.79-3.62 (m, 4H), 3.56-3.36 (m, 6H), 0.31-0.01 (m, 9H).

Step 5: methyl 2-chloro-5-[2-(morpholin-4-yl)-4-oxo-5,6-dihydro-4H-[1,3]thiazolo[5,4-c]azepin-8-yl]benzoate A solution of 2-(morpholin-4-yl)-8-(trimethylstannyl)-5,6-dihydro-4H-[1,3]thiazolo[5,4-c]azepin-4-one (0.160 g, 0.386 mmol) and methyl-5-bromo-2-chlorobenzoate (0.116 g, 0.464 mmol) in DMF (3.74 mL) was purged with argon, and then cesium fluoride (0.205 g, 1.35 mmol), copper(I) iodide (0.0184 g, 0.0966 mmol) and tetrakis(triphenylphosphine)palladium(0) (0.0446 g, 0.0386 mmol) were added. The mixture was stirred at 80° C. for 2 hours. The solution was cooled to room temperature and some of the solvent was removed in vacuo. The residue was diluted with EA and water. The layers were separated and the aqueous layer was extracted twice more with EA. The combined organic layer was then washed with water and brine then dried over anhydrous sodium sulfate and concentrated. The residue was purified using column chromatography on silica gel (12 gr Analogix column, gradient DCM to 60% EA in DCM over 15 minutes) to give the product (0.129 g, 80%). LCMS: (AA) ES+ 420, 422. $^1$H NMR (400 MHz, d$_6$-DMSO) δ: 8.05 (t, J=5.0 Hz, 1H), 7.80 (d, J=2.1 Hz, 1H), 7.61-7.44 (m, 2H), 6.48 (t, J=7.1 Hz, 1H), 3.84 (s, 3H), 3.70-3.62 (m, 4H), 3.61-3.53 (m, 2H), 3.42-3.34 (m, 4H).

Step 6: methyl 2-chloro-5-[2-(morpholin-4-yl)-4-oxo-5,6,7,8-tetrahydro-4H-[1,3]thiazolo[5,4-c]azepin-8-yl]benzoate To a solution of methyl 2-chloro-5-[2-(morpholin-4-yl)-4-oxo-5,6-dihydro-4H-[1,3]thiazolo[5,4-c]azepin-8-yl]benzoate (0.130 g, 0.310 mmol) in a Parr bottle in ethanol (8 mL) under an atmosphere of argon was added palladium hydroxide (0.073 g, 0.52 mmol). The flask was placed on the Parr apparatus and then the flask was purged several times with argon and filled with 60 psi hydrogen. Stirred at room temperature for 16 hours, reaction was incomplete by LC/MS. Added an additional portion of palladium hydroxide (0.025 g, 0.18 mmol) and stirred on the Parr apparatus at room temperature under 60 psi hydrogen for 16 hours. There was further progress by LC/MS but still incomplete reaction, so another portion of palladium hydroxide (0.025 g, 0.18 mmol) was added and stirring was continued on the Parr apparatus at room temperature under 60 psi hydrogen for 2 hours. The mixture was filtered through celite (washed celite with methanol) then concentrated. The residue was purified by preparative HPLC to give the product (0.070 g, 54%). LCMS: (AA) ES+ 422, 424. $^1$H NMR (300 MHz, d$_6$-DMSO) δ: 7.97 (t, J=4.3 Hz, 1H), 7.54 (d, J=2.1 Hz, 1H), 7.49 (d, J=8.3 Hz, 1H), 7.28-7.19 (m, 1H), 4.51-4.28 (m, 1H), 3.83 (s, 3H), 3.71-3.51 (m, 4H), 3.40-3.20 (m, 4H), 3.18-3.02 (m, 2H), 2.27-2.13 (m, 1H), 2.00-1.84 (m, 1H).

Example 31

Synthesis of 4-(4-chlorophenyl)-5,5-dimethyl-2-(pyridin-4-yl)-5,6-dihydrothieno[2,3-c]pyridin-7(4H)-one (Compound 191)

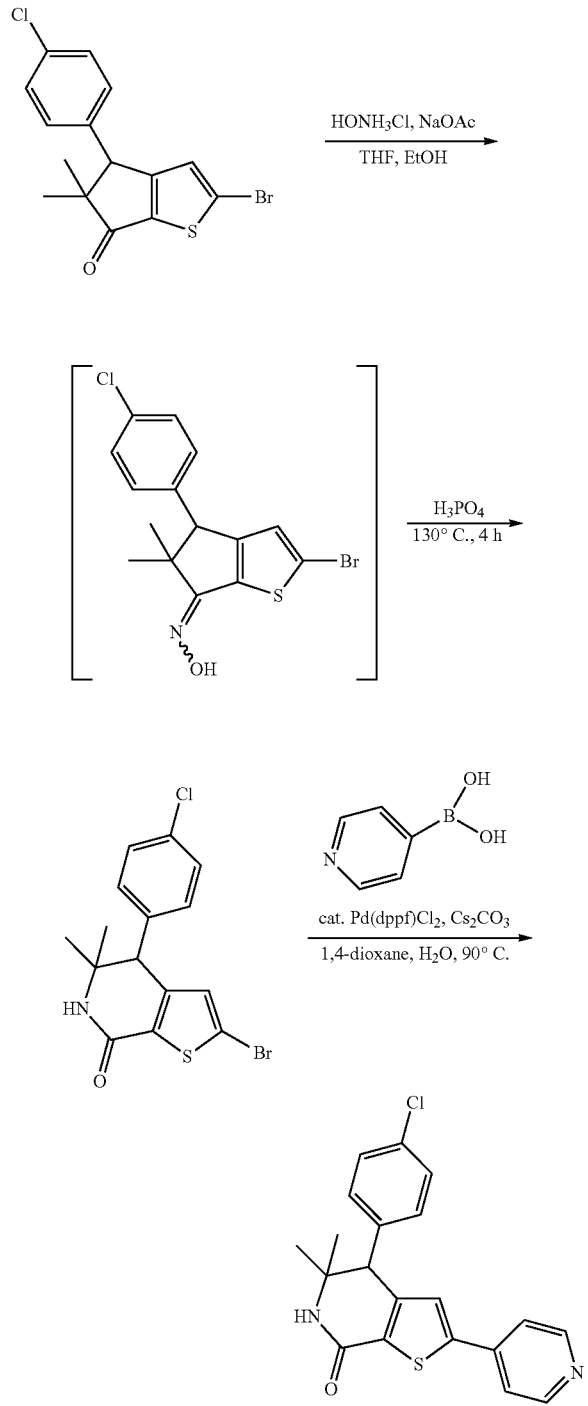

Step 1: Preparation of 2-bromo-4-(4-chlorophenyl)-5,5-dimethyl-5,6-dihydrothieno[2,3-c]pyridin-7(4H)-one To a 50 mL round bottomed flask was added a solution of 2-bromo-4-(4-chlorophenyl)-5,5-dimethyl-4,5-dihydro-6H-cyclopenta[b]thiophen-6-one (0.277 g, 0.779 mmol) in tetrahydrofuran (4.00 mL, 49.3 mmol) and ethanol (4.00 mL, 68.5 mmol). Hydroxylamine hydrochloride (0.274 g, 3.94 mmol) and sodium acetate (0.314 g, 3.83 mmol) was added and the resulting yellowish suspension was stirred at rt for 18 hours. The reaction mixture was heated to 50° C. and allow to stir for 18 hours. The reaction was quenched by the addition of a saturated aqueous solution of sodium bicarbonate (5.00 mL). EtOAc (5.00 mL) was added and the mixture was vigorously stirred for 30 minutes. The organic layer was separated and the aqueous phase was extracted with EtOAc (10 mL×3). The combined organic layers were dried over anhydrous $Na_2SO_4$, filtered and concentrated under reduced pressure. The crude material was used without further purification. A 20 mL vial was charged with crude (6Z)-2-bromo-4-(4-chlorophenyl)-N-hydroxy-5,5-dimethyl-4,5-dihydro-6H-cyclopenta[b]thiophen-6-imine. Polyphosphoric acid (4.0 g, 16.67 mmol) was added and the mixture was heated to 130° C. and allowed to stir for 4 hours. The black reaction was cooled to ambient temperature and diluted with water (20 mL). The mixture was basified to pH 9 by the addition of $K_2CO_3$ (20.0 g) which was added in portions. The mixture was extracted with EtOAc (10 mL×3) and the combined organic layers were dried over anhydrous $Na_2SO_4$, filtered and concentrated under reduced pressure. The crude material was dry loaded onto silica gel and then purified using column chromatography on silica gel (12 g Isco column, gradient 0% to 75% EtOAc in hexane over 30 minutes) to afford the product (0.0440 g, 14.4%) as a brown oil. LC/MS (AA) ES+ 370, 372, 374, 375. 1H NMR (dmso-d6, 400 MHz): d 9.59 (1H, s), 7.40-7.38 (2H, m), 7.21-7.18 (2H, m), 6.29 (1H, s), 1.74 (3H, s), 1.62 (3H, s).

Step 2: Preparation of 4-(4-chlorophenyl)-5,5-dimethyl-2-(pyridin-4-yl)-5,6-dihydrothieno[2,3-c]pyridin-7(4H)-one To a 20 mL vial was added a solution of 2-bromo-4-(4-chlorophenyl)-5,5-dimethyl-5,6-dihydrothieno[2,3-c]pyridin-7(4H)-one (0.0440 g, 0.119 mmol) and pyridine-4-boronic acid (0.02726 g, 0.2218 mmol) in 1,4-dioxane (3.0 mL) and water (0.300 mL). Cesium carbonate (0.1160 g, 0.3561 mmol) was added followed by [1,1'-bis(diphenylphosphino)ferrocene]palladium(II)dichloride (0.0117 g, 0.0142 mmol). The reaction mixture was heated to 90° C. and allowed to stir for 18 h. The reaction was cooled to ambient temperature and quenched by the addition of a saturated aqueous solution of sodium bicarbonate (10 mL) and extracted with EtOAc (10 mL×3). The combined organic layers were dried over anhydrous $Na_2SO_4$, filtered and concentrated under reduced pressure. The crude material as purified by prep HPLC to afford the product (0.0060 g, 13%) as a yellow solid. LC/MS (AA) ES+ 369, 371, 373. 1H NMR (dmso-d6, 400 MHz): d 8.59-

8.57 (2H, m), 7.91 (1H, s), 7.68-7.66 (2H, m), 7.60 (1H, s), 7.40-7.38 (2H, m), 7.19-7.17 (2H, m), 4.21 (1H, s), 1.36 (3H, s), 0.94 (3H, s).

Example 32

Synthesis of 8-(4-chlorophenyl)-2-(morpholin-4-yl)-5,6,7,8-tetrahydro-4H-[1,3]thiazolo[5,4-c]azepin-4-one (Compound 180)

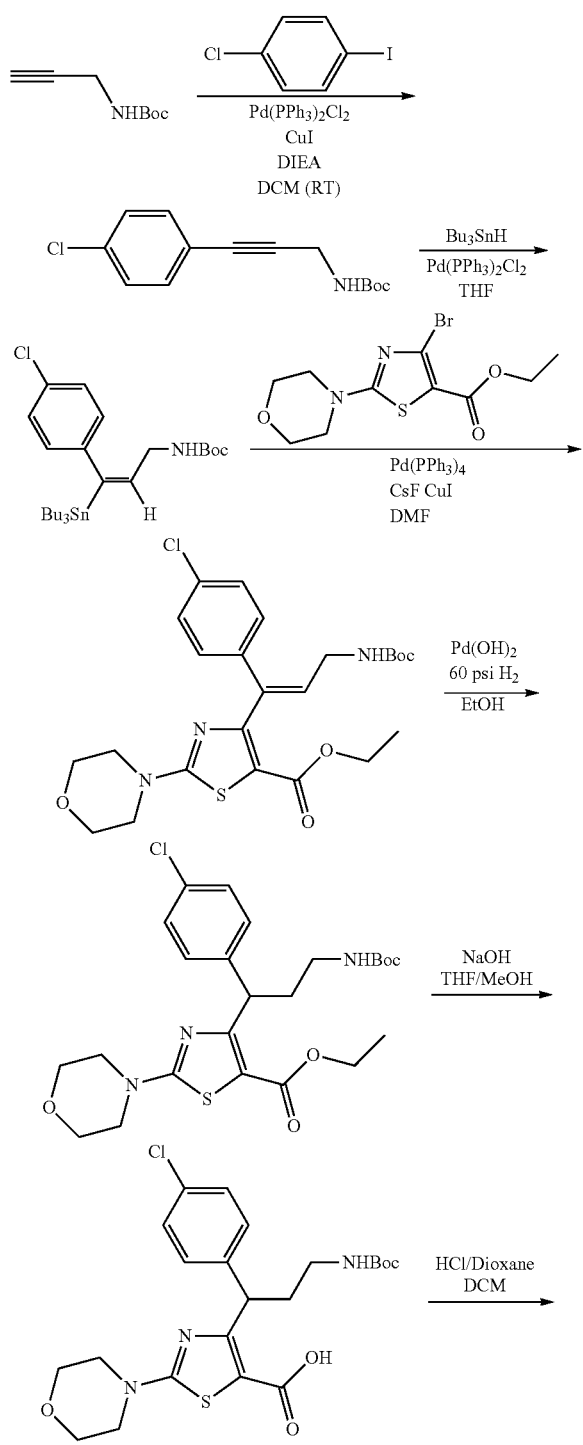

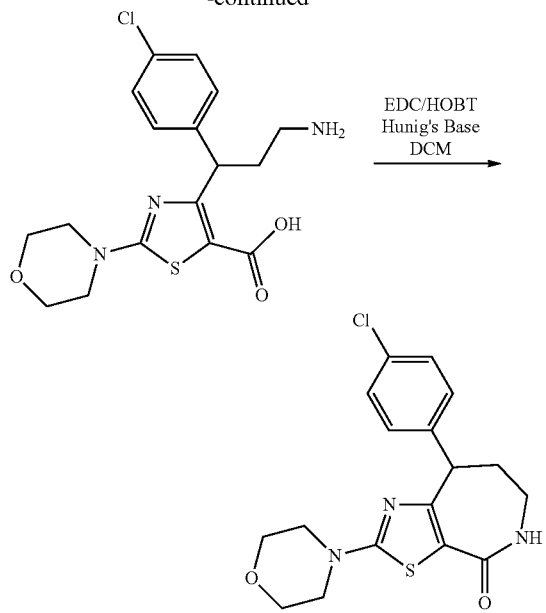

Step 1: tert-butyl [3-(4-chlorophenyl)prop-2-yn-1-yl]carbamate

To a solution of 1-chloro-4-iodobenzene (6.40 g, 26.8 mmol) and N-boc propargylamine (5.00 g, 32.2 mmol) in dichloromethane (117 mL) was added copper (I) iodide (0.204 g, 1.07 mmol) and bis(triphenylphosphine)palladium (II) chloride (0.754 g, 1.07 mmol). The solution was degassed with argon for 10 minutes, then N,N-diisopropylethylamine (14.3 mL, 81.9 mmol) was added and the mixture was stirred at room temperature for 16 hours. The solvent was evaporated, then the residue was diluted with EA and water. The layers were separated and the aqueous layer was extracted twice more with EA. The combined organic layers were dried over anhydrous sodium sulfate, filtered, then concentrated. The residue was purified using column chromatography on silica gel (80 g Analogix column, gradient hexanes to 20% EA in hexanes over 20 minutes) to give the product (5.97 g, 84%). LCMS: (AA) ES+ 210, 212 (Boc group fragmentation). $^1$H NMR (400 MHz, d$_6$-DMSO) δ: 7.47-7.39 (m, 4H), 7.35 (s, 1H), 3.97 (d, J=5.6 Hz, 2H), 1.39 (s, 9H).

Step 2: tert-butyl [(2E)-3-(4-chlorophenyl)-3-(tributylstannyl)prop-2-en-1-yl]carbamate To a solution of tert-butyl [3-(4-chlorophenyl)prop-2-yn-1-yl]carbamate (5.97 g, 22.5 mmol) in THF (240 mL) under an atmosphere of argon was added bis(triphenylphosphine) palladium(II) chloride (0.788 g, 1.12 mmol) and tri-n-butyltin hydride (9.55 mL, 35.5 mmol). The solution was stirred at room temperature for 90 minutes. The solvent was evaporated and the residue was purified using column chromatography on silica gel (220 g Analogix column, gradient hexane to 20% EA in hexane over 30 minutes) to give the product (11.2 g, 90%). LCMS: (AA) ES+ 556, 558. $^1$H NMR (400 MHz, d$_6$-DMSO) δ: 7.37-7.31 (m, 2H), 6.96 (m, 2H), 5.83-5.60 (m, 1H), 3.60-3.37 (m, 2H), 1.44-1.36 (m, 6H), 1.34 (m, 9H), 1.26-1.15 (m, 6H), 0.89-0.77 (m, 15H).

Step 3: ethyl 4-[(1E)-3-[(tert-butoxycarbonyl) amino]-1-(4-chlorophenyl)prop-1-en-1-yl]-2-(morpholin-4-yl)-1,3-thiazole-5-carboxylate A solution of tert-butyl [(2E)-3-(4-chlorophenyl)-3-(tributylstannyl)prop-2-en-1-yl]carbamate (2.17 g, 3.89 mmol) and 4-bromo-2-morpholin-4-yl-1,3-thiazole-5-carboxylate (1.50 g, 4.67 mmol) in DMF (38 mL) was purged with argon, then cesium fluoride (2.07 g, 13.6 mmol), copper(I) iodide (0.185 g, 0.973 mmol) and tetrakis(triphenylphosphine)palladium(0) (0.450 g, 0.389 mmol) were added. The mixture was stirred at 80° C. for 4 hours. The solution was cooled to room temperature, then part of the solvent was evaporated. The residue was diluted with EA and water. The layers were separated and the aqueous layer was extracted twice more with EA. The combined organic layers were washed with water and brine then dried over anhydrous sodium sulfate and concentrated. The residue was purified using column chromatography on silica gel (80 g Analogix column, gradient hexanes to 40% EA in hexanes over 20 minutes) to give the product (0.743 g, 38%). LCMS: (AA) ES+ 508, 510. $^1$H NMR (400 MHz, d$_6$-DMSO) δ: 7.45-7.31 (m, 2H), 7.30-7.17 (m, 2H), 7.12 (t, J=5.6 Hz, 1H), 5.84 (m, 1H), 4.12-3.92 (m, 2H), 3.81-3.60 (m, 6H), 3.57-3.39 (m, 4H), 1.36 (s, 9H), 1.14-1.03 (m, 3H).

Step 4: ethyl 4-{3-[(tert-butoxycarbonyl)amino]-1-(4-chlorophenyl)propyl}-2-(morpholin-4-yl)-1,3-thiazole-5-carboxylate To a solution of ethyl 4-[(1E)-3-[(tert-butoxycarbonyl)amino]-1-(4-chlorophenyl)prop-1-en-1-yl]-2-(morpholin-4-yl)-1,3-thiazole-5-carboxylate (0.328 g, 0.646 mmol) in ethanol (8 mL) in a Parr bottle under an atmosphere of argon was added palladium hydroxide (0.0323 g, 0.230 mmol). The flask was purged several times with argon then filled with hydrogen to 60 psi and rapidly stirred at room temperature for 3 hours. The reaction was incomplete by LCMS. An additional portion of palladium hydroxide (0.0300 g, 0.214 mmol) was added and the reaction was stirred at room temperature under 60 psi hydrogen for 16 hours. There was further progress by LCMS but still incomplete reaction, so another portion of palladium hydroxide (0.0300 g, 0.214 mmol) was added and the reaction was stirred at room temperature under 60 psi hydrogen for 3 days. The mixture was filtered through celite, the celite was washed with methanol to extract all product, and the filtrate was concentrated. The residue was purified using column chromatography on silica gel (24 g Analogix column, gradient hexane to 40% EA in hexane over 15 minutes) to give the product (0.286 g, 87%). LCMS: (AA) ES+ 510, 512. $^1$H NMR (300 MHz, d$_4$-MeOH) δ: 7.40 (d, J=8.5 Hz, 2H), 7.23 (d, J=8.5 Hz, 2H), 5.02 (dd, J=8.9, 6.6 Hz, 1H), 4.24 (q, J=6.8 Hz, 2H), 3.86-3.70 (m, 4H), 3.61-3.45 (m, 4H), 3.02-2.85 (m, 2H), 2.42-2.21 (m, 1H), 2.18-2.01 (m, 1H), 1.40 (s, 9H), 1.30 (t, J=7.1 Hz, 3H).

Step 5: 4-{3-[(tert-butoxycarbonyl)amino]-1-(4-chlorophenyl)propyl}-2-(morpholin-4-yl)-1,3-thiazole-5-carboxylic acid To a solution of ethyl 4-{3-[(tert-butoxycarbonyl)amino]-1-(4-chlorophenyl)propyl}-2-(morpholin-4-yl)-1,3-thiazole-5-carboxylate (0.322 g, 0.631 mmol) in THF (7.8 mL) and MeOH (2.6 mL) was added a solution of sodium hydroxide in water (1 M, 7.76 mL, 7.76 mmol). The solution was stirred at room temperature for 3 days. The solvents were evaporated and the residue was diluted with water then 1N hydrogen chloride aqueous solution was added until pH 7 was reached. The mixture was extracted twice with EA and the combined organic layers were washed with brine then dried over anhydrous sodium sulfate and concentrated to give the product (0.321 g, 105%) which was used directly in the next step. LCMS: (AA) ES+ 482, 484.

Step 6: 4-[3-amino-1-(4-chlorophenyl)propyl]-2-(morpholin-4-yl)-1,3-thiazole-5-carboxylic acid hydrochloride To a solution of 4-{3-[(tert-butoxycarbonyl)amino]-1-(4-chlorophenyl)propyl}-2-(morpholin-4-yl)-1,3-thiazole-5-carboxylic acid (0.304 g, 0.631 mmol) in DCM (5.9 mL) was added a solution of hydrogen chloride in dioxane (4 M, 3.1 mL, 12 mmol) and the mixture was stirred at room temperature for 1 hour. The solvent was evaporated and the residue was then azeotroped with toluene and dried under vacuum to give the product (0.284 g, 108%) which was used directly in the next step. LCMS: (AA) ES+ 382, 384.

Step 7: 8-(4-chlorophenyl)-2-(morpholin-4-yl)-5,6,7,8-tetrahydro-4H-[1,3]thiazolo[5,4-c]azepin-4-one To a solution of 4-[3-amino-1-(4-chlorophenyl)propyl]-2-(morpholin-4-yl)-1,3-thiazole-5-carboxylic acid hydrochloride (0.264 g, 0.631 mmol) in DCM (12.7 mL) was added 1-hydroxybenzotriazole (0.103 g, 0.763 mmol), N-(3-dimethylaminopropyl)-N'-ethylcarbodiimide hydrochloride (0.239 g, 1.24 mmol) and N,N-diisopropylethylamine (0.320 mL, 1.84 mmol) and the mixture was stirred at room temperature for 16 hours. The reaction mixture was diluted with DCM, then the layers were separated and the organic layer was washed with water then brine and dried over anhydrous sodium sulfate then concentrated. The residue was purified using column chromatography on silica gel (12 gr Analogix column, gradient DCM to 10% MeOH in DCM over 15 minutes) to give the product. The racemic product was then separated into enantiomers on a Chiralpak IA 20×250 mm column using 70/10/20 hexane/IPA/EtOH mixture, with retention time 10.4 min for peak 1 (53 mg, 23%) and 14.5 min for peak 2 (53 mg, 23%). Absolute configuration for the enantiomers is unknown. LCMS: (AA) ES+ 364, 366. $^1$H NMR (400 MHz, d$_6$-DMSO) δ: 7.95 (t, J=4.4 Hz, 1H), 7.34 (d, J=8.4 Hz, 2H), 7.08 (d, J=8.4 Hz, 2H), 4.34 (dd, J=7.1, 5.3 Hz, 1H), 3.64-3.57 (m, 4H), 3.31-3.24 (m, 4H), 3.14-3.01 (m, 2H), 2.28-2.13 (m, 1H), 2.04-1.84 (m, 1H).

Compounds in the following table are prepared from appropriate starting materials in a method analogous to that of Example 32.

| 152 | LC/MS: (AA) ES+ 371, 373 |
|---|---|
| 165 | LC/MS: (FA) ES+ 381 |
| 167 | LC/MS: (AA) ES+ 407, 409 |
| 173 | LC/MS: (AA) ES+ 398, 400 |
| 195 | LC/MS: (AA) ES+ 379, 381 |

Example 33

Synthesis of 4-(4-chlorophenyl)-2-(morpholin-4-yl)-6-oxo-5,6-dihydro-4H-thieno[2,3-c]pyrrole-3-carbonitrile (Compound 134)

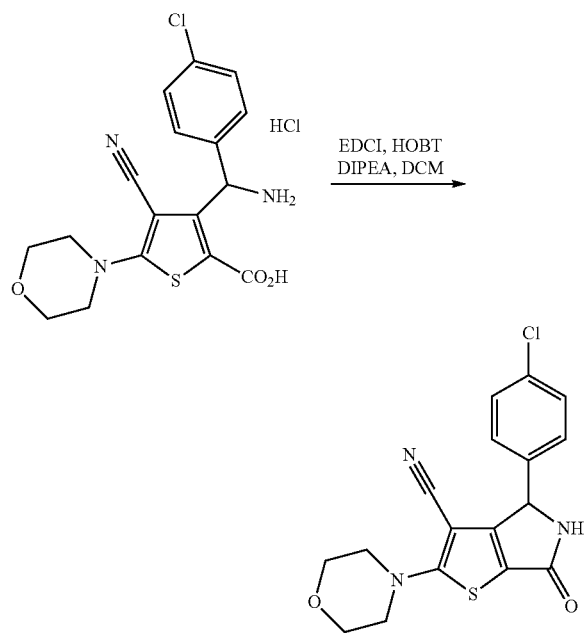

Step 1: 4-(4-chlorophenyl)-2-(morpholin-4-yl)-6-oxo-5,6-dihydro-4H-thieno[2,3-c]pyrrole-3-carbonitrile To a mixture of 3-[amino(4-chlorophenyl)methyl]-4-cyano-5-(morpholin-4-yl)thiophene-2-carboxylic acid.HCl (0.206 g, 0.497 mmol), 1-Hydroxybenzotriazole hydrate (92.1 mg, 0.601 mmol) and N-(3-Dimethylaminopropyl)-N'-ethylcarbodiimide hydrochloride (188 mg, 0.981 mmol) in dry Methylene chloride (10.0 mL, 156 mmol) was added N,N-Diisopropylethylamine (0.252 mL, 1.45 mmol). The resulted clear solution was stirred at r.t. for 21 hours. The reaction solution was diluted with DCM (~30 mL), washed with water (3×), brine, dried over anhydrous $Na_2SO_4$, filtered and rotavaped to give a crude product. Chromatograph in a silica gel column using MeOH/DCM (0/100 to 3/97) afforded a racemic product (0.138 g, yield 74.8%).

Step 2: Enantiomeric separation to 4-(4-chlorophenyl)-2-(morpholin-4-yl)-6-oxo-5,6-dihydro-4H-thieno[2,3-c]pyrrole-3-carbonitrile The racemic 4-(4-chlorophenyl)-2-(morpholin-4-yl)-6-oxo-5,6-dihydro-4H-thieno[2,3-c]pyrrole-3-carbonitrile was separated into enantiomers on a Chiralpak IA 5μ 20×250 column using 70/10/20 Hexane-iPrOH-EtOH mixture, r.t. Retention times in the same condition in a 4.6×250 mm column were 21.1 min (45.1 mg, 32.7%) and 27.1 min (53.6 mg, 38.4%). Absolute configuration of the obtained enantiomers was unknown. LCMS: (FA) $ES^+$ 360, 362. $^1$H NMR (400 MHz, d-chloroform) δ: 7.36 (m, 2H), 7.26 (m, 2H), 6.14 (s, 1H), 5.53 (s, 1H), 3.85-3.82 (m, 4H), 3.57-3.54 (m, 4H).

Compounds in the following table are prepared from appropriate starting materials in a method analogous to that of Example 33.

| | |
|---|---|
| 134 | LC/MS: (FA) ES+ 360, 362 |
| 169 | LC/MS: (FA) ES+ 376 |
| 187 | LC/MS: (FA) ES+ 392, 394 |

Example 34

Synthesis of 4-(3,4-dichlorophenyl)-2-(morpholin-4-yl)-4,5,6,7-tetrahydro-8H-thieno[2,3-c]azepin-8-one (Compound 185)

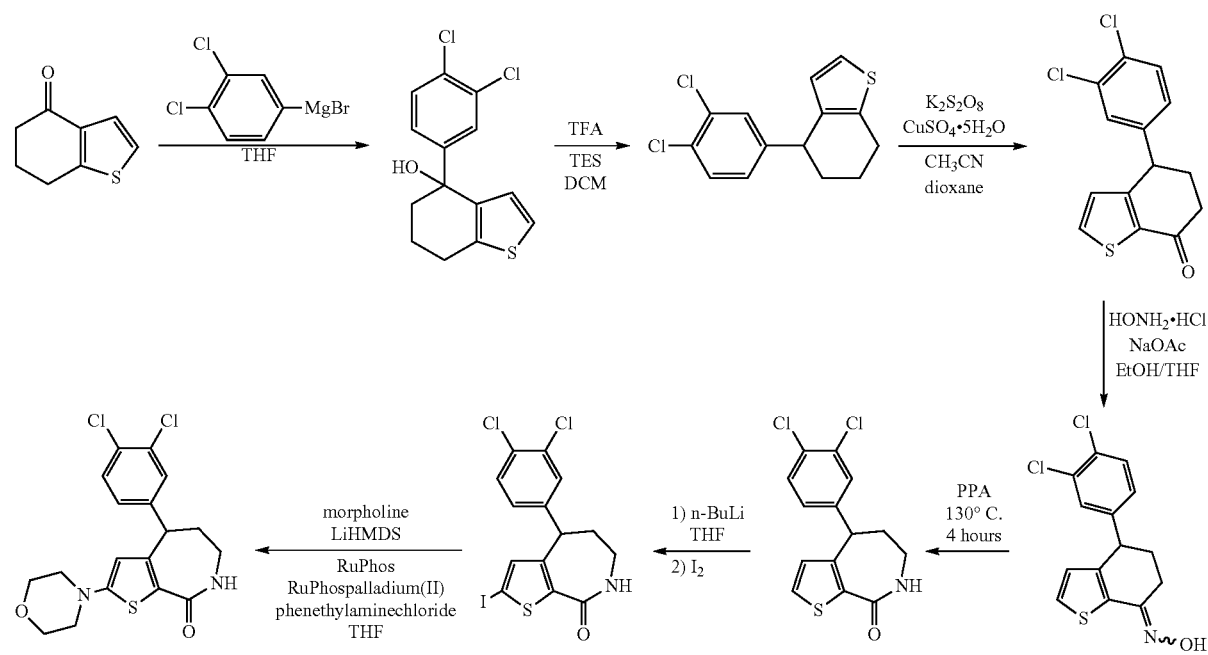

Step 1: 4-(3,4-dichlorophenyl)-4,5,6,7-tetrahydro-1-benzothiophene-4-ol

In a 500 mL round bottomed flask equipped with a stirbar was placed 6,7-dihydro-4-benzo[b]thiophenone (3.17 g, 20.8 mmol) and dry tetrahydrofuran (100 mL, 2000 mmol). The resulting solution was stirred under an atmosphere of nitrogen while a solution of 3,4-dichlorophenylmagnesiumbromide in tetrahydrofuran (0.50M, 0.0 mL, 25.0 mmol) was added in a slow stream over ~10 minutes' time (a very slight exotherm was observed). The reaction was stirred for 2.5 h at rt then was quenched by the slow addition of a saturated solution of $NH_4Cl$. The resulting mixture was stirred briefly, then ethyl acetate was added and the mixture was transferred to a separatory funnel. The layers were separated and the aqueous layer was extracted with additional ethyl acetate. The organic extracts were combined, washed with saline, dried over sodium sulfate, filtered and evaporated to leave crude product as a purplish oil. The residue was purified using column chromatography on silica gel (120 g RediSep column, gradient 0% EA in hexane to 20% EA in hexane over 30 minutes) to give the product (4.53 g, 73% yield) as a clear oil. LCMS: (FA) ES$^+$ 281, 283 (product—$H_2O$). $^1$H NMR (400 MHz, DMSO) δ 7.56-7.50 (d, J=8.4 Hz, 1H), 7.50-7.45 (d, J=1.8 Hz, 1H), 7.24-7.18 (d, J=5.2 Hz, 1H), 7.16-7.08 (dd, J=8.4, 1.8 Hz, 1H), 6.59-6.51 (d, J=5.2 Hz, 1H), 5.86-5.74 (s, 1H), 2.88-2.74 (t, J=5.9 Hz, 2H), 1.97-1.81 (m, 3H), 1.74-1.59 (m, 1H).

Step 2: 4-(3,4-dichlorophenyl)-4,5,6,7-tetrahydro-1-benzothiophene

To a stirring solution of 4-(3,4-dichlorophenyl)-4,5,6,7-tetrahydro-1-benzothiophene-4-ol (4.50 g, 15.0 mmol) in methylene chloride (75 mL) were added triethylsilane (11 mL, 69 mmol) and trifluoroacetic acid (12.0 mL, 156 mmol). The solution became reddish orange but no exotherm was observed. The reaction was stirred for 2.5 hr at rt under an atmosphere of nitrogen. The resulting somewhat fluorescent reddish orange solution was concentrated on the rotovap. Ethyl acetate and water were added (~100 ml each), the mixture was stirred, and a saturated solution of NaHCO3 was slowly added until the mixture became basic. The mixture was transferred to a separatory funnel, the organic layer was separated, and the aqueous layer was extracted again with ethyl acetate. The combined organic layers were washed with brine, dried over sodium sulfate, filtered, and concentrated to leave crude product as a light brown oil. The residue was purified using column chromatography on silica gel (80 g RediSep column, eluant 100% hexane) give the product (3.25 g, 76% yield) as a clear oil. LCMS: (FA) product did not give an ionization peak. $^1$H NMR (400 MHz, DMSO) δ 7.59-7.50 (d, J=8.3 Hz, 1H), 7.37-7.31 (d, J=2.1 Hz, 1H), 7.26-7.19 (d, J=5.2 Hz, 1H), 7.12-7.01 (dd, J=8.3, 2.1 Hz, 1H), 6.48-6.40 (d, J=5.2 Hz, 1H), 4.11-4.00 (t, J=6.2 Hz, 1H), 2.91-2.71 (m, 2H), 2.14-2.00 (m, 1H), 1.91-1.62 (m, 3H).

Step 3: 4-(3,4-dichlorophenyl)-5,6-dihydro-1-benzothiophen-7(4H)-one 4-(3,4-Dichlorophenyl)-4,5,6,7-tetrahydro-1-benzothiophene (3.25 g, 11.5 mmol), 1,4-dioxane (93 mL), acetonitrile (93 mL), water (100 mL), copper(II) sulfate pentahydrate (11.46 g, 45.90 mmol), and potassium persulfate (12.41 g, 45.90 mmol) were combined in a round bottomed flask equipped with a stirbar. The mixture was stirred overnight at 90° C. under an atmosphere of nitrogen during which time the blue color of the reaction disappeared to leave a light brown solution with some light greenish solid. The reaction was cooled to rt then additional copper(II) sulfate pentahydrate (11.46 g, 45.90 mmol) and potassium persulfate (12.41 g, 45.91 mmol) were added and the reaction was stirred at 90° C. under an atmosphere of nitrogen for an additional 5 hours. The reaction was cooled to rt and quenched with a solution of saturated sodium bisulfite. Saturated NaHCO$_3$ solution was added until the mixture was basic, then ethyl acetate was added, the biphasic mixture was transferred to a separatory funnel and the organic layer was separated. The aqueous layer was extracted with additional ethyl acetate. The organic layers were combined, dried over anhydrous sodium sulfate, filtered, and concentrated to leave crude product as darkish orange oil. The residue was purified using column chromatography on silica gel (330 g RediSep column, gradient 0% EA in hexane to 25% EA in hexane over 30 minutes) give the product 1.29 g (38% yield) product as a light tan solid. LCMS: (FA) ES$^+$ 297, 299. 1H NMR (400 MHz, DMSO) δ 8.00-7.93 (d, J=5.0 Hz, 1H), 7.64-7.57 (d, J=8.3 Hz, 1H), 7.55-7.49 (d, J=2.1 Hz, 1H), 7.22-7.14 (dd, J=8.3, 2.1 Hz, 1H), 6.72-6.65 (d, J=5.0 Hz, 1H), 4.41-4.32 (dd, J=9.2, 4.8 Hz, 1H), 2.72-2.59 (m, 1H), 2.57-2.51 (m, 1H), 2.39-2.19 (m, 2H).

Step 4: 4-(3,4-dichlorophenyl)-N-hydroxy-5,6-dihydro-1-benzothiophen-7(4H)-imine A 100 mL round bottomed flask charged with 4-(3,4-dichlorophenyl)-5,6-dihydro-1-benzothiophen-7(4H)-one (1.29 g, 4.34 mmol), tetrahydrofuran (11.0 mL) and ethanol (12.5 mL). The mixture was stirred and sodium acetate (1.117 g, 13.62 mmol) and hydroxylamine hydrochloride (0.9242 g, 13.30 mmol) were added. The mixture was stirred for 16 h at 50° C. under an atmosphere of Nitrogen. The reaction was then cooled to rt, giving a pale yellow solution with much white ppt. The reaction was quenched into ~75 ml saline solution w/stirring and the resulting mixture was transferred to a separatory funnel and extracted with ethyl acetate (2×). the extracts were combined, washed with saline, dried over sodium sulfate, filtered, and evaporated to leave 1.27 g (94% yield) product as pale yellow powder. LCMS: (FA) ES$^+$ 312, 314. 1H NMR indicated that the product was an ~3:1 mixture of geometric oxime isomers.

Step 5: 4-(3,4-dichlorophenyl)-4,5,6,7-tetrahydro-8H-thieno[2,3-c]azepin-8-one In a 250-ml round bottomed flask equipped with a stirbar was placed 4-(3,4-dichlorophenyl)-N-hydroxy-5,6-dihydro-1-benzothiophen-7(4H)-imine (1.25 g, 4.00 mmol) and polyphosphoric acid (40 g, 200 mmol). The resulting mixture was heated at 130° C. under an atmosphere of nitrogen with stirring for ~4 hours, leaving a dark brown mixture. The mixture was allowed to cool to rt then water and ethyl acetate were added. The mixture was stirred briefly then transferred to a separatory funnel. The organic layer was separated then the aqueous layer was extracted with additional ethyl acetate. The organic layers were combined, washed with brine, dried over sodium sulfate, filtered, and evaporated to leave crude product as a brown oil. The residue was purified using column chromatography on silica gel (120 g RediSep column, gradient 0% ethyl acetate in dichloromethane to 90% ethyl acetate in dichloromethane over 20 minutes) give the product 1.08 g (86% yield) product as a light tan solid. LCMS: (FA) ES$^+$ 312, 314. 1H NMR (400 MHz, DMSO) δ 8.24-8.12 (s, 1H), 7.65-7.59 (d, J=5.2 Hz, 1H), 7.60-7.51 (d, J=8.3 Hz, 1H), 7.45-7.36

(d, J=2.1 Hz, 1H), 7.11-7.01 (dd, J=8.3, 2.1 Hz, 1H), 6.64-6.51 (d, J=5.2 Hz, 1H), 4.56-4.42 (dd, J=8.8, 5.5 Hz, 1H), 3.25-3.03 (m, 2H), 2.34-2.18 (m, 1H), 2.10-1.95 (m, 1H).

Step 6: 4-(3,4-dichlorophenyl)-2-iodo-4,5,6,7-tetrahydro-8H-thieno[2,3-c]azepin-8-one To a stirring solution of 4-(3,4-dichlorophenyl)-4,5,6,7-tetrahydro-8H-thieno[2,3-c]azepin-8-one (1.05 g, 3.36 mmol) in tetrahydrofuran (30 mL) at −78° C. was added a solution of n-butyllithium in hexane (2.5 M, 6.73 mL, 16.82 mmol) in rapid drops under an atmosphere of argon. The reaction solution became purplish after ~2 ml had been added and became intensely purple by the end of the addition. The reaction solution was stirred at −78° C. for 30 minutes then iodine (7.95 g, 31.3 mmol) was added as a solid in a single portion with good stirring—the purple color was instantly quenched to give a reddish brown mixture. The resulting mixture was stirred at −78° C. for 5 minutes then the dry ice/acetone bath was removed and the reaction was allowed to warm to rt with stirring for one hour. A saturated sodium bisulfate solution (150 mL) was added to the reaction mixture with good stirring—most of the color faded to give a lemon yellow mixture. Ethyl acetate was added and the mixture was transferred to a separatory funnel. The organic layer was separated, the aqueous layer was extracted with ethyl acetate, the combined organic layers were washed with saline, dried over sodium sulfate, filtered, and concentrated to leave crude product as a light orange solid. The crude product was stirred with DCM—most solids did not dissolve. The mixture was sonicated well, diluted with t-butyl methyl ether, and the white precipitate was isolated on a fritted funnel. It was washed it with additional TBME and air-dried to leave 787 mg product as a white powder. The filtrate was evaporated to leave an orange residue which was purified using column chromatography on silica gel (80 g RediSep column, gradient 0% ethyl acetate in hexane to 100% ethyl acetate in hexane over 30 minutes) to give 440 mg additional product as a white solid. Total yield 1.227 g (83% yield). LCMS: (FA) ES+ 438, 440. 1H NMR (400 MHz, DMSO) δ 8.27-8.20 (d, J=4.5 Hz, 1H), 7.61-7.53 (d, J=8.3 Hz, 1H), 7.47-7.42 (d, J=2.0 Hz, 1H), 7.09-7.02 (dd, J=8.3, 2.1 Hz, 1H), 6.81-6.75 (s, 1H), 4.51-4.41 (dd, J=8.6, 5.3 Hz, 1H), 3.22-3.05 (d, J=5.5 Hz, 2H), 2.27-2.14 (m, 1H), 2.09-1.99 (m, J=7.9 Hz, 1H).

Step 7: 4-(3,4-dichlorophenyl)-2-(morpholin-4-yl)-4,5,6,7-tetrahydro-8H-thieno[2,3-c]azepin-8-one RuPhospalladium(II)phenethylaminechloride (37.01 mg, 0.05079 mmol), 2-dicyclohexylphosphino-2',6'-di-i-propoxy-1,1'-biphenyl (23.70 mg, 0.05079 mmol), dichlorophenyl)-2-iodo-4,5,6,7-tetrahydro-8H-thieno[2,3-c]azepin-8-one (445.0 mg, 1.016 mmol) and tetrahydrofuran were combined in a rbf equipped with a stirbar. The flask was sealed with a septum then evacuated and refilled with argon three times. Morpholine (155 uL, 1.78 mmol) was added via syringe (all solids dissolved to give a clear pale yellow solution) followed by a solution of lithium bis(trimethylsilyl) amide in tetrahydrofuran (1.0M, 2.23 mL, 2.23 mmol). The sealed reaction was vigorously stirred @ 40° C. After 2 hours' heating, the reaction was a clear reddish orange color. The reaction was heated another hour at 50° C. then was cooled to rt and quenched into saline. The mixture was extracted with ethyl acetate (2×), the extracts were combined, washed with saline, dried and filtered to leave crude product as a pale orange semisolid which was purified using column chromatography on silica gel (80 g RediSep column, gradient 0% ethyl acetate in dichloromethane to 100% ethyl acetate in dichloromethane over 12.5 minutes) give the product 89 mg (22% yield) product as a pale yellow powder. LCMS: (FA) ES+ 397, 399. 1H NMR (400 MHz, DMSO) δ 7.86-7.73 (t, J=4.5 Hz, 1H), 7.60-7.52 (d, J=8.3 Hz, 1H), 7.43-7.36 (d, J=2.0 Hz, 1H), 7.10-7.01 (dd, J=8.3, 2.1 Hz, 1H), 5.66-5.56 (s, 1H), 4.40-4.28 (dd, J=8.1, 5.1 Hz, 1H), 3.73-3.58 (t, J=4.8 Hz, 4H), 3.16-3.04 (m, 2H), 3.05-2.95 (t, J=4.9 Hz, 4H), 2.26-2.10 (m, 1H), 2.06-1.87 (m, 1H).

Example 35

Synthesis of 4-(4-chlorophenyl)-7-methyl-2-(morpholin-4-yl)-4,5,6,7-tetrahydro-8H-thieno[2,3-c]azepin-8-one (Compound 141)

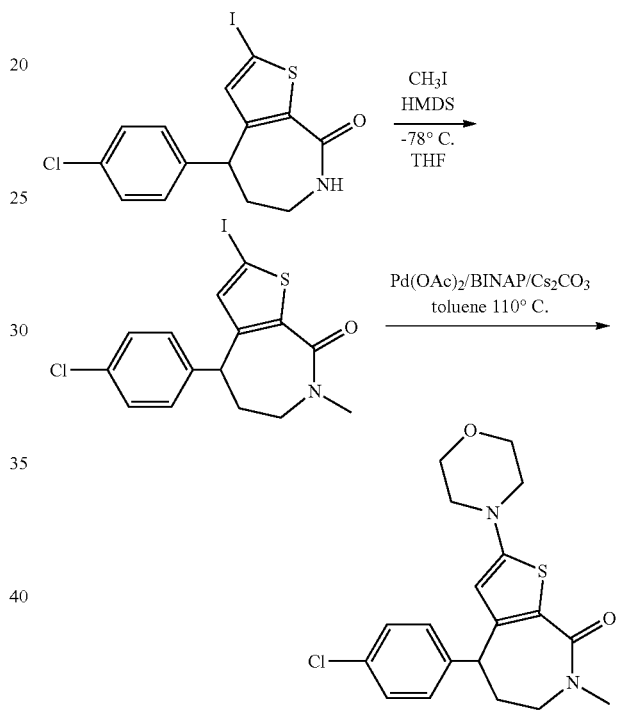

Step 1, Preparation of 4-(4-chlorophenyl)-2-iodo-7-methyl-4,5,6,7-tetrahydro-8H-thieno[2,3-e]azepin-8-one To a solution of 4-(4-chlorophenyl)-2-iodo-4,5,6,7-tetrahydro-8H-thieno[2,3-c]azepin-8-one (95.0 mg, 0.235 mmol, prepared in an analogous manner as described in Example 33) in tetrahydrofuran (8.6 mL) at −78° C. under an atmosphere of argon was added LiHMDS in hexane (1 M, 0.259 mL, 0.259 mmol). After stirring at −78° C. for 5 min, methyl iodide (0.293 mL, 4.70 mmol) was added and the resulting yellow solution was stirred at rt for 16 hr. The mixture was quenched with saturated NH₄Cl aqueous solution, the volatiles were removed and the obtained residue was purified by silica gel column chromatography (elution with 0-50% EA/hexane) to give the title compound as a white solid (52.8 mg, 53% yield). LCMS: (FA) ES+, 417/419. ¹H NMR (300 MHz, DMSO) δ 7.37 (d, J=8.4 Hz, 2H), 7.13 (d, J=8.4 Hz, 2H), 6.75 (d, J=11.3 Hz, 1H), 4.36 (dt, J=30.3, 15.3 Hz, 1H), 3.59-3.34 (m, 2H), 3.03 (d, J=8.8 Hz, 3H), 2.38-2.15 (m, 1H), 2.12-1.92 (m, 1H).

Step 2, Preparation of 4-(4-chlorophenyl)-7-methyl-2-(morpholin-4-yl)-4,5,6,7-tetrahydro-8H-thieno[2,3-e]azepin-8-one To a mixture of 4-(4-chlorophenyl)-2-iodo-7-methyl-4,5,6,7-tetrahydro-8H-thieno[2,3-c]azepin-8-one (45.6 mg, 0.109 mmol), 1,1'-binaphthalene-2,2'-diylbis(diphenylphosphine) (2.080 mg, 0.0033 mmol), dicesium carbonate (51.4 mg, 0.158 mmol) in toluene (0.4 mL) was added morpholine (0.01 mL, 0.1 mmol) and the purged with $N_2$ three times. To that mixture was added bis(dibenzylideneacetone)palladium (0) (0.96 mg, 0.0017 mmol) and the atmosphere was again purged with $N_2$, then the mixture was stirred for 16 hr at 100° C. The reaction mixture was allowed to cool to rt and then diluted with ethyl acetate (2 mL) and water (2 mL). The resulting bi-phasic mixture was vigorously stirred for 30 min. The organic phase was separated and the aqueous phase was extracted with ethyl acetate (3×5 mL). The combined organic layers were dried over anhydrous $MgSO_4$, filtered and concentrated. The crude mixture was purified by preparative HPLC to give the title compound as a white solid (7.4 mg, 17.9% yield). LCMS: (FA) ES$^+$, 376.9/378.8. $^1$H NMR (300 MHz, DMSO)δ 7.35 (d, J=8.4 Hz, 2H), 7.12 (d, J=8.4 Hz, 2H), 5.57 (s, 1H), 4.38-4.16 (m, 1H), 3.76-3.53 (m, 4H), 3.38 (dd, J=16.9, 11.5 Hz, 2H), 3.31 (s, 3H), 3.06-2.98 (m, 4H), 2.26 (dd, J=13.8, 7.0 Hz, 1H), 2.10-1.77 (m, 1H).

Example 36

2-(morpholin-4-yl)-4-(2-naphthyl)-7-oxo-4,5,6,7-tetrahydrothieno[2,3-c]pyridine-3-carbonitrile (Compound 135)

Step 1: ethyl 4-cyano-3-[2-(1,3-dioxo-1,3-dihydro-2H-isoindol-2-yl)-1-(2-naphthyl)ethyl]-5-(morpholin-4-yl)thiophene-2-carboxylate A dry 40 mL vial charged with a mixture of potassium tert-butoxide (0.110 g, 0.984 mmol) in anhydrous N,N-dimethylformamide (2.0 mL) was cooled to −50° C. with an acetonitrile-dry ice bath under nitrogen. To the vial was added a suspension of ethyl 4-cyano-5-morpholin-4-yl-3-(2-naphthylmethyl)thiophene-2-carboxylate (0.200 g, 0.492 mmol) in anhydrous N,N-dimethylformamide (2.0 mL) dropwise. After 10 min of stirring the resulting black solution, a solution of N-bromomethylphthalimide (0.142 g, 0.590 mmol) in anhydrous N,N-dimethylformamide (1.0 mL) was added dropwise and the mixture was stirred at −52° C.~−45° C. for 90 min. The reaction was quenched with acetic acid (0.084 mL, 1.5 mmol) and warmed up to r.t. The solution was diluted with water (~30 mL), and the resulting pale yellow solid was collected by filtration. The crude solid was dissolved in DCM (30 mL), washed with brine, dried over anhydrous $Na_2SO_4$, filtered, and concentrated. Purification on a silica gel column (continuous gradient of EtOAc/hexane 0~50%) afforded the title product (0.126 g, yield 45.3%). LCMS: (FA) ES$^+$ 566. $^1$H NMR (400 MHz, d-chloroform) δ: 7.95 (s, 1H), 7.90-7.75 (m, 5H), 7.73-7.63 (m, 2H), 7.50-7.40 (m, 3H), 6.03 (m, 1H), 4.87-4.73 (m, 2H), 4.20-4.10 (m, 2H), 3.82-3.75 (m, 4H), 3.51-3.42 (m, 4H), 1.20-1.13 (m, 3H).

Step 2: 2-(morpholin-4-yl)-4-(2-naphthyl)-7-oxo-4,5,6,7-tetrahydrothieno[2,3-c]pyridine-3-carbonitrile To a solution of ethyl 4-cyano-3-[2-(1,3-dioxo-1,3-dihydro-2H-isoindol-2-yl)-1-(2-naphthyl)ethyl]-5-(morpholin-

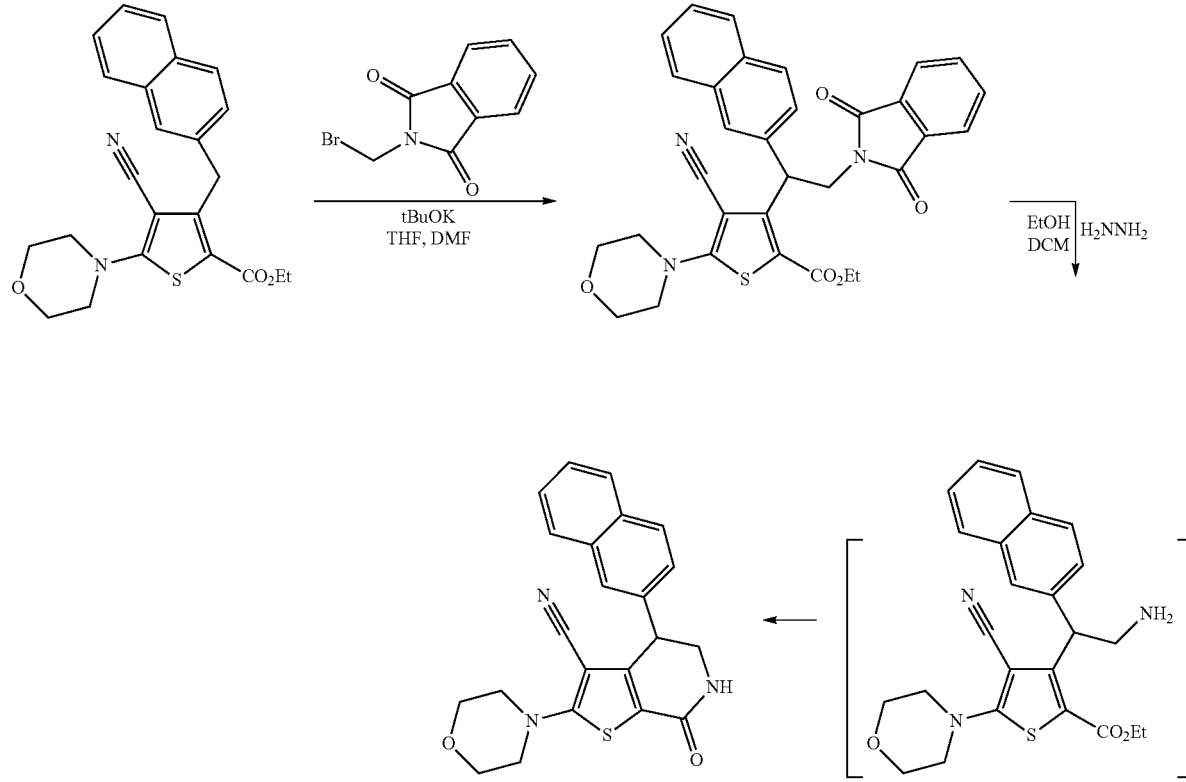

4-yl)thiophene-2-carboxylate (0.126 g, 0.223 mmol) in ethanol (4.0 mL) and methylene chloride (1.0 mL) was added hydrazine (23.3 mg, 0.727 mmol). After 40 h of stirring at rt, hydrazine (25 mg, 0.78 mmol) was added and the mixture was stirred at rt for another 22 h. The mixture was filtered and concentrated. Purification on a silica gel column (continuous gradient of MeOH/DCM 0-20%) to afford a white solid product (0.0672 g, yield 77.1%). LCMS: (FA) ES+ 390. $^1$H NMR (400 MHz, d-chloroform) δ: 7.86-7.71 (m, 3H), 7.59 (s, 1H), 7.50-7.42 (m, 2H), 7.37 (dd, J=8.5, 1.8 Hz, 1H), 5.79 (d, J=4.0 Hz, 1H), 4.32 (d, J=3.5 Hz, 1H), 4.19-4.07 (m, 1H), 3.85-3.74 (m, 4H), 3.62 (ddd, J=12.5, 4.5, 2.3 Hz, 1H), 3.59-3.51 (m, 4H).

Compounds in the following table are prepared from appropriate starting materials in a method analogous to that of Example 36.

| | |
|---|---|
| 124 | LC/MS: (FA) ES+ 350, 352 |
| 135 | LC/MS: (FA) ES+ 390 |
| 149 | LC/MS: (FA) ES+ 374, 376 |
| 159 | LC/MS: (FA) ES+ 408, 410 |
| 179 | LC/MS: (FA) ES+ 372 |
| 189 | LC/MS: (FA) ES+ 367 |
| 190 | LC/MS: (FA) ES+ 388, 390 |
| 194 | LC/MS: (FA) ES+ 363, 365 |
| 205 | LC/MS: (FA) ES+ 363, 365 |

Example 37

Synthesis of rel-(4R,5R)-4-(3,4-dichlorophenyl)-2-(morpholin-4-yl)-7-oxo-4,5,6,7-tetrahydrothieno[2,3-c]pyridine-5-carboxamide (Compound 146)

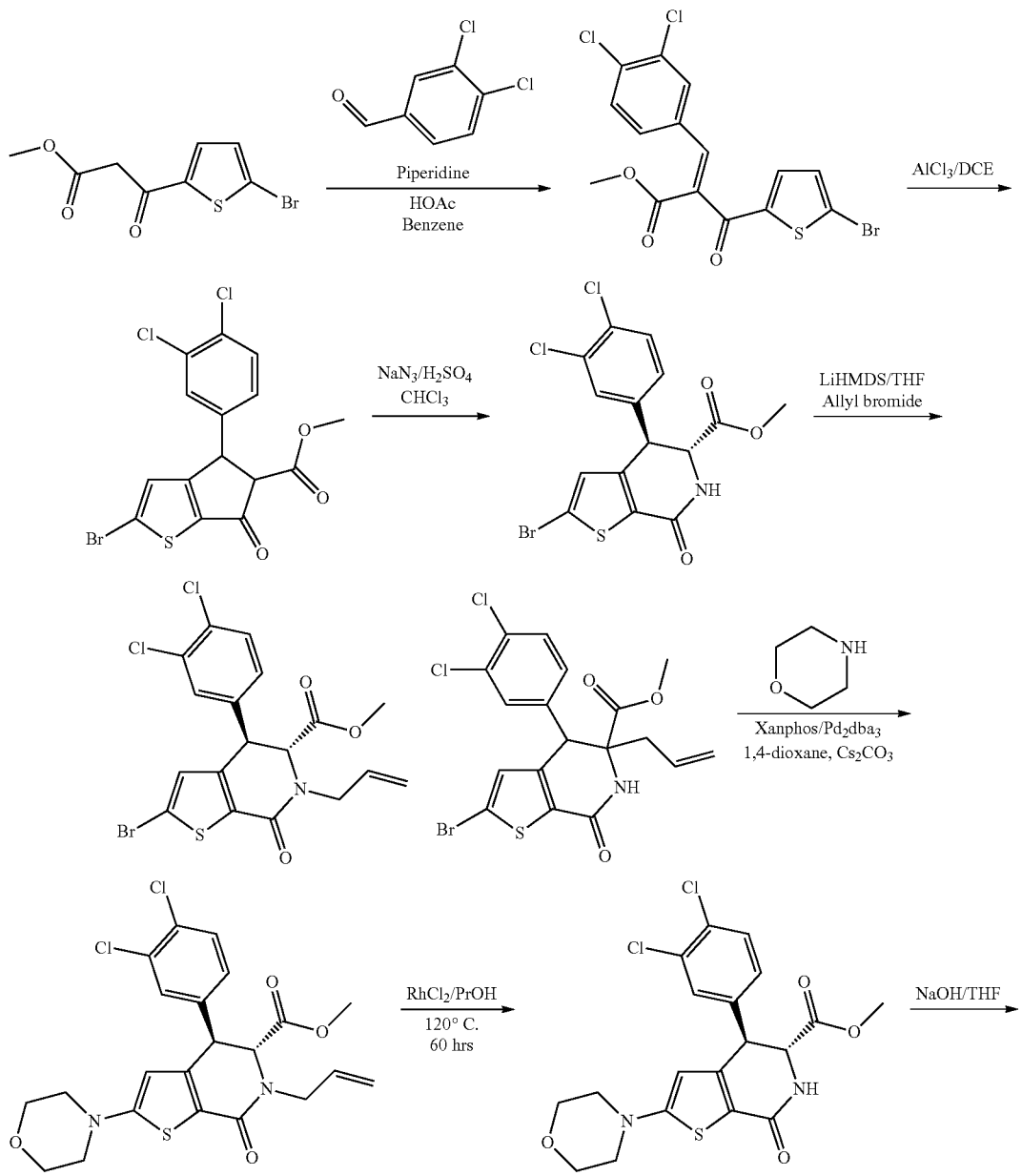

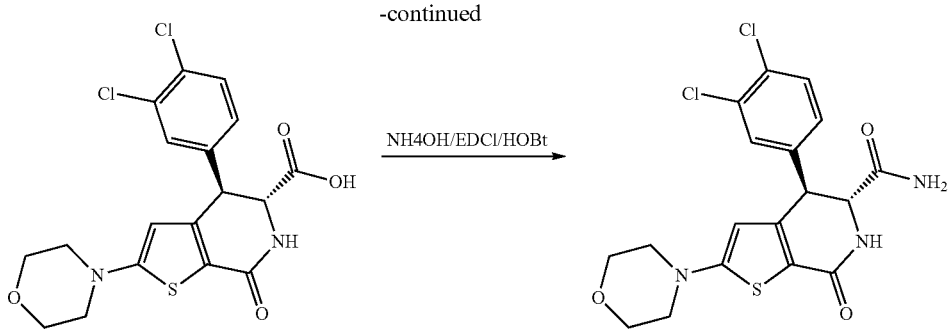

-continued

Step 1: methyl (2Z)-2-[(5-bromo-2-thienyl)carbonyl]-3-(3,4-dichlorophenyl)acrylate To a 250 mL round bottom flask was added a solution of methyl 3-(5-bromo-2-thienyl)-3-oxopropanoate (25.11 g, 95.44 mmol), 3,4-dichloro-benzaldehyde (21.71 g, 124.1 mmol) and piperidine (0.944 mL, 9.54 mmol) in anhydrous benzene (682 mL). Acetic acid (3.80 mL, 66.8 mmol) was added and the reaction mixture was fitted with a Dean-Stark trap. The oil bath was heated to 110° C. and the reaction stirred at reflux for 18 hours. The reaction was cooled to ambient temperature and concentrated under reduced pressure. The crude material was dry loaded onto silica gel and purified by silica gel chromatography to afford the product as a yellow oil (36.7 g, 91.6%). LCMS: (AA) ES+: 421. $^1$H NMR (400 MHz, $d_6$-DMSO) δ 7.83 (s, 1H), 7.53-7.45 (m, 1H), 7.34 (t, J=10.0 Hz, 1H), 7.24 (dd, J=8.4, 2.7 Hz, 2H), 7.03 (d, J=4.1 Hz, 1H), 3.81 (s, 3H).

Step 2: methyl 2-bromo-4-(3,4-dichlorophenyl)-6-oxo-5,6-dihydro-4H-cyclopenta[b]thiophene-5-carboxylate A mixture of methyl (2Z)-2-[(5-bromo-2-thienyl)carbonyl]-3-(3,4-dichlorophenyl)acrylate (36.64 g, 87.22 mmol) and aluminum trichloride (14.0 g, 105 mmol) in 1,2-dichloroethane (687.2 mL) was heated at 80° C. under argon overnight. The mixture was then cooled to rt and water (20.4 mL) was added. The mixture was stirred for 30 min and then dryloaded on silica gel. Purified on two ISCO columns, 400 g, EtOAc in hex, 0-80% to afford the product as a yellow solid (31.6 g, 81.3%). LCMS: (AA) ES–: 417, 419. 1H NMR (400 MHz, CDCl$_3$) δ 7.42 (d, J=8.3 Hz, 1H), 7.24 (d, J=2.1 Hz, 1H), 7.02-6.94 (m, 2H), 4.88 (d, J=3.5 Hz, 1H), 3.83 (s, 3H), 3.76 (d, J=3.5 Hz, 1H).

Step 3: methyl 2-bromo-4-(3,4-dichlorophenyl)-7-oxo-4,5,6,7-tetrahydrothieno[2,3-c]pyridine-5-carboxylate To a mixture of sulfuric acid (5.01 mL, 94.0 mmol) and chloroform (49.6 mL, 6.20E2 mmol) was added methyl 2-bromo-4-(3,4-dichlorophenyl)-6-oxo-5,6-dihydro-4H-cyclopenta[b]thiophene-5-carboxylate (5.01 g, 11.9 mmol) followed by sodium azide (3.72 g, 57.2 mmol) in small portions over 3 h with vigorous stirring at 15° C. After addition, the mixture was stirred at rt overnight. The reaction was quenched by ice, basified with sodium bicarbonate, and extracted with DCM. The DCM layer was washed with brine, followed by sodium bicarbonate solution and brine. Dried and evaporated to afford crude product which was purified by silica gel chromatography to afford product as off-white solid (2.50 g, 48.2%). LCMS: (AA) ES+: 435, 437, 1H NMR (400 MHz, CDCl$_3$) δ 7.43-7.38 (m, 1H), 7.28 (d, J=2.2 Hz, 1H), 7.00 (dd, J=8.3, 2.2 Hz, 1H), 6.77 (s, 1H), 5.92 (t, J=9.3 Hz, 1H), 4.67 (d, J=3.3 Hz, 1H), 4.28 (t, J=3.6 Hz, 1H), 3.76 (s, 3H).

Step 4: methyl 6-allyl-2-bromo-4-(3,4-dichlorophenyl)-7-oxo-4,5,6,7-tetrahydrothieno[2,3-c]pyridine-5-carboxylate and methyl 5-allyl-2-bromo-4-(3,4-dichlorophenyl)-7-oxo-4,5,6,7-tetrahydrothieno[2,3-c]pyridine-5-carboxylate To a solution of methyl 2-bromo-4-(3,4-dichlorophenyl)-7-oxo-4,5,6,7-tetrahydrothieno[2,3-c]pyridine-5-carboxylate (0.320 g, 0.735 mmol) in tetrahydrofuran (19 mL, 230 mmol) was added lithium bis(trimethylsilyl)amide (1.103 mmol, 1.103 mmol) in tetrahydrofuran (0.956 mL, 11.8 mmol) at −78° C. under argon. The mixture was stirred for 30 min before allyl bromide (1.27 mL, 14.7 mmol) was added. The reaction mixture was warmed to rt and stirred for 3 hr. The mixture was quenched by addition of sat. NH$_4$Cl and then extracted with EtOAc. The organic layer was separated, dried, and concentrated in vacuo. The residue was purified by silica gel chromatography to afford methyl 6-allyl-2-bromo-4-(3,4-dichlorophenyl)-7-oxo-4,5,6,7-tetrahydrothieno[2,3-c]pyridine-5-carboxylate, the first fraction, as a white solid (58 mg, 16%). LCMS: (AA) ES–: 474, 476, 1H NMR (400 MHz, CDCl$_3$) δ 7.36 (dd, J=8.3, 4.1 Hz, 1H), 7.17 (d, J=2.1 Hz, 1H), 6.87 (dt, J=9.8, 4.9 Hz, 1H), 6.79 (s, 1H), 5.36-5.23 (m, 1H), 5.03-4.93 (m, 2H), 4.71 (ddt, J=15.2, 5.2, 1.4 Hz, 1H), 4.63 (s, 1H), 4.18 (d, J=1.5 Hz, 1H), 3.74 (s, 3H), 3.46-3.35 (m, 1H).

Methyl 5-allyl-2-bromo-4-(3,4-dichlorophenyl)-7-oxo-4,5,6,7-tetrahydrothieno[2,3-c]pyridine-5-carboxylate, the second fraction, was obtained as a white solid (119 mg, 34%). LCMS: (AA) ES+: 476, 478, 1H NMR (400 MHz, CDCl$_3$) δ 7.35-7.27 (m, 1H), 7.24 (d, J=2.1 Hz, 1H), 6.96 (dd, J=8.4, 2.2 Hz, 1H), 6.82 (s, 1H), 6.29 (s, 1H), 5.65 (ddt, J=17.3, 10.1, 7.4 Hz, 1H), 5.14 (ddd, J=18.2, 13.5, 1.2 Hz, 2H), 4.24 (d, J=14.5 Hz, 1H), 3.58 (s, 3H), 2.75 (ddd, J=61.1, 13.6, 7.4 Hz, 2H).

Step 5: methyl 6-allyl-4-(3,4-dichlorophenyl)-2-(morpholin-4-yl)-7-oxo-4,5,6,7-tetrahydrothieno[2,3-c]pyridine-5-carboxylate (Compound 166)

A mixture of methyl 6-allyl-2-bromo-4-(3,4-dichlorophenyl)-7-oxo-4,5,6,7-tetrahydrothieno[2,3-c]pyridine-5-carboxylate (0.63 g, 1.3 mmol), tris(dibenzylideneacetone)dipalladium(0) (64.7 mg, 0.0706 mmol), 4,5-bis(diphenylphosphino)-9,9-dimethylxanthene (80.7 mg, 0.139 mmol) and cesium carbonate (1.30 g, 3.98 mmol) was evacuated and filled with argon, followed by addition of 1,4-dioxane (37 mL) and morpholine (0.347 mL, 3.98 mmol). The mixture was heated in a sealed microwave tube at 100° C. for 10 h. The mixture was dry loaded on silica gel and purified by chromatography to afford the product as a white solid (0.398 g, 62%). LCMS: (AA) ES+: 481, 483, 1H NMR (400 MHz, CDCl$_3$) δ 7.35 (d, J=8.3 Hz, 1H), 7.20 (d, J=2.1 Hz, 1H), 6.92 (dd, J=8.3, 2.1 Hz, 1H), 5.71 (s, 1H), 5.36-5.22 (m, 1H), 5.00-4.90 (m, 2H), 4.78 (dd, J=15.2, 4.9 Hz, 1H), 4.55 (s, 1H), 4.12 (t, J=3.0 Hz, 1H), 3.85-3.77 (m, 4H), 3.73 (d, J=8.0 Hz, 3H), 3.42-3.31 (m, 1H), 3.18 (dd, J=12.0, 7.1 Hz, 4H).

Step 6: methyl rel-(4R,5R)-4-(3,4-dichlorophenyl)-2-(morpholin-4-yl)-7-oxo-4,5,6,7-tetrahydrothieno[2,3-c]pyridine-5-carboxylate (Compound 127)

A mixture of methyl rel-(4R,5R)-6-allyl-4-(3,4-dichlorophenyl)-2-(morpholin-4-yl)-7-oxo-4,5,6,7-tetrahydrothieno[2,3-c]pyridine-5-carboxylate (0.344 g, 0.714 mmol) and rhodium(III)chloride, (22.2 mg, 0.106 mmol) in 1-propanol (9.0 mL) was heated in a sealed tube under argon at 120° C. for 50 h. The reaction mixture was evaporated and purified by silica gel chromatography to afford the product as a white solid (0.278 g, 88%). LCMS: (AA), ES+: 441, 443, 1H NMR (400 MHz, CDCl$_3$) δ 7.38 (d, J=8.3 Hz, 1H), 7.34-7.25 (m, 1H), 7.04 (dd, J=8.3, 2.0 Hz, 1H), 5.68 (s, 1H), 5.57 (s, 1H), 4.59 (d, J=2.9 Hz, 1H), 4.20-4.19 (m, 1H), 3.81-3.79 (m, 4H), 3.74 (s, 3H), 3.20-3.18 (m, 4H).

Step 7: rel-(4R,5R)-4-(3,4-dichlorophenyl)-2-(morpholin-4-yl)-7-oxo-4,5,6,7-tetrahydrothieno[2,3-c]pyridine-5-carboxylic acid (Compound 142)

A mixture of methyl rel-(4R,5R)-4-(3,4-dichlorophenyl)-2-(morpholin-4-yl)-7-oxo-4,5,6,7-tetrahydrothieno[2,3-c]pyridine-5-carboxylate (274.0 mg, 0.6208 mmol) in tetrahydrofuran (10.0 mL) and sodium hydroxide (4.50 mmol, 4.50 mmol) in water (4.50 g) was stirred at rt. After 4 h, the mixture was acidified by 1N HCl and the precipitate was collected as pure product (0.250 g, 94%). LCMS: (AA), ES+: 425, 427.

Step 8: rel-(4R,5R)-4-(3,4-dichlorophenyl)-2-(morpholin-4-yl)-7-oxo-4,5,6,7-tetrahydrothieno[2,3-c]pyridine-5-carboxamide To a mixture of rel-(4R,5R)-4-(3,4-dichlorophenyl)-2-(morpholin-4-yl)-7-oxo-4,5,6,7-tetrahydrothieno[2,3-c]pyridine-5-carboxylic acid (0.100 g, 0.234 mmol), N-(3-dimethylaminopropyl)-N'-ethylcarbodiimide hydrochloride (0.090 g, 0.47 mmol), 1-hydroxybenzotriazole hydrate (0.072 g, 0.47 mmol) in methylene chloride (4 mL) was added a solution of 33% ammonium hydroxide in water (0.40 mL, 4.7 mmol). The mixture was stirred at rt overnight. The mixture was concentrated and the residue was purified by silica gel chromatography. Final purification by HPLC afforded the product as a white solid. LCMS: (AA), ES+: 426, 428, 1H NMR (400 MHz, DMSO) δ 7.58 (d, J=8.3 Hz, 1H), 7.53-7.47 (m, 2H), 7.37 (d, J=4.2 Hz, 1H), 7.20 (s, 1H), 7.10 (dd, J=8.5, 2.0 Hz, 1H), 6.00 (s, 1H), 4.52 (s, 1H), 3.96 (dd, J=4.3, 2.2 Hz, 1H), 3.73-3.63 (m, 4H), 3.12 (d, J=5.6 Hz, 4H).

Compounds in the following table are prepared from appropriate starting materials in a method analogous to that of Example 37.

| | |
|---|---|
| 123 | LC/MS: (AA) ES+ 406, 408 |
| 125 | LC/MS: (AA) ES+ 420, 422 |
| 126 | LC/MS: (FA) ES+ 393, 395 |
| 132 | LC/MS: (AA) ES+ 440, 442, 444 |
| 136 | LC/MS: (FA) ES+ 436, 438 |
| 153 | LC/MS: (AA) ES+ 436, 438 |
| 157 | LC/MS: (AA) ES+ 406, 408 |
| 162 | LC/MS: (AA) ES+ 434, 436 |
| 168 | LC/MS: (AA) ES+ 404, 406 |
| 170 | LC/MS: (AA) ES+ 450, 452 |
| 177 | LC/MS: (FA) ES+ 450, 452 |
| 197 | LC/MS: (AA) ES+ 420, 422 |
| 200 | LC/MS: (AA) ES+ 450, 452 |
| 203 | LC/MS: (AA) ES+ 420, 422 |
| 204 | LC/MS: (AA) ES+ 436, 438 |
| 212 | LC/MS: (AA) ES+ 406, 408 |

Example 38

Synthesis of 5-allyl-4-(3,4-dichlorophenyl)-2-(morpholin-4-yl)-7-oxo-4,5,6,7-tetrahydrothieno[2,3-c]pyridine-5-carboxylic acid (Compound 196)

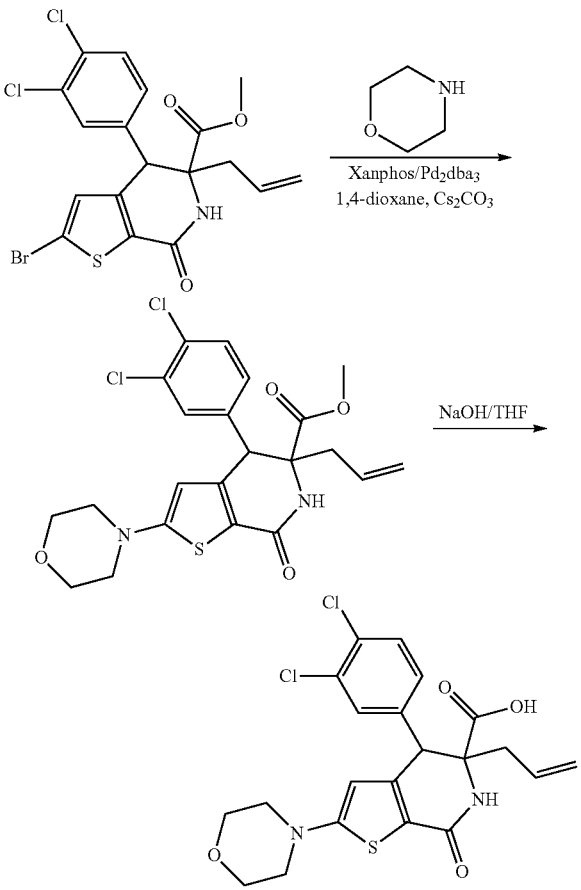

Step 1: methyl 5-allyl-4-(3,4-dichlorophenyl)-2-(morpholin-4-yl)-7-oxo-4,5,6,7-tetrahydrothieno[2,3-c]pyridine-5-carboxylate (Compound 154)

A mixture of methyl 5-allyl-2-bromo-4-(3,4-dichlorophenyl)-7-oxo-4,5,6,7-tetrahydrothieno[2,3-c]pyridine-5-carboxylate (0.51 g, 1.1 mmol), tris(dibenzylideneacetone)dipalladium(0) (98.3 mg, 0.107 mmol), 4,5-bis (diphenylphosphino)-9,9-dimethylxanthene (124 mg, 0.215 mmol) and cesium carbonate (1.29 g, 3.97 mmol) was evacuated and filled with argon, followed by addition of 1,4-dioxane (12 mL) and morpholine (0.281 mL, 3.22 mmol). The mixture was heated at 100° C. overnight. The mixture was then concentrated in vacuo and the residue was purified by silica gel chromatography. Final purification by HPLC afforded pure product as a white solid (0.136 g, 26%). LCMS (AA) ES+: 482, 484. 1H NMR (400 MHz, DMSO) δ 7.55 (d, J=8.4 Hz, 1H), 7.31 (d, J=2.0 Hz, 1H), 7.22 (s, 1H), 7.07 (dd, J=8.4, 2.0 Hz, 1H), 5.98 (s, 1H), 5.70 (dt, J=17.0, 7.2 Hz, 1H), 5.06 (t, J=13.4 Hz, 2H), 4.41 (s, 1H), 3.66 (t, J=4.7 Hz, 4H), 3.41 (s, 3H), 3.19-3.05 (m, 4H), 2.68 (ddd, J=31.0, 13.9, 7.4 Hz, 2H).

Step 2: 5-allyl-4-(3,4-dichlorophenyl)-2-(morpholin-4-yl)-7-oxo-4,5,6,7-tetrahydrothieno[2,3-c]pyridine-5-carboxylic acid A mixture of methyl 5-allyl-4-(3,4-dichlorophenyl)-2-(morpholin-4-yl)-7-oxo-4,5,6,7-tetrahydrothieno[2,3-c]pyridine-5-carboxylate (0.118 g, 0.245 mmol), methanol (2.0 mL), tetrahydrofuran (2.0 mL) and a solution of 1.0 M sodium hydroxide in water (1.50 mL, 1.50 mmol) was stirred at rt overnight. Additional methanol (2.0 mL) and 1.0 M Sodium hydroxide in water (1.50 mL, 1.50 mmol) was added. The mixture was stirred at rt for 2 days. The mixture was concentrated to remove most of volatile solvents and then acidified by 1M HCl. The precipitate was collected and dried in air to afford crude product. Final purification by HPLC afforded pure product as a white solid (43.3 mg, 23%). LCMS (FA) ES+: 467, 469. 1H NMR (400 MHz, DMSO) δ 7.45 (d, J=8.3 Hz, 1H), 7.38 (s, 1H), 7.25 (br s, 1H), 7.12 (d, J=8.2 Hz, 1H), 6.50 (s, 1H), 6.04 (s, 1H), 5.74-5.63 (m, 1H), 4.99-4.89 (m, 2H), 4.18 (s, 1H), 3.68 (br s, 4H), 3.12 (br s, 4H), 2.54-2.50 (m, 2H, overlapping with DMSO peak).

Example 39

Synthesis of methyl 4-(3,4-dichlorophenyl)-2-(morpholin-4-yl)-6-oxo-5,6-dihydro-4H-cyclopenta[b]thiophene-5-carboxylate (Compound 139)

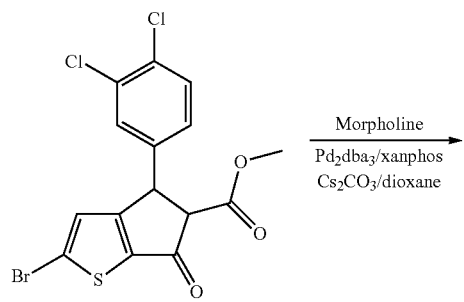

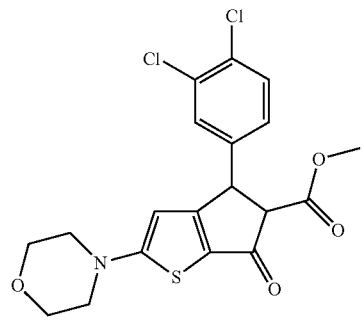

A mixture of methyl 2-bromo-4-(3,4-dichlorophenyl)-6-oxo-5,6-dihydro-4H-cyclopenta[b]thiophene-5-carboxylate (0.25 g, 0.59 mmol), morpholine (0.26 g, 2.94 mmol), tris(dibenzylideneacetone)dipalladium(0) (26.9 mg, 0.03 mmol), 4,5-bis(diphenylphosphino)-9,9-dimethylxanthene (34.0 mg, 0.06 mmol) and cesium carbonate (0.58 g, 1.76 mmol) in 1,4-dioxane (5.96 mL) was heated at 80° C. under argon for 3 h. And the temperature was raised to 100° C. and maintained overnight. The mixture was dryloaded on silica gel and purified by column chromatography (12 g cartridge, gradient hexanes to 60% EtOAc in hexanes) and then preparative HPLC to afford the product as a white solid (0.8 mg, 0.3%). LCMS: (FA) ES+ 426, 428, 430. ¹H NMR (400 MHz, CDCl₃) δ 7.37 (d, J=8.0 Hz, 1H), 7.24 (d, J=2.1 Hz, 1H), 6.99 (dd, J=8.0, 2.1 Hz, 1H), 5.77 (s, 1H), 4.73 (d, J=3.2 Hz, 1H), 3.86-3.76 (m, 7H), 3.67 (d, J=3.2 Hz, 1H), 3.35-3.26 (m, 4H).

Example 40

Synthesis of 4-(3,4-dichlorophenyl)-2-morpholino-5,6-dihydrothieno[2,3-c]pyridin-7(4H)-one (Compound 176)

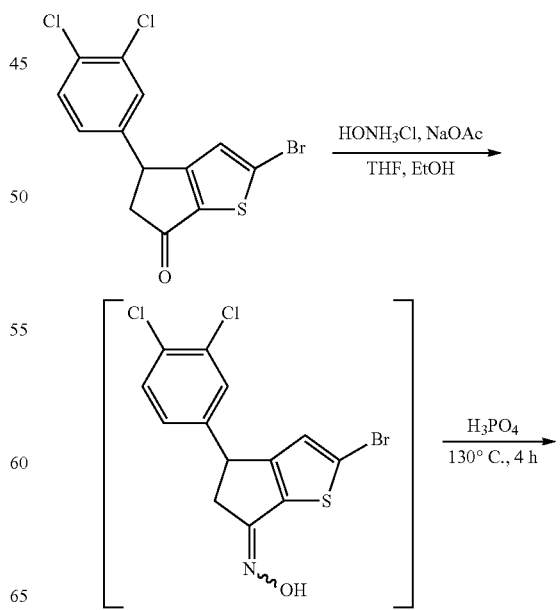

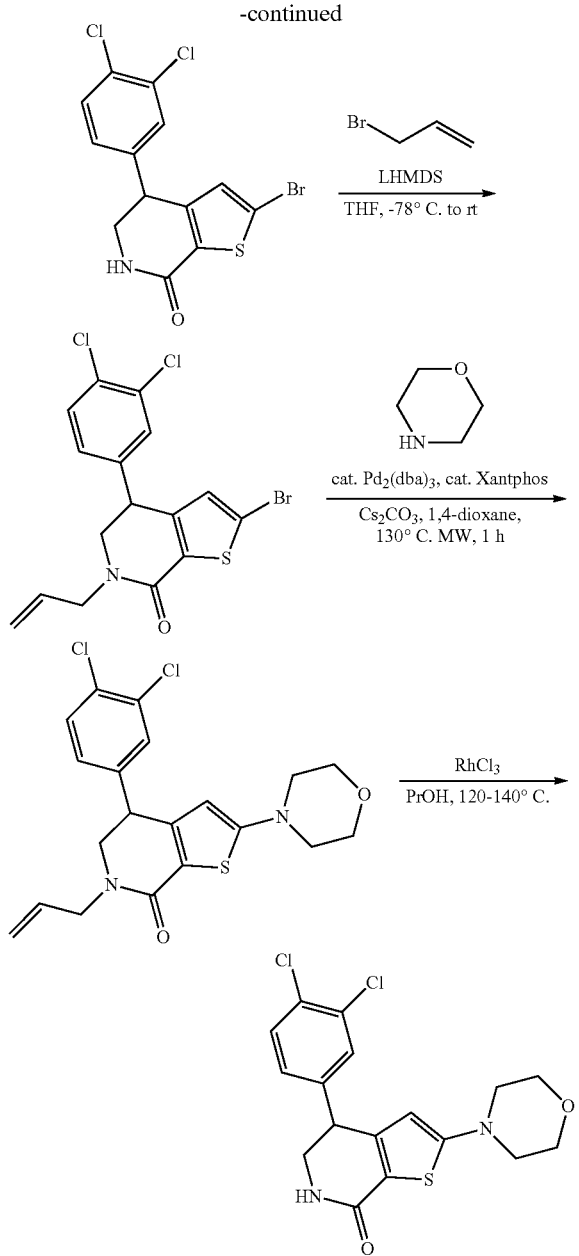

Step 1, Preparation of 2-bromo-4-(3,4-dichlorophenyl)-5,6-dihydrothieno[2,3-c]pyridin-7(4H)-one 2-Bromo-4-(3,4-dichlorophenyl)-4,5-dihydro-6H-cyclopenta[b]thiophen-6-one (0.65 g, 1.79 mmol) was dissolved in tetrahydrofuran (5.00 mL, 61.6 mmol) and ethanol (5.00 mL, 85.6 mmol). Hydroxylamine hydrochloride (0.63 g, 9.02 mmol) and sodium acetate (0.72 g, 8.77 mmol) was added and the resulting yellow suspension was allowed to stir for 18 hours. The reaction was quenched by the addition of a saturated aqueous solution of sodium bicarbonate (10.0 mL). EtOAc (5.00 mL) was added and the mixture was vigorously stirred for 30 minutes. The organic layer was separated and the aqueous phase was extracted with EtOAc (10.0 mL×3). The combined organic layers were dried over anhydrous $Na_2SO_4$, filtered and concentrated under reduced pressure. The crude yellow material was used without further purification. A mixture of crude (6Z)-2-bromo-4-(3,4-dichlorophenyl)-N-hydroxy-4,5-dihydro-6H-cyclopenta[b]thiophen-6-imine and polyphosphoric acid (5.00 g, 20.8 mmol) was heated to 130° C. and allowed to stir for 2.5 hours. The black reaction was cooled to ambient temperature and diluted with water (10.0 mL). The mixture was basified to pH 9 by the addition of $K_2CO_3$ (15.0 g) which was added in portions. The mixture was extracted with EtOAc (10.0 mL×3) and the combined organic layers were dried over anhydrous $Na_2SO_4$, filtered and concentrated under reduced pressure. The crude material was purified by silica gel column chromatography (24 g cartridge, gradient hexanes to 75% EtOAc in hexanes) to afford the product (0.27 g, 36% two steps) as a brown solid. LCMS (AA): ES⁻ 374, 376, 378, 380. ¹H NMR (DMSO-$d_6$, 400 MHz): δ 7.91 (br s, 1H,), 7.61 (d, J=8.0 Hz 1H), 7.53 (d, J=2.0 Hz 1H), 7.16 (dd, J=8.0, 2.0 Hz 1H), 7.07 (s, 1H,), 4.37 (t, J=5.6 Hz, 1H), 3.72 (ddd, J=12.8, 5.6, 2.8 Hz, 1H), 3.49 (ddd, J=12.8; 5.6, 2.8 Hz, 1H).

Step 2, Preparation 6-allyl-2-bromo-4-(3,4-dichlorophenyl)-5,6-dihydrothieno[2,3-e]pyridin-7(4H)-one A solution of 2-bromo-4-(3,4-dichlorophenyl)-5,6-dihydrothieno[2,3-c]pyridin-7(4H)-one (0.27 g, 0.72 mmol) in anhydrous tetrahydrofuran (3.00 mL,) was cooled to −78° C. A solution of 1.0 M of lithium bis(trimethylsilyl)amide in tetrahydrofuran (0.87 mL, 0.87 mmol) was added dropwise and the mixture was allowed to stir at −78° C. for 30 minutes. Allyl bromide (0.12 mL, 1.44 mmol) was added dropwise via syringe and the reaction mixture was slowly warmed to ambient temperature and continued to stir for 18 hours. The reaction was quenched by the addition of a solution of saturated aqueous ammonium chloride (2.00 mL) and extracted with EtOAc (10.0 mL×3). The combined organic layers were dried over anhydrous $Na_2SO_4$, filtered and concentrated under reduced pressure. The crude material was purified by silica gel column chromatography (24 g cartridge, gradient hexanes to 50% EtOAc in hexanes) to afford the desired product (0.29 g, 87%) as an orange oil. LCMS (AA): ES− 414, 416, 418, 420. ¹H NMR (DMSO-$d_6$, 400 MHz): δ 7.61 (d, J=8.4 Hz, 1H), 7.53 (d, J=2.4 Hz, 1H), 7.14 (dd, J=8.8, 2.4 Hz, 1H), 7.05 (s, 1H), 5.68-5.61 (m, 1H), 5.13-5.06 (m, 2H), 4.78 (t, J=6.4 Hz, 1H), 4.03-3.87 (m, 2H), 3.82 (dd, J=12.8, 6.4 Hz, 1H), 3.60 (dd, J=12.8, 6.4 Hz, 1H).

Step 3, Preparation of 6-allyl-4-(3,4-dichlorophenyl)-2-morpholino-5,6-dihydrothieno[2,3-c]pyridin-7(4H)-one A solution of 6-allyl-2-bromo-4-(3,4-dichlorophenyl)-5,6-dihydrothieno[2,3-c]pyridin-7(4H)-one (0.02 g, 0.05 mmol) and morpholine (0.01 mL, 0.14 mmol) in anhydrous 1,4-dioxane (2.00 mL) was degassed under nitrogen for 10 min. Cesium carbonate (72.7 mg, 0.22 mmol) and 4,5-bis(diphenylphosphino)-9,9-dimethylxanthene (8.32 mg, 0.01 mmol) was added followed by tris(dibenzylideneacetone)dipalladium(0) (4.4 mg, 0.0048 mmol). The reaction mixture was heated to 140° C. for 1 hour by microwave irradiation. The reaction was cooled to ambient temperature and quenched by the addition of a solution of saturated aqueous solution of sodium bicarbonate (10.0 mL) and extracted with EtOAc (10.0 mL×3). The combined organic layers were dried over anhydrous $Na_2SO_4$, filtered and concentrated under reduced pressure. The crude material was purified by silica gel column chromatography (4 g cartridge, gradient hexanes to 100% EtOAc) to afford the product (22.9 mg, 68%) as a yellow oil.

LCMS (AA): ES+ 423, 425, 427. ¹H NMR (DMSO-d₆, 400 MHz): δ 7.59 (d, J=8.4 Hz, 1H), 7.49 (d, J=2.0 Hz, 1H), 7.16 (dd, J=8.4, 2.0 Hz, 1H), 5.83 (s, 1H), 5.66-5.59 (m, 1H), 5.09-5.05 (m, 2H), 4.30 (t, J=6.0 Hz, 1H), 3.99-3.84 (m, 2H), 3.75-3.68 (m, 5H), 3.70-3.45 (m, 1H), 3.13-3.10 (m, 4H).

Step 4, Preparation of 4-(3,4-dichlorophenyl)-2-morpholino-5,6-dihydrothieno[2,3-c]pyridin-7(4H)-one A solution of 6-allyl-4-(3,4-dichlorophenyl)-2-(morpholin-4-yl)-5,6-dihydrothieno[2,3-c]pyridin-7(4H)-one (0.26 g, 0.60 mmol) in 1-propanol (10.0 mL, 134 mmol) was degassed for 10 minutes. Rhodium(III)chloride, (87.0 mg g, 0.41 mmol) was added and the reaction mixture was heated to 120° C. After 18 hours, rhodium(III)chloride (59.6 mg g) was added and the mixture was stirred for additional 18 hours. The reaction was cooled to ambient temperature and quenched by the addition of a solution of saturated aqueous solution of sodium bicarbonate (10.0 mL) and extracted with EtOAc (20.0 mL×3). The combined organic layers were dried over anhydrous Na₂SO₄, filtered and concentrated under reduced pressure. The crude material was purified by silica gel column chromatography (12 g cartridge, gradient hexanes to 100% EtOAc) to afford the pure product (114 mg g, 49%) as a white solid. The purified racemic mixture was separated into enantiomers on a Chiralpak IA 4.6×250 column using 70/15/15/01% Hexane/IPA/EtOH/DEA, 1.0 mL/minute for 40 minutes. Peak one (13.8 mg, 43.7%) was collected with retention time of 14.9 min. and peak two (14.8 mg, 46.9%) was collected with retention time of 21.5 min., both as a white solid. Absolute configuration of the obtained enantiomers is unknown. LCMS (AA): ES+ 383, 385, 387. ¹H NMR (DMSO-d₆, 400 MHz): δ 7.59 (d, J=8.4 Hz, 1H), 7.48 (d, J=2.4 Hz, 1H), 7.35 (br s, 1H), 5.88 (s, 1H), 4.19 (t, J=5.6 Hz, 1H), 3.69-3.63 (m, 5H), 3.37 (ddd, J=12.4, 6.0, 3.2 Hz, 1H), 3.13-3.11 (m, 4H).

Compounds in the following table are prepared from appropriate starting materials in a method analogous to that of Example 40.

| 128 | LC/MS: (AA) ES+ 349, 351 |
| 208 | LC/MS: (AA) ES+ 383, 385, 387 |
| 211 | LC/MS: (AA) ES+ 349, 351 |

Example 41

Synthesis of rel-(4R,5R)-4-(3,4-dichlorophenyl)-5-(hydroxymethyl)-2-(morpholin-4-yl)-5,6-dihydrothieno[2,3-c]pyridin-7(4H)-one (Compound 192)

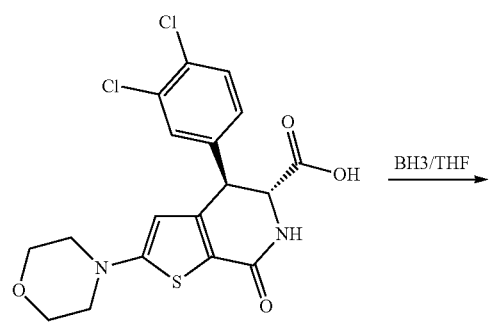

BH3/THF

-continued

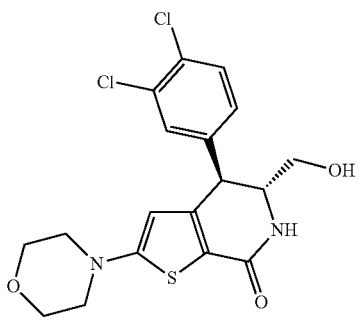

A flask was charged with rel-(4R,5R)-4-(3,4-dichlorophenyl)-2-(morpholin-4-yl)-7-oxo-4,5,6,7-tetrahydrothieno[2,3-c]pyridine-5-carboxylic acid (0.100 g, 0.234 mmol) and borane in THF (1M, 2.34 mmol, 2.34 mmol) was added. The mixture was stirred at rt for 2 hours. The reaction mixture was quenched by addition of methanol and then purified using preparative HPLC to afford the product as a white solid (25.7 mg, 26.3%). LCMS (AA) ES+: 413.4, 415.4, 1H NMR (400 MHz, CDCl₃) δ 7.43 (d, J=8.3 Hz, 1H), 7.33 (d, J=2.0 Hz, 1H), 7.08 (dd, J=8.2, 2.1 Hz, 1H), 5.82 (s, 1H), 5.47 (s, 1H), 3.99 (d, J=8.9 Hz, 2H), 3.83-3.76 (m, 4H), 3.18-3.11 (m, 4H).

Compounds in the following table are prepared from appropriate starting materials in a method analogous to that of Example 41.

| 133 | LC/MS: (AA) ES+ 379, 381 |

Example 42

Synthesis of 5-chloro-2'-(morpholin-4-yl)-6',7'-dihydro-3H-spiro[2-benzofuran-1,8'-[1,3]thiazolo[5,4-c]azepine]-3,4'(5'H)-dione (Compound 172)

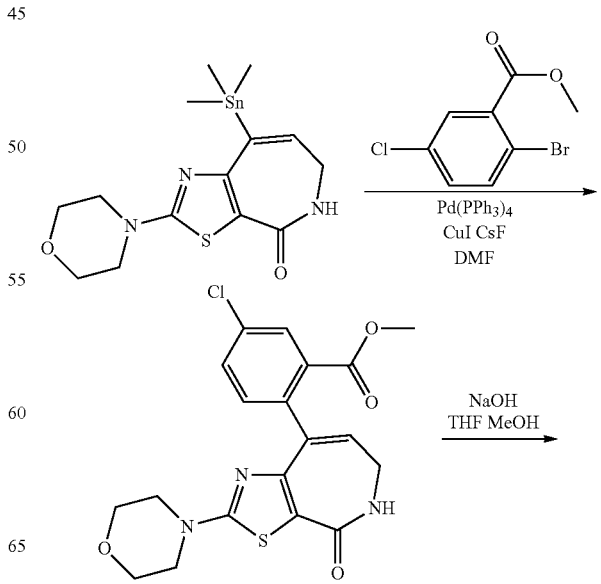

NaOH
THF MeOH

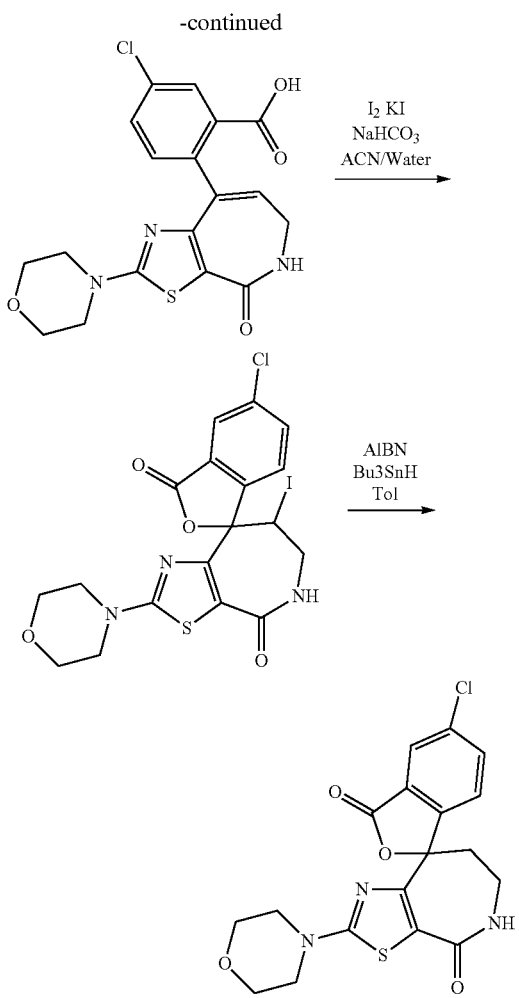

Step 1: methyl 5-chloro-2-[2-(morpholin-4-yl)-4-oxo-5,6-dihydro-4H-[1,3]thiazolo[5,4-c]azepin-8-yl]benzoate A solution of 2-(morpholin-4-yl)-8-(trimethylstannyl)-5,6-dihydro-4H-[1,3]thiazolo[5,4-c]azepin-4-one (0.160 g, 0.386 mmol) and methyl-2-bromo-5-chlorobenzoate (0.116 g, 0.464 mmol) in DMF (3.74 mL) was purged with Argon, then added cesium fluoride (0.205 g, 1.35 mmol), copper(I) iodide (0.0184 g, 0.0966 mmol) and tetrakis(triphenylphosphine)palladium(0) (0.0446 g, 0.0386 mmol). The mixture was stirred at 80° C. for 2 hours. The solution was cooled to room temperature, then evaporated some of the solvent. The residue was diluted with EA and water. The layers were separated and the aqueous layer was extracted twice more with EA. The combined organic layer was then washed with water and brine then dried over anhydrous sodium sulfate and concentrated. The residue was purified using column chromatography on silica gel (24 gr Analogix column, gradient DCM to 5% MeOH in DCM over 20 minutes) to give the product (0.129 g, 80%). LCMS: (AA) ES+ 420, 422. $^1$H NMR (300 MHz, $d_6$-DMSO) δ: 7.95 (t, J=5.0 Hz, 1H), 7.71-7.67 (m, 1H), 7.66-7.59 (m, 1H), 7.39 (d, J=8.2 Hz, 1H), 6.28 (t, J=6.9 Hz, 1H), 3.66-3.57 (m, 6H), 3.47 (s, 3H), 3.30-3.25 (m, 4H).

Step 2: 5-chloro-2-[2-(morpholin-4-yl)-4-oxo-5,6-dihydro-4H-[1,3]thiazolo[5,4-c]azepin-8-yl]benzoic acid To a solution of methyl 5-chloro-2-[2-(morpholin-4-yl)-4-oxo-5,6-dihydro-4H-[1,3]thiazolo[5,4-c]azepin-8-yl]benzoate (0.125 g, 0.298 mmol) in THF (3.7 mL) and MeOH (1.2 mL) was added a solution of 1M sodium hydroxide in water (3.66 mL, 3.66 mmol). The solution was stirred at room temperature for 16 hours. The solvents were evaporated and the residue was diluted with water and then added 1N hydrogen chloride aqueous solution until pH 7 was reached. Extracted twice with EA and the combined organic layer was then washed with brine then dried over anhydrous sodium sulfate and concentrated to give the product (0.100 g, 83%) which was used directly in the next step. LCMS: (AA) ES+ 406, 408. $^1$H NMR (400 MHz, $d_6$-DMSO) δ: 12.79 (s, 1H), 7.86 (t, J=4.9 Hz, 1H), 7.68 (d, J=2.4 Hz, 1H), 7.57 (dd, J=8.2, 2.4 Hz, 1H), 7.32 (d, J=8.2 Hz, 1H), 6.21 (t, J=6.9 Hz, 1H), 3.65-3.55 (m, 6H), 3.30-3.26 (m, 4H).

Step 3: 5-chloro-7'-iodo-2'-(morpholin-4-yl)-6',7'-dihydro-3H-spiro[2-benzofuran-1,8'-[1,3]thiazolo[5,4-c]azepine]-3,4'(5'H)-dione 5-chloro-2-[2-(morpholin-4-yl)-4-oxo-5,6-dihydro-4H-[1,3]thiazolo[5,4-c]azepin-8-yl]benzoic acid (0.0500 g, 0.123 mmol) was dissolved in acetonitrile (0.50 mL) and saturated aqueous sodium bicarbonate solution (2.5 mL), then added a solution of potassium iodide (0.102 g, 0.616 mmol) and iodine (0.0406 g, 0.160 mmol) in water (1.0 mL) dropwise and the solution was stirred at room temperature for 16 hours. The reaction mixture was diluted with EA and 15% aqueous sodium thiosulfate solution and the mixture was stirred for 20 minutes. The layers were separated and the aqueous layer was extracted twice more with EA. The combined organic layer was then washed with water and brine then dried over anhydrous sodium sulfate and concentrated. The residue was purified using column chromatography on silica gel (12 gr Analogix column, gradient DCM to 60% EA in DCM over 15 minutes) to give the product (0.0540 g, 82%). LCMS: (AA) ES+ 532, 534. $^1$H NMR (400 MHz, $d_6$-DMSO) δ: 8.44 (t, J=4.8 Hz, 1H), 8.07-7.90 (m, 1H), 7.92-7.72 (m, 2H), 5.12-4.91 (m, 1H), 3.93-3.81 (m, 1H), 3.77-3.65 (m, 1H), 3.61-3.48 (m, 4H), 3.23-3.08 (m, 4H).

Step 4: 5-chloro-2'-(morpholin-4-yl)-6',7'-dihydro-3H-spiro[2-benzofuran-1,8'-[1,3]thiazolo[5,4-c]azepine]-3,4'(5'H)-dione A solution of 5-chloro-7'-iodo-2'-(morpholin-4-yl)-6',7'-dihydro-3H-spiro[2-benzofuran-1,8'-[1,3]thiazolo[5,4-c]azepine]-3,4'(5'H)-dione (0.0430 g, 0.0809 mmol) and 2,2'-azo-bis-isobutyronitrile (0.000664 g, 0.00404 mmol) in toluene (2.0 mL) was heated at 80° C. for 10 minutes, then added tri-n-butyltin hydride (0.0644 mL, 0.239 mmol) dropwise. The solution was stirred at 80° C. for 16 hours. The reaction was incomplete by LCMS and TLC, so added additional and 2,2'-azo-bis-isobutyronitrile (2 mg) and tri-n-butyltin hydride (0.050 mL) and stirred at 80° C. for 4 hours. The reaction mixture was cooled to room temperature and the solvent was evaporated. The residue was purified by preparative HPLC to give the product (0.0100 g, 31%). LCMS: (AA) ES+ 406, 408. $^1$H NMR (400 MHz, $d_6$-DMSO) δ: 8.50-8.28 (m, 1H), 7.92 (d, J=2.0 Hz, 1H), 7.78 (dd, J=8.2, 2.0 Hz, 1H), 7.64 (d, J=8.2 Hz, 1H), 3.60-3.51 (m, 4H), 3.52-3.42 (m, 1H), 3.32 (m, 1H), 3.23-3.06 (m, 4H), 2.72-2.60 (m, 1H), 2.37-2.24 (m, 1H).

Example 43

Synthesis of 4-(4-chlorophenyl)-2-(morpholin-4-yl)-4,5,6,7-tetrahydro-8H-thieno[2,3-c]azepin-8-one (Compound 201)

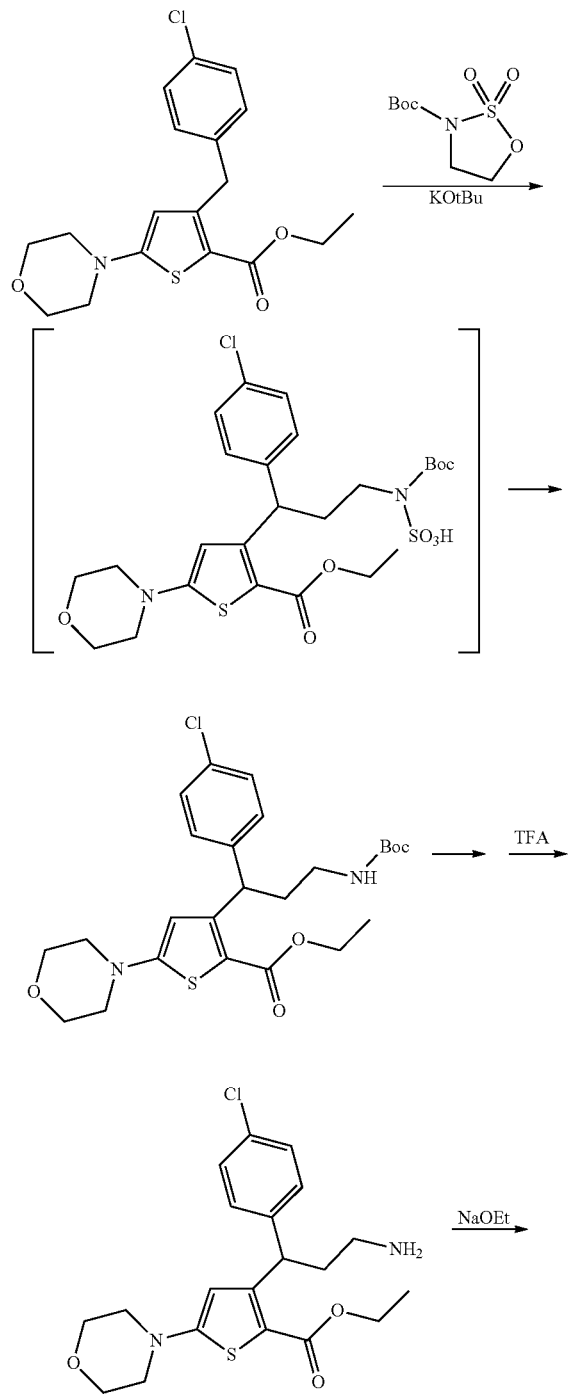

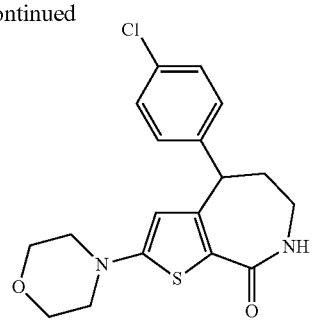

Step 1: ethyl 3-{3-[(tert-butoxycarbonyl)amino]-1-(4-chlorophenyl)propyl}-5-(morpholin-4-yl)thiophene-2-carboxylate Glasswares were flame-dried before use. A solution of ethyl 3-(4-chlorobenzyl)-5-morpholin-4-ylthiophene-2-carboxylate (0.872 g, 2.38 mmol) in N,N-dimethylformamide (16.0 mL) and tetrahydrofuran (4.00 mL) was cooled to –78° C. with vigorous stirring. The solution was evacuated under highvac and purged with argon (×4). 1.00 M Sodium hexamethyldisilazane in tetrahydrofuran (2.62 mL, 2.62 mmol) was added; the solution turned deep purple. The mixture was stirred at –78° C. under argon for 10 min. A solution of tert-butyl 1,2,3-oxathiazolidine-3-carboxylate 2,2-dioxide (1.06 g, 4.77 mmol) in N,N-dimethylformamide (4.00 mL) was added dropwise over ~1 min. The solution turned light red, and then slightly dark green in ~1 min. In 15 min, the reaction was warmed to 0° C., and then in 1 h, it was warmed to rt. After 15 min of stirring at rt, the reaction was quenched and distributed between NH$_4$Cl saturated solution and EtOAc. The aqueous layer was extracted with EtOAc (×2). The combined organic layer was washed with 10% LiCl aqueous solution (×2) and brine, dried, and concentrated. Purification on a silica gel column (continuous gradient from 5% EtOAc/hexanes to 25% EtOAc/hexanes over 30 min) provided 776 mg of ethyl 3-{3-[(tert-butoxycarbonyl)amino]-1-(4-chlorophenyl)propyl}-5-(morpholin-4-yl)thiophene-2-carboxylate (64% yield) and 303 mg of unreacted ethyl 3-(4-chlorobenzyl)-5-morpholin-4-ylthiophene-2-carboxylate (35% yield). LCMS: (AA) ES+ 510, 512; $^1$H NMR (400 MHz, CDCl$_3$) δ 7.24-7.21 (s, 4H), 5.88-5.82 (s, 1H), 5.21-5.11 (t, J=7.8 Hz, 1H), 5.06-4.94 (s, 1H), 4.34-4.22 (qd, J=7.1, 2.8 Hz, 2H), 3.83-3.73 (t, J=4.9 Hz, 4H), 3.29-3.19 (s, 1H), 3.22-3.12 (t, J=4.9 Hz, 4H), 2.99-2.85 (m, 1H), 2.25-2.12 (d, J=6.6 Hz, 1H), 2.12-2.06 (s, 1H), 1.47-1.41 (s, 9H), 1.36-1.31 (m, 3H).

Step 2: Ethyl 3-[3-amino-1-(4-chlorophenyl)propyl]-5-(morpholin-4-yl)thiophene-2-carboxylate.TFA To the solution of ethyl 3-{3-[(tert-butoxycarbonyl)amino]-1-(4-chlorophenyl)propyl}-5-(morpholin-4-yl)thiophene-2-carboxylate (821 mg, 1.61 mmol) in methylene chloride (20.0 mL) was added trifluoroacetic acid (2.00 mL, 26.0 mmol) at rt. The solution turned dark. In 1 h, the solution was concentrated. Ethyl 3-[3-amino-1-(4-chlorophenyl)propyl]-5-(morpholin-4-yl)thiophene-2-carboxylate.TFA salt was isolated as a purple syrup and used without further purification. LCMS: (AA) ES+ 409, 411; ¹H NMR (400 MHz, CDCl₃) δ 7.59 (s, br, 3H), 7.33-7.25 (d, J=8.5 Hz, 2H), 7.23-7.16 (d, J=8.5 Hz, 2H), 5.71-5.60 (s, 1H), 5.19-5.07 (dd, J=11.3, 4.8 Hz, 1H), 4.38-4.27 (m, 2H), 3.88-3.80 (t, J=4.9 Hz, 4H), 3.34-3.23 (m, 1H), 3.22-3.14 (t, J=4.9 Hz, 4H), 2.99-2.84 (s, 1H), 2.60-2.41 (ddt, J=15.3, 9.4, 4.4 Hz, 1H), 2.40-2.23 (td, J=11.0, 4.3 Hz, 1H), 1.43-1.35 (t, J=7.1 Hz, 3H).

Step 3: 4-(4-chlorophenyl)-2-(morpholin-4-yl)-4,5,6,7-tetrahydro-8H-thieno[2,3-c]azepin-8-one A 100 mL rbf was charged with a solution of ethyl 3-[3-amino-1-(4-chlorophenyl)propyl]-5-(morpholin-4-yl)thiophene-2-carboxylate.TFA (842 mg, 1.61 mmol) in ethanol (10.0 mL) and 21% sodium ethoxide (21:79, Sodium ethoxide: ethanol, 4.81 mL, 12.9 mmol). The rbf was equipped with a reflux condenser and the reaction was heated to 80° C. In 3 h, the solution was cooled and distributed between water and EtOAc. The aqueous layer was extracted with EtOAc (×2). The combined org layer was washed with brine (×2), dried, and concentrated to provide a yellow solid. Purification on a silica gel column (continuous gradient from CH₂Cl₂ to 8% MeOH/CH₂Cl₂) provided 420 mg of 4-(4-chlorophenyl)-2-(morpholin-4-yl)-4,5,6,7-tetrahydro-8H-thieno[2,3-c]azepin-8-one as a yellow solid (71.9% yield). LCMS: (AA) ES+ 363, 365; ¹H NMR (400 MHz, DMSO-d₆) δ 7.81-7.71 (s, 1H), 7.41-7.32 (m, 2H), 7.18-7.09 (m, 2H), 5.64-5.55 (s, 1H), 4.38-4.27 (dd, J=7.9, 5.1 Hz, 1H), 3.70-3.58 (t, J=4.9 Hz, 4H), 3.14-3.06 (d, J=4.3 Hz, 2H), 3.06-2.96 (t, J=4.9 Hz, 4H), 2.24-2.13 (m, 1H), 2.03-1.90 (m, 1H). Racemic 4-(4-chlorophenyl)-2-(morpholin-4-yl)-4,5,6,7-tetrahydro-8H-thieno[2,3-c]azepin-8-one (0.42 g) was separated into enantiomers on a Chiralpak IA 30×250 mm 5 micron column using a 60/40/0.1 Hexane-EtOH-DEA mixture and a flow rate of 35 mL/min. Peak one (195 mg) was collected with retention times of 10-18 min and peak two (208 mg) was collected with retention times of 26.5-38.5 min. Absolute configuration of the obtained enantiomers is unknown.

Compounds in the following table are prepared from appropriate starting materials in a method analogous to that of Example 43.

| | |
|---|---|
| 116 | LC/MS: (FA) ES+ 422, 424 |
| 120 | LC/MS: (AA) ES+ 410 |
| 131 | LC/MS: (AA) ES+ 380 |
| 150 | LC/MS: (FA) ES+ 388, 390 |
| 155 | LC/MS: (AA) ES+ 424, 426 |
| 175 | LC/MS: (AA) ES+ 379 |
| 188 | LC/MS: (FA) ES+ 404 |
| 199 | LC/MS: (FA) ES+ 422, 424 |
| 201 | LC/MS: (AA) ES+ 363, 365 |
| 202 | LC/MS: (AA) ES+ 410 |
| 209 | LC/MS: (AA) ES+ 380 |

Example 44

Synthesis of 4-(4-chlorophenyl)-2-[2-(hydroxymethyl)morpholin-4-yl]-4,5,6,7-tetrahydro-8H-thieno[2,3-c]azepin-8-one (Compound 163)

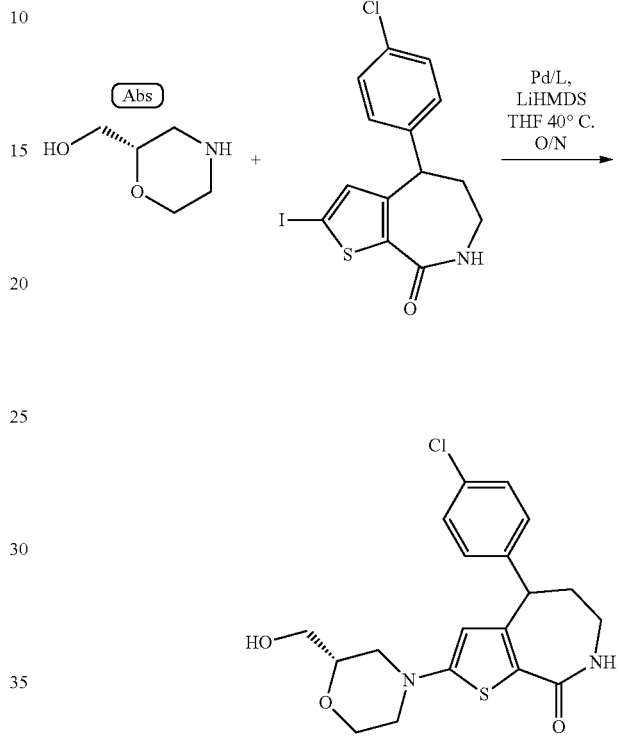

Step 1: 4-(4-chlorophenyl)-2-[2-(hydroxymethyl)morpholin-4-yl]-4,5,6,7-tetrahydro-8H-thieno[2,3-c]azepin-8-one RuPhospalladium(II)phenethylaminechloride (2.83 mg, 0.00388 mmol), 2-dicyclohexylphosphino-2',6'-di-i-propoxy-1,1'-biphenyl (1.81 mg, 0.00388 mmol), 4-(4-chlorophenyl)-2-iodo-4,5,6,7-tetrahydro-8H-thieno[2,3-c]azepin-8-one (31.3 mg, 0.0776 mmol), (2S)-morpholin-2-ylmethanol (16.0 mg, 0.137 mmol), and tetrahydrofuran (0.63 mL) were combined in a rbf equipped with a stirbar. The flask was sealed with a septum then evacuated and refilled with argon three times. To this solution was added a solution of lithium bis(trimethylsilyl)amide) in tetrahydrofuran (1.0 M, 0.31 mL, 0.31 mmol). The sealed rxn was vigorously stirred @ 40° C. for 19 hr. The reaction was cooled to rt, quenched into saline, extracted into EA, washed with saline, dried over Na₂SO₄, filtered, and concentrated in vacuo. The crude oil was purified using column chromatography on silica gel (24 g ISCO column, gradient 100% DCM to 100% EA over 50 minutes; after unreacted starting material and dehalogenated starting material eluted, the eluant was switched to 5% MeOH in EA) to give the title compound (4.8 mg, 16%) as a mixture of diastereomers. LCMS: (FA) ES+ 393, 395. 1H NMR (400 MHz, DMSO) δ 7.78 (t, J=4.6 Hz, 1H), 7.38-7.35 (m, 2H), 7.15-7.11 (m, 2H), 5.59 (s, 1H), 4.80-4.75 (m, 1H), 4.34-4.31 (m, 1H), 3.91-3.79 (m, 1H), 3.61-3.35 (m, 6H), 3.24 (d, J=11.9 Hz, 1H), 3.11-3.07 (m, 2H), 2.81-2.69 (m, 1H), 2.22-2.14 (m, 1H), 2.02-1.88 (m, 1H).

Example 45

Synthesis of rel-(4R,5R)-4-(4-chlorophenyl)-N-methyl-2-(2-methylpyridin-4-yl)-7-oxo-4,5,6,7-tetrahydrothieno[2,3-c]pyridine-5-carboxamide (Compound 138)

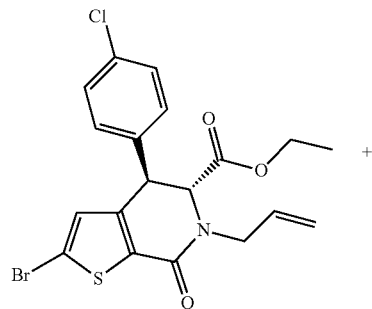

+

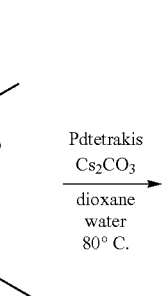

Pdtetrakis
Cs₂CO₃
─────────
dioxane
water
80° C.

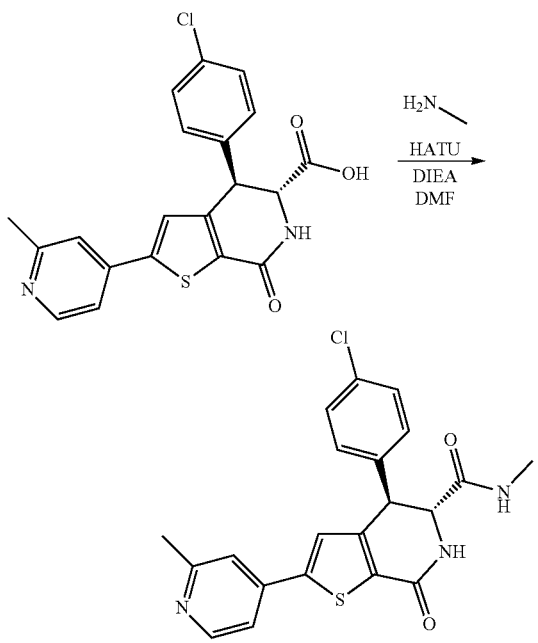

Step 1: Preparation of rel-(4R,5R)-4-(4-chlorophenyl)-2-(2-methylpyridin-4-yl)-7-oxo-4,5,6,7-tetrahydrothieno[2,3-c]pyridine-5-carboxylic acid To a solution of ethyl rel-(4R,5R)-6-allyl-2-bromo-4-(4-chlorophenyl)-7-oxo-4,5,6,7-tetrahydrothieno[2,3-c]pyridine-5-carboxylate (505.0 mg, 1.11 mmol) and 2-methyl-4-(4,4,5,5-tetramethyl-[1,3,2]dioxaborolan-2-yl)pyridine (486 mg, 2.22 mmol) in 1,4-dioxane (14.6 mL, 187 mmol) and water (1.9 mL, 110 mmol) were added tetrakis(triphenylphosphine)palladium(0) (64.2 mg, 0.055 mmol) and cesium carbonate (1.08 g, 3.33 mmol). The mixture was stirred at 80° C. for 16 hr. After the reaction was completed, the solvent was evaporated and the obtained residue was purified by column chromatography (SiO₂, elution with 0-100% [(60/20/20/20) EA/ACN/MeOH/water)]/EA to give the title compound as a yellow solid (428.7 mg, 73% yield). LCMS: (AA) ES⁺, 399/401. ¹H NMR (400 MHz, DMSO) δ 8.72 (d, J=6.1 Hz, 1H), 8.45 (d, J=6.6 Hz, 1H), 8.30 (d, J=4.4 Hz, 1H), 8.13 (s, 1H), 8.02 (d, J=8.8 Hz, 1H), 7.43 (t, J=10.0 Hz, 2H), 7.21 (dd, J=24.7, 7.7 Hz, 3H), 4.98-4.59 (m, 1H), 4.32 (d, J=2.9 Hz, 1H), 2.69 (s, 3H).

Step 2: Preparation of rel-(4R,5R)-4-(4-chlorophenyl)-N-methyl-2-(2-methylpyridin-4-yl)-7-oxo-4,5,6,7-tetrahydrothieno[2,3-c]pyridine-5-carboxamide To a mixture of rel-(4R,5R)-4-(4-chlorophenyl)-2-(2-methylpyridin-4-yl)-7-oxo-4,5,6,7-tetrahydrothieno[2,3-c]pyridine-5-carboxylic acid (326.0 mg, 0.817 mmol) and HATU (435.1 mg, 1.144 mmol) in N,N-dimethylformamide (4.28 mL, 55.3 mmol) were added methylamine as a 2M solution in tetrahydrofuran (1.64 mL, 3.27 mmol) followed by N,N-diisopropylethylamine (0.427 mL, 2.45 mmol). The mixture was stirred at rt for 16 hr. The mixture was diluted with water (4 mL) and the precipitate was filtered. The aqueous solution was extracted with DCM (3×6 mL). The solid cake and DCM layers were combined and washed with water (3 mL) and brine (3 mL), dried over sodium sulfate, and evaporated. The obtained residue purified by preparative HPLC to give the title compound as a white solid (140 mg) then the racemic mixture was separated by chiral preparative HPLC to give 30.6 mg (9.0% yield) as a white solid for peak 1. LCMS: (FA) ES⁺, 412/414. ¹H NMR (400 MHz, DMSO) δ 8.46 (d, J=5.3 Hz, 1H), 8.16 (d, J=4.4 Hz, 1H), 7.94 (d, J=4.2 Hz, 1H), 7.62 (s, 1H), 7.55 (s, 1H), 7.49-7.37 (m, 3H), 7.25 (d, J=8.5 Hz, 2H), 4.66 (d, J=1.6 Hz, 1H), 4.14 (dd, J=4.2, 2.3 Hz, 1H), 2.59 (d, J=4.5 Hz, 3H). 37.0 mg (11% yield) as a white solid for peak 2. LCMS: (FA) ES⁺, 412. ¹H NMR (400 MHz, DMSO) δ 8.46 (d, J=5.2 Hz, 1H), 8.16 (d, J=4.4 Hz, 1H), 7.95 (d, J=4.3 Hz, 1H), 7.62 (s, 1H), 7.55 (s, 1H), 7.50-7.35 (m, 3H), 7.25 (d, J=8.5 Hz, 2H), 4.66 (d, J=1.8 Hz, 1H), 4.14 (dd, J=4.3, 2.3 Hz, 1H), 2.59 (d, J=4.5 Hz, 3H).

Compounds in the following table are prepared from appropriate starting materials in a method analogous to that of Example 45.

| | |
|---|---|
| 121 | LC/MS: (FA) ES+ 403, 405 |
| 160 | LC/MS: (FA) ES+ 398, 400 |
| 206 | LC/MS: (FA) ES+ 398, 400 |
| 207 | LC/MS: (FA) ES+ 403, 405 |

Example 46

Synthesis of 3-bromo-4-(4-chlorophenyl)-2-(morpholin-4-yl)-5,6-dihydrothieno[2,3-c]pyridin-7(4H)-one (Compound 181)

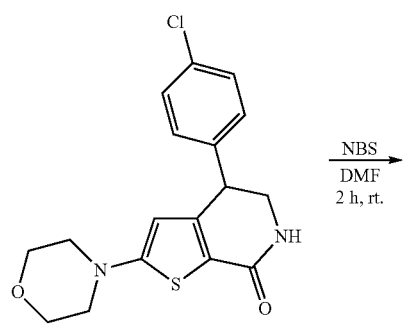

J=4.1 Hz, 1H), 4.20-4.06 (m, 2H), 3.87 (dd, J=4.6, 4.6 Hz, 4H), 3.52 (dt, J=14.4, 3.9 Hz, 1H), 3.35-3.24 (m, 2H), 3.24-3.10 (m, 2H).

Example 47

Synthesis of 4-(4-chlorophenyl)-3-(hydroxymethyl)-2-(morpholin-4-yl)-5,6-dihydrothieno[2,3-c]pyridin-7(4H)-one (Compound 178)

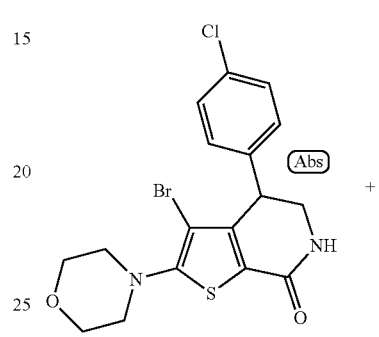

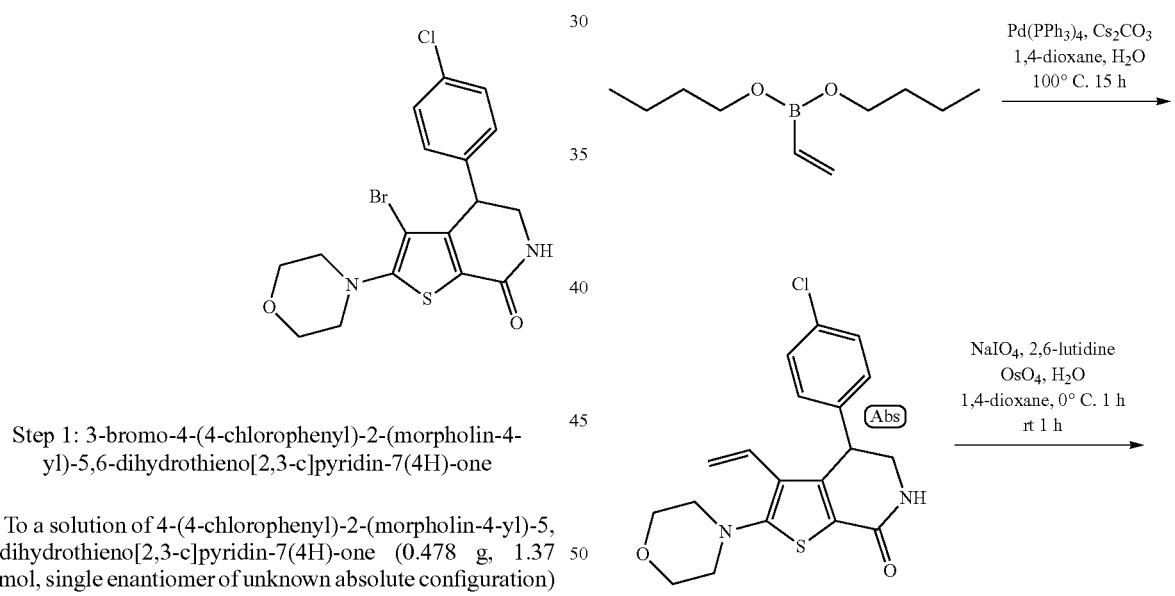

Step 1: 3-bromo-4-(4-chlorophenyl)-2-(morpholin-4-yl)-5,6-dihydrothieno[2,3-c]pyridin-7(4H)-one To a solution of 4-(4-chlorophenyl)-2-(morpholin-4-yl)-5,6-dihydrothieno[2,3-c]pyridin-7(4H)-one (0.478 g, 1.37 mmol, single enantiomer of unknown absolute configuration) in DMF (8.9 mL, 110 mmol) was added N-bromosuccinimide (0.2561 g, 1.439 mmol), and the mixture was stirred at room temperature for 2 hours. Reaction was quenched via addition of 10% aqueous sodium thiosulfate solution (30 mL), and then diluted with EtOAc (100 mL) and water (10 mL) with sonication to encourage complete dissolution of solids. The layers were separated, and aqueous layer was extracted 1×EtOAc (50 mL). The combined organic layers were washed 1× brine (10 mL), dried over $Na_2SO_4$, filtered, and concentrated in vacuo. The crude residue was adsorbed to Celite (15 mL) and dryloaded onto a silica gel column. Column chromatography (eluent: 0-100% EtOAc:hexanes) then afforded 3-bromo-4-(4-chlorophenyl)-2-(morpholin-4-yl)-5,6-dihydrothieno[2,3-c]pyridin-7(4H)-one (526 mg, 90%). LCMS: (FA) ES+ 427, 429, 431. $^1$H NMR (400 MHz, $CDCl_3$) δ: 7.26 (d, J=8.3 Hz, 2H), 7.07 (d, J=8.3 Hz, 2H), 5.41 (d,

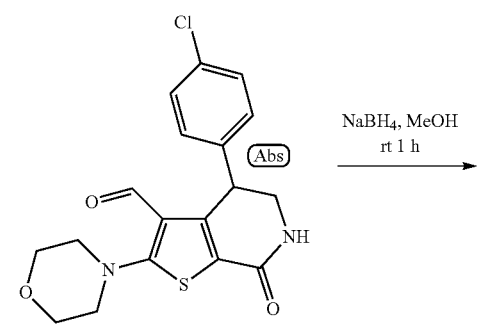

243
-continued

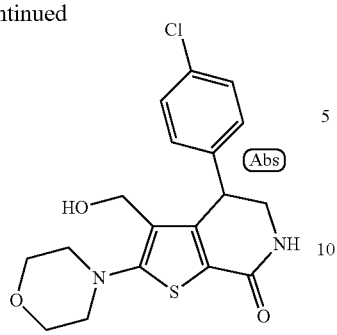

Step 1: 4-(4-chlorophenyl)-2-(morpholin-4-yl)-3-vinyl-5,6-dihydrothieno[2,3-c]pyridin-7(4H)-one (Compound 143)

In a 20 mL microwave vial a mixture of 3-bromo-4-(4-chlorophenyl)-2-(morpholin-4-yl)-5,6-dihydrothieno[2,3-c]pyridin-7(4H)-one (493.0 mg, 1.152 mmol, single enantiomer of unknown configuration), dicesium carbonate (1.13 g, 3.46 mmol), 1,4-dioxane (4.0 mL, 51 mmol), water (1.41 mL, 78.4 mmol) and vinylboronic acid dibutyl ester (381 uL, 1.73 mmol) was degassed by bubbling argon through the mixture for 10 min. Tetrakis(triphenylphosphine)-palladium(0) (66.6 mg, 0.0576 mmol) was added, the vial was sealed, and the rxn was heated at 100° C. for 15 h. The reaction was cooled to rt, diluted with water, and extracted with EA twice. The combined organics were washed with brine, dried over anhydrous sodium sulfate, filtered, and concentrated in vacuo. The crude material was (dry loaded on Celite and purified using column chromatography on silica gel (40 g ISCO column, gradient 100% hexanes to 100% EA over 60 minutes) to give the title compound (264 mg yellow solid, 61%). Final purification of 50 mg of this material by HPLC gave 30 mg pure product as a white solid. LCMS: (FA) ES+ 375, 377. 1H NMR (400 MHz, DMSO) δ 7.48 (d, J=4.6 Hz, 1H), 7.42-7.32 (m, 2H), 7.09-7.00 (m, 2H), 6.38 (dd, J=18.0, 11.8 Hz, 1H), 5.37 (dd, J=18.0, 1.7 Hz, 1H), 5.17 (dd, J=11.8, 1.6 Hz, 1H), 4.36 (d, J=4.3 Hz, 1H), 3.90 (dd, J=12.8, 5.0 Hz, 1H), 3.76-3.69 (m, 4H), 3.29 (dd, J=11.7, 5.1 Hz, 1H), 3.05-3.00 (m, 2H), 2.99-2.92 (m, 2H).

Step 2: 4-(4-chlorophenyl)-2-(morpholin-4-yl)-7-oxo-4,5,6,7-tetrahydrothieno[2,3-c]pyridine-3-carbaldehyde (Compound 193)

A suspension of 4-(4-chlorophenyl)-2-(morpholin-4-yl)-3-vinyl-5,6-dihydrothieno[2,3-c]pyridin-7(4H)-one (209.0 mg, 0.5575 mmol, single enantiomer of unknown configuration) in 1,4-dioxane (8.46 mL) and water (2.12 mL, 117 mmol) was cooled to 0° C. To the mixture was added sodium metaperiodate (0.477 g, 2.23 mmol), 2,6-lutidine (0.258 mL, 2.23 mmol), and a solution of 4% osmium tetroxide in water (68.1 uL, 0.0112 mmol). The reaction was vigorously stirred at 0° C. for 1 h. After 1 h, the ice-water bath was removed, and the reaction was stirred at rt for an hour. The reaction mixture was filtered through a celite pad, and the pad was washed with EtOAc. The filtrate was washed with 1N HCl (×2), brine, dried over Na$_2$SO$_4$, and concentrated in vacuo. The crude mixture was purified using column chromatography on silica gel (40 g ISCO column, continuous gradient 100% hexanes to 100% EA over 60 minutes) to give the title compound (176 mg orange oil, 84%). Final purification of 26 mg of this material by HPLC gave 16 mg pure product as a white solid. LCMS: (FA) ES+ 377, 379. 1H NMR (400 MHz, DMSO) δ 9.52 (s, 1H), 7.59 (d, J=4.5 Hz, 1H), 7.39-7.34 (m, 2H), 7.10-7.05 (m, 2H), 4.67 (d, J=4.4 Hz, 1H), 3.92 (dd, J=12.9, 5.1 Hz, 1H), 3.81-3.70 (m, 4H), 3.47-3.36 (m, 2H), 3.36-3.26 (m, 3H overlapping with H$_2$O peak).

Step 3: 4-(4-chlorophenyl)-3-(hydroxymethyl)-2-(morpholin-4-yl)-5,6-dihydrothieno[2,3-c]pyridin-7(4H)-one To a solution of 4-(4-chlorophenyl)-2-(morpholin-4-yl)-7-oxo-4,5,6,7-tetrahydrothieno[2,3-c]pyridine-3-carbaldehyde (52.4 mg, 0.139 mmol, single enantiomer of unknown configurate) in methanol (1.30 mL, 32.0 mmol) was added portionwise sodium borohydride (10.5 mg, 0.278 mmol). The reaction mixture was stirred at rt for 1.5 hr, then carefully quenched by the addition of an aqueous solution of 1M HCl to lower the pH to ~3-4. The mixture was extracted w/EA twice, the extracts were combined, washed w/brine, dried over Na$_2$SO$_4$, filtered, and concentrated in vacuo. HPLC purification provided the title compound as a white solid (33 mg, 62%). LCMS: (FA) ES+ 379, 381. 1H NMR (400 MHz, DMSO) δ 7.41 (d, J=4.4 Hz, 1H), 7.38-7.33 (m, 2H), 7.03-7.01 (m, 2H), 4.97 (t, J=4.9 Hz, 1H), 4.36 (d, J=4.5 Hz, 1H), 4.19 (dd, J=11.9, 5.4 Hz, 1H), 3.91-3.82 (m, 2H), 3.78-3.66 (m, 4H), 3.31-3.25 (m, 1H), 3.20-3.12 (m, 2H), 3.00-2.92 (m, 2H).

Example 48

Synthesis of 4-(4-chlorophenyl)-2-(morpholin-4-yl)-3-(phenylethynyl)-5,6-dihydrothieno[2,3-c]pyridin-7(4H)-one (Compound 137)

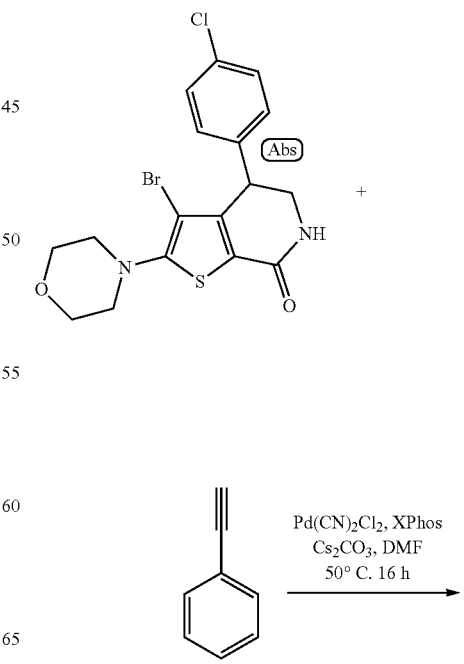

245

-continued

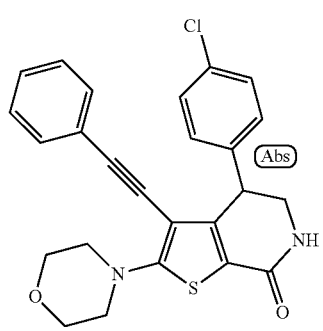

Step 1: 4-(4-chlorophenyl)-2-(morpholin-4-yl)-3-(phenylethynyl)-5,6-dihydrothieno[2,3-c]pyridin-7(4H)-one In a 10-mL microwave vial, a suspension of 3-bromo-4-(4-chlorophenyl)-2-(morpholin-4-yl)-5,6-dihydrothieno[2,3-c]pyridin-7(4H)-one (69.5 mg, 0.162 mmol, single enantiomer of unknown configuration), cesium carbonate (0.146 g, 0.448 mmol) and phenylacetylene (0.107 mL, 0.975 mmol) in N,N-dimethylformamide (0.750 mL) was degassed by bubbling argon balloon for 5-10 min., then 2-dicyclohexylphosphino-2',4',6'-tri-i-propyl-1,1'-biphenyl (12.6 mg, 0.0265 mmol) and bis(acetonitrile)palladium(II) chloride (2.11 mg, 0.00812 mmol) was added. The vial was sealed, and the mixture was heated at 50° C. for 16 h. The rxn was cooled to rt, and combined with a previous rxn of same scale. The reaction was transferred to a separatory funnel with EA. Water was added, and the layers were separated. The aqueous layer was extracted w/EA. The organic layers were combined, washed w/brine, dried over $Na_2SO_4$, filtered, and concentrated in vacuo. The crude mixture was purified using column chromatography on silica gel (40 g ISCO column, gradient 100% hexanes to 100% EtOAc over 60 minutes to obtain impure product (51 mg). Final purification by HPLC gave the title product as an off-white solid (10 mg, 7%). LCMS: (FA) ES+ 449, 451. 1H NMR (400 MHz, DMSO) δ 7.47 (d, J=4.2 Hz, 1H), 7.40-7.32 (m, 5H), 7.27-7.23 (m, 2H), 7.21-7.17 (m, 2H), 4.31-4.29 (m, 1H), 3.91 (dd, J=12.9, 5.6 Hz, 1H), 3.79-3.76 (m, 4H), 3.57-3.52 (m, 2H), 3.49-3.44 (m, 2H), 3.30-3.27 (m, 1H).

Compounds in the following table are prepared from appropriate starting materials in a method analogous to that of Example 48.

| | |
|---|---|
| 122 | LC/MS: (FA) ES+ 450, 452 |
| 130 | LC/MS: (FA) ES+ 430, 432 |

246

Example 49

Synthesis of methyl 4-(3,4-dichlorophenyl)-2-(morpholin-4-yl)-7-oxo-6,7-dihydrothieno[2,3-c]pyridine-5-carboxylate (Compound 184)

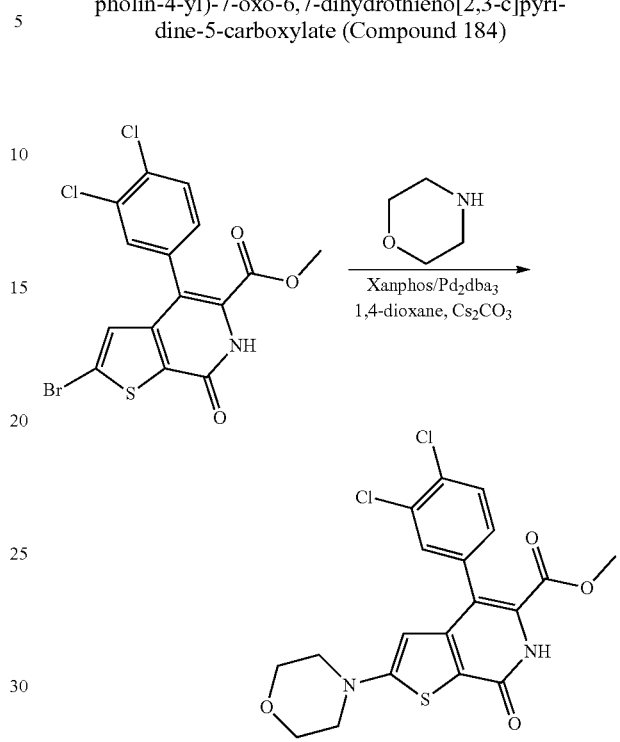

A mixture of methyl 2-bromo-4-(3,4-dichlorophenyl)-7-oxo-6,7-dihydrothieno[2,3-c]pyridine-5-carboxylate (0.081 g, 0.19 mmol), morpholine (0.0489 g, 0.561 mmol), tris(dibenzylideneacetone)dipalladium(0) (17.1 mg, 0.0187 mmol), 4,5-bis(diphenylphosphino)-9,9-dimethylxanthene (21.6 mg, 0.0374 mmol) and cesium carbonate (183 mg, 0.561 mmol) in 1,4-dioxane (3.0 mL, 38 mmol) was heated to 140° C. for 20 min, and then to 150° C. for another 90 min by microwave irradiation. The mixture was concentrated and purified by chromatography and then preparative HPLC to afford the product as a white solid (5.3 mg, 6.4%). LCMS (FA) ES+: 439.4, 441.4. $^1$H NMR (400 MHz, DMSO) δ 11.30 (s, 1H), 7.67 (d, J=8.3 Hz, 1H), 7.54 (d, J=1.9 Hz, 1H), 7.25 (dd, J=8.2, 2.0 Hz, 1H), 5.76 (s, 1H), 4.09 (d, J=5.1 Hz, 2H), 3.76-3.63 (m, 4H), 3.59 (s, 3H), 3.23-3.06 (m, 4H).

Example 50

Synthesis of 6-(morpholin-4-yl)-4-(2-naphthyl)-2-{[2-(trimethylsilyl)ethoxy]methyl}-3,4-dihydro-2H-thieno[3,2-e][1,2]thiazin-4-ol 1,1-dioxide (Compound 144)

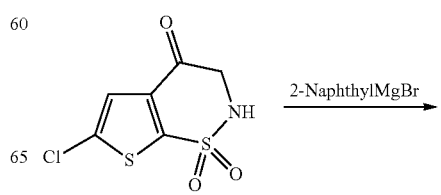

-continued

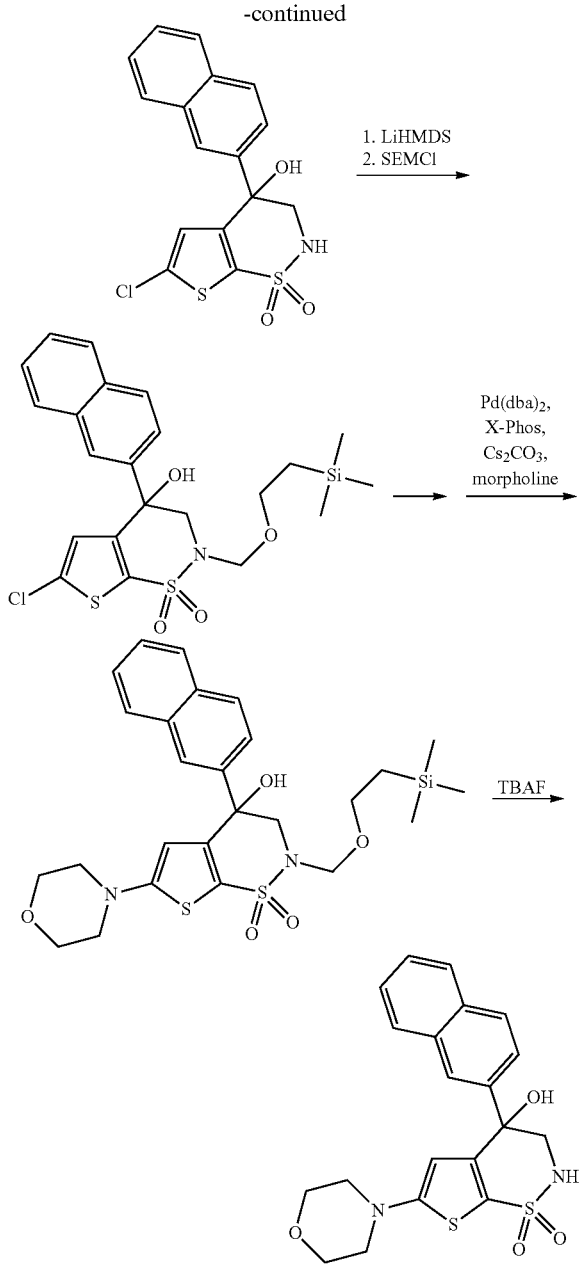

Step 1: 6-chloro-4-(2-naphthyl)-3,4-dihydro-2H-thieno[3,2-e][1,2]thiazin-4-ol 1,1-dioxide 6-chloro-2,3-dihydro-4H-thieno[3,2-e][1,2]thiazin-4-one 1,1-dioxide (0.800 g, 3.36 mmol) was dissolved in THF (30 mL) and 2-naphthylmagnesium bromide (0.5 M in THF, 33.6 mL, 16.8 mmol) was added. The solution was stirred at room temperature overnight. Reaction was quenched by addition of MeOH (20 mL) and evaporated. The residue was purified using column chromatography on silica gel (80 g Analogix column, gradient 10% EA in hexane to 40% EA in hexane over 20 minutes) to give the title compound (235 mg, 18%). LCMS (FA) ES−: 364, 366. $^1$H NMR (400 MHz, DMSO) δ 8.46-8.42 (m, 1H), 7.97-7.89 (m, 4H), 7.55-7.52 (m, 2H), 7.35-7.32 (m, 1H), 6.74 (s, 1H), 6.63 (s, 1H), 3.90-3.84 (m, 1H), 3.69-3.64 (m, 1H).

Step 2: 6-chloro-4-(2-naphthyl)-2-{[2-(trimethylsilyl)ethoxy]methyl}-3,4-dihydro-2H-thieno[3,2-e][1,2]thiazin-4-ol 1,1-dioxide To a solution of 6-chloro-4-(2-naphthyl)-3,4-dihydro-2H-thieno[3,2-e][1,2]thiazin-4-ol 1,1-dioxide (0.235 g, 0.642 mmol) in THF (5.2 mL) at −78° C. was added 1.00 M Lithium hexamethyldisilazide in THF (0.771 mL, 0.771 mmol). The reaction mixture was stirred at −78° C. for 30 min, and [β-(trimethylsilyl)ethoxy]methyl chloride (0.341 mL, 1.93 mmol) was added at the same temperature. The mixture was stirred for 1 h at −78° C. and raised to rt. After stirring at rt for 30 min, the mixture was quenched by sat. NH$_4$Cl, extracted with EA, dried and evaporated. The residue was purified by Isco silica gel chromatography (24 g cartridge), EA in hex, 0-30% using solid load to give the title compound (0.140 g, 42%). LCMS (FA) ES−: 494, 496. $^1$H NMR (400 MHz, DMSO) δ 7.95-7.92 (m, 4H), 7.55-7.52 (m, 2H), 7.32-7.29 (m, 1H), 6.77 (s, 1H), 6.74 (s, 1H), 4.91 (d, 1H), 4.64 (d, 1H), 4.20 (d, 1H), 3.95 (d, 1H), 3.52-3.47 (m, 2H), 0.85-0.76 (m, 2H), −0.05 (s, 9H).

Step 3: 6-(morpholin-4-yl)-4-(2-naphthyl)-2-{[2-(trimethylsilyl)ethoxy]methyl}-3,4-dihydro-2H-thieno[3,2-e][1,2]thiazin-4-ol 1,1-dioxide A 5 mL microwave vial was charged with 6-chloro-4-(2-naphthyl)-2-{[2-(trimethylsilyl)ethoxy]methyl}-3,4-dihydro-2H-thieno[3,2-e][1,2]thiazin-4-ol 1,1-dioxide (0.140 g, 0.282 mmol, tris(dibenzylideneacetone)dipalladium(0) (0.0129 g, 0.0141 mmol), 4,5-bis(diphenylphosphino)-9,9-dimethylxanthene (0.0163 g, 0.0282 mmol) and cesium carbonate (0.2758 g, 0.8466 mmol). The vial was flushed with Ar and 1,4-dioxane (4.4 mL) and morpholine (0.0738 mL, 0.847 mmol) were added. The reaction mixture was sealed and heated at microwave irradiation to 140° C. for 1 hour. Solvent was evaporated, and the residue was purified using column chromatography on silica gel (24 g Analogix column, gradient hexane to 50% EA in hexane over 20 minutes) to provide the title compound (0.030 g, 18%). LCMS (FA) ES+: 547. $^1$H NMR (400 MHz, DMSO) δ 7.94-7.88 (m, 4H), 7.53-7.51 (m, 2H), 7.30-7.27 (m, 1H), 6.50 (s, 1H), 5.69 (s, 1H), 4.87 (d, 1H), 4.53 (d, 1H), 4.11 (d, 1H), 3.87 (d, 1H), 3.64-3.61 (m, 4H), 3.50-3.45 (m, 2H), 3.06-3.03 (m, 4H), 0.79-0.74 (m, 2H), −0.06 (s, 9H).

Step 4: 6-(morpholin-4-yl)-4-(2-naphthyl)-3,4-dihydro-2H-thieno[3,2-e][1,2]thiazin-4-ol 1,1-dioxide 6-(morpholin-4-yl)-4-(2-naphthyl)-2-{[2-(trimethylsilyl)ethoxy]methyl}-3,4-dihydro-2H-thieno[3,2-e][1,2]thiazin-4-ol 1,1-dioxide (0.030 g, 0.055 mmol) was dissolved in THF (2.0 mL) and 1.00 M tetra-n-butylammonium fluoride in THF (0.549 mL, 0.549 mmol) was added. The solution was stirred at 40° C. overnight. The solvent was evaporated and the residue was purified using silica gel chromatography (12 g silica gel column, gradient 20% EA in hexane to 100% EA over 15 minutes) to give the product (14 mg, 55%). LCMS (FA) ES+: 417. $^1$H NMR (400 MHz, CD$_3$OD) δ 7.94 (s, 1H), 7.86-7.83 (m, 3H), 7.50-7.47 (m, 2H), 7.39-7.36 (m, 1H), 5.66 (s, 1H), 5.48 (s, 1H), 3.96 (d, 1H), 3.73-3.70 (m, 4H), 3.62 (d, 1H), 3.09-3.05 (m, 4H).

Example 51

Synthesis 2-(4-(4-chlorophenyl)-2-morpholino-7-oxo-4,5-dihydrothieno[2,3-c]pyridin-6(7H)-yl)acetic acid (Compound 213) and 2-(4-(4-chlorophenyl)-2-morpholino-7-oxo-4,5-dihydrothieno[2,3-c]pyridin-6(7H)-yl)acetamide (Compound 214)

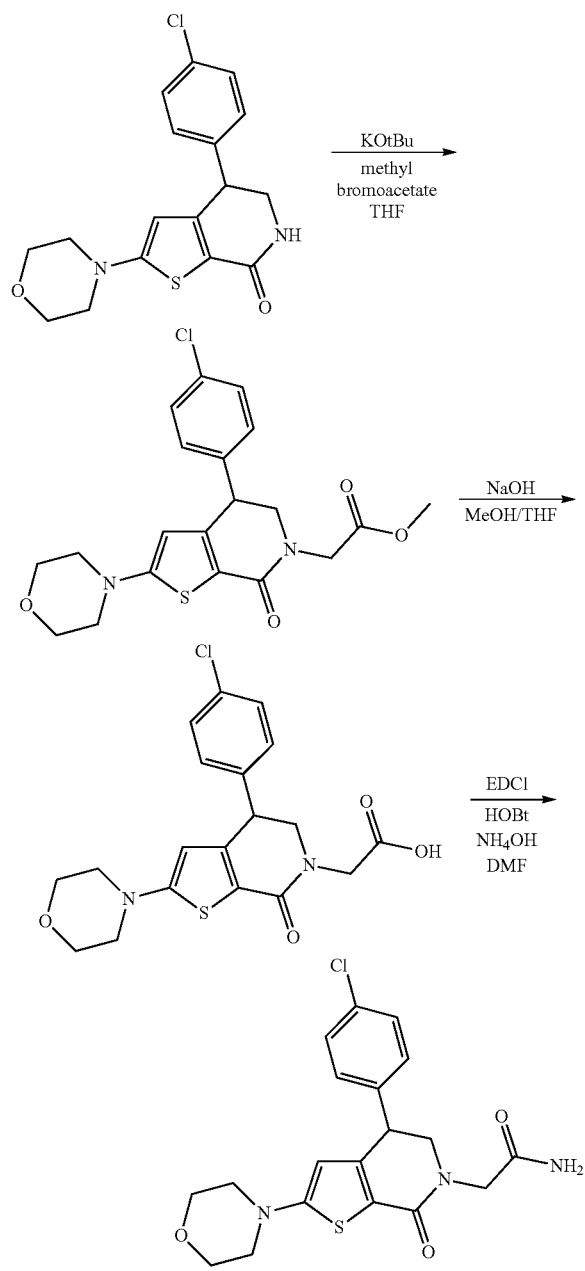

Step 1, Preparation of methyl 2-(4-(4-chlorophenyl)-2-morpholino-7-oxo-4,5-dihydrothieno[2,3-c]pyridin-6(7H)-yl)acetate To a mixture of 4-(4-chlorophenyl)-2-morpholino-5,6-dihydrothieno[2,3-c]pyridin-7(4H)-one (451 mg, 1.29 mmol) in THF (7.0 mL) in an ice bath was added 1.00 M potassium t-butoxide in THF (1.42 mL, 1.42 mmol) and the resulting solution was stirred in the ice bath for 30 minutes. Methyl bromoacetate (184 uL, 1.94 mmol) was added and the solution was stirred for 1 hour in the ice bath. The reaction was quenched with saturated NH$_4$Cl (10 mL) and diluted with ethyl acetate (20 mL). The layers were separated and the organic layer was washed with brine, dried over MgSO$_4$, filtered and concentrated in vacuo. The residue was purified by silica gel chromatography (ethyl acetate/DCM=0/100→40/60) to give 455 mg (84% yield) of the title compound as a light yellow oil. LC/MS (FA) ES+ 421. $^1$H NMR (400 MHz, CDCl$_3$) δ: 7.15-7.12 (m, 2H), 7.03-7.00 (m, 2H), 5.38 (s, 1H), 4.09 (d, 1H, J=17.2 Hz), 4.06-4.01 (m, 1H), 3.99 (d, 1H, J=17.2 Hz), 3.63-3.61 (m, 4H), 3.57-3.53 (m, 2H), 3.52 (s, 3H), 2.99-2.97 (m, 4H).

Step 2, Preparation of 2-(4-(4-chlorophenyl)-2-morpholino-7-oxo-4,5-dihydrothieno[2,3-c]pyridin-6(7H)-yl)acetic acid (Compound 213)

To a solution of methyl 2-(4-(4-chlorophenyl)-2-morpholino-7-oxo-4,5-dihydrothieno[2,3-c]pyridin-6(7H)-yl)acetate (520 mg, 1.24 mmol) in THF (13.7 mL) and methanol (6.9 mL) was added 1.0 M aqueous NaOH (10.3 mL, 10.3 mmol) and the resulting solution was stirred overnight at room temperature. The reaction was acidified with 1N HCl to pH=2 and the aqueous layer was extracted with ethyl acetate (2×30 mL). The combined organic layers were washed with brine, dried over MgSO$_4$, filtered and concentrated in vacuo. The residue was purified by silica gel chromatography (methanol/DCM=0/100→20/80) to give 299 mg of a yellow solid. This material was purified by analytical chromatography to give 161 mg (32% yield) of the title compound as a white solid. LC/MS (FA) ES+ 407. $^1$H NMR (400 MHz, DMSO-d$_6$) δ: 12.69 (bs, 1H), 7.41-7.38 (m, 2H), 7.29-7.26 (m, 2H), 5.80 (s, 1H), 4.30-4.26 (m, 1H), 4.11 (d, 1H, J=17.2 Hz), 3.95 (d, 1H, J=17.2 Hz), 3.89-3.85 (m, 1H), 3.70-3.67 (m, 4H), 3.66-3.61 (m, 1H), 3.14-3.11 (m, 4H).

Step 3, Preparation of 2-(4-(4-chlorophenyl)-2-morpholino-7-oxo-4,5-dihydrothieno[2,3-c]pyridin-6(7H)-yl)acetamide (Compound 214)

To a solution of 2-(4-(4-chlorophenyl)-2-morpholino-7-oxo-4,5-dihydrothieno[2,3-c]pyridin-6(7H)-yl)acetic acid (95.2 mg, 0.234 mmol) in DMF (3.0 mL) was added 1-hydroxybenzotriazole hydrate (39.4 mg, 0.297 mmol) and N-(3-Dimethylaminopropyl)-N'-ethylcarbodiimide hydrochloride (80.7 mg, 0.421 mmol) and the resulting solution was stirred for 30 minutes. 33% NH$_4$OH (202 uL, 2.34 mmol) was added and the resulting solution was stirred at room temperature overnight. The reaction was diluted with ethyl acetate (40 mL) and water (15 mL). The layers were separated and the organic layer was washed with water (3×10 mL). The organic layer was dried over MgSO$_4$, filtered and concentrated in vacuo to give 77 mg crude. The residue was purified by analytical chromatography to give 50 mg (53% yield) of the title compound as a white solid. LC/MS (FA) ES+ 406. $^1$H NMR (400 MHz, DMSO-d$_6$) δ: 7.42-7.39 (m, 2H), 7.28-7.26 (m and bs, 3H total), 7.01 (bs, 1H), 5.78 (s, 1H), 4.30-4.27 (m, 1H), 4.04 (d, 1H, J=17.2 Hz), 3.84-3.79 (m, 1H), 3.77 (d, 1H, J=17.2 Hz), 3.70-3.67 (m, 4H), 3.64-3.59 (m, 1H), 3.13-3.10 (m, 4H).

Formulation Example 1

Amount Per Tablet

| (1) Compound obtained in Example 1 | 10.0 mg |
|---|---|
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| (1) Compound obtained in Example 1 | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Biological Data:
PI3K and VPS34 Enzyme Assays
Cloning, Expression, and Purification of PI3Ks and VPS34
The catalytic subunits of PI3Ks are cloned into either pDEST8(p110 alpha) or pDEST10(p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:
  p110 alpha (GB:U79143)
  p110beta (GB:S67334)
  p110delta (GB: U86453)
  p110gamma (GB: X83368)
The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as follows:
  p85 alpha (GB: BC030815)
  p101(GB: AB028925)

VPS34 (accession number GB:BC033004) is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

For expression VPS34 was infected at 1MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

PI3K and VPS34 Assay Conditions
1) Human PI3Kα enzyme assay method
0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM MgCl2, 0.25 mM sodium cholate and 0.001% CHAPS, pH 7.00) containing ATP (25 uM, Promega) is added followed immediately by 10 ul PI3K reaction buffer containing di-C8 PI(4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

4) Human VPS34 enzyme assay method
100 mL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM MnCl2) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

PI3K Cell Assays

1) In-Cell Western Assay

The pSer473 AKT LI-COR In-Cell Western Assay is a quantitative immunofluorescent assay that measures phosphorylation of serine 473 AKT (pSer473 AKT) in WM266.4 and SKOV3 tumor cell lines grown in cell culture.

WM266.4 cells are propagated in Minimum Essential Media (MEM) (Invitrogen) containing L-glutamine, 10% Fetal Bovine Serum, 1 mM MEM Sodium Pyruvate, and 0.1 mM MEM Non-Essential Amino Acids and SKOV3 cells are propagated in McCoy's 5A Media (modified) (Invitrogen) containing L-Glutamine and 10% Fetal Bovine Serum. Both cell lines are kept in a humidified chamber at 37° C. with 5% $CO_2$. For the pSer473 AKT LI-COR In-Cell Western Assay, $1.5 \times 10^4$ WM266.4 and $1.5 \times 10^4$ SKOV3 cells are cultured in 100 µl of media per well in tissue culture-treated black-walled, clear bottom Optilux 96-well plates (BD Biosciences) for 16-20 hours. Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 2 hours in a humidified chamber at 37° C. with 5% $CO_2$. Immediately following compound incubation, all liquid is removed from the wells and cells are fixed with 4% paraformaldehyde in PBS (150 µl per well) for 20 minutes at room temperature. The paraformaldehyde solution is removed from wells and the cells are permeabilized with 200 µl 0.1% Triton X-100 in PBS per well for 10 min×3 at room temperature. After removal of PBS+ 0.1% Triton X-100, 150 µl Odyssey blocking buffer (LI-COR Biosciences) is added to each well and plates are incubated at room temperature for 1.5 h. Blocking buffer is removed from the wells and primary antibodies (Phospho-AKT (Ser473) (D9E) XP™ Rabbit mAb and AKT (pan) (40D4) Mouse mAb, Cell Signaling Technology) diluted in Odyssey blocking buffer are added (50 µl per well). Plates are incubated at 4° C. overnight. The cells are washed for 20 min×3 with PBS+ 0.1% Tween-20 (200 µl per well). Secondary antibodies (IRDye 680 Goat anti-Rabbit IgG (H+L) and IRDye 800CW Goat anti-Mouse IgG (H+L), LI-COR Biosciences) are diluted in Odyssey blocking buffer and added to wells (50 µl per well) followed by a 1 h incubation at room temperature, protected from light. Cells are washed for 20 min×3 with PBS+0.1% Tween-20 (200 µl per well). Wash buffer is completely removed from wells after last wash, plates are protected from light until scanned and analyzed with the Odyssey Infrared Imaging System (LI-COR Biosciences). Both pS473 AKT and AKT are simultaneously visualized with the 680 nm fluorophore indicated by a red color and the 800 nm fluorophore indicated by a green color. Relative fluorescence units derived from the scans allow for quantitative analyses of both labeled proteins and the ratio of pS473 AKT to AKT is calculated. Concentration response curves are generated by plotting the average ratios of PI3K inhibitor-treated samples relative to DMSO-treated controls to determine percent change in expression of pS473 AKT.

2) ATPlite Viability Assay

The ATPLite™ Assay (Perkin-Elmer) measures cellular adenosine-triphosphate (ATP) through the generation of a luminescent signal formed from the ATP-dependent enzyme firefly luciferase. The luminescent signal intensity can be used as a measure of cellular proliferation, and can be used to assess the anti-proliferative effects of PI3K inhibitors.

WM266.4 cells propagated in Minimum Essential Media (MEM) (Invitrogen) containing L-Glutamine, 10% Fetal Bovine Serum, 1 mM MEM Sodium Pyruvate, and 0.1 mM MEM Non-Essential Amino Acids are cultured in 384-well tissue culture-treated Black/Clear plates (Falcon) at $1 \times 10^3$ cells per well in a volume of 75 µl in a humidified chamber at 37° C. with 5% $CO_2$ for 24 h. Test compounds (2 µl in 100% DMSO) are diluted in 95 µl of cell culture media. The diluted test compounds are added (8 µl per well) to 384-well plates. Final concentration range of 3-fold serial dilution of compounds is 0.001 to 20 µM. Plates are incubated for 72 h in a humidified chamber at 37° C. with 5% $CO_2$. One control plate without compound addition is processed at the start of the 72 h incubation as a "Time Zero" reading for quantitative evaluation of cell viability at start of assay. After 72 h, all but 25 µl of cell culture media is removed from each well, followed by the addition of 25 pd of ATPlite 1 step reagent (Perkin Elmer) to each well. Luminescence is measured on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from the curves.

As detailed above, compounds of the invention inhibit PI3K. In certain embodiments, compounds inhibit one or more isoforms of PI3K. In other embodiments, compounds of the invention inhibit PI3 Kbeta and have an $IC_{50} > 1.0$ µM. For example, these compounds include 4, 5, 14. In other embodiments, compounds of the invention have an $IC_{50} < 1.0$ µM but $>0.1$ µM. For example, these compounds include compounds 3, 7, 9, 10, 11, 12, 15, 16, 19, 20, 23, 25, 27, 29, 31. In still other embodiments, compounds of the invention have an $IC_{50} < 0.1$ µM. For example, these compounds include compounds 1, 2, 6, 8, 13, 17, 18, 21, 22, 24, 26, 28, 30. Table 2 also depicts exemplary potency data at 1.11 µM for certain compounds of the invention.

TABLE 2

| | Potency Data at 1.11 µM: | | | | |
|---|---|---|---|---|---|
| Compound | PI3Kalpha % inh | PI3Kbeta % inh | PI3Kgamma % inh | PI3Kdelta % inh | VPS34 % ihn |
| 1 | 49.800 | 100.100 | 63.400 | 103.300 | 29.300 |
| 2 | 3.200 | 110.400 | 21.200 | 63.100 | 4.300 |
| 3 | 10.800 | 65.700 | | | −2.500 |
| 4 | −0.100 | 14.400 | | | |
| 5 | −3.800 | 32.800 | | | |
| 6 | 27.000 | 97.900 | 14.000 | 70.700 | 10.100 |
| 7 | 20.500 | 64.600 | 6.500 | 91.300 | 9.600 |
| 8 | 2.050 | 101.950 | 21.900 | 59.200 | 2.550 |
| 9 | 3.600 | 67.200 | 3.300 | 41.900 | −2.200 |
| 10 | 0.200 | 71.000 | 6.700 | 32.400 | 0.100 |
| 11 | 36.000 | 71.600 | 5.200 | 60.300 | −4.200 |
| 12 | 9.400 | 73.200 | 31.000 | 69.000 | −6.000 |
| 13 | 3.100 | 102.100 | 10.800 | 55.700 | 6.600 |
| 14 | 8.700 | 31.900 | | | |
| 15 | 3.100 | 65.000 | 4.000 | 26.400 | 2.000 |
| 16 | 24.500 | 54.550 | | | |
| 17 | 12.400 | 96.800 | 8.600 | 47.900 | 28.500 |
| 18 | 18.800 | 104.400 | 21.500 | 53.800 | −4.100 |
| 19 | −0.400 | 86.500 | 8.100 | 43.100 | −6.800 |
| 20 | 23.600 | 68.200 | 6.600 | 60.400 | 0.900 |
| 21 | 6.067 | 111.967 | 24.700 | 79.150 | 9.100 |
| 22 | 0.600 | 97.500 | 14.200 | 44.500 | 4.400 |
| 23 | 3.100 | 92.800 | 10.900 | 23.000 | −2.000 |
| 24 | 13.800 | 98.100 | 16.900 | 54.200 | −6.900 |
| 25 | 3.700 | 69.800 | 4.500 | 31.200 | 10.900 |
| 26 | 6.600 | 105.000 | 11.700 | 37.900 | 1.200 |
| 27 | 4.900 | 98.300 | 12.300 | 46.000 | 8.500 |
| 28 | 15.650 | 104.750 | 23.550 | 75.050 | 8.600 |
| 29 | 6.000 | 87.800 | 4.600 | 20.900 | 1.400 |
| 30 | 6.300 | 94.900 | 11.200 | 36.000 | −0.200 |
| 31 | 16.600 | 83.300 | 6.900 | 50.500 | 2.000 |
| 116 | 36.43 | 66.61 | | | |

TABLE 2-continued

Potency Data at 1.11 μM:

| Compound | PI3Kalpha % inh | PI3Kbeta % inh | PI3Kgamma % inh | PI3Kdelta % inh | VPS34 % ihn |
|---|---|---|---|---|---|
| 117 | 26.64 | 100.52 | 35.49 | 81.15 | 6.21 |
| 118 | 19.67 | 62.95 | 5.03 | 54.64 | 9.51 |
| 119 | 42.40 | 106.60 | 60.26 | 99.78 | |
| 120 | 12.90 | 44.05 | | | |
| 121 | 40.77 | 104.98 | | | |
| 122 | 97.85 | 127.80 | | | |
| 123 | 32.28 | 101.46 | 10.42 | 49.58 | |
| 124 | 12.16 | 93.50 | 9.41 | 59.24 | |
| 125 | 22.55 | 71.83 | 16.66 | 44.54 | 24.38 |
| 126 | 39.72 | 98.08 | 36.62 | 75.35 | 26.74 |
| 127 | 31.36 | 75.79 | | | |
| 128 | 18.03 | 107.54 | 45.90 | 86.97 | 36.29 |
| 129 | 2.32 | 59.86 | 3.89 | 26.46 | −2.80 |
| 130 | 58.08 | 116.45 | | | |
| 131 | 9.87 | 85.03 | | | |
| 132 | 54.02 | 114.65 | | | |
| 133 | 35.04 | 110.07 | 30.69 | 102.10 | |
| 134 | 33.04 | 93.80 | 32.17 | 76.47 | 9.44 |
| 135 | 89.78 | 121.40 | | | |
| 136 | 17.00 | 87.47 | 4.11 | 35.35 | |
| 137 | 16.10 | 80.82 | | | |
| 138 | 7.29 | 64.59 | | | |
| 139 | 14.38 | 95.64 | | | |
| 140 | 8.99 | 98.34 | 18.05 | 67.86 | 19.51 |
| 141 | 4.69 | 76.97 | 6.82 | 47.20 | 15.11 |
| 142 | 16.73 | 72.00 | | | |
| 143 | 10.03 | 82.45 | | | |
| 144 | 41.58 | 100.66 | 67.80 | 110.90 | 5.73 |
| 145 | 18.36 | 101.66 | 50.45 | 88.59 | −1.31 |
| 146 | 40.44 | 107.09 | 50.72 | 99.66 | |
| 147 | 3.15 | 65.70 | 2.45 | 9.91 | 9.65 |
| 148 | 24.59 | 118.63 | 13.18 | 98.18 | |
| 149 | 46.13 | 107.80 | 29.11 | 80.94 | 4.85 |
| 150 | 26.81 | 108.10 | 21.48 | 99.94 | |
| 151 | 43.14 | 102.63 | 41.05 | 89.96 | |
| 152 | 12.54 | 101.56 | 51.77 | 96.67 | |
| 153 | 20.40 | 87.14 | 9.08 | 39.78 | |
| 154 | 10.88 | 75.49 | | | |
| 155 | 64.67 | 113.45 | 42.58 | 104.50 | 11.64 |
| 156 | 6.34 | 94.95 | 11.17 | 36.03 | −0.21 |
| 157 | 30.11 | 110.65 | | | |
| 158 | 12.95 | 108.45 | 65.33 | 100.04 | 5.41 |
| 159 | 67.17 | 118.45 | | | |
| 160 | 11.18 | 76.80 | | | |
| 161 | 12.09 | 92.64 | 19.28 | 59.27 | 10.78 |
| 162 | 7.94 | 70.58 | 3.59 | 41.79 | |
| 163 | 5.98 | 99.63 | 11.94 | 71.42 | |
| 164 | −2.24 | 76.85 | 5.01 | 14.04 | 8.39 |
| 165 | 13.35 | 108.75 | | | |
| 166 | 7.59 | 69.25 | | | |
| 167 | 5.27 | 81.18 | | | |
| 168 | 74.55 | 117.05 | | | |
| 169 | 50.56 | 99.74 | 71.33 | 98.20 | |
| 170 | 22.53 | 83.73 | 12.47 | 51.65 | |
| 171 | 48.14 | 105.95 | 64.41 | 110.62 | 16.77 |
| 172 | 16.14 | 49.29 | | | |
| 173 | 24.12 | 102.95 | 41.53 | 109.53 | 41.77 |
| 174 | 4.56 | 82.54 | | | |
| 175 | 66.93 | 112.20 | 43.76 | 112.40 | |
| 176 | 28.06 | 105.20 | 60.09 | 107.75 | |
| 177 | 29.59 | 58.45 | | | |
| 178 | 4.71 | 40.19 | | | |
| 179 | 21.57 | 107.30 | | | |
| 180 | 13.95 | 97.40 | 28.66 | 87.34 | 55.81 |
| 181 | 8.59 | 69.53 | | | |
| 182 | 2.99 | 61.19 | 3.51 | 48.48 | 14.02 |
| 183 | 26.88 | 90.44 | 20.55 | 60.11 | 9.00 |
| 184 | 6.62 | 77.50 | | | |
| 185 | 27.72 | 106.30 | 53.39 | 109.53 | 47.78 |
| 186 | 15.14 | 92.30 | 23.31 | 74.92 | 26.79 |
| 187 | 38.40 | 103.85 | | | |
| 188 | 102.25 | 117.23 | 62.33 | 109.60 | 12.91 |
| 189 | 25.85 | 115.90 | | | |
| 190 | 57.47 | 122.80 | 35.76 | 101.40 | |
| 191 | 9.58 | 79.44 | 6.39 | 30.34 | 7.04 |
| 192 | 39.59 | 105.67 | 52.88 | 104.81 | |
| 193 | 11.08 | 79.13 | | | |
| 194 | 38.65 | 113.05 | | | |
| 195 | 16.47 | 62.54 | | | |
| 196 | 13.67 | 84.31 | | | |
| 197 | 19.34 | 84.06 | 9.08 | 47.39 | |
| 198 | 8.93 | 86.62 | 14.93 | 62.90 | 8.01 |
| 199 | 65.98 | 115.55 | | | |
| 200 | 48.20 | 53.94 | | | |
| 201 | 16.74 | 79.38 | | | |
| 202 | 88.75 | 113.55 | | | |
| 203 | 40.46 | 66.37 | | | |
| 204 | 51.34 | 60.14 | | | |
| 205 | 28.04 | 96.83 | | | |
| 206 | 41.75 | 58.49 | | | |
| 207 | 42.91 | 62.94 | | | |
| 208 | 18.37 | 96.82 | | | |
| 209 | 81.32 | 114.75 | 49.45 | 110.40 | 42.07 |
| 210 | 5.17 | 72.97 | 5.88 | 34.62 | −0.70 |
| 211 | 20.46 | 62.33 | | | |
| 212 | 54.25 | 65.59 | | | |
| 213 | 5.63 | 99.34 | | | |
| 214 | 5.13 | 110.10 | | | |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula I-A:

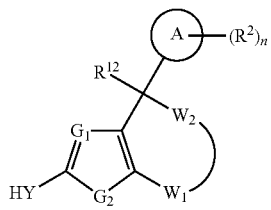

I-A or a pharmaceutically acceptable salt thereof, wherein:
$G_1$ is $CR^1$, wherein $R^1$ is H, —CN, halogen, or an optionally substituted group selected from $C_{1-6}$ straight-chain or branched aliphatic, 3-10-membered cycloaliphatic, and —Z—$R^{11}$, wherein:
Z is selected from an optionally substituted $C_{1-3}$ alkylene chain, —O—, —N($R^{1a}$)—, —S—, —S(O)—, S(O)$_2$—, —C(O)—, —CO$_2$—, —C(O)NR$^{1a}$—, —N($R^{1a}$)C(O)—, —N($R^{1a}$)CO$_2$—, —S(O)$_2$NR$^{1a}$—, —N($R^{1a}$)S(O)$_2$—, —OC(O)N($R^{1a}$)—, —N($R^{1a}$)C(O)NR$^{1a}$—, —N($R^{1a}$)S(O)$_2$($R^{1a}$)—, and —OC(O)—;
$R^{1a}$ is hydrogen or an optionally substituted $C_{1-4}$ straight-chain or branched aliphatic, and
$R^{11}$ is hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$G_2$ is S;

Ring A is an optionally substituted group selected from 6-10-membered aryl, and 5-10-membered heteroaryl having 1-5 heteroatoms independently selected from nitrogen, oxygen, and sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;

each occurrence of $R^{12b}$ is independently hydrogen or an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, and, or sulfur;

each occurrence of $R^{12c}$ is independently an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{12e}$ is independently hydrogen or an optionally substituted $C_{1-6}$ straight-chain or branched aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$-aliphatic group;

n is 0 to 4;

$R^{12}$ is hydrogen, halo, or an optionally substituted group selected from $C_{1-6}$ straight-chain or branched aliphatic, —$C(O)N(R^{5a})_2$, 3-10-membered cycloaliphatic, —$N(R^{4b})_2$, —$OR^{4a}$, and —$SR^{4a}$;

or $R^2$ and $R^{12}$ form an optionally substituted 3-10-membered cycloaliphatic;

$W_1$ is —$C(O)NR^{4a}$—;

$W_2$ is —$(C-W_3)_r$,
wherein each occurrence of $W_3$ is independently —$(R^5)_2$ or =O;

r is 1;

each occurrence of $R^{4a}$ is independently hydrogen or optionally substituted $C_{1-6}$ straight-chain or branched aliphatic;

each occurrence of $R^{4b}$ is independently hydrogen, or a group selected from optionally substituted $C_{1-6}$ straight-chain or branched aliphatic, —$OR^{4c}$, and —$N(R^{4a})_2$;

each occurrence of $R^{4c}$ is independently hydrogen or optionally substituted $C_{1-6}$ aliphatic;

each occurrence of $R^5$ is independently hydrogen, halo, or an optionally substituted group selected from $C_{1-6}$ straight-chain or branched aliphatic, —$C(O)N(R^{5a})_2$, 3-10-membered cycloaliphatic, 6-10-membered aryl, 5-10-membered heteroaryl having 1-5 heteroatoms independently selected from nitrogen, oxygen, and sulfur, —$N(R^{4b})_2$, —$OR^{4a}$, and —$SR^{4a}$;

each occurrence of $R^{5a}$ is independently hydrogen or optionally substituted $C_{1-6}$ straight-chain or branched aliphatic;

HY is an optionally substituted group selected from:

A
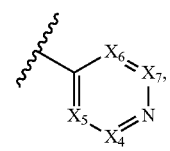

B
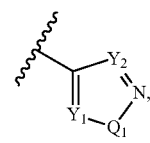

C
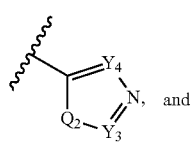

D
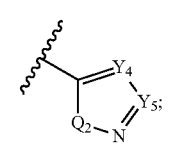

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{10}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, and 5-6-membered heteroaryl having 1-5 heteroatoms independently selected from nitrogen, oxygen, and sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7$C(O)O$R^{10a}$—, —$NR^7$C(O)N$R^7$—, —$NR^7$C(O)S$R^{10a}$—, —$NR^7$C(S)O$R^{10a}$—, —$NR^7$C(S)N$R^7$—, —$NR^7$C(S)S$R^{10a}$—, —$NR^7$C($NR^7$)O$R^{10a}$—, —$NR^7$C($NR^7$)N$R^7$—, —$NR^7$S(O)$_2$—, —$NR^7$S(O)$_2$N$R^7$—, —C(O)—, —CO$_2$—, —C(O)N$R^7$—, —C(O)N$R^7$—, —C(O)N$R^7$O—, —SO$_2$—, or —SO$_2$N$R^7$—;

each occurrence of $R^{10a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N($R^7$)—, —OC(O)N($R^7$)—, —N($R^7$)C(O)—, —N($R^7$)SO$_2$—, N($R^{10a}$)C(O)O—, —N$R^{10a}$C(O)N($R^{10a}$)—, —N($R^{10a}$)S(O)$_2$N($R^{10a}$)—, —OC(O)—, or —C(O)N($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^7$)$_2$, O$R^{10a}$, —S$R^{10a}$, —S(O)$_2$ $R^{10a}$, —C(O)$R^{10a}$, —C(O)O$R^{10a}$, —C(O)N($R^7$)$_2$, —S(O)$_2$N($R^7$)$_2$, —OC(O)N($R^7$)$_2$, —N($R^7$)C(O)$R^{10a}$, —N($R^7$)SO$_2R^{10a}$, —N($R^7$)C(O)O$R^{10a}$, —N($R^7$)C(O)N($R^7$)$_2$, or —N($R^7$)SO$_2$N($R^7$)$_2$, or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{10c}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, and sulfur;

each occurrence of $R^7$ is independently hydrogen, —C(O) $R^{7a}$, —CO$_2R^{7a}$, —C(O)N($R^{7a}$)$_2$, —C(O)N($R^{7a}$)—O$R^{7a}$, —SO$_2R^{7a}$, —SO$_2$N($R^{7a}$)$_2$, or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{7a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^6$ is independently hydrogen, —C(O) $R^{6a}$, —CO$_2R^{6a}$, —C(O)N($R^{6b}$)$_2$, —SO$_2R^{6a}$, —SO$_2$N($R^{6b}$)$_2$, or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;

wherein each occurrence of $R^{6a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteratoms independently selected from nitrogen, oxygen, and sulfur; and wherein each occurrence of $R^{6b}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, and sulfur, or 5-10-membered heteroaryl having 1-5 heteroatoms independently selected from nitrogen, oxygen, or sulfur;

or HY is

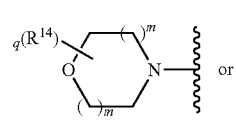

E

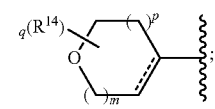

F wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —R$^{14c}$, —N(R$^{14b}$)$_2$, —OR$^{14b}$, —SR$^{14c}$, —S(O)$_2$R$^{14c}$, —C(O)R$^{14b}$, —C(O)OR$^{14b}$, —C(O)N(R$^{14b}$)$_2$, —S(O)$_2$N(R$^{14b}$)$_2$, —OC(O)N(R$^{14}$)$_2$, —N(R$^{14e}$)C(O)R$^{14b}$, —N(R$^{14e}$)SO$_2$R$^{14c}$, —N(R$^{14e}$)C(O)OR$^{14b}$, —N(R$^{14e}$)C(O)N(R$^{14b}$)$_2$, or —N(R$^{14e}$)SO$_2$N(R$^{14b}$)$_2$, or two occurrences of R$^{14b}$, taken together with a nitrogen atom to which they are bound, form an optionally substituted 4-7-membered heterocyclyl ring having 0-1 additional heteroatoms selected from nitrogen, oxygen, and sulfur;

each occurrence of R$^{14b}$ is independently hydrogen or an optionally substituted group selected from C$_1$-C$_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of R$^{14c}$ is independently an optionally substituted group selected from C$_1$-C$_6$ straight-chain or branched aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, and sulfur;

each occurrence of R$^{14d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of R$^{14e}$ is independently hydrogen or an optionally substituted C$_{1-6}$ straight-chain or branched aliphatic group; and T$_1$ is an optionally substituted C$_1$-C$_6$ alkylene chain wherein the alkylene chain optionally is interrupted by —N(R$^{14b}$)—, —O—, —S—, —S(O)—, —S(O)$_2$—, —C(O)—, —C(O)O—, —C(O)N(R$^{14ab}$)—, —S(O)$_2$N(R$^{14b}$)—, —OC(O)N(R$^{14b}$)—, —N(R$^{14b}$)C(O)—, —N(R$^{14b}$)SO$_2$—, —N(R$^{14b}$)C(O)O—, —NR$^{14b}$C(O)N(R$^{14b}$)—, —N(R$^{14b}$)S(O)$_2$N(R$^{14b}$)—, —OC(O)—, or —C(O)N(R$^{14b}$)—O— or wherein T$_1$ or a portion thereof optionally forms part of an optionally substituted 3-7 membered cycloaliphatic or heterocyclyl ring;

q is 0-6;

m is 1 or 2; and p is 0, 1, or 2.

2. The compound of claim 1, wherein HY is selected from:

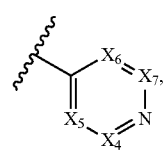

A

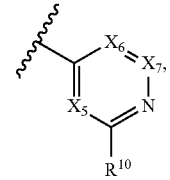

H

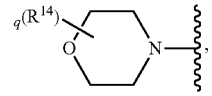

J

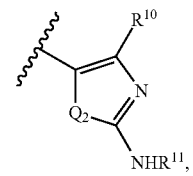

K

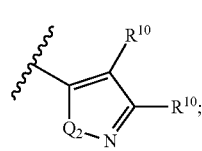

L

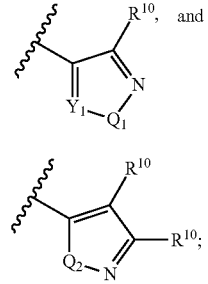

M wherein each occurrence of X$_4$, X$_5$, X$_6$, and X$_7$ is independently —CR$^{10}$ or N, provided no more than two occurrences of X$_4$, X$_5$, X$_6$, and X$_7$ are N;

each occurrence of Q$_1$ and Q$_2$ is independently S, O or —NR$^6$;

each occurrence of Y$_1$ is independently —CR$^{10}$ or N;

or wherein two adjacent occurrences of X$_6$ and X$_7$, or Y$_1$ and Q$_1$, taken together with the atom to which they are bound, form an optionally substituted fused group selected from 5-6-membered aryl and 5-6-membered heteroaryl having 1-5 heteroatoms independently selected from nitrogen, oxygen, and sulfur;

wherein each occurrence of R$^{14}$ is independently an optionally substituted C$_{1-6}$ straight-chain or branched aliphatic group.

3. The compound of claim 1, wherein HY is selected from:

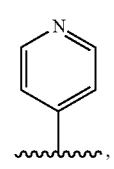

i

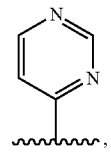

ii

-continued

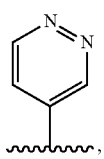
iii

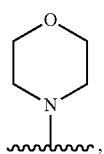
iv

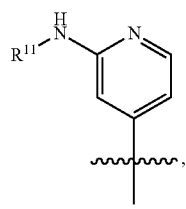
v

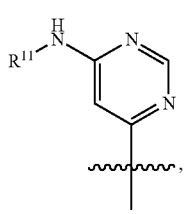
vi

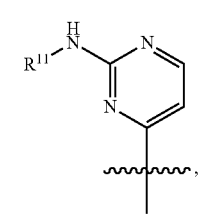
vii

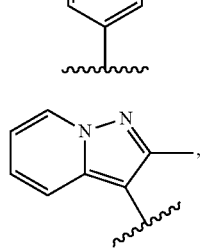
viii and

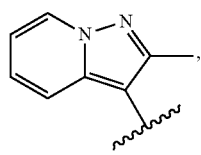
ix wherein each HY group is optionally additionally substituted with one or more occurrences of $R^{10}$ or $R^{14}$.

4. The compound of claim 1, wherein Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

5. The compound of claim 4, wherein Ring A is a phenyl group, $R^2$ is halogen and n is 1 or 2.

6. The compound of claim 1, wherein $R^{12}$ is OH.

7. The compound of claim 1 having the following formula IV:

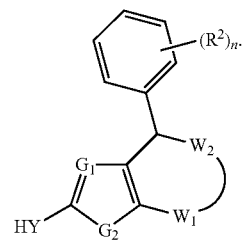
IV

8. The compound of claim 7, wherein HY is selected from:

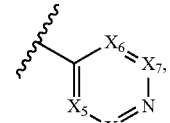
A

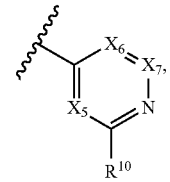
H

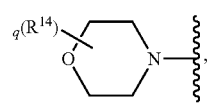
J

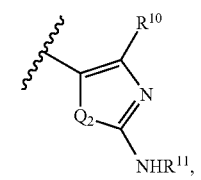
K

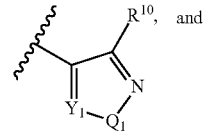
L, and

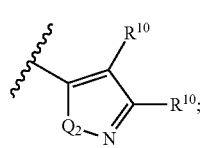
M wherein each occurrence of $X_4$, $X_5$, $X_6$, and $X_7$ is independently —$CR^{10}$ or N, provided no more than two occurrences of $X_4$, $X_5$, $X_6$, and $X_7$ are N;
each occurrence of $Q_1$ and $Q_2$ is independently S, O or —$NR^6$;
each occurrence of $Y_1$ is independently —$CR^{10}$ or N;
or wherein two adjacent occurrences of $X_6$ and $X_7$, or $Y_1$ and $Q_1$, taken together with the atom to which they are bound, form an optionally substituted fused group selected from 5-6-membered aryl and 5-6-membered heteroaryl having 1-5 heteroatoms independently selected from nitrogen, oxygen, and sulfur;
wherein each occurrence of $R^{14}$ is independently an optionally substituted $C_{1-6}$ straight-chain or branched aliphatic group.

9. The compound of claim 7, wherein HY is selected from:

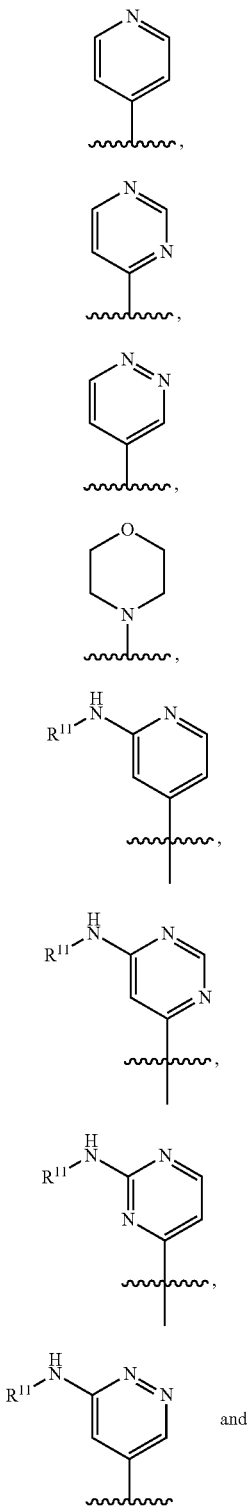

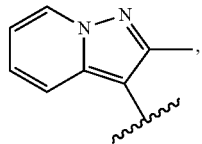

wherein each HY group is optionally additionally substituted with one or more occurrences of $R^{10}$ or $R^{14}$.

10. The compound of claim 7, wherein each occurrence of $R^2$ is independently halogen, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

11. The compound of claim 7, 8, 9, or 10, wherein $R^2$ is halogen and n is 1 or 2.

12. A compound selected from the group consisting of:

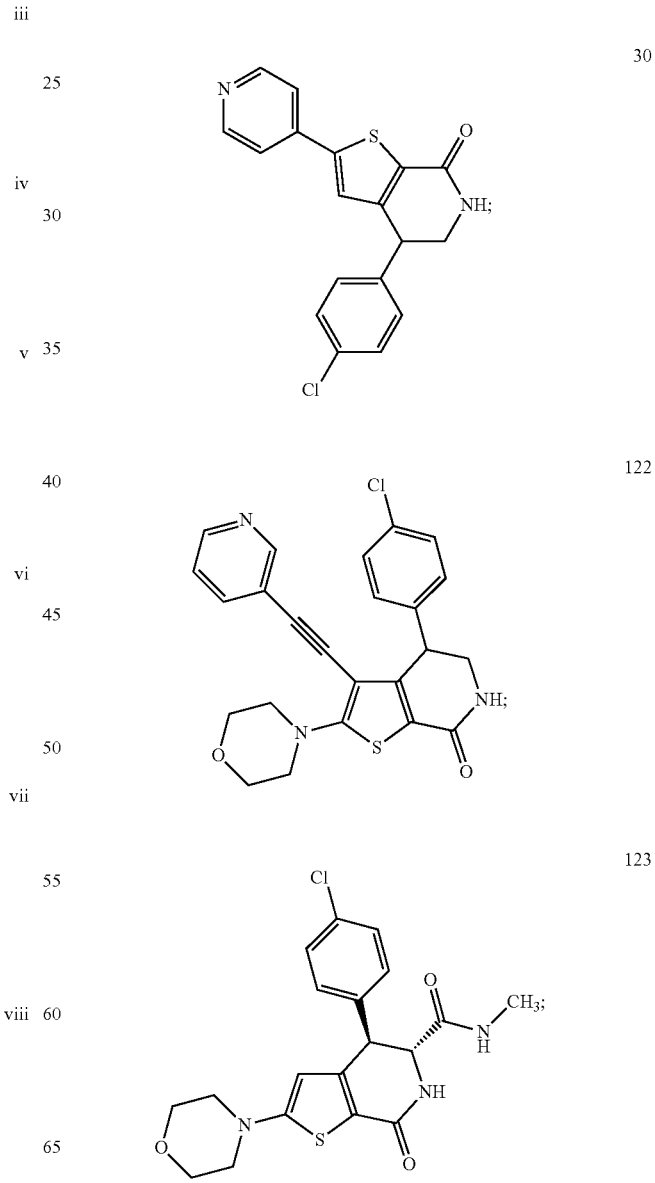

267
-continued
125 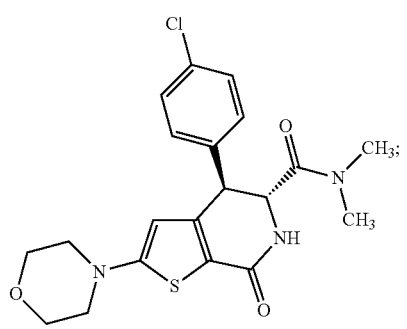
126 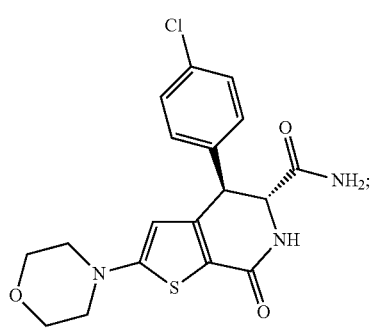
127 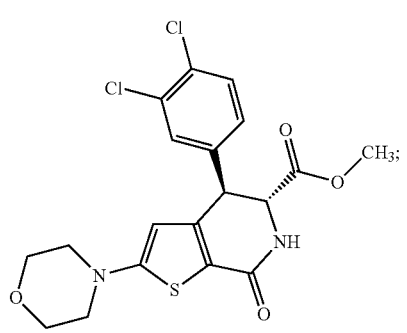
128 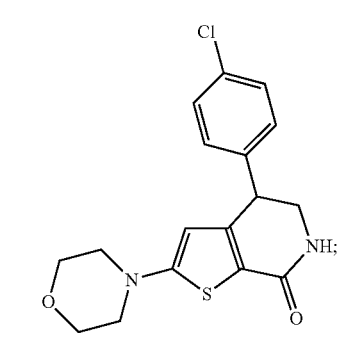
130 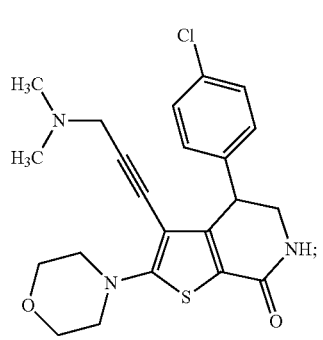
268
-continued
132 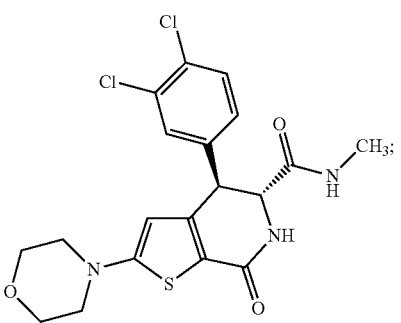
133 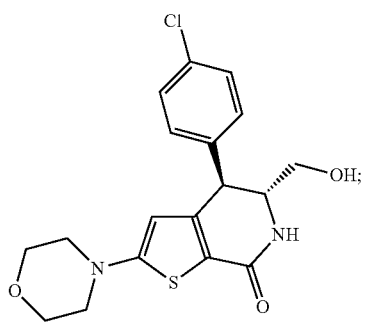
135 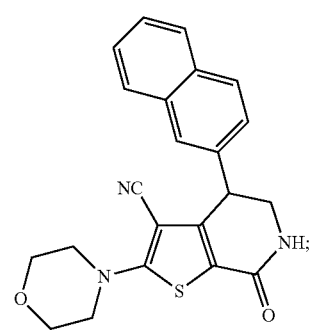
136 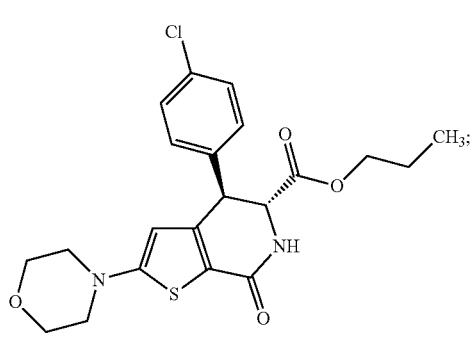
137 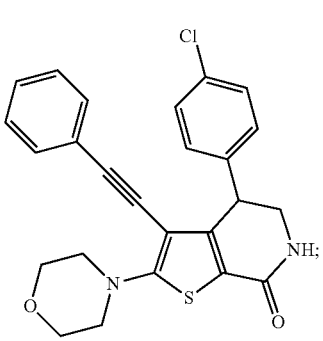

138
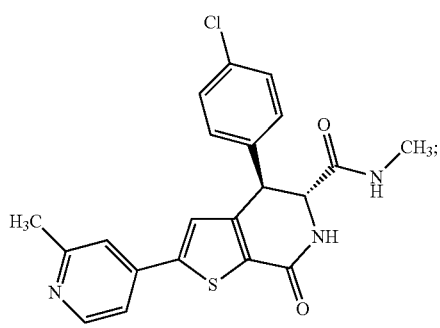
142
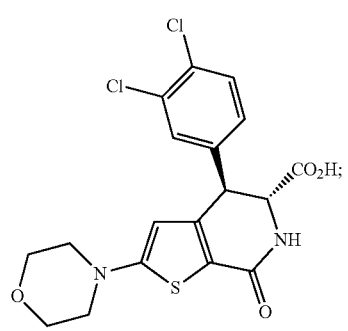
143
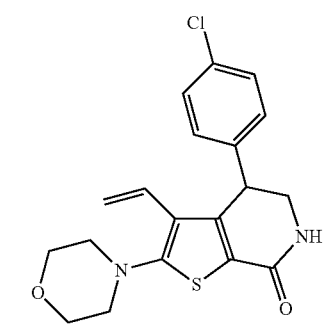
146
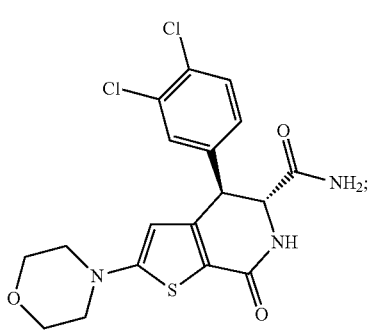
149
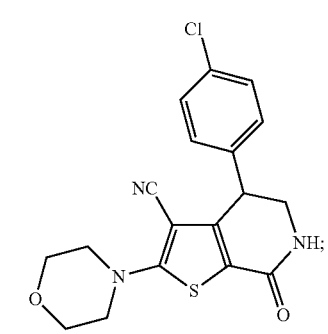
151
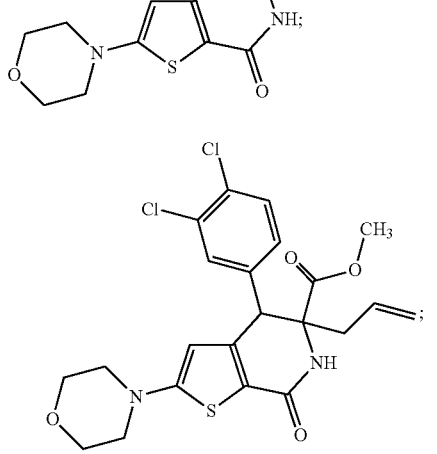
153
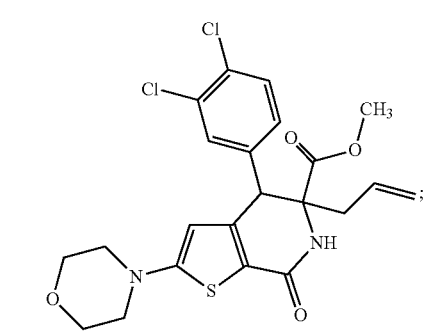
154
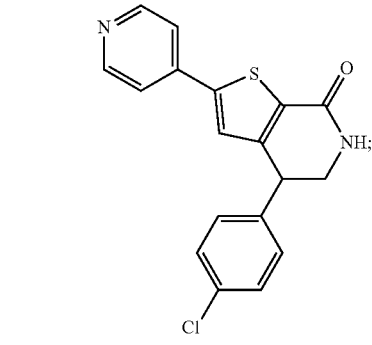
156
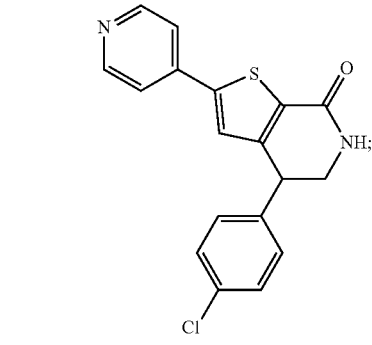
157
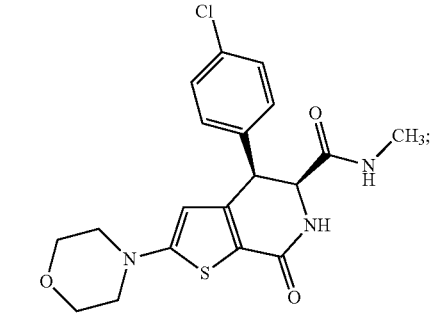

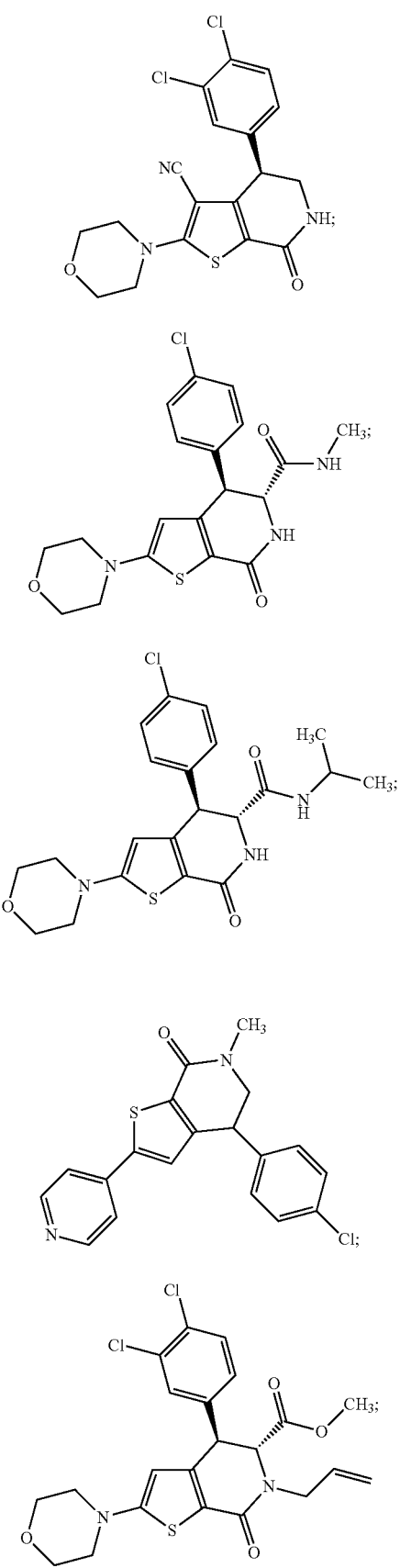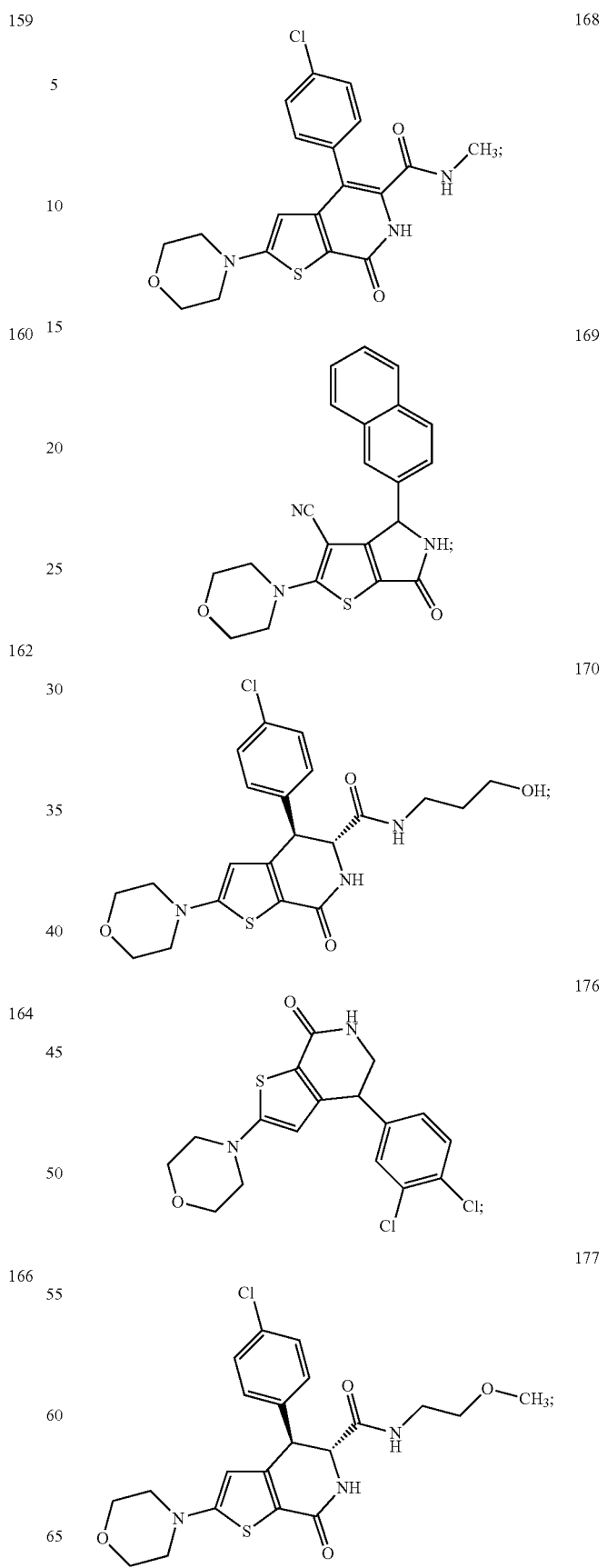

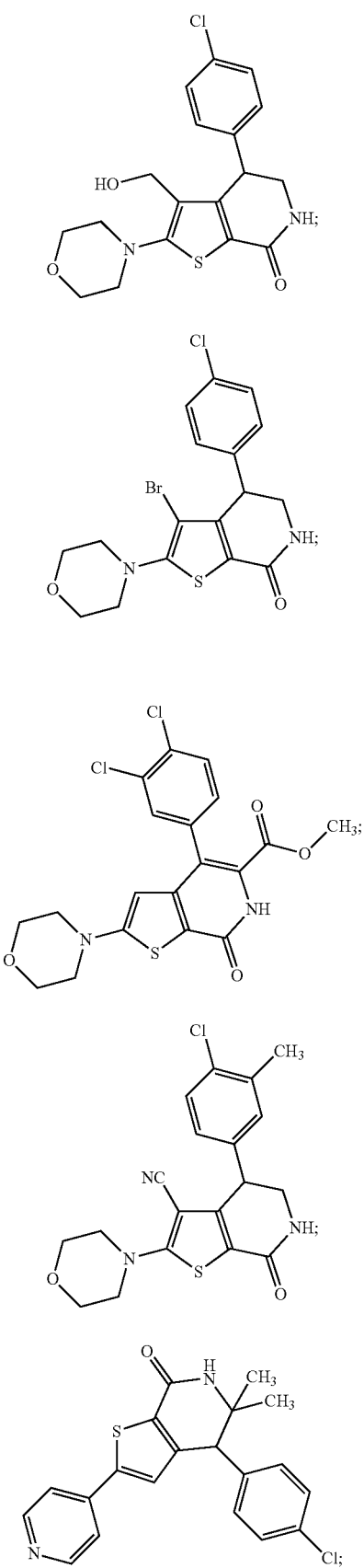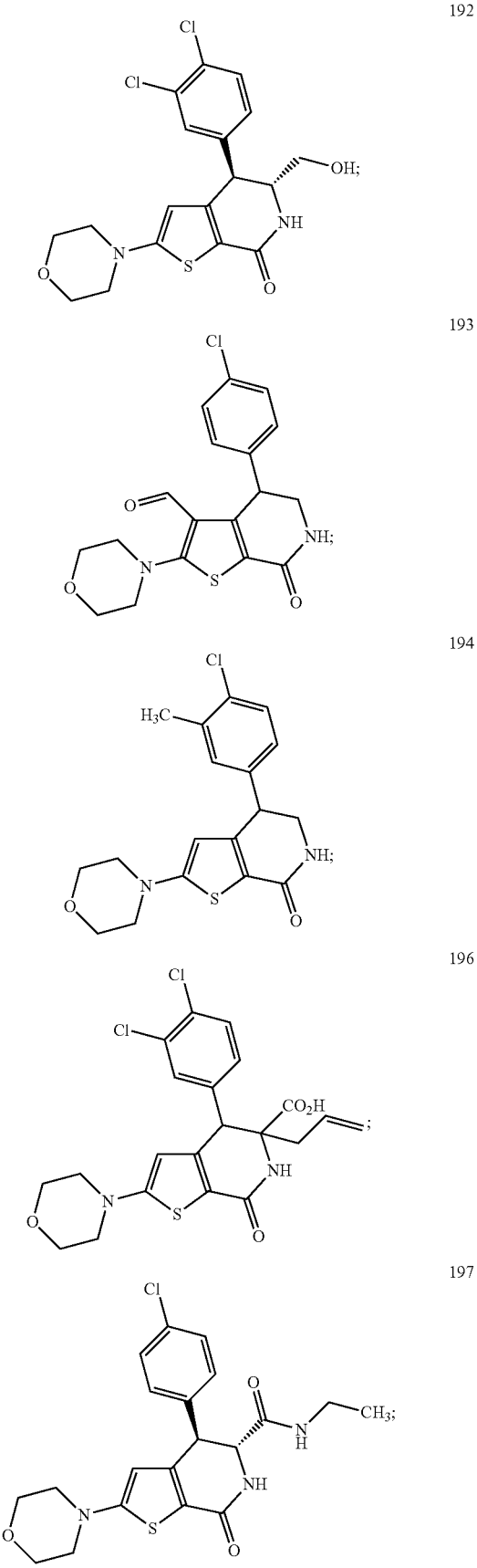

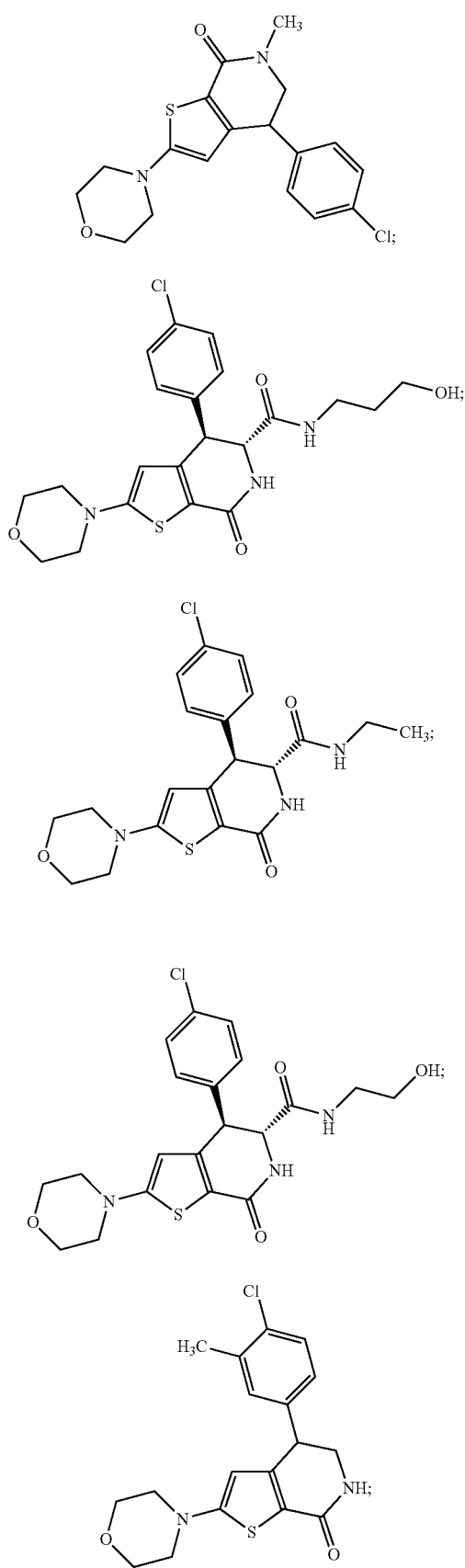
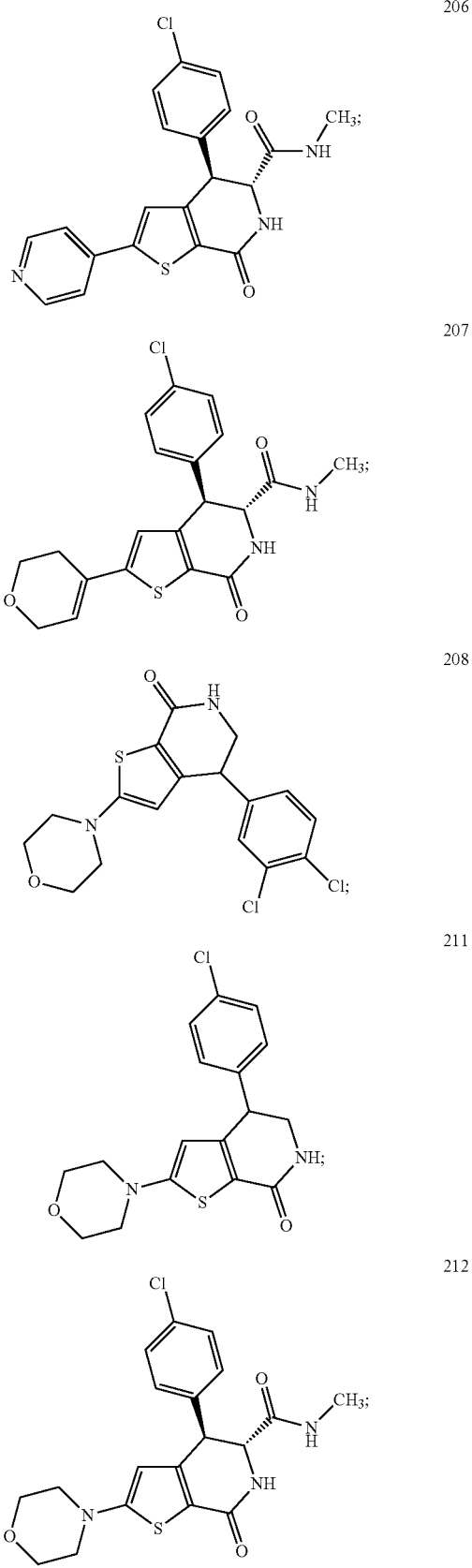

-continued

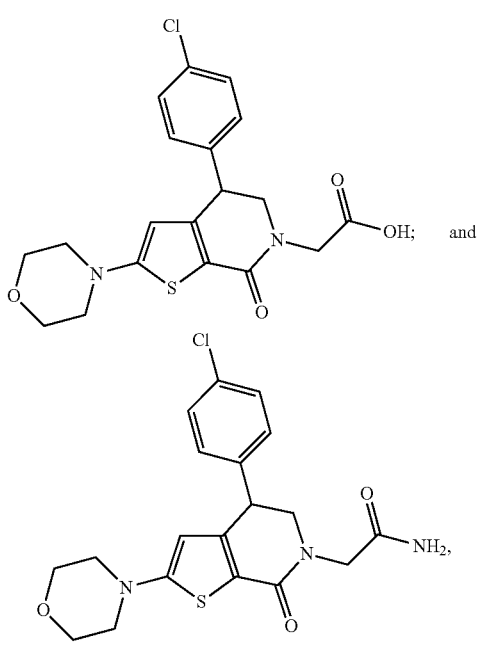

213 and stereoisomers and pharmaceutically acceptable salts thereof.

13. A compound having the structure VIII-A:

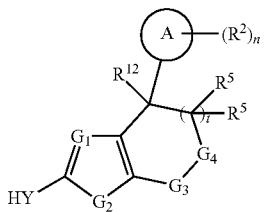

VIII-A or a pharmaceutically acceptable salt thereof, wherein:

$G_1$ is $CR^1$, wherein $R^1$ is H, —CN, halogen, or an optionally substituted group selected from $C_{1-6}$ straight-chain or branched aliphatic, 3-10-membered cycloaliphatic, and —Z—$R^{11}$, wherein:

Z is selected from an optionally substituted $C_{1-3}$ alkylene chain, —O—, —N($R^{1a}$)—, —S—, —S(O)—, S(O)$_2$—, —C(O)—, —CO$_2$—, —C(O)N$R^{1a}$—, —N($R^{1a}$)C(O)—, —N($R^{1a}$)CO$_2$—, —S(O)$_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, and —OC(O)—;

$R^{1a}$ is hydrogen or an optionally substituted $C_{1-4}$ straight-chain or branched aliphatic, and $R^{11}$ is hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur; and $G_2$ is S;

$G_3$ is C=O;

$G_4$ is $NR^{4a}$, wherein $R^{4a}$ is hydrogen or optionally substituted $C_{1-6}$ straight-chain or branched aliphatic;

Ring A is an optionally substituted group selected from 6-10-membered aryl and 5-10-membered heteroaryl having 1-5 heteroatoms independently selected from nitrogen, oxygen, and sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —$R^{12c}$, —N($R^{12b}$)$_2$, —OR$^{12b}$, —SR$^{12c}$, —S(O)$_2$R$^{12c}$, —C(O)R$^{12b}$, —C(O)OR$^{12b}$, —C(O)N($R^{12b}$)$_2$, —S(O)$_2$N($R^{12b}$)$_2$, —OC(O)N($R^{12b}$)$_2$, —N($R^{12e}$)C(O)R$^{12b}$, —N($R^{12e}$)SO$_2$R$^{12c}$, —N($R^{12e}$)C(O)OR$^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;

each occurrence of $R^{12b}$ is independently hydrogen or an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12c}$ is independently an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{12e}$ is independently hydrogen or an optionally substituted $C_{1-6}$ straight-chain or branched aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$-aliphatic group;

n is 0 to 4;

$R^{12}$ is hydrogen, halo, or an optionally substituted group selected from $C_{1-6}$ straight-chain or branched aliphatic, —C(O)N($R^{5a}$)$_2$, 3-10-membered cycloaliphatic, —N($R^{4b}$)$_2$, —O$R^{4a}$, or —S$R^{4a}$;

or $R^2$ and $R^{12}$ form an optionally substituted 3-10-membered cycloaliphatic;

HY is an optionally substituted group selected from:

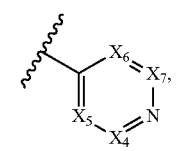 A

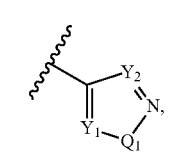 B

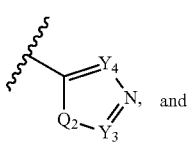 C and

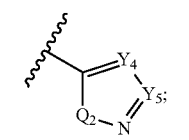 D wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$, $Y_2$, $Y_3$, $Y_4$, and $Y_5$ is independently —$CR^{1o}$ or N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl and 5-6-membered heteroaryl having 1-5 heteroatoms independently selected from nitrogen, oxygen, and sulfur;

wherein $R^{10}$ is —$R^{10b}$, —$V_1$—$R^{10c}$, -$T_1R^{10b}$, or —$V_1$-$T_1$-$R^{10b}$ wherein:

$V_1$ is —$NR^7$—, —$NR^7$—C(O)—, —$NR^7$—C(S)—, —$NR^7$—C($NR^7$)—, —$NR^7$C(O)O$R^{10a}$—, —$NR^7$C(O)N$R^7$—, —$NR^7$C(O)S$R^{10a}$—, —$NR^7$C(S)O$R^{10a}$—, —$NR^7$C(S)N$R^7$—, —$NR^7$C(S)S$R^{10a}$, —$NR^7$C($NR^7$)O$R^{10a}$—, —$NR^7$C($NR^7$)N$R^7$—, —$NR^7$S(O)$_2$—, —$NR^7$S(O)$_2$N$R^7$—, —C(O)—, —$CO_2$—, —C(O)N$R^7$—, —C(O)N$R^7$O—, —$SO_2$—, or —$SO_2NR^7$—;

each occurrence of $R^{10a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

$T_1$ is an optionally substituted $C_1$-$C_6$alkylene chain wherein the alkylene chain optionally is interrupted by —N($R^7$)—, —O—, —S—, —S(O)—, —S(O)$_2$—, —C(O)—, —C(O)O—, —C(O)N($R^7$)—, —S(O)$_2$N($R^7$)—, —OC(O)N($R^7$)—, —N($R^7$)C(O)—, —N($R^7$)SO$_2$—, —N($R^{10a}$)C(O)O—, —N$R^{10a}$C(O)N($R^{10a}$)—, —N($R^{10a}$)S(O)$_2$N($R^{10a}$)—, —OC(O)—, or —C(O)N($R^7$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^7$)$_2$, O$R^{10a}$, —S$R^{10a}$, s(O)$_2R^{10a}$, —C(O)$R^{10a}$, C(O)O$R^{10a}$, —C(O)N($R^7$)$_2$, —S(O)$_2$N($R^7$)$_2$, —OC(O)N($R^7$)$_2$, —N($R^7$)C(O)$R^{10a}$, —N($R^7$)SO$_2R^{10a}$, —N($R^7$)C(O)O$R^{10a}$, —N($R^7$)C(O)N($R^7$)$_2$, or —N($R^7$)SO$_2$N($R^7$)$_2$, or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{10c}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or $R^7$ and $R^{10c}$ taken together with a nitrogen atom to which they are bound form an optionally substituted 4-7-membered heterocyclyl ring having 0-1 additional heteroatoms independently selected from nitrogen, oxygen, and sulfur;

each occurrence of $R^7$ is independently hydrogen, —C(O)$R^{7a}$, —$CO_2R^{7a}$, —C(O)N($R^{7a}$)$_2$, —C(O)N($R^{7a}$)—O$R^{7a}$, —$SO_2R^{7a}$, —$SO_2$N($R^{7a}$)$_2$, or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{7a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^6$ is independently hydrogen, —C(O)$R^{6a}$, —$CO_2R^{6a}$, —C(O)N($R^{6b}$)$_2$, —$SO_2R^{6a}$, —$SO_2$N($R^{6b}$)$_2$) or an optionally substituted group selected from $C_{1-6}$ straight-chain or branched aliphatic, 3-10-membered cycloaliphatic, 4-10-membered heterocyclyl hav-ing 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{6a}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur; and wherein each occurrence of $R^{6b}$ is independently hydrogen or an optionally substituted group selected from $C_{1-6}$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteratoms independently selected from nitrogen, oxygen, and sulfur; or two occurrences of $R^{6b}$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;

or HY is

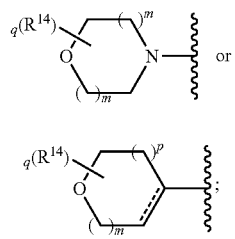

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —O$R^{14b}$, —S$R^{14c}$, —S(O)$_2$$R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2$$R^{14c}$, —N($R^{14e}$)C(O)O$R^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{14c}$ is independently an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{14e}$ is independently hydrogen or an optionally substituted $C_{1-6}$ straight-chain or branched aliphatic group; and $T_1$ is an optionally substituted $C_1$-$C_6$ alkylene chain wherein the alkylene chain optionally is interrupted by —N($R^{14b}$)—, —O—, —S—, —S(O)—, —S(O)$_2$—, —C(O)—, —C(O)O—, —C(O)N($R^{14b}$)—, —S(O)$_2$N($R^{14b}$)—, —OC(O)N($R^{14b}$)—, —N($R^{14b}$)C(O)N($R^{14b}$)SO$_2$—, —N($R^{14b}$)C(O)O—, —N$R^{14b}$C(O)N($R^{14b}$)—, —N($R^{14b}$)S(O)$_2$N($R^{14b}$)—, —OC(O)—, or —C(O)N($R^{14b}$)—O— or wherein $T_1$ or a portion thereof optionally forms part of an optionally substituted 3-7 membered cycloaliphatic or heterocyclyl ring;

q is 0-6;
m is 1 or 2;
p is 0, 1, or 2;
t is 1;

each occurrence of $R^5$ is independently —$R^{15a}$ or -$T_5$-$R^{15d}$, wherein:

each occurrence of $R^{15a}$, as valency and stability permit, is independently hydrogen, halogen, =O, =S, —CN, —NO$_2$, —$R^{15c}$, N($R^{15b}$)$_2$, —O$R^{15b}$, —S$R^{15c}$, —S(O)$_2$$R^{15c}$, —C(O)$R^{15b}$, —C(O)O$R^{15b}$, —C(O)N($R^{15b}$)$_2$, —S(O)$_2$N($R^{15b}$)$_2$, —OC(O)N($R^{15b}$)$_2$, —N($R^{15e}$)C(O)$R^{15b}$, —N($R^{15e}$)SO$_2$$R^{15c}$, —($R^{15e}$)C(O)O$R^{15b}$, —(N$^{15e}$)C(O)N($R^{15b}$)$_2$, or —N($R^{15e}$)SO$_2$N($R^{15b}$)$_2$, or two occurrences of $R^{15b}$, taken together with a nitrogen atom to which they are bound, form an optionally substituted 4-7-membered heterocyclyl ring having 0-1 additional heteroatoms selected from nitrogen, oxygen, and sulfur;

each occurrence of $R^{15b}$ is independently hydrogen or an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{15c}$ is independently an optionally substituted group selected from $C_1$-$C_6$ straight-chain or branched aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{15d}$ is independently hydrogen, —N($R^{15b}$)$_2$, —O$R^{15b}$, —S$R^{15c}$, —S(O)$_2R^{15c}$, —C(O)$R^{15b}$, —C(O)O$R^{15b}$, —C(O)N($R^{15b}$)$_2$, —S(O)$_2$N($R^{15b}$)$_2$, —OC(O)N($R^{15b}$)$_2$, —N($R^{15e}$)C(O)$R^{15b}$, —N($R^{15e}$)SO$_2R^{15c}$, —N($R^{15e}$)C(O)O$R^{15b}$, —N($R^{15e}$)C(O)N($R^{15b}$)$_2$, —N($R^{15e}$)SO$_2$N($R^{15b}$)$_2$, or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{15e}$ is independently hydrogen or an optionally substituted $C_{1-6}$ straight-chain or branched aliphatic group; and $T_5$ is an optionally substituted $C_1$-$C_6$alkylene chain wherein the alkylene chain optionally is interrupted by —N($R^{15b}$)—, —O—, —S—, —S(O)—, —S(O)$_2$—, —C(O)—, —C(O)O—, —C(O)N($R^{15b}$)—, —S(O)$_2$N ($R^{15b}$)—, —OC(O)N($R^{15b}$)—, —N($R^{15b}$)C(O)—, —N($R^{15b}$)SO$_2$—, —N($R^{15b}$)C(O)O—, —N$R^{15b}$ C(O) N($R^{15b}$)—, —N($R^{15b}$)S(O)$_2$N($R^{15b}$)—, —OC(O)—, or —C(O)N($R^{15b}$)—O— or wherein $T_5$ or a portion thereof optionally forms part of an optionally substituted 3-7 membered cycloaliphatic or heterocyclyl ring.

14. The compound of claim 13, wherein when $G_1$ is $CR_1$, $R^1$ is hydrogen, CN, optionally substituted $C_{1-6}$ straight-chain or branched aliphatic or $C_{3-6}$-cycloaliphatic, or optionally substituted alkyne.

15. The compound of claim 13, wherein HY is selected from:

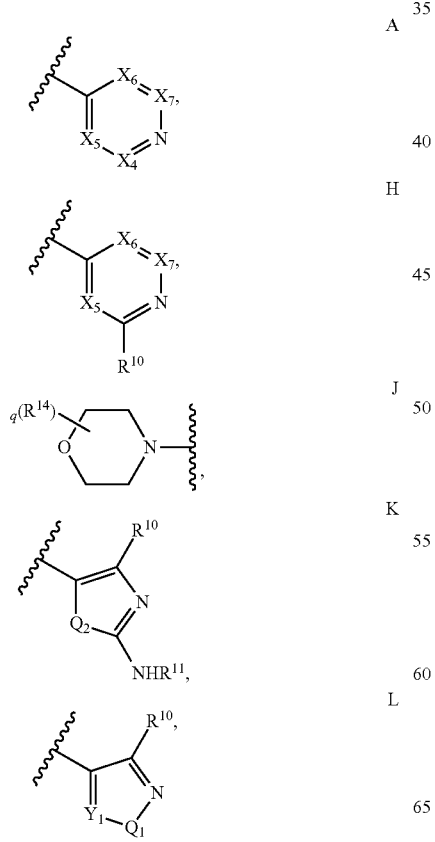

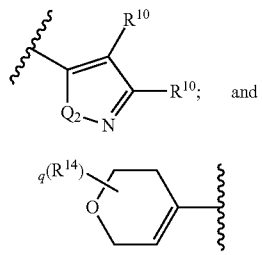

wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^6$;

each occurrence of $Y_1$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein each occurrence of $R^{14}$ is independently an optionally substituted $C_{1-6}$ straight-chain or branched aliphatic group.

16. The compound of claim 13, wherein HY is selected from:

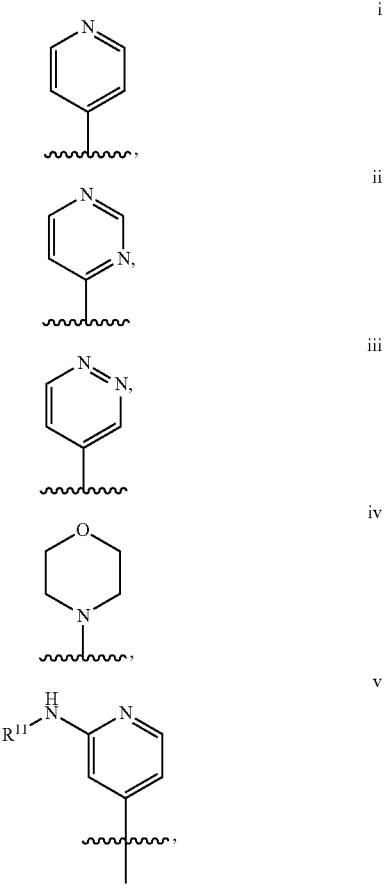

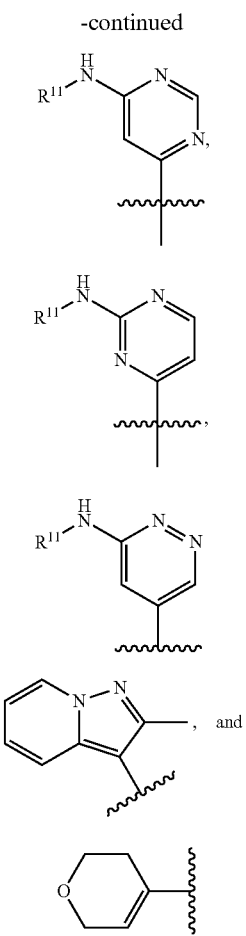

wherein each HY group is optionally additionally substituted with one or more occurrences of $R^{10}$ or $R^{14}$.

17. The compound of claim 16, wherein HY is selected from optionally substituted morpholino (iv) and dihydropyran (x).

18. The compound of claim 17, wherein HY is optionally substituted morpholino (iv).

19. The compound of claim 13, wherein Ring A is an optionally substituted phenyl, naphthyl, quinoline, isoquinoline, or benzimidazole ring.

20. The compound of claim 19, wherein Ring A is optionally substituted by $R^2$ and each occurrence of $R^2$ is independently halogen, $C_{1-3}$ alkyl, —CN, $C_{1-3}$ haloalkyl, —$OC_{1-3}$ alkyl, —$OC_{1-3}$haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

21. The compound of claim 20, wherein Ring A is a phenyl group; each occurrence of $R^2$ is independently halogen, $C_{1-3}$ alkyl, —CN, $C_{1-3}$haloalkyl, —$OC_{1-3}$ alkyl, —$OC_{1-3}$haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

22. The compound of claim 21, wherein Ring A is a phenyl group, $R^2$ is halogen and n is 1 or 2.

23. The compound of claim 13, wherein $R^{4a}$ is optionally substituted straight-chain or branched aliphatic.

24. The compound of claim 23, wherein the optionally substituted straight-chain or branched aliphatic is —(C($R^{4d}$)$_2$)$_{1-4}R^{4e}$, wherein $R^{4d}$ is hydrogen or optionally substituted $C_{1-6}$ straight-chain or branched aliphatic, $R^{4e}$ is hydrogen, optionally substituted 5-membered heteroaryl, COO$R^{4f}$ or CONR$^{4f}$, wherein $R^{4f}$ is hydrogen or optionally substituted $C_{1-6}$ straight-chain or branched aliphatic.

25. The compound of claim 13 wherein each occurrence of $R^5$ is independently hydrogen, halo, or an optionally substituted group selected from $C_{1-6}$ straight-chain or branched aliphatic, C(O)N($R^{15b}$)$_2$, —C(O)O$R^{15b}$, —CH$_2$N($R^{15b}$)$_2$, —CH$_2$O$R^{15b}$, —CH$_2$S$R^{15c}$, 3-10-membered cycloaliphatic, 6-10-membered aryl, and 5-10-membered heteroaryl having 1-5 heteroatoms independently selected from nitrogen, oxygen, and sulfur.

26. The compound of claim 25, wherein $R^{15b}$ is an optionally substituted straight-chain or branched aliphatic group and the optionally substituted straight-chain or branched aliphatic group is optionally further substituted with hydroxyl, $C_{1-6}$ alkoxyl, amino, or $C_{1-6}$ dialkylamino.

27. A pharmaceutical composition comprising a compound of any one of claim 1, 10, 12, or 13 and a pharmaceutically acceptable carrier.

* * * * *